(12) United States Patent
Schmulling et al.

(10) Patent No.: US 8,138,389 B2
(45) Date of Patent: Mar. 20, 2012

(54) METHOD FOR MODIFYING PLANT MORPHOLOGY, BIOCHEMISTRY AND PHYSIOLOGY

(76) Inventors: Thomas Schmulling, Berlin (DE); Tomas Werner, Berlin (DE)

( * ) Notice: Subject to any disclaimer, the term of this patent is extended or adjusted under 35 U.S.C. 154(b) by 0 days.

(21) Appl. No.: 12/844,343

(22) Filed: Jul. 27, 2010

(65) Prior Publication Data
US 2011/0023186 A1      Jan. 27, 2011

Related U.S. Application Data

(60) Continuation of application No. 11/801,018, filed on May 8, 2007, now Pat. No. 7,807,879, which is a division of application No. 10/014,101, filed on Dec. 10, 2001, now Pat. No. 7,259,296, which is a continuation-in-part of application No. PCT/EP01/06833, filed on Jun. 18, 2001.

(60) Provisional application No. 60/258,415, filed on Dec. 27, 2000.

(30) Foreign Application Priority Data

Jun. 16, 2000   (EP) ..................................... 00870132
Mar. 16, 2001   (EP) ..................................... 01870053

(51) Int. Cl.
*C12N 15/82* (2006.01)
(52) U.S. Cl. .................... 800/278; 800/290; 800/287
(58) Field of Classification Search .................. None
See application file for complete search history.

(56) References Cited

FOREIGN PATENT DOCUMENTS
WO          99/06571       2/1999

OTHER PUBLICATIONS

Abstract: Rounsley et al. (1998); XP002151606, Database Accession No. ID/AC=022213.
Abstract: Bevan et al. (2000); "Cytokinin oxidase-like protein", XP-002151607, Database Accession No. ID/AC=Q9SU77.
Abstract: Lin et al. (1999) "*Arabidopsis thaliana* chromosome II BAC F3P11 genomic sequence, Putative Cytokinin Oxidase", XP-002151608, Database Accession No. ID/AC=Q9ZUP1.
Abstract: Zhang et al. (1999) "Initiation an elongation of lateral roots in *Lactuca sativa*", XP002151609, Database Accession No. AN=PREV199900326622, International J. of Plant Sciences, 160(3): 511-519.
Abstract: Koda et al. (1989) "Cytokinin production by tomato root. Identification of a major cytokinin produced by the root and environmental factors affecting the production", XP002151610, Database Accession No. AN=PREV198988038194, J. of the Faculty of Agriculture Hokkaido University, 64(1):, pp. 10-20.
Abstract: Frank et al. (1999) "TSD genes negatively regulate merismetic activity in *Arabidopsis*", XP00215616, Database Accession No. AN=PREV200000242628, Biologia Plantarum (Prague), 42 (suppl): S47.
Doerner et al. (1996) "Control of root growth and development by cyclin expression" Nature, 380: 520-523.
Faiss et al. (1997) "Conditional transgenic expression of the ipt gene indicates a function for cytokinins in paracrine signaling in whole tobacco plants", The Plant Journal, 12(2): 401-415.
Houba-Herin et al. (1999) "Cytokinin oxidases from *Zea mays*: purification, cDNA cloning and expression in moss protoplasts", The Plant Journal, 17(6): 615-626.
Klee, et al. (1995) "Transgenic plants in hormone biology", Plant Hormones: Physiology, Biochemistry and Molecular Biology, ed. Davies, P.J. (Klower, Dordrdrocht, the Netherlands), pp. 340-353.
Mok (1994) "Cytokinins and Plant Development", Cytokines: Chemistry, Activity, and Function, Chapter 12, eds. Mok, D.W.S. & Mok, M.C., CRC Press, Inc., pp. 155-166.
Morris et al. (1999) "Isolation of a Gene Encoding a Glycosylated Cytokinin Oxidase from Maize", Biochemical and Biophysical Research Communications, 255: 328-333.
Motyka et al. (1996) "Changes in Cytokinin Content and Cytokinin Oxidase Activity in Response to Derepression of ipt Gene Transcription in Transgenic Tobacco Calli and Plants", Plant Physiol., 112: 1035-1043.
Rinaldi et al. (1999) "Cytokinin oxidase strikes again", Trends in Plant Sci., Elsevier Science, 4(8): 300.
Schmulling et al (1999) "Recent advances in cytokinin research: Receptor candidates, primary response genes, mutants and transgenic plants", Advances in Regulation of Plant Growth and Development, pp. 85-96.
Werner et al. (2001) "Regulation of plant growth by cytokinin" PNAS, 98(18): 10487-10492.
Hare et al. (1994) Physiologia Plantarum, 91: 128-136.
Bowie et al. (1990) Science, 247: 1306-1310.
McConnell et al. (2001) Nature, 411 6838: 709-713.
Fourgoux-Nicol (1999) Plant Molecular Biology, 40: 857-872.
Kaminek et al. (1990) Plant Physiol, 93: 1530-1538.
Lin et al. (1999) NCBI Accession No. AC005917.
Werner et al. (2003) "The Plant Cell" 15: 2532-2550.
Deaton (1999) Proceedings of Genetic and Evolutionary Computation Conference, 2 AAAI, Morgan Kaufmann, San Francisco, 1999 Orlando Florida.
Anonymous, Roche Applied Science, Nonradioactive In-Situ (2004) Hybridization Application Manual, pp. 1-206 available at: www.roche-applied-science.com/PROD_INF/MANUALS/InSitu/InSi_toc.htm.

*Primary Examiner* — Stuart F Baum
(74) *Attorney, Agent, or Firm* — Ann R. Pokalsky, Esq.; Dilworth & Barrese, LLP

(57) ABSTRACT

The present invention provides nucleotide sequences and corresponding amino acid sequences for plant cytokinin oxidase proteins. In addition, vectors, host cells, and transgenic plants comprising such sequences as well as methods for stimulating root growth and/or enhancing the formation of lateral or adventitious roots and/or altering root geotropism using such sequences are provided by the present invention. Also provided by the present invention are methods for altering various plant phenotypes including delaying onset to flowering, increasing leaf thickness, reducing vessel size, inducing parthenocarpy, increasing branching, increasing seed size and/or weight, embryo size and/or weight, and cotyledon size and/or weight using cytokinin oxidase proteins and/or nucleic acid molecules encoding cytokinin oxidase.

16 Claims, 18 Drawing Sheets

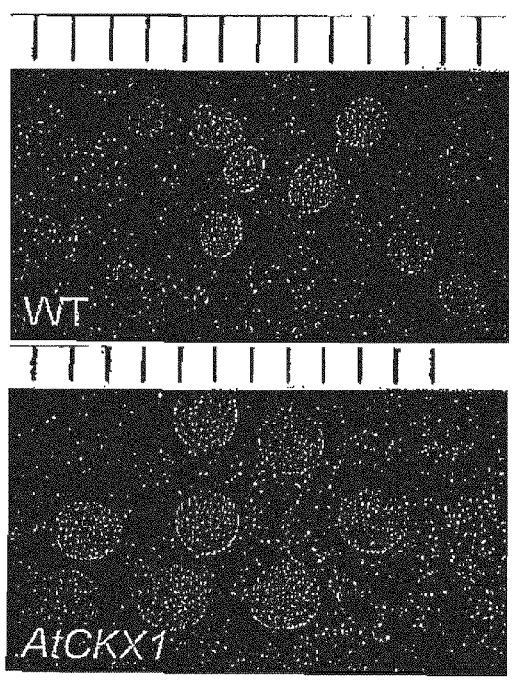 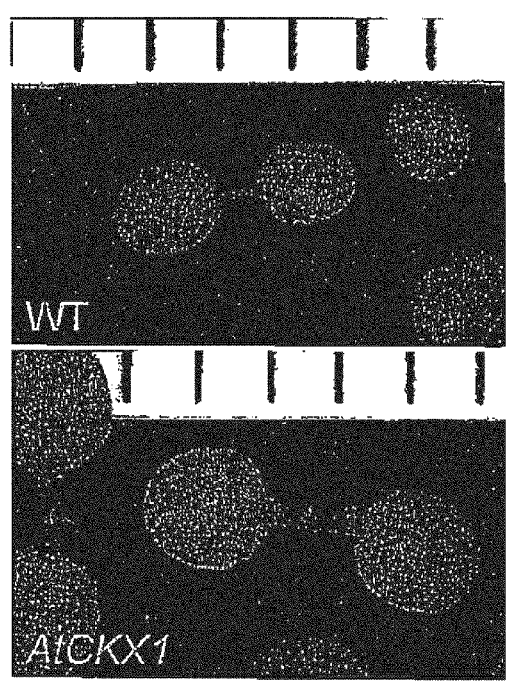
Figure 13D
Figure 13E

SEQUENCE LISTING

```
<160> NUMBER OF SEQ ID NOS: 42

<210> SEQ ID NO 1
<211> LENGTH: 2236
<212> TYPE: DNA
<213> ORGANISM: Arabidopsis thaliana

<400> SEQUENCE: 1
atgggattga cctcatcctt acggttccat agacaaaaca acaagactTT cctcggaatc      60
ttcatgatct tagttctaag ctgtatacca ggtagaacca atctttgttc caatcattct     120
gttagtaccc caaaagaatt accttcttca aatccttcag atattcgttc ctcattagtt     180
tcactagatt tggagggtta tataagcttc gacgatgtcc acaatgtggc caaggacttt     240
ggcaacagat accagttacc acctttggca attctacatc caaggtcagt ttttgatatt     300
tcatcgatga tgaagcatat agtacatctg ggctccacct caaatcttac agtagcagct     360
agaggccatg gtcactcgct tcaaggacaa gctctagctc atcaaggtgt tgtcatcaaa     420
atggagtcac ttcgaagtcc tgatatcagg atttataagg ggaagcaacc atatgttgat     480
gtctcaggtg gtgaaatatg gataaacatt ctacgcgaga ctctaaaata cggtctttca     540
ccaaagtcct ggacagacta ccttcatttg accgttggag gtacactatc taatgctgga     600
atcagcggtc aagcattcaa gcatggaccc caaatcaaca acgtctacca gctagagatt     660
gttacaggta tttcattcat gctttatctc tgcggtagtc tcaaaaaaat atgcacctgt     720
aaagaatatc catctcttca tgagcaaaaa cactgacgac tttaaataat ttttgactat     780
aaaacaagag tgcataggca caaatgtgaa atatgcaaca cacaattgta acttgcacca     840
agaaaaaagt tataaaaaca aacaactgat aagcaatata tttccaatat ttaatcaggg     900
aaaggagaag tcgtaacctg ttctgagaag cggaattctg aacttttctt cagtgttctt     960
```

```
ggcgggcttg gacagtttgg cataatcacc cgggcacgga tctctcttga accagcaccg    1020
catatggtaa agttctatct tgaacaaagt tcaaacaata tacgctatga ttctaagaac    1080
cactttcctg acacagtcaa ataactttta ataggttaaa tggatcaggg tactctactc    1140
tgacttttct gcattttcaa gggaccaaga atatctgatt tcgaaggaga aaacttttga    1200
ttacgttgaa ggatttgtga taatcaatag aacagacctt ctcaataatt ggcgatcgtc    1260
attcagtccc aacgattcca cacaggcaag cagattcaag tcagtgggaa aaactcttta    1320
ttgcctagaa gtggtcaaat atttcaaccc agaagaagct agctctatgg atcaggtaag    1380
atgtgaaagc aatatataac tagacttagt ttccacagag agctccaaat caaccgttgg    1440
ctactagcct actaacataa tgaatggttg ccgtgcagga aactggcaag ttactttcag    1500
agttaaatta tattccatcc actttgtttt catctgaagt gccatatatc gagtttctgg    1560
atcgcgtgca tatcgcagag agaaaactaa gagcaaaggg tttatgggag gttccacatc    1620
cctggctgaa tctcctgatt cctaagagca gcatatacca atttgctaca gaagttttca    1680
acaacattct cacaagcaac aacaacggtc ctatccttat ttatccagtc aatcaatcca    1740
agtaagtgag caaaatgcca aaagcaaatg cgtccagtga ttctgaaaca taaattacta    1800
accatatcca acattttgtg gtttcaggtg gaagaaacat acatctttga taactccaaa    1860
tgaagatata ttctatctcg tagccttttct cccctctgca gtgccaaatt cctcagggaa    1920
aaacgatcta gagtaccttt tgaaacaaaa ccaagagtt atgaacttct gcgcagcagc    1980
aaacctcaac gtgaagcagt atttgcccca ttatgaaact caaaaagagt ggaaatcaca    2040
ctttggcaaa agatgggaaa catttgcaca gaggaaacaa gcctacgacc ctctagcgat    2100
tctagcacct ggccaaagaa tattccaaaa gacaacagga aaattatctc ccatccaact    2160
cgcaaagtca aaggcaacag gaagtcctca aaggtaccat tacgcatcaa tactgccgaa    2220
acctagaact gtataa                                                    2236
```

<210> SEQ ID NO 2
<211> LENGTH: 575
<212> TYPE: PRT
<213> ORGANISM: Arabidopsis thaliana

<400> SEQUENCE: 2

```
Met Gly Leu Thr Ser Ser Leu Arg Phe His Arg Gln Asn Asn Lys Thr
  1               5                  10                  15

Phe Leu Gly Ile Phe Met Ile Leu Val Leu Ser Cys Ile Pro Gly Arg
                 20                  25                  30

Thr Asn Leu Cys Ser Asn His Ser Val Ser Thr Pro Lys Glu Leu Pro
             35                  40                  45

Ser Ser Asn Pro Ser Asp Ile Arg Ser Ser Leu Val Ser Leu Asp Leu
         50                  55                  60

Glu Gly Tyr Ile Ser Phe Asp Asp Val His Asn Val Ala Lys Asp Phe
 65                  70                  75                  80

Gly Asn Arg Tyr Gln Leu Pro Pro Leu Ala Ile Leu His Pro Arg Ser
                 85                  90                  95

Val Phe Asp Ile Ser Ser Met Met Lys His Ile Val His Leu Gly Ser
            100                 105                 110

Thr Ser Asn Leu Thr Val Ala Ala Arg Gly His Gly His Ser Leu Gln
        115                 120                 125

Gly Gln Ala Leu Ala His Gln Gly Val Val Ile Lys Met Glu Ser Leu
    130                 135                 140

Arg Ser Pro Asp Ile Arg Ile Tyr Lys Gly Lys Gln Pro Tyr Val Asp
```

-continued

```
            145                 150                 155                 160
        Val Ser Gly Gly Glu Ile Trp Ile Asn Ile Leu Arg Glu Thr Leu Lys
                        165                 170                 175
        Tyr Gly Leu Ser Pro Lys Ser Trp Thr Asp Tyr Leu His Leu Thr Val
                        180                 185                 190
        Gly Gly Thr Leu Ser Asn Ala Gly Ile Ser Gly Gln Ala Phe Lys His
                        195                 200                 205
        Gly Pro Gln Ile Asn Asn Val Tyr Gln Leu Glu Ile Val Thr Gly Lys
                        210                 215                 220
        Gly Glu Val Val Thr Cys Ser Glu Lys Arg Asn Ser Glu Leu Phe Phe
        225                 230                 235                 240
        Ser Val Leu Gly Gly Leu Gly Gln Phe Gly Ile Ile Thr Arg Ala Arg
                        245                 250                 255
        Ile Ser Leu Glu Pro Ala Pro His Met Val Lys Trp Ile Arg Val Leu
                        260                 265                 270
        Tyr Ser Asp Phe Ser Ala Phe Ser Arg Asp Gln Glu Tyr Leu Ile Ser
                        275                 280                 285
        Lys Glu Lys Thr Phe Asp Tyr Val Glu Gly Phe Val Ile Ile Asn Arg
                        290                 295                 300
        Thr Asp Leu Leu Asn Asn Trp Arg Ser Ser Phe Ser Pro Asn Asp Ser
        305                 310                 315                 320
        Thr Gln Ala Ser Arg Phe Lys Ser Asp Gly Lys Thr Leu Tyr Cys Leu
                        325                 330                 335
        Glu Val Val Lys Tyr Phe Asn Pro Glu Glu Ala Ser Ser Met Asp Gln
                        340                 345                 350
        Glu Thr Gly Lys Leu Leu Ser Glu Leu Asn Tyr Ile Pro Ser Thr Leu
                        355                 360                 365
        Phe Ser Ser Glu Val Pro Tyr Ile Glu Phe Leu Asp Arg Val His Ile
                        370                 375                 380
        Ala Glu Arg Lys Leu Arg Ala Lys Gly Leu Trp Glu Val Pro His Pro
        385                 390                 395                 400
        Trp Leu Asn Leu Leu Ile Pro Lys Ser Ser Ile Tyr Gln Phe Ala Thr
                        405                 410                 415
        Glu Val Phe Asn Asn Ile Leu Thr Ser Asn Asn Asn Gly Pro Ile Leu
                        420                 425                 430
        Ile Tyr Pro Val Asn Gln Ser Lys Trp Lys His Thr Ser Leu Ile
                        435                 440                 445
        Thr Pro Asn Glu Asp Ile Phe Tyr Leu Val Ala Phe Leu Pro Ser Ala
                        450                 455                 460
        Val Pro Asn Ser Ser Gly Lys Asn Asp Leu Glu Tyr Leu Leu Lys Gln
        465                 470                 475                 480
        Asn Gln Arg Val Met Asn Phe Cys Ala Ala Ala Asn Leu Asn Val Lys
                        485                 490                 495
        Gln Tyr Leu Pro His Tyr Glu Thr Gln Lys Glu Trp Lys Ser His Phe
                        500                 505                 510
        Gly Lys Arg Trp Glu Thr Phe Ala Gln Arg Lys Gln Ala Tyr Asp Pro
                        515                 520                 525
        Leu Ala Ile Leu Ala Pro Gly Gln Arg Ile Phe Gln Lys Thr Thr Gly
                        530                 535                 540
        Lys Leu Ser Pro Ile Gln Leu Ala Lys Ser Lys Ala Thr Gly Ser Pro
        545                 550                 555                 560
        Gln Arg Tyr His Tyr Ala Ser Ile Leu Pro Lys Pro Arg Thr Val
                        565                 570                 575
```

<210> SEQ ID NO 3
<211> LENGTH: 2991
<212> TYPE: DNA
<213> ORGANISM: Arabidopsis thaliana

<400> SEQUENCE: 3

```
atggctaatc ttcgtttaat gatcacttta atcacggttt taatgatcac caaatcatca      60
aacggtatta aaattgattt acctaaatcc cttaacctca ccctctctac cgatccttcc     120
atcatctccg cagcctctca tgacttcgga aacataacca ccgtgacccc cggcggcgta     180
atctgcccct cctccaccgc tgatatctct cgtctcctcc aatacgccgc aaacggaaaa     240
agtacattcc aagtagcggc tcgtggccaa ggccactcct taaacggcca agcctcggtc     300
tccggcggag taatcgtcaa catgacgtgt atcactgacg tggtggtttc aaaagacaag     360
aagtacgctg acgtggcggc cgggacgtta tgggtggatg tgcttaagaa gacggcggag     420
aaaggggtgt cgccggtttc ttggacggat tatttgcata taccgtcgg aggaacgttg     480
tcgaatggtg gaattggtgg tcaagtgttt cgaaacggtc ctcttgttag taacgtcctt     540
gaattggacg ttattactgg tacgcatctt ctaaactttg atgtacatac aacaacaaaa     600
actgttttg ttttatagta ttttcattt tttgtaccat aggttttatg ttttatagtt     660
gtgctaaact tcttgcacca cacgtaagtc ttcgaaacac aaaatgcgta acgcatctat     720
atgttttttg tacatattga atgttgttca tgagaaataa agtaattaca tatacacaca     780
tttattgtcg tacatatata ataattaaa gacaattt cacaattggt agcgtgttaa     840
tttgggattt ttgtaatgta catgcatgac gcatgcatat ggagcttttc ggttttctta     900
gatttgtgta gtatttcaaa tatatcattt attttctttc gaataaagag gtggtatatt     960
tttaaaatag caacatttca gaattttct ttgaatttac acttttaaa ttgttattgt    1020
taatatggat tttgaataaa taatttcagg gaaaggtgaa atgttgacat gctcgcgaca    1080
gctaaaccca gaattgttct atggagtgtt aggaggtttg ggtcaatttg gaattataac    1140
gagagccaga attgtttggg accatgcacc taaacgggta cgtatcatca tattttacca    1200
tttgttttag tcagcattca tttttcatta gtaattccgt ttcaatttct aaatttttt    1260
agtcaataga aaatgattct tatgtcagag cttgattatt tagtgatttt tattgagata    1320
aaataaaata taacctaacg gaaataatta ttttactaat cggataatgt ctgattaaaa    1380
cattttatga tattcacta agagagttag agacgtatgg atcacaaaac atgaagcttt    1440
cttagatggt atcctaaaac taagttaggt acaagtttg gaatttaggt caaatgctta    1500
agttgcatta atttgaacaa atctatgca ttgaataaaa aaagatatg gattatttta    1560
taaagtatag tccttgtaat cctaggactt gttgtctaat cttgtcttat gcgtgcaaat    1620
cttttgatg tcaatatata atccttgttt attagagtca agctctttca ttagtcaact    1680
actcaaatat actccaaagt ttagaatata gtcttctgac taattagaat cttacaaccg    1740
ataaacgtta caatttggtt atcattttaa aaaacagatt tggtcataat atacgatgac    1800
gttctgtttt agtttcatct attcacaaat tttatataat tattttcaag aaaatattga    1860
aatactatac tgtaatatgg tttcttata tatgtgtgta taaattaaat gggattgttt    1920
tctctaaatg aaattgtgta ggccaaatgg tttcggatgc tctacagtga tttcacaact    1980
tttacaaagg accaagaacg tttgatatca atggcaaacg atattggagt cgactattta    2040
gaaggtcaaa tatttctatc aaacggtgtc gttgacacct ctttttccc accttcagat    2100
caatctaaag tcgctgatct agtcaagcaa cacggtatca tctatgttct tgaagtagcc    2160
```

```
aagtattatg atgatcccaa tctccccatc atcagcaagg tactacacat ttacattttc    2220
atcatcgttt ttatcatacc ataagatatt taaatgattc atcattgcac cacattaaga    2280
tattcatcat catcatcgtt acatttttt ttgcatctta tgcttctcat aatctactat     2340
tgtgtaggtt attgacacat taacgaaaac attaagttac ttgcccgggt tcatatcaat    2400
gcacgacgtg gcctacttcg atttcttgaa ccgtgtacat gtcgaagaaa ataaactcag    2460
atctttggga ttatgggaac ttcctcatcc ttggcttaac ctctacgttc ctaaatctcg    2520
gattctcgat tttcataacg gtgttgtcaa agacattctt cttaagcaaa aatcagcttc    2580
gggactcgct cttctctatc caacaaaccg gaataagtac atacttctct tcattcatat    2640
ttatcttcaa gaaccaaagt aaataaattt ctatgaactg attatgctgt tattgttaga    2700
tgggacaatc gtatgtcggc gatgatacca gagatcgatg aagatgttat atatattatc    2760
ggactactac aatccgctac cccaaaggat cttccagaag tggagagcgt taacgagaag    2820
ataattaggt tttgcaagga ttcaggtatt aagattaagc aatatctaat gcattatact    2880
agtaaagaag attggattga gcattttgga tcaaatgggg atgattttc gaagaggaaa    2940 gatctatttg atcccaagaa actgttatct ccagggcaag acatcttttg a             2991

<210> SEQ ID NO 4
<211> LENGTH: 501
<212> TYPE: PRT
<213> ORGANISM: Arabidopsis thaliana

<400> SEQUENCE: 4

Met Ala Asn Leu Arg Leu Met Ile Thr Leu Ile Thr Val Leu Met Ile
 1               5                  10                  15

Thr Lys Ser Ser Asn Gly Ile Lys Ile Asp Leu Pro Lys Ser Leu Asn
            20                  25                  30

Leu Thr Leu Ser Thr Asp Pro Ser Ile Ile Ser Ala Ala Ser His Asp
        35                  40                  45

Phe Gly Asn Ile Thr Thr Val Thr Pro Gly Gly Val Ile Cys Pro Ser
    50                  55                  60

Ser Thr Ala Asp Ile Ser Arg Leu Leu Gln Tyr Ala Ala Asn Gly Lys
65                  70                  75                  80

Ser Thr Phe Gln Val Ala Ala Arg Gly Gln Gly His Ser Leu Asn Gly
                85                  90                  95

Gln Ala Ser Val Ser Gly Gly Val Ile Val Asn Met Thr Cys Ile Thr
            100                 105                 110

Asp Val Val Ser Lys Asp Lys Lys Tyr Ala Asp Val Ala Ala Gly Lys
        115                 120                 125

Thr Leu Trp Val Asp Val Leu Lys Lys Thr Ala Glu Lys Gly Val Ser
    130                 135                 140

Pro Val Ser Trp Thr Asp Tyr Leu His Ile Thr Val Gly Gly Thr Leu
145                 150                 155                 160

Ser Asn Gly Gly Ile Gly Gly Gln Val Phe Arg Asn Gly Pro Leu Val
                165                 170                 175

Ser Asn Val Leu Glu Leu Asp Val Ile Thr Gly Lys Gly Glu Met Leu
            180                 185                 190

Thr Cys Ser Arg Gln Leu Asn Pro Glu Leu Phe Tyr Gly Val Leu Gly
        195                 200                 205

Gly Leu Gly Gln Phe Gly Ile Ile Thr Arg Ala Arg Ile Val Leu Asp
    210                 215                 220

His Ala Pro Lys Arg Ala Lys Trp Phe Arg Met Leu Tyr Ser Asp Phe
225                 230                 235                 240
```

```
Thr Thr Phe Thr Lys Asp Gln Glu Arg Leu Ile Ser Met Ala Asn Asp
            245                 250                 255
Ile Gly Val Asp Tyr Leu Glu Gly Gln Ile Phe Leu Ser Asn Gly Val
        260                 265                 270
Val Asp Thr Ser Phe Phe Pro Pro Ser Asp Gln Ser Lys Val Ala Asp
    275                 280                 285
Leu Val Lys Gln His Gly Ile Ile Tyr Val Leu Glu Val Ala Lys Tyr
290                 295                 300
Tyr Asp Pro Asn Leu Pro Ile Ile Ser Lys Val Ile Asp Thr Leu
305                 310                 315                 320
Thr Lys Thr Leu Ser Tyr Leu Pro Gly Phe Ile Ser Met His Asp Val
            325                 330                 335
Ala Tyr Phe Asp Phe Leu Asn Arg Val His Val Glu Glu Asn Lys Leu
        340                 345                 350
Arg Ser Leu Gly Leu Trp Glu Leu Pro His Pro Trp Leu Asn Leu Tyr
    355                 360                 365
Val Pro Lys Ser Arg Ile Leu Asp Phe His Asn Gly Val Val Lys Asp
370                 375                 380
Ile Leu Leu Lys Gln Lys Ser Ala Ser Gly Leu Ala Leu Leu Tyr Pro
385                 390                 395                 400
Thr Asn Arg Asn Lys Trp Asp Asn Arg Met Ser Ala Met Ile Pro Glu
            405                 410                 415
Ile Asp Glu Asp Val Ile Tyr Ile Ile Gly Leu Leu Gln Ser Ala Thr
        420                 425                 430
Pro Lys Asp Leu Pro Glu Val Glu Ser Val Asn Glu Lys Ile Ile Arg
    435                 440                 445
Phe Cys Lys Asp Ser Gly Ile Lys Ile Lys Gln Tyr Leu Met His Tyr
450                 455                 460
Thr Ser Lys Glu Asp Trp Ile Glu His Phe Gly Ser Lys Trp Asp Asp
465                 470                 475                 480
Phe Ser Lys Arg Lys Asp Leu Phe Asp Pro Lys Lys Leu Leu Ser Pro
            485                 490                 495
Gly Gln Asp Ile Phe
            500

<210> SEQ ID NO 5
<211> LENGTH: 3302
<212> TYPE: DNA
<213> ORGANISM: Arabidopsis thaliana

<400> SEQUENCE: 5
atggcgagtt ataatcttcg ttcacaagtt cgtcttatag caataacaat agtaatcatc      60
attactctct caactccgat cacaaccaac acatcaccac aaccatggaa tatcctttca     120
cacaacgaat cgccggaaa actcacctcc tcctcctcct ccgtcgaatc agccgccaca     180
gatttcggcc acgtcaccaa atcttccct tccgccgtct taatcccttc ctccgttgaa     240
gacatcacag atctcataaa actctctttt gactctcaac tgtctttcc tttagccgct     300 cgtggtcacg gacacagcca ccgtggccaa gcctcggcta agacggagt tgtggtcaac     360 atgcggtcca tggtaaaccg ggatcgaggt atcaaggtgt ctaggacctg tttatatgtt     420
gacgtggacg ctgcgtggct atggattgag gtgttgaata aaactttgga gttagggtta     480
acgccggttt cttggacgga ttatttgtat ttaacagtcg gtgggacgtt atcaaacggc     540
ggaattagtg gacaaacgtt tcggtacggt ccacagatca ctaatgttct agagatggat     600
```

```
gttattactg gtacgtacca cgatcttttt cacacagaga ttaaaaaaaa cagtaatagt    660
gattttaact tcgtacgttt ctgatagaca acaaagaact tcgtacgttt ttcgaagttt    720
tttcgtcttt ttcattttag atctgcgcgg ccattttgg ttatgctatt gtttgtttgt     780
attgtttgtc tctgtttatt tatttctcga acttgttgat agcttttctt cttttcacac    840
atcaatctaa tcacctttt tggtcttaag attagaaaga agatacggac taggtaaaaa    900
taggtggttg taaacgtaga cgcattaaaa aaatattggt tttttattt tttgataagc     960 aaaattggtg gttggtctaa gattataaac ttgatattaa tgcaaaggtc gatctagcaa   1020
tagaagatta atcaatattc ttggtgtttt aacaacagat tatttcatca ttaaaatcgt   1080
gaaacaaaga aattttggta gtatacatta cgtgtagttt tgttagttta ttaaaaaaaa   1140
tagtatatag ttttgttaaa acgcgattta tttagtaaca cattagtata ttacacgttt   1200
aaccaactaa acttttttt ttgaataatt atgttctata tttcttactc aaattatgca    1260
aatttcgtgg attcgaagtc aaatttctgc gaaatttaca tggtcatata ttataaaact   1320
gttcatataa cccggtgaac aaacagacaa ttaagggttt gaatggttac ggcggttggg   1380
gcggacacaa ccgtcaatag atcagaccgt tttttattta ccattcatca attatattcc   1440
gcagtggttt ggggtaaaaa aaatagaaga aaaccgcagc ggaccaattc cataccgttt   1500
ttacatacaa ataaacatgg tgcgcaacgg tttattgtcc gcctcaaaaa tgaaatggac   1560
taaaccgcag ataaattaga ccgctttgtc cgctgcctcc attcatagac taaaaaaaaa   1620
caaccaaaaa aaaatggtc ccacgcccat gattttacac gaggtttctt gtggcgtaag   1680
gacaaaactc aaaagttcat aacgtttggt cctaaccagg tgtaatggat taagtaacag   1740
tcaattttct tattatagct gtatccatta tgtccacata tgcatccata tacattacac   1800
tgttggtctc aagtgtagtt agattacgaa gactttcaag ttccattttt tggttaggag   1860
ataaacataa tttaatgata ccgactttag cactctaggc tcaaaacaag tacagaagag   1920
aatagtttta tttcaaactc gttgcattgt tgtatcaatt aattgtgtta gtctttgtat   1980
attcttacat aacggtccaa gtttgttgaa atagtttact tactaaactt ttcctaatgg   2040
ggtcaaattt tatttatag gaaaaggaga gattgcaact tgttccaagg acatgaactc    2100
ggatcttttc ttcgcggtgt taggaggttt gggtcaattc ggcattataa caagagccag   2160
aattaaactt gaagtagctc cgaaaagggt atgtaaatt tgtaaattat gcaactacg    2220 aaaattctat gaaatttatg aatgaacata tatgcatttt tggatttttg taggccaagt   2280
ggttaaggtt tctatacata gatttctccg aattcacaag agatcaagaa cgagtgatat   2340
cgaaaacgga cggtgtagat ttcttagaag gttccattat ggtggaccat ggcccaccgg   2400
ataactggag atccacgtat tatccaccgt ccgatcactt gaggatcgcc tcaatggtca   2460
aacgacatcg tgtcatctac tgccttgaag tcgtcaagta ttacgacgaa acttctcaat   2520
acacagtcaa cgaggtccgt acatacatac aatcataaat catacatgta taattgggag   2580
atctttatgc attattcaat tatattaatt tactttagtt atttaactta tgcaggaaat   2640
ggaggagtta agcgatagtt taaaccatgt aagagggttt atgtacgaga aagatgtgac   2700
gtatatggat ttcctaaacc gagttcgaac cggagagcta aacctgaaat ccaaaggcca   2760
atgggatgtt ccacatccat ggcttaatct cttcgtacca aaaactcaaa tctccaaatt   2820
tgatgatggt gttttaagg gtattatcct aagaaataac atcactagcg gtcctgttct    2880
tgtttatcct atgaatcgca acaagtaagt ttaactcgat attgcaaaat ttactatcta   2940
cattttcgtt ttggaatccg aaatattctt acaagctaat tttatgcggc gttttaggt    3000
```

```
ggaatgatcg gatgtctgcc gctatacccg aggaagatgt attttatgcg gtagggtttt   3060
taagatccgc gggttttgac aattgggagg cttttgatca agaaaacatg gaaatactga   3120
agttttgtga ggatgctaat atggggggtta tacaatatct tccttatcat tcatcacaag   3180
aaggatgggt tagacatttt ggtccgaggt ggaatatttt cgtagagaga aaatataaat   3240
atgatcccaa aatgatatta tcaccgggac aaaatatatt tcaaaaaata aactcgagtt   3300
ag                                                                 3302
```

<210> SEQ ID NO 6
<211> LENGTH: 523
<212> TYPE: PRT
<213> ORGANISM: Arabidopsis thaliana

<400> SEQUENCE: 6

```
Met Ala Ser Tyr Asn Leu Arg Ser Gln Val Arg Leu Ile Ala Ile Thr
 1               5                   10                  15

Ile Val Ile Ile Thr Leu Ser Thr Pro Ile Thr Thr Asn Thr Ser
            20                  25                  30

Pro Gln Pro Trp Asn Ile Leu Ser His Asn Glu Phe Ala Gly Lys Leu
        35                  40                  45

Thr Ser Ser Ser Ser Val Glu Ser Ala Ala Thr Asp Phe Gly His
    50                  55                  60

Val Thr Lys Ile Phe Pro Ser Ala Val Leu Ile Pro Ser Ser Val Glu
 65                  70                  75                  80

Asp Ile Thr Asp Leu Ile Lys Leu Ser Phe Asp Ser Gln Leu Ser Phe
                85                  90                  95

Pro Leu Ala Ala Arg Gly His Gly His Ser His Arg Gly Gln Ala Ser
            100                 105                 110

Ala Lys Asp Gly Val Val Val Asn Met Arg Ser Met Val Asn Arg Asp
        115                 120                 125

Arg Gly Ile Lys Val Ser Arg Thr Cys Leu Tyr Val Asp Val Asp Ala
    130                 135                 140

Ala Trp Leu Trp Ile Glu Val Leu Asn Lys Thr Leu Glu Leu Gly Leu
145                 150                 155                 160

Thr Pro Val Ser Trp Thr Asp Tyr Leu Tyr Leu Thr Val Gly Gly Thr
                165                 170                 175

Leu Ser Asn Gly Gly Ile Ser Gly Gln Thr Phe Arg Tyr Gly Pro Gln
            180                 185                 190

Ile Thr Asn Val Leu Glu Met Asp Val Ile Thr Gly Lys Gly Glu Ile
        195                 200                 205

Ala Thr Cys Ser Lys Asp Met Asn Ser Asp Leu Phe Phe Ala Val Leu
    210                 215                 220

Gly Gly Leu Gly Gln Phe Gly Ile Ile Thr Arg Ala Arg Ile Lys Leu
225                 230                 235                 240

Glu Val Ala Pro Lys Arg Ala Lys Trp Leu Arg Phe Leu Tyr Ile Asp
                245                 250                 255

Phe Ser Glu Phe Thr Arg Asp Gln Glu Arg Val Ile Ser Lys Thr Asp
            260                 265                 270

Gly Val Asp Phe Leu Glu Gly Ser Ile Met Val Asp His Gly Pro Pro
        275                 280                 285

Asp Asn Trp Arg Ser Thr Tyr Tyr Pro Pro Ser Asp His Leu Arg Ile
    290                 295                 300

Ala Ser Met Val Lys Arg His Arg Val Ile Tyr Cys Leu Glu Val Val
305                 310                 315                 320
```

```
Lys Tyr Tyr Asp Glu Thr Ser Gln Tyr Thr Val Asn Glu Glu Met Glu
            325                 330                 335

Glu Leu Ser Asp Ser Leu Asn His Val Arg Gly Phe Met Tyr Glu Lys
        340                 345                 350

Asp Val Thr Tyr Met Asp Phe Leu Asn Arg Val Arg Thr Gly Glu Leu
    355                 360                 365

Asn Leu Lys Ser Lys Gly Gln Trp Asp Val Pro His Pro Trp Leu Asn
370                 375                 380

Leu Phe Val Pro Lys Thr Gln Ile Ser Lys Phe Asp Asp Gly Val Phe
385                 390                 395                 400

Lys Gly Ile Ile Leu Arg Asn Asn Ile Thr Ser Gly Pro Val Leu Val
                405                 410                 415

Tyr Pro Met Asn Arg Asn Lys Trp Asn Asp Arg Met Ser Ala Ala Ile
            420                 425                 430

Pro Glu Glu Asp Val Phe Tyr Ala Val Gly Phe Leu Arg Ser Ala Gly
        435                 440                 445

Phe Asp Asn Trp Glu Ala Phe Asp Gln Glu Asn Met Glu Ile Leu Lys
    450                 455                 460

Phe Cys Glu Asp Ala Asn Met Gly Val Ile Gln Tyr Leu Pro Tyr His
465                 470                 475                 480

Ser Ser Gln Glu Gly Trp Val Arg His Phe Gly Pro Arg Trp Asn Ile
                485                 490                 495

Phe Val Glu Arg Lys Tyr Lys Tyr Asp Pro Lys Met Ile Leu Ser Pro
            500                 505                 510

Gly Gln Asn Ile Phe Gln Lys Ile Asn Ser Ser
            515                 520

<210> SEQ ID NO 7
<211> LENGTH: 2782
<212> TYPE: DNA
<213> ORGANISM: Arabidopsis thaliana

<400> SEQUENCE: 7
atgactaata ctctctgttt aagcctcatc accctaataa cgcttttttat aagtttaacc      60
ccaaccttaa tcaaatcaga tgagggcatt gatgttttct acccatatc actcaacctt      120
acggtcctaa ccgatccctt ctccatctct gccgcttctc acgacttcgg taacataacc      180
gacgaaaatc ccggcgccgt cctctgccct tcctccacca cggaggtggc tcgtctcctc      240
cgtttcgcta acgaggatt ctcttacaat aaaggctcaa ccagccccgc gtctactttc      300
aaagtggctg ctcgaggcca aggccactcc ctccgtggcc aagcctctgc acccggaggt      360
gtcgtcgtga acatgacgtg tctcgccatg gcggctaaac cagcggcggt tgttatctcg      420
gcagacggga cttacgctga cgtggctgcc gggacgatgt gggtggatgt tctgaaggcg      480
gcggtggata gaggcgtctc gccggttaca tggacggatt atttgtatct cagcgtcggc      540
gggacgttgt cgaacgctgg aatcggtggt cagacgttta cacggccc tcagattagt      600
aacgttcatg agcttgacgt tattaccggt acgtaaatac caaaacttca ctaatctcgt      660
tacaatttttt taatttttttg gtaatatataaa ttttgtacgg ctcaactctt aattaagaat      720
gaaacagtat ctatgatctt ctagatgctc tttttttgtc tgcaagcttt aattgtagta      780
acatcagcga tatatatatc acatgcatgt gtattattga tgataatata taatgtttta      840
gttacaaatt tgattctcaa ggtaaaactc acacgccata accagtataa aactccaaaa      900
atcacgttttt ggtcagaaat acatatcctt cattaacagt agttatgcta aatttgtga      960
ttataaataa ctccggagtt tgttcacaat actaaatttc aggaaaaggt gaaatgatga     1020
```

```
cttgctctcc aaagttaaac cctgaattgt tctatggagt tttaggaggt ttgggtcaat    1080
tcggtattat aacgagggcc aggattgcgt tggatcatgc acccacaagg gtatgtatca    1140
tgcatctata gtgtaatcaa tttataattt taatgtagtg gtcctaaatc caaaatttga    1200
tttgatttgg ttggaacgta cgtatatata ataagtcaaa aggctgattt tgaagacgaa    1260
tttatatact tttgttgaat taaatctgat tttgcttacg ttttattaga ttctgcgtaa    1320
taaatcctag gacttgctcg agtgtaatct tgtcttatgc ttgcaaatct tgttgatgtc    1380
aatatctaat cttttttatt atatttccct acgtaagttt tagatatagt tattttaaac    1440
tgctataaat tgtgtacgta tagactttag ataaaaagtt gtggtcgctt gcacctattt    1500
gtttatcgct atagtgattc aaaggtctat atatgattct tggttttttct ttttgaaaaa    1560 aatagaccat acaatccaag gaagatgatc ttaaatggac taatttatgg atataaattg    1620
atatacaaat ctgcaggtga aatggtctcg catactctac agtgacttct cggcttttaa    1680
aagagaccaa gagcgtttaa tatcaatgac caatgatctc ggagttgact ttttggaagg    1740
tcaacttatg atgtcaaatg gcttcgtaga cacctctttc ttcccactct ccgatcaaac    1800
aagagtcgca tctcttgtga atgaccaccg gatcatctat gttctcgaag tagccaagta    1860
ttatgacaga accacccttc ccattattga ccaggtacta aaatccatta ttcatgatga    1920
ttatcttcac acaatcagta tcatccacaa ttaccatcat cacttgtcat atatgatcca    1980
aagtaaatat atcacatgat ataaataaat cgttcaaatc tttttttta aagaataaaa    2040 gaatcatttt caagcattac tcatacacat ctacgaatca ccgtgaccat atataaccat    2100
acgcttatta aataatcatt tttgtttgta ggtgattgac acgttaagta gaactctagg    2160
tttcgctcca gggtttatgt tcgtacaaga tgttccgtat ttcgatttct tgaaccgtgt    2220
ccgaaacgaa gaagataaac tcagatcttt aggactatgg gaagttcctc atccatggct    2280
taacatcttt gtcccggggt ctcgaatcca agatttcat gatggtgtta ttaatggcct    2340
tcttctaaac caaacctcaa cttctggtgt tactctcttc tatcccacaa accgaaacaa    2400
gtaaatattt acttttttgat tttgtttttat ttgaaagtat atcccaataa tgtatgttaa    2460
attgttaaca agaatttatt ttattaatag atggaacaac cgcatgtcaa cgatgacacc    2520
ggacgaagat gttttttatg tgatcggatt actgcaatca gctggtggat ctcaaaattg    2580
gcaagaactt gaaaatctca acgacaaggt tattcagttt tgtgaaaact cgggaattaa    2640
gattaaggaa tatttgatgc actatacaag aaaagaagat tgggttaaac attttggacc    2700
aaaatgggat gattttttaa gaaagaaaat tatgtttgat cccaaaagac tattgtctcc    2760
aggacaagac atatttaatt aa    2782
```

<210> SEQ ID NO 8
<211> LENGTH: 524
<212> TYPE: PRT
<213> ORGANISM: Arabidopsis thaliana

<400> SEQUENCE: 8

```
Met Thr Asn Thr Leu Cys Leu Ser Leu Ile Thr Leu Ile Thr Leu Phe
  1               5                  10                  15

Ile Ser Leu Thr Pro Thr Leu Ile Lys Ser Asp Glu Gly Ile Asp Val
             20                  25                  30

Phe Leu Pro Ile Ser Leu Asn Leu Thr Val Leu Thr Asp Pro Phe Ser
         35                  40                  45

Ile Ser Ala Ala Ser His Asp Phe Gly Asn Ile Thr Asp Glu Asn Pro
     50                  55                  60
```

```
Gly Ala Val Leu Cys Pro Ser Ser Thr Thr Glu Val Ala Arg Leu Leu
 65                  70                  75                  80

Arg Phe Ala Asn Gly Gly Phe Ser Tyr Asn Lys Gly Ser Thr Ser Pro
                 85                  90                  95

Ala Ser Thr Phe Lys Val Ala Ala Arg Gly Gln Gly His Ser Leu Arg
            100                 105                 110

Gly Gln Ala Ser Ala Pro Gly Gly Val Val Asn Met Thr Cys Leu
            115                 120                 125

Ala Met Ala Ala Lys Pro Ala Ala Val Val Ile Ser Ala Asp Gly Thr
        130                 135                 140

Tyr Ala Asp Val Ala Ala Gly Thr Met Trp Val Asp Val Leu Lys Ala
145                 150                 155                 160

Ala Val Asp Arg Gly Val Ser Pro Val Thr Trp Thr Asp Tyr Leu Tyr
                165                 170                 175

Leu Ser Val Gly Gly Thr Leu Ser Asn Ala Gly Ile Gly Gln Thr
                180                 185                 190

Phe Arg His Gly Pro Gln Ile Ser Asn Val His Glu Leu Asp Val Ile
        195                 200                 205

Thr Gly Lys Gly Glu Met Met Thr Cys Ser Pro Lys Leu Asn Pro Glu
        210                 215                 220

Leu Phe Tyr Gly Val Leu Gly Gly Leu Gly Gln Phe Gly Ile Ile Thr
225                 230                 235                 240

Arg Ala Arg Ile Ala Leu Asp His Ala Pro Thr Arg Val Lys Trp Ser
                245                 250                 255

Arg Ile Leu Tyr Ser Asp Phe Ser Ala Phe Lys Arg Asp Gln Glu Arg
                260                 265                 270

Leu Ile Ser Met Thr Asn Asp Leu Gly Val Asp Phe Leu Glu Gly Gln
            275                 280                 285

Leu Met Met Ser Asn Gly Phe Val Asp Thr Ser Phe Pro Leu Ser
        290                 295                 300

Asp Gln Thr Arg Val Ala Ser Leu Val Asn Asp His Arg Ile Ile Tyr
305                 310                 315                 320

Val Leu Glu Val Ala Lys Tyr Tyr Asp Arg Thr Thr Leu Pro Ile Ile
                325                 330                 335

Asp Gln Val Ile Asp Thr Leu Ser Arg Thr Leu Gly Phe Ala Pro Gly
            340                 345                 350

Phe Met Phe Val Gln Asp Val Pro Tyr Phe Asp Phe Leu Asn Arg Val
            355                 360                 365

Arg Asn Glu Glu Asp Lys Leu Arg Ser Leu Gly Leu Trp Glu Val Pro
        370                 375                 380

His Pro Trp Leu Asn Ile Phe Val Pro Gly Ser Arg Ile Gln Asp Phe
385                 390                 395                 400

His Asp Gly Val Ile Asn Gly Leu Leu Leu Asn Gln Thr Ser Thr Ser
                405                 410                 415

Gly Val Thr Leu Phe Tyr Pro Thr Asn Arg Asn Lys Trp Asn Asn Arg
            420                 425                 430

Met Ser Thr Met Thr Pro Asp Glu Asp Val Phe Tyr Val Ile Gly Leu
        435                 440                 445

Leu Gln Ser Ala Gly Gly Ser Gln Asn Trp Gln Glu Leu Glu Asn Leu
        450                 455                 460

Asn Asp Lys Val Ile Gln Phe Cys Glu Asn Ser Gly Ile Lys Ile Lys
465                 470                 475                 480

Glu Tyr Leu Met His Tyr Thr Arg Lys Glu Asp Trp Val Lys His Phe
```

|     |     |     | Gly | Pro | Lys | Trp | Asp | Asp | Phe | Leu | Arg | Lys | Lys | Ile | Met | Phe | Asp | Pro |
|-----|-----|-----|-----|-----|-----|-----|-----|-----|-----|-----|-----|-----|-----|-----|-----|-----|-----|-----|
|     |     |     | 485 |     |     |     |     | 490 |     |     |     |     | 495 |     |     |     |     |     |

Lys Arg Leu Leu Ser Pro Gly Gln Asp Ile Phe Asn
        500                 505                 510
                515                     520

<210> SEQ ID NO 9
<211> LENGTH: 2805
<212> TYPE: DNA
<213> ORGANISM: Arabidopsis thaliana

<400> SEQUENCE: 9

```
atgacgtcaa gctttcttct cctgacgttc gccatatgta aactgatcat agccgtgggt      60
ctaaacgtgg gccccagtga gctcctccgc atcggagcca tagatgtcga cggccacttc     120
accgtccacc cttccgactt agcctccgtc tcctcagact tcggtatgct gaagtcacct     180
gaagagccat ggccgtgctc tcatccatca tcggccgaag acgtggcacg actcgtcaga     240
acagcttacg gttcagccac ggcgtttccg gtctcagccc gaggccacgg ccattccata     300
aacggacaag ccgcggcggg gaggaacggt gtggtggttg aaatgaacca cggcgtaacc     360
gggacgccca agccactcgt ccgaccggat gaaatgtatg tggatgtatg gggtggagag     420
ttatgggtcg atgtgttgaa gaaaacgttg gagcatggct agcaccaaaa atcatggacg     480
gattacttgt atctaaccgt tggaggtaca ctctccaatg caggaatcag tggtcaagct     540
tttcaccatg gtcctcaaat tagtaacgtc cttgagctcg acgttgtaac tggttagtat     600
taaaacattc aagttcatat attttaaatg cttttgtctg aagttttact aataacaaga     660
aattgatacc aaaaagtagg gaaaggagag gtgatgagat gctcagaaga agagaacaca     720
aggctattcc atggagttct tggtggatta ggtcaatttg gatcatcac tcgagcacga     780
atctctctcg aaccagctcc ccaaagggta atatttttt aatgactagc atcaaaaat     840
ccctggcggg tccatacgtt gtaatctttt tagtttttac tgttgatggt atttttata     900
tattttggat aataaaaccc taaaatggta tattgtgatg acaggtgaga tggatacggg     960
tattgtattc gagcttcaaa gtgtttacgg aggaccaaga gtacttaatc tcaatgcatg    1020
gtcaattaaa gtttgattac gtggaaggtt ttgtgattgt ggacgaagga ctcgtcaaca    1080
attggagatc ttctttcttc tctccacgta acccgtcaa gatctcctct gttagttcca    1140
acggctctgt tttgtattgc cttgagatca ccaagaacta ccacgactcc gactccgaaa    1200
tcgttgatca ggtcactttc attattcact tagaaaaaag cgatatttc atttttata    1260
ttgatgaata tctggaagga tttaacgcta tgcgactatt gggaaatcat tatgaaaaaa    1320
tatttagttt atatgattga agtggtctct catagtattt ttgttgtgtc gactttatta    1380
taacttaaat ttggaagagg acatgaagaa gaagccagag aggatctaca gagatctagc    1440
ttttccacct gaacttaata atgcacattt atataattat ttttcttctt ctaaagttta    1500
gtttatcact agcgaattaa tcatggttac taattaagta gtggacaggg tcatggacca    1560
ctcactcacc aaataatgat tcctctttac tcttaagttt aatttaata aaaccaactc    1620
tactggaatc ttaacttatc cttggttttg gtaggctttt atagcaacac ggtttttta    1680
attttcctat tccagatttt gtatattaaa tgtcgatttt ttttctttt gtttcaggaa    1740
gttgagattc tgatgaagaa attgaatttc ataccgacat cggtctttac aacggattta    1800
caatatgtgg actttctcga ccgggtacac aaggccgaat tgaagctccg gtccaagaat    1860
ttatgggagg ttccacaccc atggctcaac ctcttcgtgc caaaatcaag aatctctgac    1920
```

```
ttcgataaag gcgttttcaa gggcattttg ggaaataaaa caagtgggcc tattcttatc   1980 tacccccatga acaaagacaa gtaagtcttg acattaccat tgattactac ttctaaattt   2040
cttctctaga aaaaagaata aaacgagttt tgcattgcat gcatgcaaag ttacacttgt   2100
ggggattaat tagtggtcca agaaaaaaag tttgtcaaaa ttgaaaaaaa ctagacacgt   2160
ggtacatggg attgtccgaa aaacgttgtc cacatgtgca tcgaaccagc taagattgac   2220
aacaacactt cgtcggctcg tatttctctt tttgttttgt gaccaaatcc gatggtccag   2280
attgggttta tttgttttta agttcctaga actcatggtg ggtgggtccc aatcagattc   2340
tcctagacca aaccgatctc aacgaaccct ccgcacatca ttgattatta cattaatata   2400
gatattgtcg ttgctgacgt gtcgtaattt gatgttattg tcagatggga cgagaggagc   2460
tcagccgtga cgccggatga ggaagttttc tatctggtgg ctctattgag atcagcttta   2520
acggacggtg aagagacaca gaagctagag tatctgaaag atcagaaccg tcggatcttg   2580
gagttctgtg aacaagccaa gatcaatgtg aagcagtatc ttcctcacca cgcaacacag   2640
gaagagtggg tggctcattt tggggacaag tgggatcggt tcagaagctt aaaggctgag   2700
tttgatccgc gacacatact cgctactggt cagagaatct ttcaaaaccc atctttgtct   2760
ttgtttcctc cgtcgtcgtc ttcttcgtca gcggcttcat ggtga               2805
```

<210> SEQ ID NO 10
<211> LENGTH: 536
<212> TYPE: PRT
<213> ORGANISM: Arabidopsis thaliana

<400> SEQUENCE: 10

```
Met Thr Ser Ser Phe Leu Leu Leu Thr Phe Ala Ile Cys Lys Leu Ile
 1               5                  10                  15

Ile Ala Val Gly Leu Asn Val Gly Pro Ser Glu Leu Leu Arg Ile Gly
            20                  25                  30

Ala Ile Asp Val Asp Gly His Phe Thr Val His Pro Ser Asp Leu Ala
        35                  40                  45

Ser Val Ser Ser Asp Phe Gly Met Leu Lys Ser Pro Glu Glu Pro Leu
    50                  55                  60

Ala Val Leu His Pro Ser Ser Ala Glu Asp Val Ala Arg Leu Val Arg
65                  70                  75                  80

Thr Ala Tyr Gly Ser Ala Thr Ala Phe Pro Val Ser Ala Arg Gly His
                85                  90                  95

Gly His Ser Ile Asn Gly Gln Ala Ala Ala Gly Arg Asn Gly Val Val
            100                 105                 110

Val Glu Met Asn His Gly Val Thr Gly Thr Pro Lys Pro Leu Val Arg
        115                 120                 125

Pro Asp Glu Met Tyr Val Asp Val Trp Gly Gly Glu Leu Trp Val Asp
    130                 135                 140

Val Leu Lys Lys Thr Leu Glu His Gly Leu Ala Pro Lys Ser Trp Thr
145                 150                 155                 160

Asp Tyr Leu Tyr Leu Thr Val Gly Gly Thr Leu Ser Asn Ala Gly Ile
                165                 170                 175

Ser Gly Gln Ala Phe His His Gly Pro Gln Ile Ser Asn Val Leu Glu
            180                 185                 190

Leu Asp Val Val Thr Gly Lys Gly Glu Val Met Arg Cys Ser Glu Glu
        195                 200                 205

Glu Asn Thr Arg Leu Phe His Gly Val Leu Gly Gly Leu Gly Gln Phe
    210                 215                 220
```

-continued

| | | | | | | | | | | | | | |
|---|---|---|---|---|---|---|---|---|---|---|---|---|---|
|Gly|Ile|Ile|Thr|Arg|Ala|Arg|Ile|Ser|Leu|Glu|Pro|Ala|Pro|Gln|Arg|
|225| | | | |230| | | | |235| | | | |240|

Gly Ile Ile Thr Arg Ala Arg Ile Ser Leu Glu Pro Ala Pro Gln Arg
225                 230                 235                 240

Val Arg Trp Ile Arg Val Leu Tyr Ser Ser Phe Lys Val Phe Thr Glu
            245                 250                 255

Asp Gln Glu Tyr Leu Ile Ser Met His Gly Gln Leu Lys Phe Asp Tyr
        260                 265                 270

Val Glu Gly Phe Val Ile Val Asp Glu Gly Leu Val Asn Asn Trp Arg
            275                 280                 285

Ser Ser Phe Phe Ser Pro Arg Asn Pro Val Lys Ile Ser Ser Val Ser
290                 295                 300

Ser Asn Gly Ser Val Leu Tyr Cys Leu Glu Ile Thr Lys Asn Tyr His
305                 310                 315                 320

Asp Ser Asp Ser Glu Ile Val Asp Gln Glu Val Glu Ile Leu Met Lys
                325                 330                 335

Lys Leu Asn Phe Ile Pro Thr Ser Val Phe Thr Thr Asp Leu Gln Tyr
            340                 345                 350

Val Asp Phe Leu Asp Arg Val His Lys Ala Glu Leu Lys Leu Arg Ser
        355                 360                 365

Lys Asn Leu Trp Glu Val Pro His Pro Trp Leu Asn Leu Phe Val Pro
370                 375                 380

Lys Ser Arg Ile Ser Asp Phe Asp Lys Gly Val Phe Lys Gly Ile Leu
385                 390                 395                 400

Gly Asn Lys Thr Ser Gly Pro Ile Leu Ile Tyr Pro Met Asn Lys Asp
                405                 410                 415

Lys Trp Asp Glu Arg Ser Ser Ala Val Thr Pro Asp Glu Val Phe
            420                 425                 430

Tyr Leu Val Ala Leu Leu Arg Ser Ala Leu Thr Asp Gly Glu Thr
        435                 440                 445

Gln Lys Leu Glu Tyr Leu Lys Asp Gln Asn Arg Arg Ile Leu Glu Phe
            450                 455                 460

Cys Glu Gln Ala Lys Ile Asn Val Lys Gln Tyr Leu Pro His His Ala
465                 470                 475                 480

Thr Gln Glu Glu Trp Val Ala His Phe Gly Asp Lys Trp Asp Arg Phe
                485                 490                 495

Arg Ser Leu Lys Ala Glu Phe Asp Pro Arg His Ile Leu Ala Thr Gly
            500                 505                 510

Gln Arg Ile Phe Gln Asn Pro Ser Leu Ser Leu Phe Pro Pro Ser Ser
            515                 520                 525

Ser Ser Ser Ser Ala Ala Ser Trp
530                 535

<210> SEQ ID NO 11
<211> LENGTH: 1936
<212> TYPE: DNA
<213> ORGANISM: Arabidopsis thaliana

<400> SEQUENCE: 11
atgcttatag taagaagttt caccatcttg cttctcagct gcatagcctt taagttggct      60
tgctgcttct ctagcagcat tcttctttg aaggcgcttc ccctagtagg ccatttggag     120
tttgaacatg tccatcacgc ctccaaagat tttggaaatc gataccagtt gatccctttg     180
gcggtcttac atcccaaatc ggtaagcgac atcgcctcaa cgatacgaca catctggatg     240
atgggcactc attcacagct tacagtggca gcgagaggtc gtggacattc actccaaggc     300
caagctcaaa caagacatgg aattgttata cacatggaat cactccatcc ccagaagctg     360

```
caggtctaca gtgtggattc ccctgctcca tatgttgatg tgtctggtgg tgagctgtgg    420
ataaacattt tgcatgagac cctcaagtac gggcttgcac caaaatcatg acggattac    480
ctgcatttaa ctgtaggtgg tactctgtcc aatgctggaa taagcggcca ggcattccga    540
catgaccac agatcagcaa tgttcatcaa ctggagattg tcacaggtta gttcagagtt     600
gcagtattcg tgttttgaaa gcatagactc tatatggttg gtgactatta caacatgaa     660
gagattcccg agaatagcta cccactaatg tcatgcctat ttattgactg caggaaaagg    720
cgagatccta aactgtacaa agaggcagaa cagcgactta tttaatggtg ttcttggtgg    780
tttaggtcag tttggcatca taacgcgggc aagaatagca ttggaaccag caccaaccat    840
ggtaaacaat aaataaataa aaaacttaaa aactgaacac gcgtgtgtcc tcctaactct    900
gtataatgga caggtaaaat ggataagagt gttatacctg gattttgcag cttttgccaa    960
ggaccaagag caactaatat ctgcccaggg ccacaaattc gattacatag aagggtttgt   1020
gataataaac aggacaggcc tcctgaacag ctggaggttg tctttcaccg cagaagagcc   1080
tttagaagca agccaattca gtttgatgg aaggactctg tattgtctgg agctagccaa    1140
gtatttgaag caagataaca aagacgtaat caaccaggtg agaaaacaga gtagaagcaa   1200
tcggtagaat cttctttggt agatgacatt cattggaact gaaaatatat atatatttgt   1260
ccaatccagg aagtgaaaga aacattatca gagctaagct acgtgacgtc gacactgttt   1320
acaacggagg tagcatatga agcattcttg gacagggtac atgtgtctga ggtaaaactc   1380
cgatcgaaag ggcagtggga ggtgccacat ccatggctga acctcctggt accaagaagc   1440
aaaatcaatg aatttgcaag aggtgtattt ggaaacatac taacggatac aagcaacggc   1500
ccagtcatcg tctacccagt gaacaaatca agtaagaaa gaaagaaaga aagagctagt    1560
catgattttg tttcttttca cttgttgaca aaacaaaagc atgttggtga gcaggtggga   1620
caatcaaaca tcagcagtaa caccggagga agaggtattc tacctggtgg cgatcctaac   1680
atcggcatct ccagggtcgg caggaaagga tggagtagaa gagatcttga ggcggaacag   1740
aagaatactg gaattcagtg aagaagcagg gatagggttg aagcagtatc tgccacatta   1800
cacgacaaga gaagagtgga gatcccattt cggggacaag tggggagaat tgtgaggag    1860
gaaatccaga tatgatccat tggcaattct tgcgcctggc caccgaattt ttcaaaaggc   1920
agtctcatac tcatga                                                    1936
```

<210> SEQ ID NO 12
<211> LENGTH: 504
<212> TYPE: PRT
<213> ORGANISM: Arabidopsis thaliana

<400> SEQUENCE: 12

Met Leu Ile Val Arg Ser Phe Thr Ile Leu Leu Ser Cys Ile Ala
1               5                   10                  15

Phe Lys Leu Ala Cys Cys Phe Ser Ser Ile Ser Ser Leu Lys Ala
                20                  25                  30

Leu Pro Leu Val Gly His Leu Glu Phe Glu His Val His His Ala Ser
            35                  40                  45

Lys Asp Phe Gly Asn Arg Tyr Gln Leu Ile Pro Leu Ala Val Leu His
        50                  55                  60

Pro Lys Ser Val Ser Asp Ile Ala Ser Thr Ile Arg His Ile Trp Met
    65                  70                  75                  80

Met Gly Thr His Ser Gln Leu Thr Val Ala Ala Arg Gly Arg Gly His
                85                  90                  95

Ser Leu Gln Gly Gln Ala Gln Thr Arg His Gly Ile Val Ile His Met
            100                 105                 110

Glu Ser Leu His Pro Gln Lys Leu Gln Val Tyr Ser Val Asp Ser Pro
            115                 120                 125

Ala Pro Tyr Val Asp Val Ser Gly Glu Leu Trp Ile Asn Ile Leu
130                 135                 140

His Glu Thr Leu Lys Tyr Gly Leu Ala Pro Lys Ser Trp Thr Asp Tyr
145                 150                 155                 160

Leu His Leu Thr Val Gly Gly Thr Leu Ser Asn Ala Gly Ile Ser Gly
            165                 170                 175

Gln Ala Phe Arg His Gly Pro Gln Ile Ser Asn Val His Gln Leu Glu
            180                 185                 190

Ile Val Thr Gly Lys Gly Glu Ile Leu Asn Cys Thr Lys Arg Gln Asn
            195                 200                 205

Ser Asp Leu Phe Asn Gly Val Leu Gly Gly Leu Gly Gln Phe Gly Ile
            210                 215                 220

Ile Thr Arg Ala Arg Ile Ala Leu Glu Pro Ala Pro Thr Met Asp Gln
225                 230                 235                 240

Glu Gln Leu Ile Ser Ala Gln Gly His Lys Phe Asp Tyr Ile Glu Gly
            245                 250                 255

Phe Val Ile Ile Asn Arg Thr Gly Leu Leu Asn Ser Trp Arg Leu Ser
            260                 265                 270

Phe Thr Ala Glu Glu Pro Leu Glu Ala Ser Gln Phe Lys Phe Asp Gly
            275                 280                 285

Arg Thr Leu Tyr Cys Leu Glu Leu Ala Lys Tyr Leu Lys Gln Asp Asn
            290                 295                 300

Lys Asp Val Ile Asn Gln Glu Val Lys Glu Thr Leu Ser Glu Leu Ser
305                 310                 315                 320

Tyr Val Thr Ser Thr Leu Phe Thr Thr Glu Val Ala Tyr Glu Ala Phe
            325                 330                 335

Leu Asp Arg Val His Val Ser Glu Val Lys Leu Arg Ser Lys Gly Gln
            340                 345                 350

Trp Glu Val Pro His Pro Trp Leu Asn Leu Leu Val Pro Arg Ser Lys
            355                 360                 365

Ile Asn Glu Phe Ala Arg Gly Val Phe Gly Asn Ile Leu Thr Asp Thr
            370                 375                 380

Ser Asn Gly Pro Val Ile Val Tyr Pro Val Asn Lys Ser Lys Trp Asp
385                 390                 395                 400

Asn Gln Thr Ser Ala Val Thr Pro Glu Glu Val Phe Tyr Leu Val
            405                 410                 415

Ala Ile Leu Thr Ser Ala Ser Pro Gly Ser Ala Gly Lys Asp Gly Val
            420                 425                 430

Glu Glu Ile Leu Arg Arg Asn Arg Arg Ile Leu Glu Phe Ser Glu Glu
            435                 440                 445

Ala Gly Ile Gly Leu Lys Gln Tyr Leu Pro His Tyr Thr Thr Arg Glu
            450                 455                 460

Glu Trp Arg Ser His Phe Gly Asp Lys Trp Gly Glu Phe Val Arg Arg
465                 470                 475                 480

Lys Ser Arg Tyr Asp Pro Leu Ala Ile Leu Ala Pro Gly His Arg Ile
            485                 490                 495

Phe Gln Lys Ala Val Ser Tyr Ser
            500

<210> SEQ ID NO 13

```
<211> LENGTH: 31
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 13
cggtcgacat gggattgacc tcatccttac g                              31

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 14
gcgtcgactt atacagttct aggtttcggc agtat                          35

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 15
gcggtaccag agagagaaac ataaacaaat ggc                            33

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 16
gcggtaccca attttacttc caccaaaatg c                              31

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 17
gcggtacctt cattgataag aatcaagcta ttca                           34

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 18
gcggtaccca aagtggtgag aacgactaac a                              31

<210> SEQ ID NO 19
<211> LENGTH: 28
<212> TYPE: DNA
```

```
<213> ORGANISM: Artificial Sequence
<220> FEATURE:
<223> OTHER INFORMATION: Description of Artificial Sequence:
      oligonucleotide: primer or probe

<400> SEQUENCE: 19
gcggtacccc cattaaccta cccgtttg                                           28

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 20
gcggtaccag acgatgaacg tacttgtctg ta                                      32

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 21
ggggtacctt gatgaatcgt gaaatgac                                           28

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 22
ggggtaccct ttcctcttgg ttttgtcctg t                                       31

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 23
gctctagatc aggaaaagaa ccatgcttat ag                                      32

<210> SEQ ID NO 24
<211> LENGTH: 32
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 24
gctctagatc atgagtatga gactgccttt tg                                      32

<210> SEQ ID NO 25
<211> LENGTH: 1728
<212> TYPE: DNA
<213> ORGANISM: Arabidopsis thaliana
```

-continued

<400> SEQUENCE: 25

```
atgggattga cctcatcctt acggttccat agacaaaaca acaagacttt cctcggaatc      60
ttcatgatct tagttctaag ctgtatacca ggtagaacca atctttgttc caatcattct     120
gttagtaccc caaaagaatt accttcttca aatccttcag atattcgttc ctcattagtt     180
tcactagatt tggagggtta tataagcttc gacgatgtcc acaatgtggc caaggacttt     240
ggcaacagat accagttacc acctttggca attctacatc caaggtcagt ttttgatatt     300
tcatcgatga tgaagcatat agtacatctg gctccacct  caaatcttac agtagcagct     360
agaggccatg gtcactcgct tcaaggacaa gctctagctc atcaaggtgt tgtcatcaaa     420
atggagtcac ttcgaagtcc tgatatcagg atttataagg ggaagcaacc atatgttgat     480
gtctcaggtg gtgaaatatg gataaacatt ctacgcgaga ctctaaaata cggtctttca     540
ccaaagtcct ggacagacta ccttcatttg accgttggag gtacactatc taatgctgga     600
atcagcggtc aagcattcaa gcatggaccc caaatcaaca acgtctacca gctagagatt     660
gttacaggga aggagaagt  cgtaacctgt tctgagaagc ggaattctga acttttcttc     720
agtgttcttg gcgggcttgg acagtttggc ataatcaccc gggcacggat ctctcttgaa     780
ccagcaccgc atatggttaa atggatcagg gtactctact ctgacttttc tgcattttca     840
agggaccaag aatatctgat ttcgaaggag aaaacttttg attacgttga aggatttgtg     900
ataatcaata gaacagacct tctcaataat tggcgatcgt cattcagtcc caacgattcc     960
acacaggcaa gcagattcaa gtcagatggg aaaactcttt attgcctaga agtggtcaaa    1020
tatttcaacc cagaagaagc tagctctatg gatcaggaaa ctggcaagtt actttcagag    1080
ttaaattata ttccatccac tttgttttca tctgaagtgc catatatcga gtttctggat    1140
cgcgtgcata tcgcagagag aaaactaaga gcaaagggtt tatgggaggt tccacatccc    1200
tggctgaatc tcctgattcc taagagcagc atataccaat ttgctacaga gttttcaac    1260
aacattctca caagcaacaa caacggtcct atccttatt  atccagtcaa tcaatccaag    1320
tggaagaaac atacatcttt gataactcca aatgaagata tattctatct cgtagccttt    1380
ctccccctctg cagtgccaaa ttcctcaggg aaaaacgatc tagagtacct tttgaaacaa    1440
aaccaaagag ttatgaactt ctgcgcagca gcaaacctca acgtgaagca gtatttgccc    1500
cattatgaaa ctcaaaaaga gtggaaatca cactttggca aagatgggaa acatttgca    1560
cagaggaaac aagcctacga ccctctagcg attctagcac ctggccaaag aatattccaa    1620
aagacaacag gaaaattatc tcccatccaa ctcgcaaagt caaaggcaac aggaagtcct    1680
caaaggtacc attacgcatc aatactgccg aaacctagaa ctgtataa               1728
```

<210> SEQ ID NO 26
<211> LENGTH: 1506
<212> TYPE: DNA
<213> ORGANISM: Arabidopsis thaliana

<400> SEQUENCE: 26

```
atggctaatc ttcgttaat  gatcactta atcacggttt taatgatcac caaatcatca      60
aacggtatta aaattgattt acctaaatcc cttaacctca ccctctctac cgatccttcc     120
atcatctccg cagcctctca tgacttcgga aacataacca ccgtgacccc cggcggcgta     180
atctgcccct cctccaccgc tgatatctct cgtctcctcc aatacgccgc aaacggaaaa     240
agtacattcc aagtagcggc tcgtggccaa ggccactcct taaacggcca agcctcggtc     300
tccggcggag taatcgtcaa catgacgtgt atcactgacg tggtggtttc aaaagacaag    360
```

```
aagtacgctg acgtggcggc cgggacgtta tgggtggatg tgcttaagaa gacggcggag      420 aaagggtgt cgccggtttc ttggacggat tatttgcata taaccgtcgg aggaacgttg       480
tcgaatggtg gaattggtgg tcaagtgttt cgaaacggtc ctcttgttag taacgtcctt     540
gaattggacg ttattactgg gaaaggtgaa atgttgacat gctcgcgaca gctaaaccca     600
gaattgttct atggagtgtt aggaggtttg ggtcaatttg gaattataac gagagccaga    660
attgttttgg accatgcacc taaacgggcc aatggtttc ggatgctcta cagtgatttc      720 acaacttta caaaggacca agaacgtttg atatcaatgg caaacgatat tggagtcgac      780
tatttagaag gtcaaatatt tctatcaaac ggtgtcgttg cacctctttt tttcccacct     840
tcagatcaat ctaaagtcgc tgatctagtc aagcaacacg gtatcatcta tgttcttgaa    900
gtagccaagt attatgatga tcccaatctc cccatcatca gcaaggttat tgacacatta    960
acgaaaacat taagttactt gcccgggttc atatcaatgc acgacgtggc ctacttcgat    1020
ttcttgaacc gtgtacatgt cgaagaaaat aaactcagat cttgggatt atgggaactt     1080 cctcatcctt ggcttaacct ctacgttcct aaatctcgga ttctcgattt tcataacggt   1140
gttgtcaaag acattcttct taagcaaaaa tcagcttcgg gactcgctct tctctatcca   1200
acaaaccgga ataaatggga caatcgtatg tcggcgatga taccagagat cgatgaagat  1260
gttatatata ttatcggact actacaatcc gctaccccaa aggatcttcc agaagtggag   1320
agcgttaacg agaagataat taggttttgc aaggattcag gtattaagat taagcaatat  1380
ctaatgcatt atactagtaa agaagattgg attgagcatt ttggatcaaa atgggatgat   1440
ttttcgaaga ggaaagatct atttgatccc aagaaactgt tatctccagg gcaagacatc   1500
ttttga                                                               1506

<210> SEQ ID NO 27
<211> LENGTH: 1572
<212> TYPE: DNA
<213> ORGANISM: Arabidopsis thaliana

<400> SEQUENCE: 27
atggcgagtt ataatcttcg ttcacaagtt cgtcttatag caataacaat agtaatcatc     60
attactctct caactccgat cacaaccaac acatcaccac aaccatggaa tatcctttca   120
cacaacgaat tcgccggaaa actcacctcc tcctcctcct ccgtcgaatc agccgccaca   180
gatttcggcc acgtcaccaa aatcttccct tccgccgtct taatcccttc ctccgttgaa   240
gacatcacag atctccataa actctctttt gactctcaac tgtctttttcc tttagccgct    300 cgtggtcacg gacacagcca ccgtggccaa gcctcggcta agacggagt tgtggtcaac   360 atgcggtcca tggtaaaccg ggatcgaggt atcaaggtgt ctaggacctg tttatatgtt  420
gacgtggacg ctgcgtggct atggattgag gtgttgaata aaactttgga gttagggtta   480
acgccggttt cttggacgga ttatttgtat ttaacagtcg gtgggacgtt atcaaacggc   540
ggaattagtg gacaaacgtt tcggtacggt ccacagatca ctaatgttct agagatggat   600
gttattactg gaaaaggaga gattgcaact tgttccaagg acatgaactc ggatcttttc    660
ttcgcggtgt taggaggttt gggtcaattc ggcattataa caagagccag aattaaactt   720
gaagtagctc cgaaaagggc caagtggtta aggtttctat acatagattt ctccgaattc    780
acaagagatc aagaacgagt gatatcgaaa acggacggtg tagatttctt agaaggttcc    840
attatggtgg accatggccc accgataac tggagatcca cgtattatcc accgtccgat    900
cacttgagga tcgcctcaat ggtcaaacga catcgtgtca tctactgcct tgaagtcgtc   960
```

| | |
|---|---:|
| aagtattacg acgaaacttc tcaatacaca gtcaacgagg aaatggagga gttaagcgat | 1020 |
| agtttaaacc atgtaagagg gtttatgtac gagaaagatg tgacgtatat ggatttccta | 1080 |
| aaccgagttc gaaccggaga gctaaacctg aaatccaaag gccaatggga tgttccacat | 1140 |
| ccatggctta atctcttcgt accaaaaact caaatctcca aatttgatga tggtgttttt | 1200 |
| aagggtatta tcctaagaaa taacatcact agcggtcctg ttcttgttta tcctatgaat | 1260 |
| cgcaacaagt ggaatgatcg gatgtctgcc gctatacccg aggaagatgt attttatgcg | 1320 |
| gtagggtttt taagatccgc gggttttgac aattgggagg cttttgatca agaaaacatg | 1380 |
| gaaatactga gttttgtga ggatgctaat atggggggtta caatatctt tccttatcat | 1440 |
| tcatcacaag aaggatgggt tagacatttt ggtccgaggt ggaatatttt cgtagagaga | 1500 |
| aaatataaat atgatcccaa aatgatatta tcaccgggac aaaatatatt tcaaaaaata | 1560 |
| aactcgagtt ag | 1572 |

<210> SEQ ID NO 28
<211> LENGTH: 1575
<212> TYPE: DNA
<213> ORGANISM: Arabidopsis thaliana

<400> SEQUENCE: 28

| | |
|---|---:|
| atgactaata ctctctgttt aagcctcatc accctaataa cgcttttat aagtttaacc | 60 |
| ccaaccttaa tcaaatcaga tgagggcatt gatgttttct acccatatc actcaacctt | 120 |
| acggtcctaa ccgatccctt ctccatctct gccgcttctc acgacttcgg taacataacc | 180 |
| gacgaaaatc ccggcgccgt cctctgccct tcctccacca cggaggtggc tcgtctcctc | 240 |
| cgtttcgcta acgaggatt ctcttacaat aaaggctcaa ccagccccgc gtctactttc | 300 |
| aaagtggctg ctcgaggcca aggccactcc ctccgtggcc aagcctctgc acccggaggt | 360 |
| gtcgtcgtga acatgacgtg tctcgccatg gcggctaaac cagcggcggt tgttatctcg | 420 |
| gcagacggga cttacgctga cgtggctgcc gggacgatgt gggtggatgt tctgaaggcg | 480 |
| gcggtggata gaggcgtctc gccggttaca tggacggatt atttgtatct cagcgtcggc | 540 |
| gggacgttgt cgaacgctgg aatcggtggt cagacgttta gacacggccc tcagattagt | 600 |
| aacgttcatg agcttgacgt tattaccgga aaaggtgaaa tgatgacttg ctctccaaag | 660 |
| ttaaaccctg aattgttcta tggagttta ggaggtttgg gtcaattcgg tattataacg | 720 |
| agggccagga ttgcgttgga tcatgcaccc acaagggtga atggtctcg catactctac | 780 |
| agtgacttct cggcttttaa aagagaccaa gagcgtttaa tatcaatgac caatgatctc | 840 |
| ggagttgact ttttggaagg tcaacttatg atgtcaaatg gcttcgtaga cacctctttc | 900 |
| ttcccactct ccgatcaaac aagagtcgca tctcttgtga atgaccaccg gatcatctat | 960 |
| gttctcgaag tagccaagta ttatgacaga accacccttc ccattattga ccaggtgatt | 1020 |
| gacacgttaa gtagaactct aggtttcgct ccagggttta tgttcgtaca agatgttccg | 1080 |
| tatttcgatt tcttgaaccg tgtccgaaac gaagaagata aactcagatc tttaggacta | 1140 |
| tgggaagttc ctcatccatg gcttaacatc tttgtcccgg gtctcgaat ccaagatttt | 1200 |
| catgatggtg ttattaatgg ccttcttcta aaccaaacct caacttctgg tgttactctc | 1260 |
| ttctatccca caaaccgaaa caaatggaac aaccgcatgt caacgatgac accggacgaa | 1320 |
| gatgtttttt atgtgatcgg attactgcaa tcagctggtg gatctcaaaa ttggcaagaa | 1380 |
| cttgaaaatc tcaacgacaa ggttattcag ttttgtgaaa actcgggaat taagattaag | 1440 |
| gaatatttga tgcactatac aagaaaagaa gattgggtta acatttttgg accaaaatgg | 1500 |

```
gatgattttt taagaaagaa aattatgttt gatcccaaaa gactattgtc tccaggacaa    1560
gacatattta attaa                                                    1575

<210> SEQ ID NO 29
<211> LENGTH: 1611
<212> TYPE: DNA
<213> ORGANISM: Arabidopsis thaliana

<400> SEQUENCE: 29
atgacgtcaa gctttcttct cctgacgttc gccatatgta aactgatcat agccgtgggt     60
ctaaacgtgg gccccagtga gctcctccgc atcggagcca tagatgtcga cggccacttc    120
accgtccacc cttccgactt agcctccgtc tcctcagact tcggtatgct gaagtcacct    180
gaagagccat ggccgtgct tcatccatca tcggccgaag acgtggcacg actcgtcaga    240
acagcttacg gttcagccac ggcgtttccg gtctcagccc gaggccacgg ccattccata    300
aacggacaag ccgcggcggg gaggaacggt gtggtggttg aaatgaacca cggcgtaacc    360
gggacgccca agccactcgt ccgaccggat gaaatgtatg tggatgtatg gggtggagag    420
ttatgggtcg atgtgttgaa gaaaacgttg gagcatggct agcaccaaa atcatggacg    480 gattacttgt atctaaccgt tggaggtaca ctctccaatg caggaatcag tggtcaagct    540
tttcaccatg gtcctcaaat tagtaacgtc cttgagctcg acgttgtaac tgggaaagga    600
gaggtgatga tgctcaga agaagagaac acaaggctat ccatggagt tcttggtgga    660 ttaggtcaat ttgggatcat cactcgagca cgaatctctc tcgaaccagc tccccaaagg    720
gtgagatgga tacgggtatt gtattcgagc ttcaaagtgt ttacggagga ccaagagtac    780
ttaatctcaa tgcatggtca attaaagttt gattacgtgg aaggttttgt gattgtggac    840
gaaggactcg tcaacaattg gagatcttct ttcttctctc cacgtaaccc cgtcaagatc    900
tcctctgtta gttccaacgg ctctgttttg tattgccttg agatcaccaa gaactaccac    960
gactccgact ccgaaatcgt tgatcaggaa gttgagattc tgatgaagaa attgaatttc   1020
ataccgacat cggtctttac aacggattta caatatgtgg actttctcga ccgggtacac   1080
aaggccgaat tgaagctccg gtccaagaat ttatgggagg ttccacaccc atggctcaac   1140
ctcttcgtgc caaaatcaag aatctctgac ttcgataaag gcgttttcaa gggcattttg   1200
ggaaataaaa caagtggccc tattcttatc taccccatga acaaagacaa atgggacgag   1260
aggagctcag ccgtgacgcc ggatgaggaa gttttctatc tggtggctct attgagatca   1320
gctttaacgg acggtgaaga gacacagaag ctagagtatc tgaaagatca gaaccgtcgg   1380
atcttggagt tctgtgaaca agccaagatc aatgtgaagc agtatcttcc tcaccacgca   1440
acacaggaag agtgggtggc tcattttggg gacaagtggg atcggttcag aagcttaaag   1500
gctgagtttg atccgcgaca catactcgct actggtcaga gaatctttca aaacccatct   1560
ttgtctttgt ttcctccgtc gtcgtcttct tcgtcagcgg cttcatggtg a            1611

<210> SEQ ID NO 30
<211> LENGTH: 1515
<212> TYPE: DNA
<213> ORGANISM: Arabidopsis thaliana

<400> SEQUENCE: 30
atgcttatag taagaagttt caccatcttg cttctcagct gcatagcctt taagttggct     60
tgctgcttct ctagcagcat ttcttctttg aaggcgcttc ccctagtagg ccatttggag    120
tttgaacatg tccatcacgc ctccaaagat tttggaaatc gataccagtt gatccctttg    180
```

```
gcggtcttac atcccaaatc ggtaagcgac atcgcctcaa cgatacgaca catctggatg    240
atgggcactc attcacagct tacagtggca gcgagaggtc gtggacattc actccaaggc    300
caagctcaaa caagacatgg aattgttata cacatggaat cactccatcc ccagaagctg    360
caggtctaca gtgtggattc ccctgctcca tatgttgatg tgtctggtgg tgagctgtgg    420
ataaacattt tgcatgagac cctcaagtac gggcttgcac caaaatcatg gacggattac    480
ctgcatttaa ctgtaggtgg tactctgtcc aatgctggaa taagcggcca ggcattccga    540
catggaccac agatcagcaa tgttcatcaa ctggagattg tcacaggaaa aggcgagatc    600
ctaaactgta caagaggca gaacagcgac ttatttaatg gtgttcttgg tggtttaggt    660
cagtttggca tcataacgcg ggcaagaata gcattggaac cagcaccaac catggaccaa    720
gagcaactaa tatctgccca gggccacaaa ttcgattaca tagaagggtt tgtgataata    780
aacaggacag gcctcctgaa cagctggagg ttgtctttca ccgcagaaga gcctttagaa    840
gcaagccaat tcaagtttga tggaaggact ctgtattgtc tggagctagc caagtatttg    900
aagcaagata acaaagacgt aatcaaccag gaagtgaaag aaacattatc agagctaagc    960
tacgtgacgt cgacactgtt tacaacgag gtagcatatg aagcattctt ggacagggta   1020
catgtgtctg aggtaaaact ccgatcgaaa gggcagtggg aggtgccaca tccatggctg   1080
aacctcctgg taccaagaag caaaatcaat gaatttgcaa gaggtgtatt tggaaacata   1140
ctaacggata caagcaacgg cccagtcatc gtctacccag tgaacaaatc aaagtgggac   1200
aatcaaacat cagcagtaac accggaggaa gaggtattct acctggtggc gatcctaaca   1260
tcggcatctc cagggtcggc aggaaaggat ggagtagaag agatcttgag gcggaacaga   1320
agaatactgg aattcagtga agaagcaggg ataggggttga agcagtatct gcccacattac   1380 acgacaagag aagagtggag atcccatttc ggggacaagt ggggagaatt tgtgaggagg   1440
aaatccagat atgatccatt ggcaattctt gcgcctggcc accgaatttt tcaaaaggca   1500
gtctcatact catga                                                    1515

<210> SEQ ID NO 31
<211> LENGTH: 84
<212> TYPE: DNA
<213> ORGANISM: Arabidopsis thaliana

<400> SEQUENCE: 31
tcagcttcgg gactcgctct tctctatcca acaaaccgga ataaatggga caatcgtatg    60
tcggcgatga taccagagat cgat                                           84

<210> SEQ ID NO 32
<211> LENGTH: 28
<212> TYPE: PRT
<213> ORGANISM: Arabidopsis thaliana

<400> SEQUENCE: 32

Ser Ala Ser Gly Leu Ala Leu Leu Tyr Pro Thr Asn Arg Asn Lys Trp
 1               5                  10                  15

Asp Asn Arg Met Ser Ala Met Ile Pro Glu Ile Asp
            20                  25

<210> SEQ ID NO 33
<211> LENGTH: 2814
<212> TYPE: DNA
<213> ORGANISM: Arabidopsis thaliana

<400> SEQUENCE: 33
```

| | |
|---|---|
| atgaatcgta tgacgtcaag ctttcttctc ctgacgttcg ccatatgtaa actgatcata | 60 |
| gccgtgggtc taaacgtggg ccccagtgag ctcctccgca tcggagccat agatgtcgac | 120 |
| ggccacttca ccgtccaccc ttccgactta gcctccgtct cctcagactt cggtatgctg | 180 |
| aagtcacctg aagagccatt ggccgtgctt catccatcat cggccgaaga cgtggcacga | 240 |
| ctcgtcagaa cagcttacgg ttcagccacg gcgtttccgg tctcagcccg aggccacggc | 300 |
| cattccataa acgacaagc cgcggcgggg aggaacggtg tggtggttga aatgaaccac | 360 |
| ggcgtaaccg ggacgcccaa gccactcgtc cgaccggatg aaatgtatgt ggatgtatgg | 420 |
| ggtggagagt tatgggtcga tgtgttgaag aaaacgttgg agcatggctt agcaccaaaa | 480 |
| tcatggacgg attacttgta tctaaccgtt ggaggtacac tctccaatgc aggaatcagt | 540 |
| ggtcaagctt ttcaccatgg tcctcaaatt agtaacgtcc ttgagctcga cgttgtaact | 600 |
| ggttagtatt aaaacattca agttcatata ttttaaatgc ttttgtctga agttttacta | 660 |
| ataacaagaa attgatacca aaagtaggga aaggagagg tgatgagatg ctcagaagaa | 720 |
| gagaacacaa ggctattcca tggagttctt ggtggattag gtcaatttgg gatcatcact | 780 |
| cgagcacgaa tctctctcga accagctccc caaagggtaa tatttttta atgactagct | 840 |
| atcaaaaatc cctggcgggt ccatacgttg taatcttttt agttttact gttgatggta | 900 |
| ttttttatat atttttggata ataaaaccct aaaatggtat attgtgatga caggtgagat | 960 |
| ggatacgggt attgtattcg agcttcaaag tgtttacgga ggaccaagag tacttaatct | 1020 |
| caatgcatgg tcaattaaag tttgattacg tggaaggttt tgtgattgtg gacgaaggac | 1080 |
| tcgtcaacaa ttggagatct tctttcttct ctccacgtaa ccccgtcaag atctcctctg | 1140 |
| ttagttccaa cggctctgtt ttgtattgcc ttgagatcac caagaactac cacgactccg | 1200 |
| actccgaaat cgttgatcag gtcactttca ttattcactt agaaaaaagc gatattttca | 1260 |
| ttttttatat tgatgaatat ctggaaggat ttaacgctat gcgactattg ggaaatcatt | 1320 |
| atgaaaaaat atttagttta tatgattgaa agtggtctcc atagtatttt tgttgtgtcg | 1380 |
| actttattat aacttaaatt tggaagagga catgaagaag aagccagaga ggatctacag | 1440 |
| agatctagct tttccacctg aacttaataa tgcacattta tataattatt tttcttcttc | 1500 |
| taaagtttag tttatcacta gcgaattaat catggttact aattaagtag tggacagggt | 1560 |
| catgaccac tcactcacca aataatgatt cctcttact cttaagttta attttaataa | 1620 |
| aaccaactct actggaatct taacttatcc ttggttttgg taggctttta tagcaacacg | 1680 |
| gttttttaa ttttcctatt ccagattttg tatattaaat gtcgattttt tttctttttg | 1740 |
| tttcaggaag ttgagattct gatgaagaaa ttgaatttca taccgacatc ggtctttaca | 1800 |
| acggattac aatatgtgga ctttctcgac cgggtacaca aggccgaatt gaagctccgg | 1860 |
| tccaagaatt tatgggaggt tccacaccca tggctcaacc tcttcgtgcc aaaatcaaga | 1920 |
| atctctgact tcgataaagg cgttttcaag ggcattttgg gaaataaaac aagtggccct | 1980 |
| attcttatct accccatgaa caaagacaag taagtcttga cattaccatt gattactact | 2040 |
| tctaaattc ttctctagaa aaaagaataa aacgagtttt gcattgcatg catgcaaagt | 2100 |
| tacacttgtg gggattaatt agtggtccaa gaaaaaaagt ttgtcaaaat tgaaaaaaac | 2160 |
| tagacacgtg gtacatggga ttgtccgaaa acgttgtcc acatgtgcat cgaaccagct | 2220 |
| aagattgaca acaacacttc gtcggctcgt atttctcttt ttgttttgtg accaaatccg | 2280 |
| atggtccaga ttgggtttat ttgttttaa gttcctagaa ctcatggtgg gtgggtccca | 2340 |
| atcagattct cctagaccaa accgatctca acgaaccctc cgcacatcat tgattattac | 2400 |

| | |
|---|---|
| attaatatag atattgtcgt tgctgacgtg tcgtaatttg atgttattgt cagatgggac | 2460 |
| gagaggagct cagccgtgac gccggatgag gaagttttct atctggtggc tctattgaga | 2520 |
| tcagctttaa cggacggtga agagacacag aagctagagt atctgaaaga tcagaaccgt | 2580 |
| cggatcttgg agttctgtga acaagccaag atcaatgtga agcagtatct tcctcaccac | 2640 |
| gcaacacagg aagagtgggt ggctcatttt ggggacaagt gggatcggtt cagaagctta | 2700 |
| aaggctgagt ttgatccgcg acacatactc gctactggtc agagaatctt tcaaaaccca | 2760 |
| tctttgtctt tgtttcctcc gtcgtcgtct tcttcgtcag cggcttcatg gtga | 2814 |

<210> SEQ ID NO 34
<211> LENGTH: 1620
<212> TYPE: DNA
<213> ORGANISM: Arabidopsis thaliana

<400> SEQUENCE: 34

| | |
|---|---|
| atgaatcgta tgacgtcaag ctttcttctc ctgacgttcg ccatatgtaa actgatcata | 60 |
| gccgtgggtc taaacgtggg ccccagtgag ctcctccgca tcggagccat agatgtcgac | 120 |
| ggccacttca ccgtccaccc ttccgactta gcctccgtct cctcagactt cggtatgctg | 180 |
| aagtcacctg aagagccatt ggccgtgctt catccatcat cggccgaaga cgtggcacga | 240 |
| ctcgtcagaa cagcttacgg ttcagccacg gcgtttccgg tctcagcccg aggccacggc | 300 |
| cattccataa acggacaagc cgcggcgggg aggaacggtg tggtggttga atgaaccac | 360 |
| ggcgtaaccg ggacgcccaa gccactcgtc cgaccggatg aaatgtatgt ggatgtatgg | 420 |
| ggtggagagt tatgggtcga tgtgttgaag aaaacgttgg agcatggctt agcaccaaaa | 480 |
| tcatggacgg attacttgta tctaaccgtt ggaggtacac tctccaatgc aggaatcagt | 540 |
| ggtcaagctt ttcaccatgg tcctcaaatt agtaacgtcc ttgagctcga cgttgtaact | 600 |
| gggaaaggag aggtgatgag atgctcagaa gaagagaaca caaggctatt ccatggagtt | 660 |
| cttggtggat taggtcaatt tgggatcatc actcgagcac gaatctctct cgaaccagct | 720 |
| ccccaaaggg tgagatggat acgggtattg tattcgagct tcaaagtgtt tacggaggac | 780 |
| caagagtact taatctcaat gcatggtcaa ttaaagtttg attacgtgga aggttttgtg | 840 |
| attgtggacg aaggactcgt caacaattgg agatcttctt tcttctctcc acgtaacccc | 900 |
| gtcaagatct cctctgttag ttccaacggc tctgttttgt attgccttga atcaccaag | 960 |
| aactaccacg actccgactc cgaaatcgtt gatcaggaag ttgagattct gatgaagaaa | 1020 |
| ttgaatttca taccgacatc ggtctttaca acggatttac aatatgtgga ctttctcgac | 1080 |
| cgggtacaca aggccgaatt gaagctccgg tccaagaatt tatgggaggt tccacaccca | 1140 |
| tggctcaacc tcttcgtgcc aaaatcaaga atctctgact tcgataaagg cgttttcaag | 1200 |
| ggcatttttgg gaaataaaac aagtggccct attcttatct accccatgaa caaagacaaa | 1260 |
| tgggacgaga ggagctcagc cgtgacgccg gatgaggaag ttttctatct ggtggctcta | 1320 |
| ttgagatcag ctttaacgga cggtgaagag acacagaagc tagagtatct gaaagatcag | 1380 |
| aaccgtcgga tcttggagtt ctgtgaacaa gccaagatca atgtgaagca gtatcttcct | 1440 |
| caccacgcaa cacaggaaga gtgggtggct cattttgggg acaagtggga tcggttcaga | 1500 |
| agcttaaagg ctgagtttga tccgcgacac atactcgcta ctggtcagag aatctttcaa | 1560 |
| aacccatctt tgtctttgtt tcctccgtcg tcgtcttctt cgtcagcggc ttcatggtga | 1620 |

<210> SEQ ID NO 35
<211> LENGTH: 539
<212> TYPE: PRT

<213> ORGANISM: Arabidopsis thaliana

<400> SEQUENCE: 35

Met Asn Arg Met Thr Ser Ser Phe Leu Leu Leu Thr Phe Ala Ile Cys
1               5                   10                  15

Lys Leu Ile Ile Ala Val Gly Leu Asn Val Gly Pro Ser Glu Leu Leu
            20                  25                  30

Arg Ile Gly Ala Ile Asp Val Asp Gly His Phe Thr Val His Pro Ser
        35                  40                  45

Asp Leu Ala Ser Val Ser Ser Asp Phe Gly Met Leu Lys Ser Pro Glu
    50                  55                  60

Glu Pro Leu Ala Val Leu His Pro Ser Ser Ala Glu Asp Val Ala Arg
65                  70                  75                  80

Leu Val Arg Thr Ala Tyr Gly Ser Ala Thr Ala Phe Pro Val Ser Ala
                85                  90                  95

Arg Gly His Gly His Ser Ile Asn Gly Gln Ala Ala Gly Arg Asn
            100                 105                 110

Gly Val Val Val Glu Met Asn His Gly Val Thr Gly Thr Pro Lys Pro
            115                 120                 125

Leu Val Arg Pro Asp Glu Met Tyr Val Asp Val Trp Gly Gly Glu Leu
130                 135                 140

Trp Val Asp Val Leu Lys Lys Thr Leu Glu His Gly Leu Ala Pro Lys
145                 150                 155                 160

Ser Trp Thr Asp Tyr Leu Tyr Leu Thr Val Gly Gly Thr Leu Ser Asn
                165                 170                 175

Ala Gly Ile Ser Gly Gln Ala Phe His His Gly Pro Gln Ile Ser Asn
            180                 185                 190

Val Leu Glu Leu Asp Val Val Thr Gly Lys Gly Glu Val Met Arg Cys
            195                 200                 205

Ser Glu Glu Glu Asn Thr Arg Leu Phe His Gly Val Leu Gly Gly Leu
210                 215                 220

Gly Gln Phe Gly Ile Ile Thr Arg Ala Arg Ile Ser Leu Glu Pro Ala
225                 230                 235                 240

Pro Gln Arg Val Arg Trp Ile Arg Val Leu Tyr Ser Ser Phe Lys Val
                245                 250                 255

Phe Thr Glu Asp Gln Glu Tyr Leu Ile Ser Met His Gly Gln Leu Lys
            260                 265                 270

Phe Asp Tyr Val Glu Gly Phe Val Ile Val Asp Glu Gly Leu Val Asn
            275                 280                 285

Asn Trp Arg Ser Ser Phe Phe Ser Pro Arg Asn Pro Val Lys Ile Ser
290                 295                 300

Ser Val Ser Ser Asn Gly Ser Val Leu Tyr Cys Leu Glu Ile Thr Lys
305                 310                 315                 320

Asn Tyr His Asp Ser Asp Ser Glu Ile Val Asp Gln Glu Val Glu Ile
                325                 330                 335

Leu Met Lys Lys Leu Asn Phe Ile Pro Thr Ser Val Phe Thr Thr Asp
            340                 345                 350

Leu Gln Tyr Val Asp Phe Leu Asp Arg Val His Lys Ala Glu Leu Lys
            355                 360                 365

Leu Arg Ser Lys Asn Leu Trp Glu Val Pro His Pro Trp Leu Asn Leu
        370                 375                 380

Phe Val Pro Lys Ser Arg Ile Ser Asp Phe Asp Lys Gly Val Phe Lys
385                 390                 395                 400

Gly Ile Leu Gly Asn Lys Thr Ser Gly Pro Ile Leu Ile Tyr Pro Met

```
                   405                 410                 415
Asn Lys Asp Lys Trp Asp Glu Arg Ser Ser Ala Val Thr Pro Asp Glu
            420                 425                 430

Glu Val Phe Tyr Leu Val Ala Leu Leu Arg Ser Ala Leu Thr Asp Gly
            435                 440                 445

Glu Glu Thr Gln Lys Leu Glu Tyr Leu Lys Asp Gln Asn Arg Arg Ile
            450                 455                 460

Leu Glu Phe Cys Glu Gln Ala Lys Ile Asn Val Lys Gln Tyr Leu Pro
465                 470                 475                 480

His His Ala Thr Gln Glu Glu Trp Val Ala His Phe Gly Asp Lys Trp
                485                 490                 495

Asp Arg Phe Arg Ser Leu Lys Ala Glu Phe Asp Pro Arg His Ile Leu
            500                 505                 510

Ala Thr Gly Gln Arg Ile Phe Gln Asn Pro Ser Leu Ser Leu Phe Pro
            515                 520                 525

Pro Ser Ser Ser Ser Ser Ala Ala Ser Trp
            530                 535

<210> SEQ ID NO 36
<211> LENGTH: 842
<212> TYPE: DNA
<213> ORGANISM: Arabidopsis thaliana

<400> SEQUENCE: 36
aagcttaaat gacaatttag taccttgggt tggtcatgat ttagagcgga acaaatatac      60
catacatcaa acgaggatat acagagaaaa ttcatggaag tatggaattt agaggacaat     120
ttctcttctg ggctacaacg gaccggccca ttcgctcatt tacccagagg tatcgagttt     180
gtggactttt gatgccgcta gagactattg gcatcggatt gaaaaaaatg tttacttcgt     240
tgttaacaat tttctgaatg caatatttc cttgtcatga atatttaaac ttgttattac     300
tttcttttag cttaggtgtg gacaattatg gagtttactt caaacgagga agaatcttaa     360
acgctcggtt caggtctcga aaacaaacca actcacaatc ctgacttaat tgaggaaaac     420
aatgcaaaac cacatgcatg cttccatatt tctatcaaa tcttataaga aaaaacacta     480
ctaagtgaaa tgattctgta tatatataac caatgccttt tgttttgtga tattttatgt     540
atatataact attgactttt gtcatctatg gatagtgtct cgggctcttg gcaaacatat     600
ttcaaagaaa agttaatgac tgtaattaat taatctgaag ctagaaacag aaccccgagg     660
taaaagaaaa agacagagca catgaagttt agtacttta tatatttaat atatcattct     720
ttcttattgc ttatctctaa agcaaaaact tccctaaacc ctaagccaaa ggactcagat     780
cgatgcagaa ccaagaaggc ttgttttgga tttgagagcc aaatgcaaag aaaaaaactc     840
tt                                                                    842

<210> SEQ ID NO 37
<211> LENGTH: 92721
<212> TYPE: DNA
<213> ORGANISM: Arabidopsis thaliana

<400> SEQUENCE: 37
aaagggccac aacttgtagt acacaaaatg taatagtaga cttcatttgc ggacatgcat      60
caccagtgtt ccaaaactgt caagttgagg cctgaaacgt gacatagcaa tgttataatt     120
gttctgtcaa tggaaggaca gagcaatgtt ataactgctc aacaacgtga taagtcgggc     180
gaaagtttgg gattttcaat tcaaaaatgt gaaaatatac taaatatgta ctcatatact     240
```

```
aaatatacta aaaagtattt ttgtgaattt atttgagttt atgtatgtta acgtgtatgg   300
ccgtttgata tgggaagtgg atgtttattt ttggccaagg gagatagtag tgttgctaat   360
attgtttttt tgaacgactt gatccctcat tgaaggttta gttctatatt aaacttgtct   420
gtaatttgaa gaagtcatcg agcaaagcct tgggtggctt tgtttgtatg tatctttgtt   480
tggtttggtt aaatgatttt taaaggtaat atgttgaatt gatcaatgga tgtgaaagga   540
tgatcaagaa actatgttca tgaaaatttt gaaatttgtg ttcaacttttt atgcaaaaga   600 tgagcagaat tacgatcctt tcaaagcctt ttttttttcac caccatatttt tctctcagct   660 attgtaaagt gattggttta gttacatttc acgtaaactt tagtgataat caaaatatttt   720 tatcttaatg acattagacc cttgactttg tattgtatct cacatttttt cttctagtta   780
tttcttaggt tctttaaaaa ataattactg tatttaacta aattagatat gccatatttt   840
atttcttgtt ccaagtacca aagagcctag gcacgacaat gtgtgtattc actctttaat   900
ggttctataa caaaatttta gtgaaaatgg tgttgtttgt tttaggctat ttatcaatat   960
cttcgaggtt catgattcta tttgttattt cattttgata ttattctgcc atgcccttta  1020 cccatttttgc accacctcca tcatgaggtt tgatattgat atccattaga aaatattatg  1080
aaaacatctt tgacacaaaa aattatgaaa ccaaatgtaa tattcaacaa actaaaattt  1140 tcattttttat tggtttacaa acataatcca aaccacgtac gtaactctct tttttggttt  1200
atcacataaa tatcacaatt tacaaaccat acatttacat gcatataatt aaaaatattg  1260 cacccttcaaa taaatgtttt tacaaaaatc cccaatgaga aactagccaa ttaaacaacg  1320
acattagaaa accggactct tgatttccaa tcgcgaatcg cagaccggag cgtatggttc  1380
ggtgtgagct tgaagtggtc tagcttttgt cgagtcaccg gtgaaatgtt atgtttctca  1440
agccacgcta agatcgcttt cctctcgtac gtgaatccat cggcagcaat ctctggctcc  1500
tccattatct cctacatcca acaatccaaa taaataaata aaatctaaac cggttcaaat  1560
ttcttgttac tacatttgtg taccgaacca ggtaaccttt tactcacccg taagattgga  1620
cagaagtaat gactcggtgc acgtaaattg cttccttctt tctttacttt cgaattcgcc  1680
gtctccacaa gccgtttcaa aaccggtata acctctgatt taagatccgg tctatctcgg  1740
catcgaaatt cagcacattt taaaccgatc cgagccaatt cctcggtttc tgccaaaggc  1800
caatcggtaa ccgattatc tagcatttcg gttaacgtcc ctttctttac cgcgttttcg  1860
accgctggta caatcccgct cgggttacga gccgtcaaca actgaagaat gattatgccg  1920
aacgcatata gatccgactt tggtctaatt gttccggttc tgtggtattc tggatcaata  1980
taatgcaatg taccggcaag aaccgagttt cggtacatcg tgacattatc gggtgcaaca  2040
tccgtaacca gcttggctag gccaacgtca gcgattttgc taacgtagtt ccggtttaac  2100
aagatatttc ccggttttaa gtcacggtga acaattggtt ccggtttaga gctgtgtaag  2160
aaggccaaac cgcaagctac ctcgaaaatt accctaaacc ggataaacca aggcaaaggc  2220
ggtttatttt ttcggtgaaa tatatattcc tcgaggcttc catttttccaa gtactcgtaa  2280 accaaacaac cattctccgg acaagctccg aggaggagaa ccacgtgtgg gtgtcggagt  2340
tggcttagaa cctcaaccta tagagaaata ttaccaaacc gaaataaat caaccggatc  2400 aaatcaaaag agttaaccga aaccagacat aatttaaccg atacctcttt caagaactct  2460
tgtttcttct ccggtgtatc tagccggaca actttaacag ccgccggagt actatcaagg  2520
ctacattggt aaactttccc gtatcctcct tctccaatca ctttctctgg cgagaatcct  2580
tctgtggctg ttacaatttc ctcaattgtg tattttctgt accggtgatc agtccctaaa  2640
```

```
agctgatcga tcactttctt cttctccaag taagtcctta aagcattcac ctccgcgatc   2700
tgtcgctgac aaaactctct tgcgagcaac gctttcgcgg tttcgacctc tttcaccgcc   2760
ttcatgtacc gctctttctc cagcgccgcg gtgttcctct gcaactcttc tttctccaca   2820
gcattgttca ctcttttaga ttcattcaaa tattcagtcg aaagcatttt aacctaacag   2880
aaacccaaa ataaacactt tacttggaga aaagcaagc aaaatgattc accagtgagt   2940
ttggaaaact attttataga aacaataaaa tcagatataa aataaacact tctttcacag   3000
ataagttttg atggccatca caaatataca aatttctctt cccaaaatca tctctaatca   3060
ttttcttgca gattttaggg ttcaagatca gaaatctata ccttgttttg tgtggagaag   3120
agctcttcac aagcttgttt atatttaaag actgtacttt gtagctcatt cttcaaacgt   3180
tcgacctctt cttcaatctc aacctgtcaa acaacaccaa atctttcaaa aacctcggtt   3240
acgtcataat agctagtctc atcattgcag caaagatga tggtaaagta accttcttgg   3300
attttcttga tgtttccggg ggtgaacgat cagagtctcg gtgttcgcta acgatgttct   3360
caacatttga ttggggcttg gtacatgttt tatcaaaatc tgagtaattc agctgaggaa   3420
tatcggatcc tctccgtcgc ctaaaaatct ctggagttgt tgcactagaa gccttactac   3480
tttgaggcgt tttgggttta ttacaagtaa ggcttaatgc ctcaaatctc agctctcttg   3540
ccgatgctga cctccttgtt cctgcctctt caacatccaa aagaaagaga aaaacttcag   3600
gccttcaaga catcatagtt tatattatat gcattatcat ttatatattt tataaatatga   3660
atctatactt gatagatgca tgttcgttgc aaatttcttc gtataacaaa tttatattca   3720
aagttataat gttatgcaac tagtttactt tttgttaact aagattgttg ttatatattt   3780
ttcaaaatta ggttcaattc aaaaaaatga gtcaattgac cattaaaatt atttttattt   3840
ttgtttgttt aagaatgtca gaattgagaa tgtactatat attaaaacaa cctaaaaccg   3900
ctattcattt cctatgaatt ctgatggata tttgactagc tatatgtata ttttaccagt   3960
tgactgtcga ggatcgggta acgttggaga ccgtagagtg tggaaactag ccgcccagtc   4020
tctcaagaag tcatgggcag tcgcggctgc gtgtggactt gtgcacggct ctggttacca   4080
cgattaaaga gaagttttaa gaaatgagaa aatattgtgt tatcaaataa aatgttttgc   4140
ctataaatta ccatgtttaa gaaattacat caactatgga tgtagtatta aacaataatt   4200
ttctttaaaa aaaaacgaa acacaaaatc ctaattttta cctcggttga ttaatggatc   4260
catagatttt gtagtgattc tgtctttaca cacaatgtat acttcacatg tttctggtgc   4320
gtatcttaaa acgtcagtg gtactcctgt acctttttgtt ctcctagacc gaaaatatcg   4380
ctgttagtgt atataaccga gttaattaag aagaacgtaa accaaaaccg aactatgtaa   4440
atttaccatg tgaatatgtt tgaagtaaat gatcccataa ccaaactgtt aactcctgat   4500
ttggatatca atctgacaag tgcttttgca ggatcgtcgt actctagcaa tagagtctct   4560
accttacact gaaggttaca atatttcagg gagtttaaag tttgtctctt aatttatcta   4620
gattataaaa ccgaaataaa acaaaaccaa ccttggtact cctagtactc ttgcacattt   4680
tcaaaagggg aacaaagact gtttcatatt cttttttcac gtctcttaca tacatttcca   4740
ccacactctc ctccacttct tccaccggca atctatctcc ggctgtaaca acccacattc   4800
tcgtaaacat taatatcaaa atatctttaa attacaatga taaattaagt atttaaaaag   4860
atgtcaaaca aaaatttga taagtcgaat tagctaattt acttttttaac atacaaaaaa   4920
cggaacaatt tcacctcatt aaaatcaaac tacgaaaaag taattactta atcatttgat   4980
tatcatacga acataaattg taagatttgt gaaacttact tttcacattt tcttccttca   5040
```

-continued

```
tgttctatat atttggtgtg aaaaaaaaaa aaaaaaaaac tcagtaatta ttatttcctt    5100
tctgtcttt  ggttttttact tcattttatc tttatatcat ttacattagg tttttaataa    5160
caataacaag aaaaatgtga atgattgaga gagacttact cggagtagga atagaagtaa    5220
tggtagggat gacgtggatc atcacaaatt tatcagcctt cggtaaaaga ttatcgacag    5280
cccaccgtac ggcacgacga cttcctgcac cgcctaattt gtctccgatc aaacccttca    5340
cggccaccgc cacaaacagc tgaccctctt ccgcctttgg accaccaccg ccactcattt    5400
cttgcgtcag catcaccacc atctaatcaa ttatacttac gtataccaca agtaaccaaa    5460
gaataacttt tgttgttgt  gactgaggaa cccttgtggg ctgatacact tttgtagttt    5520
tgtttctgaa tttgggtggg gaaatgctat tccagagatg gatattactc tgatcacgac    5580
tatattgtat tgatctcttt atatatatat atataagagt cgtttaggac caagtgttta    5640
aaaatgtaaa aaaaaaaaaa tttgattagt agccgaacaa tgattggtcg tctttcggtc    5700
tatttgttgc tttggtttgt ttaatcaata attaaagtcc taagatatgt tttaatataa    5760
acttgaacaa acaaaatata tgagtttgat tgtagaaatg ctttaattaa cactctaagt    5820
ctaaagtata aacaaaataa caacatcaaa aactaagtga ttgtagtgta ggcgtaataa    5880
tattttgata gtccgttcta aaattagttt ataaatgcta ttttttttatg gaccactatt    5940
aattattaaa tctcaaaaga attatttcta aacaatgttg tttacttaag tgatatagtg    6000
cagtacaata taaaattttt cgtattagtt tataaataca tagcttaaaa aatataagag    6060
aatacgaagt agactcatag gattggatta tataaaatca gtctattgac tttaggaaca    6120
aacaaaagat ataatttgat ctgttttgaa ttttgttggt aatcaccgat atggatcttg    6180
cagtcctgga tatataatta atagtaaaat atgtttggcc aacattagga agaaatcgat    6240
gggatggaaa tcgccttcaa aggaatatat attccattta atacttttca aattcgaatt    6300
tttttggacg gccaatttgt taattataat tagtgtgcag ctttattatc tgaagttttc    6360
tagttctatc tacatgatat ttgaacggtt tagatagaga ttttttatgtc tgtcagttgt    6420
ataatatgta tcatatacta tgaccagttg taccaatgtg ggcaatgtga tcaatataat    6480
gtaacctact aacttataac ctatgtatt  gttgcaaaat aattatgtat gaagtaattt    6540
tgaatttatt tgaattttc  cctgactttg tccgtgtcaa caaacaattc gaaatgcctc    6600
gactttttta gaacaggttc tagcaaaata acttagctca gtaagctttc agaataaata    6660
aagtagtcat tttctatcag aagatgacat aatttagttt tttcttctgt gcaaacaatg    6720
acataacaaa aacaaatga  cattacttag ttacggtact agattaatct tgaagtggta    6780
tgtggtcgca acaatctgaa tcttttagta aaaggcatga gattgttgtg gccttgtgag    6840
ataagtcaca ttttgttccg gttaaaatat gaaattattc agtatttttt gtcgcagacc    6900
aacctatata ttaaaattct ttataatttt tttttaatac attgtcttga atttccacga    6960
tttcttgcac ataatagttg tttaggattt gatcatctga tacggtaacg tacagatcca    7020
aatttccgat caaaccggtt tgatttggct gagtaatgat gtttgcaatt gttttctaat    7080
atgtaaccaa aagttgacca aaacagtcta atgatttttt cattaatttt ttgctcagca    7140
caaatgagga tatacccgaa taattaagaa ttatatataa aaaaaaaaca ctaataatgc    7200
actgatcgtt tacgagaacg acataattaa actaattaaa gatcttaacg attgtcgact    7260
ctccaatgtt cttatacaca cacaaatata aatatgatta gtccaatcta tatagtcgaa    7320
cagtaattta cagcagactt agatcgatct ttcgtataga agaaagagac gttaccaatg    7380
acattactga aataacttct ttttttttt  taactacata gaattattaa cacattctaa    7440
```

```
tacagcatac attaatacat atatactctc actacgtgta aatgatagaa gacgatcaat    7500
attggctaga ggtccatctt tggttaattg ttccatatat gtagatctaa gctatatata    7560
cataatactt tcggaatttt tttgtatttc ttaaaacatt aaatatgcaa atgtaaacgg    7620
aaacaaatca aacaaaactt ttaatttgat gtcaagaaaa cgatatcata tttttttatt    7680
ttagcccaag ctgtttttgg gtgtttatta gtatacaatt tatatttaat tggagcgaag    7740
cctacatata gaaagtttag agcatcatgt agacgtcatg tgaattctag gtccaaaatt    7800
atgtacacac tacataaaat atcataacat caaacgaaaa acacatatac cacacacgaa    7860
aaaagggaaa aagaaaaga aataaccacc atcacttagt ttctgattct ggacaagtag    7920
ttcatgaatc atctaatata ttagtcatta ttgatttctt aaagatttat tgatcaattc    7980
atacatatat ttctatttct agccaaatat ataatagagc tagattttta tttttttgt     8040
tcataaaaag aaaacagctt taattgataa cagttgttca ttgttatttt tgctacttag    8100
acgatggatc atgcatgaaa aggtaccaag taattcaaac agtactgtta ttggtagatt    8160
ttagatatat gcataaatgt gggggacaaa aaaatatag atacataaat ataatggaaa     8220
tggtaaaaga acaaaatag ataaaacata gataaaggga gaagaaaag tactttttta      8280
cttaagaata tatttctgtc cacaacaaga tttgctagga cgaaaaatca gtaactattt    8340
ctcaattctt ctatgtagct cttttaaaata ctaaaggtca tccgatgacc ggcatcaaac   8400
ccttatccgc aacttgatac gcacgctttg ttcctttgcg atcatgcgtg aaatcttctc    8460
attctcatga tgataaacct tccttatgtc ttgctcctta attttttct ttgttaaagt     8520
gccttgctcc tctttgtaac tcaaagctca tcatttgtac aaaaattaga tcattttgta   8580
gcctttatta tgttatatat attgatgtga ttagtgtttg taatttgata gaaaaaacgt    8640
acgactctga gctttacaac ggctatttgg caatttacaa cggatatggc gacttacgct    8700
attttactgt aaagattgaa atgatatttt gtgtgtcgtt aggtaaaaca ttagtgaaaa    8760
caaaaggtgg atagacaaga tatggtcata tctatctaac catacacaga gacgtttgct    8820
gccatgcatg catgatgcat atatatatat atatgtggat ataaaatata tttaatttat   8880
atacacatag tccatagata gatagataaa tagacgtaga gagggagaga gcaggagaca    8940
agaagagagt aagcacgcag agctttcgag catgagcatg ctagaaaaag agccatgtgt    9000
gctcactctc ttctgtcgcc ttcgttattg ctattccctt acctcctta gttgacttgc     9060
ttcatcttct tgcatgcata tgattttgat gttatattag cctcggtccc taaaattact   9120
atatgatatg atgatatgat atgaaacagt ttgtctgatt ttagggtcta tatataagga    9180
ttgctagggt ctatatatga tgatgcatgc atagatttca tcatcatcat ccactgacca   9240
ctagctacgt ttaatttata gaaagattcc gccggattaa actcttattt cctgtcaatt   9300
tgagcaacaa gattctctct tttcaattat atatacataa cacatgtcta taatatacgt    9360
acaaaccaat aaaattggac tcttaacaaa attttgagag tgagagatcc cacttaaaac    9420
gaaataaact atttgtttgg tcattgcatg cgtaaacgac cacttgaaca attaagtata    9480
cataacatag gtctagatct atgtgaaaga ttcccaaact taagatctct agctagaaca    9540
ttcattgatc ctccaatcaa aaaccaaagg aataaaaagt aatctttgta agggcgaatg    9600
taaaaccgaa acgtaagcta gaggaattga tattaaaatg gaagtaaaag cgaatattac    9660
taaaggtttt ggagttaatt aaataaagac aaaagatgca aggacaacga attatgaaca    9720
tcttcgaaat acgtttttaa tattgttttg gcatttgatt tgatttgatt ctccttccac    9780
attcccttgt tcatatgtgt ttgtgtctca cgcaagcact acataagcgg tccccctaaa    9840
```

```
tacgtttcta gaaacgtcaa cgtttattca atcataccaa aatttacatg tgtattcatc   9900
aatcagccga ccataaacta catggtccat tagtcattac ctatactgca attttttctag  9960
cttttaacag ccattatgta cttcacagtt tggaatactg gtatgacgaa gaaaagtcga  10020
ggtaaaaaac gtattagaat aaatgtttat cgtccaaaga tcgcaccagc aaagaataag  10080
aaacctaaac caacaaagga acaattaatg gaccctgaat tttctgatga agacgtactt  10140
accagcttgg gttttgatga tggcggttac ataataccac taccgaaaaa atctctcatg  10200
ttgattaatc taccagattc ttttcgagat gagttgcaaa cgatgcatgt cagttttat  10260
ctccgagaag ttggcaaact tatgtttggg tgaggacaaa tatgctctag tgaatagtac  10320
taagaagttg atgcttacag atggtctagg acggcttcat ttgttttgga tgaattcaat  10380
ttttttccg aatcagtatt tgcgaatgag atttatgtag ccctagatgt gagatttatg  10440
aaagctggaa gtgccaaaaa gaaaggtgga gattttaatt gtaacaaaaa cgcacagagt  10500
cttctttatg atttttcctt ggtagatata gatgaggaga tatatgggtc aaaatttgaa  10560
gagacggaag accaaaagaa gtggaacaaa aaattttgaa ttgatttgtc ttcatcatat  10620
tgtgctatta acattaaaca cgaaatagag catctgaatc ttgaattcta tggaatctct  10680
aaaacgaata gacagatctc cgcggaggaa gtgaaattct ctactcatac tgcattcaaa  10740
attaattgag ttttttcaatt acattggagg tttatccttt gatactttcg gtttggtgat  10800
ttgaatgaaa tgttggttt gacagaaaaa tgaataacac ttgcattaaa atcatcaaaa  10860
attgaataac actagaatct aaggaggtgt attcgatctt atatttaag ttatttgagt  10920
ttttatataa ttttgatttt ttaaagaatt tggatgaatt taaggaggtt gttatgattt  10980
atggtaaaat cctctcaaat tccacctaaa accatgagat ttaaaattat atattttaa  11040
ctaagaaaat ccacttaagt ctcttaaagt cactaaaatc caatctttaa aatgttttca  11100
ataacgaaag attttaaag gagattttaa aatcagtaatt caatagcatt agatttcatg  11160
atacttttaa aaattcataa ttgaataaca taggatatgt tagtttgaat aagatatcct  11220
aggtgttaat ttactatttt taaaaaggta agattttttt tcatgttttt aaaaaatgtg  11280
agagtttttt tacctatttt tctattaaaa tgaaatgtat aaaattaaaa ttttgttttt  11340
aaataaaatt actaaattaa atattacaaa atatgtatat attactattt agaattcaaa  11400
tattatcgat acaaaattaa attatttct tcaattcgtc tatttaagca agctagtaat  11460
ttgatcgaca aaaaaaaaac aagctagtaa aatataatta acagaattac taaatcggcc  11520
ggtttaggga ttgctttctc tcagtcgtca attgcactaa accactggtg gtaatatcgc  11580
tggcgtttcg caagtatcac cgggaattgc aaagaagcag aggaccatgt acggagacgc  11640
tacaaactgg aatgaagatg agtatagaga atcaattttg aaggagcgag agatagagac  11700
acgcaccgtc ttcagaaccg cctgggctcc tccggcgaga atctctaatc cagacgcatt  11760
tgttgtagcc tccagcgatg gaactttagc ttttccattca ctgaactcgc ttgtgtctca  11820
atcggcgagt tttggctact cgaaaggtca agatgttatg gtggctgaac ctgagagagt  11880
ggttagggca cacgaaggtc ctgcttatga tgttaagttc tatggtgaag acgaagatgc  11940
tttgctactt aggtagagac ttaaatctct ctttgttgat tgatgagtct ttgatgaatt  12000
gtaattgaga gtttgaaatt ttgatctggt tatgtgtagt tgtggtgatg atggtagagt  12060
taggggatgg aaatggagag aatttgctga atcagatgtg tctcttcatt tgaaaggtgt  12120
gtgtgtgcca ttttttgtggt ttttgatatg aatgatgctt tttggagctt agtggttgtt  12180
tttcttatga tctacagaga atcatctgaa gccattgctt gaactgatta atccacaaca  12240
```

```
caagtgagta tgagttttgt tcattttta ttctacttga taactctgtt actgaaaatg    12300
ctataattgt gggttcaaat gtcagtgttc gtaatagttg tgtgtataat caccattctt    12360
tttcttatag aggtccttgg ggtgcgcttt caccgatgcc tgagatcaat gccatgtctg    12420
ttgatcctca ggttggaatt gtatttaaat ttcattgctt ggttagacag tctcacagga    12480
taactgtttc accctctctc acttctttcg ttttgatagt caggaagtgt atttacagca    12540
gctggtgatt cttgcgcata ttgttgggac gtggtatgta tttgaccatg atagatgtat    12600
gtcctatgtg aatccagata tcttaacttt ctaaaatcat ttatgtgtat ccaacaattt    12660
caggagagtg taagattaa aatgaccttt aaaggtcatt cagactattt gcatactgta    12720
gtttctcgta gttctgcaag tcaggtaatg atgttaccat aaatattaga aatgcaccta    12780
tccaaatctg agttccacat ttggatttt gtctgattgt agtctctttc tccagatatt    12840
gacgggttca gaggatggga ctgcgagaat ctggggtaac atgctcccga ccatatttct    12900
ttatgctgta atttctagta ttaggtcata cgtggttata aacttttga aatcatttga    12960 gtcttcatgt tggtacttaa gatccaatgc tcctcagttt tgttggctgc ttcttacaac    13020
tctatgatga ttcattttgg tgattacaga actttccact atgttatgtt ttggttcatg    13080
tggtttactt tagttgtcta gactaagctt tgttcgctca agggcttctt tctgttttgt    13140
caaccagatt gcaaacggg aaaatgtgtt aaagtaattg gttcccagga taaaaagtcc    13200
cgccttcgcg ttagttctat ggcccttgat gggagtgaaa gctggttggt aagaactaag    13260
caactagata atctaacatt ttcgcaacct gctatttgtt tgaagggatt gttgcctcca    13320
gtaacctaag aatatagttc ctttctcctg aagaatcact tagaagttta aatactgaac    13380
atgtatttac tgttattggt atgattttct cctctttcag gtttgtggac agggcaaaaa    13440
tttagcttta tggaatcttc ccgcctcaga atgcgtacaa acaatacca tccctgcaca    13500 tgtacaggat gtgatgtttg atgaaaagca agtaagcaga acaagattag attgaaattt    13560
aagcagtgta atttaaagcc ttgggaggcc gtgggtgtta tttgtttatc aaggcttaat    13620
aggtttatgt agtatctctt tgaatcatcc ctcttcaacg aagtttatta aaaaaattac    13680
tgacttttct aaactagaaa cagaggtcaa cacctagttt taattcctgt gctaaagttt    13740
aaacatcttt ttaaaaatgt tgtctttaac aagtatcgca ctatcagatt ttgactgtag    13800
gagcagaacc acttctaaga cgtttcgact taaatggagc tttgctttct caaattcact    13860
gtgctccttg ttcagtattt tccatttcct tgcatccagc aggagtatgt ttccaatccc    13920 ttctttctc cccatttcct atatatgtgt ttgcttttct cccatttcct atgttactgc    13980
taatattctg caaatatgtt acccttctg gactagaaac tcaatgttta accgttgatc    14040
caattctttt gtatttgcag gtagttgctg tgggaggtta tggaggtatt gttgatgtca    14100
tctctcaatt tggaagccat ctctgcacat ttcgtagcag ttcattgtaa aactccttac    14160
agtttcttga tttggctcga taccctaaag aggtaccgaa atgtgtcagt cagattattg    14220
cagaggttaa gaaaccttt ctttgttttt cttaggatct tgctcctgac taaagaccaa    14280
ttagttgttt ggttaagtgt aattggtttg tggttccgta gttgctatca aatttgaacc    14340
attaaaatga cattggaccg gtttagtctg atcacgtaca ttaactgccg ttagagtttc    14400 aatttttgc gagtcctgtt ttcttatgac caccattgat caaatatttg gatccataac    14460
taaatgattc tcactcttcc aagtaaaatt ttaccatatt atgcaattta atacatggac    14520
aaaacatata gtttccatat ccacaaaaat aagtcctcaa aaacatcact aatctaaacc    14580
tcaaacatca ctcctgataa gagaaaccaa actccagcga tcaacaaaac caagaagaa    14640
```

```
gaaaatgaag aagctgtgga agcaacaatc tgaataggga aattgcattg tccctgagat   14700
atattctttg tggtaatggt ggccaaacct tggaagatac aagcatcctc atcctggttc   14760
tttacttgaa aatacatgtt aaacgcatat gaagcgttcc catttgcatc aagagtattg   14820
caagaagacc cgtaaccaag cgcagtgcaa tccgaaaaag tgcaggcgta atctatgtta   14880
gcagcgagtt ttgtcaaatc tttggcttct gtattaaaca tacaccactt cttaggttga   14940
tacgtcacgt tctcggcacc aatcaacaac ttgttctgtc cttgacctga tagatctata   15000
ggaaactttg gttgcccgtc gaatttgaat attccccagt ggcgttcaaa ctctcccggt   15060
gctatacttt tcgcatcctc atcaagtaat ccaaacaagt atacctcaat gtaggttggt   15120
ctcagtggag tgcctctgtt ttccccaagc cttggtaaaa gaccgttgta gaatctgtaa   15180
gcactgcctg cgaaaaatac gttttcaaaa catttcattg catctaaaga actggaaaat   15240
gttagatgtc ttaccactat ttgcgtgttt gtcaccctct gttggccaac cgacttctcc   15300
aacgatgatt ggcatatctc catgaccaac agctttcaaa gccgatacca aagtgtcgaa   15360
attggcatcg aaaacgtttg tgtaagcaat accattgtca tctactggtt tagcaccatc   15420
aaagaaggcg taattgagtg gaaaatcatc attcccatag aggcttaaga aagggtagat   15480
gttaatggtg atgggtgcac tgttattgcc aagaaagtca acaatctgag tcatttgacc   15540
gatgatatca ggacggaatc ttcctgcaga tggcacaggg ttgcttgatg gtgaatcgta   15600
gacatccgcg tttaaaggga ctgtcgcttt gacggagctt cctagtccag cttcattcaa   15660
agcgttttgg atgttttgaa gtgcagggaa tgtgaggttt ataaatgatc cattgtatga   15720
tttgaggaat ggctcatttc caacagctac aaacctgaaa acacatccac aagagattag   15780
acatataaac attttgacaa tgttcttacc agattaacat tttcagagaa ttgatttcac   15840
aaccgaacac attagaacca atatataaca agcagaggga gaaactcact aacgtgatat   15900
tgacaccacc attgaagtta taacgagtga cattcttatg aacccaatct ttagctcggt   15960
cataacttcc cataaccttta agctgatcat taggaatagc aaccataact tcaagaccag   16020
agccagaaag tgcactcata gtggtctcat ccgcatcaaa aagcttaact ttgttaatgt   16080
tattgtcctt aagcatttga accactttct ttggtgaaag cttatgtgta gccattgttc   16140
cccagttgac acctagccca tctaccataa caatacccat gattccaaat ccaacgacga   16200
aggccaacag attcatcgtc ctgagaaaca atgaaatggc ttaccaggtg ttttcaccca   16260
aattcaaacc cttaacttga acactcgtaa aatctcactt aaaccccaga aattgaagat   16320
atttacattt tcctaaatgg aggtcaatca aaacatcata aagttcaaag cttttcacgc   16380
aaaatctacg agataaccaa aaataaagcc aaagatacga ttttttaacaa aaaaaaatga   16440 gaatggggac tagaccttc cactgagagt aacaatcgtc aagcaaaaag attgattctt   16500
ttttctctct ttaactttc cggaaaaaaa gttttaagct ttgatctttc tctgattgag   16560
cttgacggtg aataatatgc tttgtgattg gttcttggaa cttggaagta tttggtaaaa   16620
gcccaaatta aaagttttaa gtaaacattg cacttttaga atttttattgt attgttttta   16680 tggtcagtaa ataatgaccc aatgtgtttt atgtttgaca aatgttttag agtggttatt   16740
ggtagatgaa ttttttctaat tttcagattt tattgtcaat aattcatgga ttcttttaaa   16800
gttttagtaa aatacattgt tattgggttg taagctttta aattctattc aaaaaaaaaa   16860
ttattcaaat agtttagtta ttataaattc tctaattcta acaaatatat cttaatatta   16920
agatatgaaa ttctatgttt ttactcatga agcacaactt tcttaatcta tatatacatt   16980
tttggagggg attttttgaag ataatgttga agatttgaac cataattcaa caattaattc   17040
```

```
aaatgggtgg gttttacccg gtttaactct gttcggatcc tggataacat gtttaattct    17100
gttctgatct tggataacat taattttggg aaaagttacc taaaacctaa taattaaaaa    17160
cgaaaattaa tgatttactt accaaattta atataaacaa tatctctaaa ctaaccatat    17220 ttttattta ccttaactaa tttcctaaaa tatttctacc taatttaaac ataaatatat    17280
aaatcttctt tcattttat ttgatcttat actttattta ttttgaattt atataaaata    17340
tatatagtta ataaaatatt atatttttct gaatatgatg taatttaaat ttttaaaac    17400 ggacatatat tattcaacct atgaagaaat aatatatgta caatgtccca catcgcttag    17460
aaaaattgga caatggttca gacccatatt ataaaaggac caaaatgatt ctgattacga    17520
atgagcagaa agcttgattt atcaggcgtc caaaattaaa atagttatcc gattttactc    17580
ggatttttta ttttaaagaa ttgaaacttt aaaatatttc aagaaattat aaatattata    17640
actttatcaa aagttaaata ttataatttt aaaatctttt tataaagttt atctttaaaa    17700
aatgcttgaa atatttataa ttttaaaact tataaagttt taaagtataa gtttttaaaa    17760
ttataaattg aattttacaa gaaatttaaa tattataaat atataaaaaa tatattaata    17820
cgagacgata tattcagga aaaatcttaa atataacaat caaaattcaa tgatgaattt    17880
tgggtcgata ttgtattttt ttaagtttca aatttataa tattgaaatt tataagaaaa    17940
tgacaaaatt atgtttaatt ttacgggact gggttatatg gtaggacggg tttgggtgga    18000
taataattac gattttagaa tgttccacat cgcttaaaaa aattggacaa tggtcaagag    18060
ccatactata aaaggacca aaatgatttc gattacgaat gagcatgaaa cttgatttat    18120
gaggtgtcca aaattaaaat ggtttgttta ctagggttat ttatttaaa aaattgaaac    18180 gttaaaaagt ttaaaaaatt ataaattaaa tattacaaga aatttaaaca atataaaga    18240 tattaatacg ggacgatata ctgctagaga aatcttagat ataacactca aaattcaatg    18300
atgaaatttg gatcaatatt aatcattttg aaagtttcta attttataaa tatttgaaat    18360
ttataataaa atgacaaatt tgtgtttaat ttcacgggac ggggttatat ggtgtgacgg    18420
atttgagtgg ataataacat gggatagtat gctatggaaa aaacatataa taacaatcat    18480
aatataatta tataatctta aacactaaac aaaattaaca atattaaaaa aaaaacttaa    18540
aactttaatt ttttttaaaa aaattttgat tcttatatta gaaatttaaa cattataaat    18600
atttaaactt tatactacgg gtgaaatttt agaattgact gtttaggttg ataagaattt    18660
acgatagaac taggagttaa atcctagaat gacaattaaa atataattat acaattaaat    18720
actaccacga gtgaaatcct agaattgacg agtttgaatc gatattaata tgggatagtg    18780
tactacgggt gatatttag aattgactgg tttgggttga taataatttg cgatagaatt    18840
aggagtgaaa tcctagaatg acaattaaaa tataattata caactaaata ctatcacggg    18900
tgaaatccta gaattgacgg gcttgatttg atatcaatat gggatggtgt actacgggtg    18960
atattttaga attgactggt ttgggttgat aataatttgc gatagaatta ggagtgaaat    19020
cctagaatga caattaaaat ataattatac aattaaatac taccacgggt gaaatcttag    19080
aattgacggg tttgattcga tattaatatg ggatggtgta ctacgggtga atccgagaa    19140 acaacaatca aaatacaatt ataaaatatt aaacatttaa caaaataaac aaatacaact    19200
taaaacttta aaatttgagt tataaaattt cttctcgcgg tgaattatac atttaaatca    19260
aacaatagca taaatttatt aaatcatcat aaaaaatatt caattatttt ttattttaata    19320 aaaatatagg cccgcgggtt aatatctagt actatgcata tccaaaaaat tttacaaatt    19380
tatgaaacaa caaaaaaaca caaacccaaa cccaacgatc aaaacaacaa caacctttga    19440
```

```
tttttcttttt agcaaatctc atgtgtagca aagattatta tgcaaatcat gtcacaaccc   19500
aaatttcgtg agacataacc atggataaaa tatacaaaat aggatattag aagggaaatt   19560
gcaaatgcca gtaaaatttc tctcacctat tctcgacaaa aaacattatt ctgaattgaa   19620
ataattgatt gatactctat acaaaatggt catgtagaaa gaatcatcct tataaacaaa   19680
ttaaaacata cctaaaactg gagaatatga tatgttaatt aggacagcta ggaaaaacaa   19740
aatattgtaa tcatttctaa aaaagcataa atatacaata tctcttatac agagaatttg   19800
gtaaaatata tcttatacat agaattttgg taaaataaat tttgatataa atctattaca   19860
attagtgaca accaatcatg atatttggtt aaaacaatcc atgcatattt gttaatccac   19920
aaaaaaagtt taaatatcta actctgaaat ctctaaaatc tttacaccta tgcatctacc   19980
aataatgatt ctgaaagttt cagaaaaatg tctggaaata taactgtg ttgggttttc   20040 atttgaaaat tatgatctct tactagtaat aacgtcatgg aaattgcaac acagaaaaag   20100
acttataaag ttttctgata tttttctaat ttaggatttt cttttttaaaa aatacaaaga   20160 aaaaccgact atagaaatgt tggtgtaaat taaacaggag gaagagtttt atccaataat   20220
acagtataca agtaacaaga tgaagaacct cgggaacttg atacgtttga gggttaacag   20280
tgaatcatat tttttatata accaagtcat aaactagaga aaccatataa attgaacaaa   20340 cgaaaaaga caatctcact tccatggtta gtaatctttc atttagaaag atcttaaggg   20400
aaatatataa ttgtatattc tctctctata ccacacaatt ccgatgaaca cacaatctgg   20460
tatattgtac atttgtttat aatgcttggc acgacggctt gtgataaggc tttatcgtct   20520
cataaaagga aaacgtagtc attcgatcat ctcccaaagt ttcaatcttc tctactgtct   20580
tcgtttattt caaatgatta tgagttgatt aattattcaa aacacagaag atctctctat   20640
acatatatat atatatatat atagaaacct ttcaaaccat ttcgcaaatt ggttgtttct   20700
cactttctct agcgtaaatc tcgatgagct taagttaaaa cttaccttca gggtcatttg   20760
ttttgttatg tgacaatctt ctagattaat attccactta ctacttcctg cttaaaatat   20820
ttagttacat cacatgacca tgtaattgaa tttatcctct ttataatata aactacgaaa   20880
atctgaagaa gaaaaaaatt atcgaaaaga gaatcatatt ctggtactag caaaataaat   20940
ttggtagaag atatatatat attttttctat atgtaaactt caaaattaat gcctaagata   21000
tgctaaaaat ttgcgaagga gtcaggggga aagcttgaga ggaccaatgc atggcattgc   21060
ttttactgac agtaaacagt gtcacgctca cgacccattc ttcccgttcc atttggtttt   21120
atttatttca aagtttaata ttccttttgt ataacattca aatcttcaca tgattgattg   21180
tgtgaaaacc ccacagattt tactacaata gggggagttg acttaaaata gctattgatg   21240
tcgaaaaaat gtatttagt tataaattat actaagaaa attttgatt tgtctgttgt   21300 ttaagcatat gtattgttaa acttaaaaaa atatgtattg ttaatcttaa aaatgtagga   21360
gtacacatca aatactcgag cataatcaaa accgtattca tagaccgatg tgagaatcaa   21420
atagaagata atgtgatttt ttaaaatatc gtatctccaa atcaatcact tagaagataa   21480
tgtaattctt tatgtgctac ataaataaat atatatatat atatatatat atatcttgta   21540
tatatgtctt gacaaaaaat tgccagtcaa aaaccatgac tgaatcaaac tataagtcgg   21600
attgaatcaa actataagtc ggatgagtat taatttccat tatgtttcta tactttacaa   21660
accggaaaat agatattata gataccaaaa aagtagattt gtgtatatta ttagaagatt   21720
tggaatttca tcattatcag gatctaaagt acttccctaa ttaaatcatg tcggttgaaa   21780
aagctcaatg aatgtttgaa atttggaaag tttattaaat tcggatcttt ttttttttgtt   21840
```

```
tgtcgtccca aacattttta ttttattaca aataatcaac ttatccttac tactaaatca   21900
tttcatatct ttgataccaa caaatcattt catattctat tttgatgttt aagaaaacac   21960
tatttaccag ttacaaaata ttataaggat tgttgtttag aaaaaaaagt acaagttgaa   22020 ttcttttgt caaatataaa attgactttt taatatataa ttgacttatt gaacatgatt   22080
acagaattaa tcatctacaa aactttccaa gtttataata aatacatttc aaagactatt   22140
agttcttctt aaaatatttc taaaagtgat caaagactac cacatataat tcagaaaaag   22200
tagaagttga tttcttttg tcaaataaat aattgactta aaatagtttg gaaagccatt   22260
gaacttgatt atagaattga taatgtacat aaaaaaaattc caagtttata ataaatacat   22320
ttttcaaatg ctatatcagt tcttcttaaa atatttcact aaaaaaacac tcaaatatag   22380
aataaattta ttgaataaca taccaactgt aaaacagaat ttgacaaaaa aaaaaaaaaa   22440
atgaaatgaa gatgaagaca aaaataaatc accagaggat cttatgcaaa aaaatatatg   22500
aatacacaat aaaccatatt gatatttta aaataaaata aaaacagaaa aatatcccaa   22560
caccgctttt caattaaaaa tcttccgtca ccattgttgt catcttcctc tctcgtgaat   22620
cctttttcct ttcttcttct tcttctcttc agagaaaact ttgcttctct ttctataagg   22680
aaccagacac gaatcccatt cccaccgatt tcttagcttc ttccttcaat ccgctctttc   22740
cctctccatt agattctgtt tcctctttca atttcttctg catgcttctc gattctctct   22800
gacgcctctt ttctcccgac gctgtttcgt caaacgcttt tcgaaatggc gattttggat   22860
tctgctggcg ttactacggt gacggagaac ggtggcggag agttcgtcga tcttgatagg   22920
cttcgtcgac ggaaatcgag atcggattct tctaacggac ttcttctctc tggttccgat   22980
aataattctc cttcggatga tgttggagct cccgccgacg ttagggatcg gattgattcc   23040
gttgttaacg atgacgctca gggaacagcc aatttggccg gagataataa cggtggtggc   23100
gataataacg gtggtggaag aggcggcgga gaaggaagag gaaacgccga tgctacgttt   23160
acgtatcgac cgtcggttcc agctcatcgg agggcgagag agagtccact tagctccgac   23220
gcaatcttca aacaggttta aaatctcaga aatcttcgaa tttggtgttt gcttgttgtt   23280
ttatatggaa ttgagtttgg tgattgtttt gcattgcaga gccatgccgg attattcaac   23340
ctctgtgtag tagttcttat tgctgtaaac agtagactca tcatcgaaaa tcttatgaag   23400
gtttgctgtt acttgtttct ccttttagga attgaattgc ttgaaaattt atcagagacg   23460
aataactttg ttgttgctat cattcatgta gtatggttgg ttgatcagaa cggatttctg   23520
gtttagttca agatcgctgc gagattggcc gcttttcatg tgttggtaaa agaagatgtt   23580 ttttattcc agcaatgtta cattgttata cgtataatga tgagtttagt gatcaagttc   23640
ctctttgatt cttctttctt gttgcagtat atcccttcg atctttcctt tggctgcctt   23700
tacggttgag aaattggtac ttcagaaata catatcagaa cctgtgagta attactattc   23760
tccagccatt actgtaattt ttattgaaga caagtttgta tcatgaagaa cttacaagtt   23820
ctgttttgaa aatgctcaag gttgtcatct ttcttcatat tattatcacc atgacagagg   23880
ttttgtatcc agtttacgtc accctaaggt gatactgttt ttctggtctc agtttgtgat   23940
actgttttta agtttagttg tctgacccgg tgatcttgaa aatggacagg tgtgattctg   24000 ctttttate aggtgtcact ttgatgctcc tcacttgcat tgtgtggcta aagttggttt   24060
cttatgctca tactagctat gacataagat ccctagccaa tgcagctgat aaggtaaaat   24120
acgaaaaaga agcgtatgta ttagtcactt gcactgtgtt actgttttaa ccaaacactg   24180
ttatgaactt taggccaatc ctgaagtctc ctactacgtt agcttgaaga gcttggcata   24240
```

```
tttcatggtc gctcccacat tgtgttatca ggtaactgca aagtgcatca accattctta    24300
tacttgcaag agtttcttgt ctaaacctcg gatctttgct tttccccagc caagttatcc    24360
acgttctgca tgtatacgga agggttgggt ggctcgtcaa tttgcaaaac tggtcatatt    24420
caccggattc atgggattta aatagaaca agtacgtttt cacatcttgc tttattagtt    24480
ttccttggtg aaaatcatca tccctgcgtt gtcaccactt gacttcatgt tctttttgtta   24540
cattttggca gtatataaat cctattgtca ggaactcaaa gcatcctttg aaaggcgatc    24600
ttctatatgc tattgaaaga gtgttgaagc tttcagttcc aaatttatat gtgtggctct    24660
gcatgttcta ctgcttcttc cacctttggt atgctgtgat cccatctctt tcaaaataat    24720
ttgcaaattc gaaaaaccga aaaaggctaa atctcatacg aatttgatat ttttagtttc    24780
ttagagtcgg tgatgtaatt tcagttactg aacgcaaatc tcttgtccaa aggttaaaca    24840
tattggcaga gcttctctgc ttcggggatc gtgaattcta caaagattgg tggaatgcaa    24900
aaagtgtggg agatgtgagc tattttactc aaaagaaaac ttatgatttt taatgttgtc    24960
gttgttttg ggtcatctaa ctaaccaaat tcatgtattc actgtcttcc tttatcagta    25020
ctggagaatg tggaatatgg tatggttctc ttcctaaaca tcaccttctt ttgtacacaa    25080
aatagaagaa gagagctaat taagatcttg ttttccttga cagcctgttc ataaatggat    25140
ggttcgacat atatacttcc cgtgcttgcg cagcaagata ccaaaggtga gtgagatata    25200
taccgatatg caattgtcga gatttgtttc tgtgatataa atttaaccct ccacacactt    25260
gtttttcaga cactcgccat tatcattgct ttcctagtct ctgcagtctt tcatgaggta    25320
tacatacttt ctacattgcc ctgtctctag acgcatgaac acacgctagt gaaagaaatg    25380
ctaatattca aagcattgtt tttacttaac gatcttgtgt tacaaatttc cttttgacag    25440
ctatgcatcg cagttccttg tcgtctcttc aagctatggg cttttcttgg gattatgttt    25500
caggttaaaa aattactaaa ctgctgcagt cgattttac taaactctaa tctcatattc     25560
tgaccaacca atttgtttga gtaggtgcct ttggtcttca tcacaaacta tctacaggaa    25620
aggtttggct caacggtatg ctctcaaaac ccgagaaaat agaacgaata actctttctt    25680
tcatagccta gccatttaaa tcgcaatgct gaaacttaat aataaaggtg atctgttttg    25740
gaatgggatc atattattag gtggggaaca tgatcttctg gttcatcttc tgcattttcg    25800
gacaaccgat gtgtgtgctt ctttattacc acgacctgat gaaccgaaaa ggatcgatgt    25860
catgaaacaa ctgttcaaaa aatgactttc ttcaaacatc tatggcctcg ttggatctcc    25920
gttgatgttg tggtggttct gatgctaaaa cgacaaatag tgttataacc attgaagaag    25980
aaaagaaaat tagagttgtt gtatctgcaa aaattttggt agagacacgc gaacccgttt    26040
ggatttttgtt atggtgtaaa gaaatttcaa tcaaaaaact gttgtaataa ttgttaccaa    26100
aaagaaatgc ttttctggaa acgaggggaa aaatagtagt tttgttaggt tttactgttt    26160
ggaccaaatc tagtaaaaaa cttttttgtaa taaggaaaaa aaagaacaa atgtgataaa    26220
tgcatgggga ttgtatgaaa ccttccaata aagttgattg gtggtcccgt tttggggatg    26280
gccattattt atttatctttt ttttagcgt atttatttat gtcgtatgta tccaaggga    26340
gacaagactc taaattgcaa taagtgttga ggcccgaaca tcatcattga caatatcagt    26400
taatacatta catatggcaa atggtagaga aaatgtcgat gtgcagcaaa cacttttacc    26460
cattcgaatt atgttatgaa gctttcttt acctttcaa acacttagct cattagatgc     26520
tatataaagt gataccttaa atgaatttaa tactgaaatc tagatttcga gaagaaaata    26580
tgcaacataa ctcttaggat atggaatact aataatctaa tatgtattta ataggtggag    26640
```

```
caagcaacga aataatcaac cttttctttg tgttatatta aacctcatcg gcaaattatt   26700
tagctttaat agatatatct tatcttttt ttggtgcgaa tatagagata ccttatctaa   26760
aggtccaagt ctttaacaat ttgcataaat taaattaaaa tatttcattg tacaagaaat   26820
tcaaatgaaa ctcatagtgt ataaacattt agtcgagtta caaagaaaca aagttattta   26880
tggttacttc tttccttaaa aggaaaagaa aatggttacg agaggaacca cgtgaagatc   26940
acgtagagag gttggtcaaa catagaaatt cagttggaag taaatttaat ttttaacgct   27000
ccaccgactc tcggagacag ctgcctctga ctcagcgcct catgttgact tggcagtcta   27060
ttattaatat tgtcgacttt ttttttttgt tggactataa aagcgatatt ttgtgtccta   27120
tttttttttt ttttttgacaa agtgatatac tatttacatt taagattaat tattttttatt   27180 actcaaatta gtagttatat atttcaattt aattcaatct gaaattcatc tcaattttct   27240
atccacgaaa gaaagacatg aaaatcaact gaagtatggt ttctgttttt atatacttt   27300 taagaatttt ttatgctact agaagaaatt tagaatactg tatatatttt tggatgaaaa   27360
tttaaaataa tctttagaat gcgaaattag aaaataacta cacaataaca ttatatctct   27420 aattttttt tttatatagt ttccaaataa acaaaacaac aactgtatca cgttttgtta   27480
atttcattta cctaatcaag acattcttaa atttccaaaa tttaaggaaa gtatatgtag   27540
tcaacaaaaa tgattatcta cttaacatgg tatggttctc ttctttaaga aatcagttaa   27600
tataactaaa ttttgcaaaa taatgagatc gcattattgt aaatacatat tgtctttac   27660 tatttttat ttatatttat aaaaatgtta ccagacaaag gtaacataca atttatttaa   27720
aactcgcacg aaaaaaactcc attctcttac aatactttta caaataaaaa atgtaacaaa   27780
taacttccat acattggcta tataaactct tttagaaaaa cttcaacata ccttatgtat   27840
ttatttgaag tatcaatata taaaattgaa acaaaagatt ctttccttct cgtaaaagaa   27900
agaaacaaaa aaagaaatca ttcgtcgact ttattacaaa accctctcac aacaccatca   27960
cttcttcttc gtcttctgtc tgagtccaaa atggaagact acagatccag atcgtacggt   28020
gacgggagaa catcagacct tcaacaatac tctgctcacc gaagatccga cggtccagat   28080
tcattcagtg gtaacggtat gcaagatctt aggtcttaca gtacttccta cacagattac   28140
ccgacccgga tacccgaaga ccagaacccg aagaaggaa gatcatcttc atcgtcttct   28200
tggggatttg tggatccaga tttacaaagg aagaagagag ttgttagtta cagagcttat   28260
actgttgaag gtaagcttaa aggttctttc agaaaaagct tcaaatggat caaagataaa   28320
tgcaacaaat tacttaatta attctgtcaa atgtgtttta cataagataa taaacttttg   28380
tcacttcgat cggttgagtt tcaatctttt tttgtgtatg tgtgtgtgtg tttgtgtgtg   28440
tgttcttagc ttatgagttg tgatcgatag tgatttgta acaacaatac ttaatagatg   28500
agtaagtgat ttcttattca atttttgacg tatcaaaaca agttacaatg ttttaaacat   28560
tttaattaaa acgtgatta ttcatttctt tatcattgaa aacatccatg agttattatt   28620
atcatgtttt gtagtagttt cgtttcatat tatgcgtgtc taaaaagata acttgtttta   28680
tgcatgtgat tatcttgtaa aaacgattag ttcaggtatg ttaagtaatt acggcatgaa   28740
tgttaaagtt cttacgtttt taatttgcga tactcttcct tcagttttga tgaataattt   28800
ttcttatgaa ttatgaagtg gttttgtttc attgtgtgtc taaagtgtt tacacgaaac   28860 tttgttaatt aagtgaatcc aacgttttta gcgttacatg attataataa cgtcttgatt   28920
tgtagcgatt ggtgtgtttg agaaactatt tttatttgta ttgattagta tatacataag   28980
aagggactaa tttttttgtaa acaatgtatc actttgtaaa gactagatat gatttataaa   29040
```

```
atatgttgtt ttttttaata atgattggtg agtttgatga aaatggactg tggaggaaaa    29100
caaatagcag tcaaacaccg attagaacac cacttacgta cgtcttctaa tcgatatttt    29160
actgctactt gtgttcctca agagtacttc aaactcacat cattatacaa ataaaattaa    29220
tatatcttaa tcatacttct tgaattttta tgaccaaaac aacatacaaa atcacatatt    29280
ttagaattca atattagca tttctcttaa tattattata catgataaca acaaaacact    29340
tttagaattt tggggctttt ccatacacaa ctctgcaaaa tcacgaaaaa atgacatata    29400
tacgcaaaca aaactcccac aattctacat gatggattaa ggatagtcaa gaaataaacc    29460
tacaagtgtt tgtatttgaa atatattaca acttttttt aacataggtg tacgaaggaa    29520
ttcttaacta aattataaag ttgttttgaa ttatgctatg ttcctacgct tatacgataa    29580
atgatatatt tcttgttgat tactgaattt tggtttgctt atgcgataaa atgaagtcag    29640
acgagtctct ctttccttct gttttttttt tttttaattg tatattacgt gactttgttg    29700
tttgtttgtt gattccaatt tattacatgt tatgtttggc tatgccaaaa tcttaaagcc    29760
gaacttttga aaatgaagcc ctgcatatat agtaagagat tacgttgtaa ttataggttt    29820
tgaatacgta aaagtctctc cctaccgaca tagtgttcgt cttcatgttt ctagaaagta    29880
caaattgagt aagtaatttt tgtcaaacaa atttgaccaa ttagacaaat aaaagttcat    29940
ataaattttc aagatatgaa acataaaaca agatattaac ttactcttat cccccactgg    30000
attttatatc attccgcaaa tattatcaga gaggaaggat cttaaaattc gaagagtttc    30060
tctatacaaa tggaggagac aaatgaatat ttgaagaatc atagtttaag cactttcgtt    30120
tggtataata aatctatatt atctctctct tatatatcat cagttctcta gctgtgaaaa    30180
tagcctttct tcagaagaat catagacaac gtcactgagt gagtacaggt tttgttttat    30240
agctgctttg tatgaatcag tcagagagct ttgctttggg gttctacatc gtctccattt    30300
gattgtggcg ttgctgctgt ctcatcgcct gcattgttat tgatccgtaa accatcaatg    30360
cctttgagtg cggtttcata gtttgcattg tcactcccgc cactaaatgg ttcacgactg    30420
ctcgtgtcca caactcgtct tgacgatgat ccctctgatc ggcccaagtt caaagatcca    30480
ggtagctgag aaatcaatgg atcacaatga acatcccgac tcaaaagaag gtacccgaga    30540
agaaaaaaaa acagcatgac aagaaactta ccagcttgtc ctttgcaatt gcagaatcat    30600
ttccattctt gtctttctgc ttcagggtaa aatccggatt tgtcctctga tttgggacat    30660
ctatggcaga caaacacgcc cttagtatat aaatcaatgg acaactatgc ggctgcattt    30720
tcataaagaa ggataataag cattcaaaaa tatacctgga cgcttctcag aattgccaac    30780
cgcagggttt aatccagaac tagttccaac accaccatcc tgaaaaaaga aacatagaaa    30840
gatcttgcat tattcatctg tgtatgtata tgtatcatga acgggataga aactttaaag    30900
tatcaagagt gtacatgggg acgaggttga gggtttccag attgtgattg ctgatacttg    30960
tatactgtcc agtcaaacac aaaatcaaac tgaaaacctg gacaaacaa atactcatt    31020 ttgagtcaac agatgcttct gtatgaactt aatagcctga gaggaagaag agagatagag    31080
aaaatgaatg accttcccgg ataaaaaggt tgcggaatag tctcttcaaa tatgcatagt    31140
ctggcttatc atcaaaccta agtgagcggc agtaatggaa gtaagatgca aactctgttg    31200
gatgacctct gcataacgtc tgcaaagtta cagtactatc tatgatcaac cgtctctacc    31260
tgatcataat cctttgaaac atggattcgt ataagtttct aaatgtaaac catataagaa    31320
gaacttactt cgatggaagt tgaaaccttc ttttcgctga tcttatcata cttctgtttc    31380
ttgtttccag ctttcagccc ttgccaaggg agactacaag agaataagat attagagatg    31440
```

```
gattgggaga caagaatcag aacagaaaga aaagttactt aatgactctc accttccctt    31500
gaggaaatac atgaggatgt aaccaagcga ttctatatca tctctccgac tttgctctac    31560
caagtgaaaa atgtcaaaaa gtaatcagtg aaagaggaga aaaagatccg cgattatcat    31620
gagggtttat agaaagtgat ggagtatacc aatccctagg tgagtgttca agctggcata    31680
cctcggagtc ccaattagac ttttattctc cctgaatcat ttacacgtaa aatccaaaca    31740
ataaagaacc cgttgtcagg aaatctgaag ctgacataca atatgctgaa aatgctgaat    31800
ctgtgacatc caaaatcttg ttacctgtat gggatatgtc tatgagttga gctgtctcta    31860
tatttcttag ccaaaccata gtctatgatg tagacctaga gaaagagacc aaaatcagtc    31920
atacaatagc gagaccccaa aaacaaatcc aactgagaga atttgcaaaa gtaagaaaac    31980
ctgatttgcc cgcctcccta agcccatgag aaaattatcc ggctttatat cacgatgaag    32040
atacgactta gaatgaatga actcgagacg atttatctga cacaagataa acccaacagt    32100
gagagagtta cattaagaat gacaagacac caatccaaag cataattacc atttgatcag    32160
caagcataag aacagtcttc aagctaaact gcctcttgca ataactaaac aaatcttcaa    32220
gacttggacc aagcaaatcc atgactaaga cattgtagtc cccctcaaca ccataccatt    32280
tcatatttgg aatcccagct acattaacga acatacacaa gaaatgaata accaaatgag    32340
aattcaataa caatagagat aaacatttca ttgcatactt ccaccctgaa gaactctata    32400
tatcctcgac tcatatgaca attgcggatg cgcagtcttc acactttcct gcacacacac    32460
aaaaaaaact aagttttgat gatccaagtt gggactttga agagatgaaa cactcacaag    32520
cttaatagca acttcttcgt tagtctgaac atcagttcct gcaatcaaaa cagtctcatc    32580
aaacgactat tgaagagatt ttatatgtat agagagggga ggaacgaacc gaggtaaatc    32640
tctccgaaag agccgctccc aattttgcgg ccaaggcgaa acttgttccc aacacgaggt    32700
tccatcccca attgaaaaaa ccctaacttt gtggttttat ctatctacta cgtcgagcgg    32760
atttctcgat ttctcatgcg gaggagagtg aagtgcgatg atcaaaacta gggcttttgc    32820
gaagaagagg ggaagaatcg agcaggttga aattggaagt gagtaggtga ggaaatttag    32880
ggagattcca tggtgttttg gttaagcaac cagaagcaag caagatgaag aagactgcgc    32940
gtgtgtgtgt gtctcgctta gcctgttgct tttggtcttt tctattcctt ttctcaattt    33000
attaaatatc tttattcggt gaaaaaaata tacagtatat ttcttagaaa ctttataata    33060
agaataagga ttttgttttt atattttcct aaattccata aatctcttaa gtttacaaat    33120
tcatatatct tttaacattt aaacaaataa ccagacttct agtaatatat ataaatttat    33180
ttagggagtg ttattggttt gtgatgtatt cgaagtttca gtgacttaaa atgttatgaa    33240
gaatttgttg ttattcaata aagattttc aattttttgt taaagtttgg tgttattagt     33300
ttaagatttg taaaaagtaa tataaaatct tcataaatgt agagttattg gattcatatt    33360
tttataaagt tattaaattt tttgtgtaat tcatttaaaa caaagaatct atgattatta    33420
taatgaatta aattattgtg ttattggttt atgactttct acccttttttt ttataaaata   33480 aagttgtgaa aaatatcata ccctttttt ttacaaaata aagttgtgaa aaatatcata     33540
aaaataaaga aattgtttga gaaactttac aaaattatta aaaactaatc aacaagttta    33600 ttaatgaacct taaaccaaaa taggtacata taatattaga tagatcatgc aaatgcgttt   33660
ggtggttatg ttacttttgt atcatttgat tggcatgatg ttctacattt ttttaccatt    33720
tctctattct taagtcgaaa tctttaggac caaataagca tttttcccta aactaacaaa    33780
gcagcatctc actagatgtt ttccaatcag atttgcttac tatagtgtgc taatatgaaa    33840
```

```
tttgagtgac tcatgacaat gcatcaatcc agattaagca ttaacatgtg atcagctagc    33900
attcatgaga atatgagaat tgtcttcgag ctaaaagaaa gtagactctt ttttcacttg    33960
agaaactcat gacatacttt tttttttatat acatttgttt tttgatgatt aggttaaact    34020
tttgtaataa ataaattttt agttaaataa ataaacttct atcatcaaaa gactcgtgag    34080
tttcttccta tgttgcaatg aaatggaaac gaaaacgcga atacgaaacg tttcggaaac    34140
gagaaacgat tttttcttaa aattagggat tggaaacgat tttttcttaa aattagggat    34200
tggaaacgta tacacataca tacatatata tatatatata tatataacat taacataaaa    34260
ctatattaaa gaaaaaatgg tttaaacaat acaagtccaa aacatcaata ttaaataaat    34320
aaactaaaat tctaaaagat aaaaattaaa aggttcaagt tcaaatagtt aatttagacc    34380
aacattttca ttttcattag tttcatcaaa gataatataa agctcttttc aaatctggtt    34440
tatcaaaaga aatatcttaa aactcaaagt cttccaaaat tagttatatg tattaataat    34500
tttaataatt ttaattttag ttattaaatt tcaaagttg aaaaaaattt gtcgtatgtc    34560
tatttgggaa acatgagttt ctatctttaa aacgtaagtt tccatcgtgt ttccaaacat    34620
aaatttttaa aaaacgcgtt tccgttacgt ttttcatgtt tccggagagt ttctgttttc    34680
gtaacgtttc ggaaatggga aatagacctc ggggcgagtt tccatgcaac ctagatttct    34740
tctaaccaat agaaatgctc ttaaaagcct tttttttaaaa aaaatcaaca gaaatgctct    34800
taaatgttaa aaacaaatat tcatgccaaa ttttgatgta aaaatttgtt attttcgctt    34860
tagttgtgtc ttatttcggt ctggtcattt tctcaaagcc ttttagtta tttatatata    34920 tattctctgt ctcgtatttg tccccaaaaa tctagggttt taaggtttct tatccttcct    34980
cttcctccgc cagattcttt tcttgcgaag atgagcaacg acaaggacag catgaacatg    35040
tccgatctct ccaccggtaa gatattataa tcttattgtc ctatagaatg aggcctggat    35100
tctcttttgt tctcttgatt tattgaaaaa agcttctctt gttttgtgtt ttgcttatag    35160
ctcttaacga ggaggatcgt gccgggcttg ttaatgctct taaggtgagt tttttcttca    35220
cgatatgatt tgcgtatgac tatctggaga ttgggctatt catctttgta acttttaggg    35280
attgttttct cttcctgact agttttgaga aattgatttg attcttatgg cttagagaat    35340
ttgactttgg ttttgaggat tgtctatgca tcttaatttg gttgtttgaa agtttgtgac    35400
ttttcctgat ttgatttacg tgtttgctgc agaacaagtt gcagaatttg ctgacaac    35460 actctgatgt ccttgaaaac ttgactccac cagtcaggaa gcgtgtcgag tttctaagag    35520
agattcaggt gagtaaattt tcagctttta gatgatcttg gattttgtat tggttttgaa    35580
ttagctggct gttcaggtct aatgagtttt tggtggagca aatttatctg attccttttg    35640
tattttaacc tttgcagaac caatatgatg agatggaagc aaaattcttt gaggagagag    35700
cagctcttga agctaagtat caaaagttat atcagccttt ataccaag gtttgaatac    35760 ggtctttgat tctgcgagat tcttatggtc tttagtttcc tattattaga atatctttga    35820
aacacatgat gacacctcaa ttgataaagg tttaataaga cttctctctg ttgctactta    35880
cgtgaatgat tagtgcttca tggttttcac ttctttctgc atcattcgtg attgtaactg    35940
atattgatgg tcttctgcct tctgcatcac agcgatatga gattgtgaat ggtgtggtcg    36000
aagttgaagg tgcagctgaa gaagtaaaat ccgaacaagg agaagataaa tcagctgaag    36060
gtgtgtttat cgattctttt actgaaacat gtttattttt agtatcttat gatgatgatg    36120
gtgaactcat gatttttata tgatatgaaa ctgtctttct gcagagaaag gagtaccaga    36180
tttctggctt attgcattga agaacaatga aattactgcg gaagaggttc gttattagaa    36240
```

```
tattcttctt tttggtttat aaaatggcga ttctctttat cattatgtgg tttttccac    36300 ggttttagat aactgagcga gatgaagggg ctctcaagta tctcaaagat atcaagtgga    36360
gtagggttga agaaccaaaa gggttcaagc ttgagttttt ctttgatcag aatccttact    36420
tcaagaacac tgtcttgacc aagacatatc acatgattga tgaagatgag cctatccttg    36480
agaaggccct cgggtaatgt tttgctctat caagtattta ctgtttatgt tctgaagaca    36540
ataagtcttt attgactgtc gtttactgct gttcaggacg gagattgagt ggtatcctgg    36600
aaagtgtttg acacagaaga ttctaaaaaa gaagccaaag aaaggatcca aaacacaaa    36660 gccgatcact aagactgagg actgtgagag tttcttcaac tttttcagtc cacctcaagt    36720
tcctgacgat gatgaggatc ttgatgatga catggtattt ccatctccat aagcagttta    36780
gtttttagag tcagtaatta agattgtgtt ggattttaat ctgatcatct aatattcaca    36840
ggctgatgaa ctccaaggac aaatggagca tgattatgat atcgggtgtg tacctttcta    36900
tttcatattc agttctcttc acttagttca gttctaggat ctgagtctgt ccactgttta    36960
tcctgtagtt caacaatcaa agagaaaatc atctcgcatg ctgtgtcatg gttcactggt    37020
gaagctgttg aggcagatga ccttgatatt gaggacgacg atgatgagat tgatgaagat    37080
gatgatgaag aggacgagga agatgatgag gatgacgagg aggaggatga tgaggatgat    37140
gacgaggagg aagaagcaga tcaaggaaag aagagcaaaa agaaggtaaa ttatgtggtt    37200
ttgttctact taaaaccttc ctacatagga aactaaaacc tctgaaactg atttggtggt    37260
ttatcttttg ttttgttgca gtcatcagct gggcacaagg tttaacaatc aatcaatctc    37320
gatctttttt ttttgttgat aatgcaatgg ctaacctgag gtatcctttt ttaatgaaca    37380
gaaggctgga agaagtcaac ttgcggaagg tcaagcaggt gagaggccac cggaatgtaa    37440
gcagcagtga agaagtgaag aatcttggct tagttatgat gaagaagaag agtgaagagt    37500
gtctttgagc cgaggttgtg tttctttaat ttgcagagtc atggtccggt ttattatata    37560
tcagttttgg gtgattggtt tgctatttaa aaaaaaaaaa tgggttcttt ggtttggttt    37620
gtgtctcttg attttttcctt ttgtaatgat cttatgaatt tgtttcgagt taatgtcgtt    37680
ctctggtcag atttcgaatt caattctatt tatcctccct cgttaatgag agaatttgtg    37740
agacaatcta gtttacttaa gattgatcga attttataaa ccaacattac caaaccgtca    37800
aataattaaa accaatcaat cttatttatc ggtttgcata acccatcaat gagccggttt    37860
agacatcggt ttgagtttct ctgggaaaga caaaagtcaa aaacatctct gccgacttgt    37920
aaaagaccga tcaacagaaa cccaaaaaaa atagttgaaa cggagggaaa cgaaaaccta    37980
aaaccctaaa aaactcttcc ttttttttt ccagtgaaat ttctcttctt ctccgttttc    38040
atacaagtct gacttctggg tagttggaat tttccagttt ttggtttgtt tctgtatctg    38100
tggtttaaaa aagtggagaa gaagcttttt agtgcttttc tatggcgagg attctccgaa    38160
acgtttattc actgagaagc tctctgtttt cgtcagaggt atgtttatcg tgtttctcat    38220
ttgggtatta cgagaaatta aaaaaactct gttactgtcg ttttcattgc ttatttgggt    38280
attcattcat gagaaagaat ccgaaatgtt gtctcttaat ttgaattcat tcttttttc    38340 tgggtaatgt ttattgacaa gggtttcatg gggttttgca gttacttaga agaagtgtgg    38400
ttggaacatc gtttcagctc cgaggctttg ctgccaaagg ttgtcttaag cttttacctt    38460
ttgtttctat gaatcgattt tactcaaatt ggttttttgat tttgatgaat atatgtattt    38520
ccacagatta ctagagctaa atccgtttgc gtttctgatt gcttagctca ctgtggttgt    38580
taaagttgag gtttttgcca ttaactctgc aattgttttt gttttgaagc taaaaagaaa    38640
```

```
tccaagtcag atggaaatgg atcatctgaa gaaggtatgt cgaaaaagga gattgctctt    38700
cagcaagcac ttgatcagat taccagttca tttggcaaag ggtccataat gtatctcggt    38760
cgtgctgttt ctcctagaaa tgtcccggtt ttctctaccg gatctttgc ccttgatgta     38820
gctttgggag ttggtggcct tcctaaggta tatatactta tctcttttgg tgatattatt    38880
ctttccccaa tatgtgtgtt ttagagtttt tataggttgg ttctattagc taagttaatt    38940
gaggtttatg tataagtctg tattctcttt gaagaatcta ataatattgg tctccccatt    39000
gtgaattcca tagggcgtg ttgtggagat atatggtcct gaagcatcgg gaaagacaac     39060
acttgctctt catgttattg cagaagcaca aaaacaagga ggttattcct tgtttctttt    39120
aactcctcgg ctatgttctt tacagagcca tacgtcgtat cctaaagaag ttttttgcat    39180
acaggaacct gtgtctttgt agatgctgag catgctcttg attcgtcact tgctaaggca    39240
atcggtgtaa atacagaaaa tctgcttcta tcacagcctg attgtggcga acaggccctt    39300
agtcttgtgg atactttaat ccgaagtggt tcagttgatg ttattgtagt tgacagtgta    39360
agtaaggtga tttatatggg atggataatg ggttgatgct tttgctattg gatctatatt    39420
tcgctctctc atgttttcat gtgattttgt tttacaggtg gctgctcttg tacctaaagg    39480
agaacttgag ggcgagatgg gtgatgcaca tatggctatg caagccagat tgatgagcca    39540
agctttgcgt aaattgagcc attcttatc gttatcgcaa acacttctga tctttataaa     39600
tcaggtaaga gaacgttact agctgagatt tgtattcgaa atgtaaagtc tcttatgcaa    39660
atgtatcttt acttccccat gtttcatatt caggtgagat caaaactatc tacgtttgga    39720
ggatttggag gtccaacaga agttacttgt ggtggaaatg ctttgaagtt ttatgcttct    39780
atgcgtttga atatcaagcg aattggactt atcaagaaag gcgaagaggt aaacttccga    39840
aacccgctta cacattttgg gttcgaaggt cttatcctac gacctgtctt atgttcgtga    39900
tgtgtgttta actgatcact taacctttct attgtctcct tagttcttca gaatgattaa    39960
atgcttgtgt ttgaaacctg agattgtatg cttgtgcaga caacgggaag tcaagtctcc    40020
gtgaagatag tgaagaacaa actcgctccg ccgtttagaa ctgctcagtt tgagcttgaa    40080
ttcggcaaag gaatctgcaa gatcacggag ataatcgacc tgagcataaa gcacaagttc    40140
atcgcgaaaa acggaacatt ctacaatctc aacggtaaaa actaccatgg aaaagaggct    40200
ttaaagagat tccttaaaca gaacgaatct gatcaagaag agctcatgaa gaagctccaa    40260
gacaagctca tcgccgatga agctgcagat aaggaaactg aatctgaatc tgaggaagaa    40320
gattccctga gagttgtggt ttcacctgac aacacagatg atgaatcacc agctcttgtt    40380
gttggagctg ctgcagtggt tgttgaggca gcatgattag cgacctccgg tttagtataa    40440
tattcttcct ttggcctaga gttttccggt ttaacgcggt ttggattcgg tttccttctc    40500
ctcatgtaat ttatgtgcta gttaaatcac atttacatat aaccgttgtt gtgggtgaga    40560
aaattttgta gttttatgg ggaaatttaa tgttaacgaa aagcagaata tttaaatgtt     40620
attgatcaat tttacttcca ccaaaatgct attattatat agtaactata ttatagtttt    40680
agatattaga cctcacaaat gacatatcac attaagttaa tcaaaagatg tcttgccctg    40740
gagataacag tttcttggga tcaaatagat cttttcctctt cgaaaaatca tcccatttg    40800
atccaaaatg ctcaatccaa tcttctttac tagtataatg cattagatat tgcttaatct    40860
taatacctga atccttgcaa aacctaatta tcttctcgtt aacgctctcc acttctggaa    40920
gatcctttgg ggtagcggat tgtagtagtc cgataatata tataacatct tcatcgatct    40980
ctggtatcat cgccgacata cgattgtccc atctaacaat aacagcataa tcagttcata    41040
```

```
gaaatttatt tactttggtt cttgaagata aatatgaatg aagagaagta tgtacttatt   41100
ccggtttgtt ggatagagaa gagcgagtcc cgaagctgat ttttgcttaa gaagaatgtc   41160
tttgacaaca ccgttatgaa aatcgagaat ccgagattta ggaacgtaga ggttaagcca   41220
aggatgagga agttcccata atcccaaaga tctgagttta ttttcttcga catgtacacg   41280
gttcaagaaa tcgaagtagg ccacgtcgtg cattgatatg aacccgggca agtaacttaa   41340
tgttttcgtt aatgtgtcaa taacctacac aatagtagat tatgagaagc ataagatgca   41400
aaaaaaaatg taacgatgat gatgatgaat atcttaatgt ggtgcaatga tgaatcattt   41460
aaatatctta tggtatgata aaaacgatga tgaaaatgta aatgtgtagt accttgctga   41520
tgatggggag attgggatca tcataatact tggctacttc aagaacatag atgataccgt   41580
gttgcttgac tagatcagcg actttagatt gatctgaagg tgggaaaaaa gaggtgtcaa   41640
cgacaccgtt tgatagaaat atttgacctt ctaaatagtc gactccaata tcgtttgcca   41700
ttgatatcaa acgttcttgg tcctttgtaa aagttgtgaa atcactgtag agcatccgaa   41760
accatttggc ctacacaatt tcatttagag aaaacaatcc catttaattt atacacacat   41820
atataaagaa accatattac agtatagtat ttcaatattt tcttgaaaat aattatataa   41880
aatttgtgaa tagatgaaac taaaacagaa cgtcatcgta tattatgacc aaatctgttt   41940
tttaaaatga taaccaaatt gtaacgttta tcggttgtaa gattctaatt agtcagaaga   42000
ctatattcta aactttggag tatatttgag tagttgacta atgaaagagc ttgactctaa   42060
taaacaagga ttatatattg acatcaaaaa gatttgcacg cataagacaa gattagacaa   42120
caagtcctag gattacaagg actatacttt ataaaataat ccatatcttt tttttattca   42180
atgcatagat tttgttcaaa ttaatgcaac ttaagcattt gacctaaatt ccaaacttgt   42240
acctaacttt agttttagga taccatctaa gaaagcttca tgttttgtga tccatacgtc   42300
tctaactctc ttagtgtaat atcataaaat gttttaatca gacattatcc gattagtaaa   42360
ataattattt ccgttaggtt atattttatt ttatctcaat aaaaatcact aaataatcaa   42420
gctctgacat aagaatcatt ttctattgac taaaaaaatt tagaaattga aacggaatta   42480
ctaatgaaaa atgaatgctg actaaaacaa atggtaaaat atgatgatac gtacccgttt   42540
aggtgcatgg tccaaaacaa ttctggctct cgttataatt ccaaattgac ccaaacctcc   42600
taacactcca tagaacaatt ctgggtttag ctgtcgcgag catgtcaaca tttcaccttt   42660
ccctgaaatt atttattcaa aatccatatt aacaataaca atttaaaaag tgtaaattca   42720
aagaaaaatt ctgaaatgtt gctatttttaa aaatatacca cctctttatt cgaaagaaaa   42780
taaatgatat atttgaaata ctacacaaat ctaagaaaac cgaaaagctc catatgcatg   42840
cgtcatgcat gtacattaca aaaatcccaa attaacacgc taccaattgt gaaaatttgt   42900
ctttaattat ttatatatgt acgacaataa atgtgtgtat atgtaattac tttatttctc   42960
atgaacaaca ttcaatatgt acaaaaaaca tatagatgcg ttacgcattt tgtgtttcga   43020
agacttacgt gtggtgcaag aagtttagca caactataaa acataaaacc tatggtacaa   43080
aaaatgaaaa atactataaa acaaaaacag ttttttgttgt tgtatgtaca tcaaagtttta   43140
gaagatgcgt accagtaata acgtccaatt caaggacgtt actaacaaga ggaccgtttc   43200
gaaacacttg accaccaatt ccaccattcg acaacgttcc tccgacggtt atatgcaaat   43260
aatccgtcca agaaaccggc gacacccctt tctccgccgt cttcttaagc acatccaccc   43320
ataacgtccc ggccgccacg tcagcgtact tcttgtctttt tgaaaccacc acgtcagtga   43380
tacacgtcat gttgacgatt actccgccgg agaccgaggc ttggccgttt aaggagtggc   43440
```

```
cttggccacg agccgctact tggaatgtac ttttccgtt tgcggcgtat tggaggagac    43500
gagagatatc agccggtggag gaggggcaga ttacgccgcc gggggtcacg gtggttatgt    43560
ttccgaagtc atgagaggct gcggagatga tggaaggatc ggtagagagg gtgaggttaa    43620
gggatttagg taaatcaatt ttaataccgt ttgatgattt ggtgatcatt aaaaccgtga    43680
ttaaagtgat cattaaacga agattagcca tttgtttatg tttctctctc tctctgattt    43740 gattttgaa gaagagaatt acaacgaaag aattagatat cgctataatt tgttacttat    43800
atagacaccg taggaatgta tgtataacat aaaatatgga atcctaccaa aaaaaaaaag    43860
acaataaata ttgaagtcaa aatgaaatct caaataattc ctaaaaatga aaaaggaaa    43920 tcttactgtt ttgtcaactt gttgaattaa tacttcaagg cacatcctca tatttagata    43980
tataataaat cttgttgact atagttagcc atatctatcc ataaatatct ttttagaatt    44040
tgaatttagt attaaccaac aaaaaaattt acattaattt tcttggaata aaatcgagta    44100
aagctttcac taaggtttgt tgagaaaaat attaaagagt gaaactgaat taaaaaaaac    44160
ttatgtttat gtatgtgcat ttccatgaac cagcatgtca taacataaaa gcctagaggg    44220
gagggtcgag gggagagtcg ggtagttcaa ggagttgatt tggttgcaaa tgattcggtg    44280
aatatgccgt tgaaagtaaa ctgccgattg gagaggcatg cattacgttc ttgccaactt    44340
gactaaagat catatacgta ggtcgtggtt tattttgcg ggaaccaaaa cttttgggat    44400
tttgattcaa agacatcata acagataaga tgatcgagat gtagtaagac aaggaatgtt    44460
ttacatggat gtaggcgtgt tctgactcat gtaagtactt agaacgagga tttacggaaa    44520 caacccttt atgttatgaa ttttacgttc tcgaaaattg tgaatttttt ttagagtagc    44580
ctctctaata ggtttatata tgaaatttag gaggattatt tggaaaattc cttccgctta    44640
atgataaaat tcattcgttt taagttttaa ccttatgttt ctcctctttc acggtcatgc    44700
tctcgactga tcttttcata actatatata tgacatagtt tgagtatcta agtactgtga    44760
agtgaagatt agttttttat aaaatatttt aaaagtctat gccaccattt ctctgacaag    44820
ttatatctat acgatttctc tctctctcaa ttgataaaac aagcaagaaa taaataaaat    44880
tgttttgatt atagtagaac actatagttt gataaacgaa gaacgagaaa aaaatctaca    44940
aaattgtgat tatagtagaa cactatagta gtcgagttat ttatggacac caaaaataac    45000
cactagaact tttaattctg gaacaaagtt gggaatatct tggtagatat ggcaccgata    45060
atcacaatga tatgatgttt cgctaaagtc atgacaggtg gcgaaatggt ctttgtttag    45120
ttatagttga ttacttgatc tttgtttgca tagagataat tgcaatttt ctttgttctt    45180 tactagtata actaccttaa actattgaag agatttgaag aatatcagaa ctgttgtcat    45240
atttgtttgc agtttctgtt ctataacttc tgttaaaata atcactttct gacattgttg    45300
cagatattgg ttgaggaatg ctctgagtgt tcagagaacc gtataggact taatcgcagc    45360
gggtggagct ggatgcgtct ttaagataac gaattagttt ctggttcttg tgatcagttg    45420
tgtttaatgt atattcatgg gtgatagatt taatcactca taatcttatg ttacaatcct    45480
ttgtgctatt ttagttatgt tcattagagt atttatgata agaactcact agctgcgagg    45540
aggagatgga acttgccaga gaaccactca gattcaagag gaggacaaca aagatgaatg    45600
gacatggggt tggtacttat ttggaagaat actcctacta ggttactgtt tgagatgatg    45660
gataagcttc tgaatgagag aatgacgaag aggagtggat gtgtcatgta aaccaaatac    45720
tgagctacta agaactgatt tcaagaattt gtttagattt tgatttggaa tcatagcaaa    45780
accatatgtg atacgttttg gatcagaaaa aaaaaacgat ccaaggcagc caattgttgc    45840
```

```
gggcaggccc gtctgccatc tttagataat tagatgtaac taaaatatta ttattattat   45900
taaataagaa tggattttgt caatttgttt ttgtctaatt acttatctga ttagaaatag   45960
tttgatttca atgattggat gattagtcca tctgtccata tactatgaaa actatgatat   46020
ataccacatt ttcacattct accacttctt tcatcctttt tttttaaatc taccatattt   46080
cccaaaccaa aaaactaatt tacactcaaa tctatctttt tagtttatac tgttactagc   46140
aaaagtccaa cgcgttgcat ggtgtaatta atatacttaa atgtataata aaatgtaact   46200
aaatatatac tgaaacattt tttgttactt ttaaaatata ataattatat ttatatttta   46260
tattgcacta atttgttgtt agtggtagaa gcttttttgta cactacaaaa ctaaacattt   46320
gtaatatttg gttttttaaat agatgatgtt ttcaactttc aataaataat tgattaactt   46380
tttagtattg gttttaacta tttatactat gtaaattatt ttattattgg ttgaattgta   46440
ttcaaacatc taataaatga tgatttagtt tagaaaataa aaaaataata attagattaa   46500
tgtgcaatag aaataaagaa ggatcatcat gtctacttaa gtgaaaaaac attagatcca   46560
aaatatcgtt tggttaaagt gcattttatt aaccgtgtga atgaagacca tatgtggcaa   46620
cactacatga agcttgtttt attgaaatat aggattttta taggcttta ctcgacggtg   46680
gccattcaca gaatcctatt agacaaaaaa gaatagtcac aaatcctaaa tatctttagt   46740
ttgatatttt ggaaacattg acaagtgcac caataaaaac ttgcactaaa attcagtga   46800
aagtcggatt agataccaaa tattggaaag aaaaaatgat gcatgctaga gacacacact   46860
taaaatttt gtaaagtgaa acggattaaa gaaccaaatt aactaaacca tttatcaagt   46920
taactaattt accaccataa ttaaatttta atattaaaac taaaatatac aatgatcatt   46980
ttaaattgaa tttaattatt tatataaata gaaaaccatt ttccaataat atttctataa   47040
tatattttat catttaataa taatatatta gcatcaaatt atattaataa tcgaccacaa   47100
cctaatgacc caaaaacaaa gacgaccata tagaatttaa acttatgaaa atcttaaata   47160
tagttatgta gctaaaacta tacacgagat taatatatat tgtggtgtgc ttgtgacaat   47220
gaagacaaca acgacgcatg ctacaaaaat aagtcaaatt ttctattgga atcatgaacc   47280
cactcaacca ctgttttctt acacaattgg ttttagcga taaaaacac cgtgtaatag   47340
taaaatcttg aaattgagtg tgagaaatac ataacgtcgc taatagatac atgaactgtt   47400
cgactactgt ttttatacac aattagtctt tagcggaaaa tatcgtgtaa tgataaaaat   47460
tttgaaattg agtatgagaa ataatatatc tgaaattata aacttttta ccaatgaaaa   47520
tcataccgag agtttaaatt tatatctaga aaataagcat ggccattaga caccaaaaaa   47580
actcttaatt tactcactta gaagttaaaa cacatttcc ccattgtttt tgatggtatg   47640
cattcaataa aacgttagta attgaataaa taaaaaatta tggtaatttg gatatattgt   47700
agttatatgc aattatgcat ttaataatag gttttaaaat gaatgagtag tcaacgacgt   47760
cgctatcgat ttttttttgt gattagttat tgatttcctt tataatttc tttttttttt   47820
tttattttct ttataattac gatcatatgt ttataaaaat aatattttta atgattttat   47880
gattagacct tcactattgg gtcttcatat acaatcttta caatttcatt tgtcattttt   47940
actcatcttt gagaaacatc agaatcgtat tttacttcat ctgactctgt tgttttacc   48000
gcttatgttg aaccgatgaa attattgttt ttgttttcat gttttttattt attttatttta   48060
catgactaat tttatgattt aaatccatga ttataaacct taaattgttt tattttagtg   48120
gatatttata atttagggaa aattagtagg atttcctatt atttctagta acgtgaagtc   48180
attgtagaaa acaaatagtc aaagaagtta tgggtccaat ataaatcatt ataaatttag   48240
```

```
atttttcta aattttatg ttaaatttt aaattaaata tttataataa aaatgaaatt    48300
ttaaattttt agacaccaat aactaaaatg ttaataaaat tatttttat ccaaaattat    48360 aaaattaata tcataacatc taaaaattaa tagttaattg agatgataag ggtaaaattg    48420 aaatttatt tttgttatga gatcgtgagt atgaaaataa cgacatttaa ttgcttgggt    48480
attaaattgc acagttttat tatttcatgt atttaccttc aaccaaaaa caattaggta    48540 ttaaacgtcc aaacaaagaa tatttaggt ttgttttgg attttttccc ttttattgt    48600 ttatagttga ataattttat tcccgtgtaa agttctcaaa cgatacgttt cttctttatt    48660
atataagata ttatttcttt attttatttt ttgttttctc tctctttctt cttctcttt    48720 tttcctctct aaatatatta ttcctctctt tcttcccttc ccttgaattt taccacaata    48780
ataaattttc aaaagtcaaa tagacgatct aaacttgttc tcgatccact attattcatt    48840
cgattgtaat ttgttcccga tcaaattcta ttactcattc aatatgaact tgtccccggt    48900
ataattatat tactcattcg atttgaactt gtccccgata aaggtattag atctggacat    48960
gccatgcaag atgggtaata taattagatc gggacaagtt ctattacttt ttctatagtc    49020
ttttttaaaa ttaacactct gttaaattta gggacaactg gctttgatga ttgtccttcg    49080
tcatatgagg tgggtttatc cgctagaaat cttaacttac ttttcgggga tttcattcac    49140
tatatttcat aattattgtc tacggtaaat gttaactaca tttaatgcaa cattttgttc    49200
ttattctccg ccataaagct gttttctgg cacaagttac catttttctc taacacaaac    49260
tttcacactt ttaagggaca aaattgtcaa taaaatacta taataccata aatatggtag    49320
ttttagaaag gtcaatacaa ttgtggtaga tttggaaaga atcttttcaa aagttgtaaa    49380
ctagtcaata ttcccaaaat ttagggtaat ataatattag tttttttcaa gtcaaatgta    49440
atctcaattt acttccaaaa caaacaaaa taaattaatg tgttgaattt ttaatgcaca    49500
tcatatattt ggatctctaa ttaattctt tgactgcatt ctgcaaacat tatctataaa    49560
tacttatttg atagtgtaat ttttattcat ccttaaatta ctcaatcaat ttttatttct    49620
aaaagaacaa attattgtta tggaaccact aggagatcgt cgtccttgct gcgtatgtat    49680
caccaaaaat agaaattgtc ctagattctg cgaatatgcg gaatactttc catatgagtt    49740
gtatactttt tttaaaaact tttttttcctt actattatct tctgctaaac attttacttg    49800
atattaatta attttaatt tcaggcgaag tcattatgaa agtactaatg aattgtttgg    49860
cacaccaaag atcattaaga tgatgaggca tgctcctgaa gaaaaaaac aaatgcttgc    49920 aacttccata atcatggaag gtaatgcttg gacaaatgat cctgtaagtg gtggatttgg    49980
tatggtgcaa aagatcatgt ggaagattat gttacacaaa gcctaccttc atgaactcga    50040
ggagaagatt aaggaagaga aggaaaaaat cgagcttcat ctttaagtga tacattgtag    50100
catatattat ttatgcatca aataatgatt atttaatata aaatcatatt taagatgaat    50160
attaaattac cgtcgagcaa gttaatacct tatatttctt attcatattt cttgtgatta    50220
aattgtttgt gtatttagat gatcataaat gaaactttga aatctagaga aacatattgt    50280
acatataata aagtaaaagt ataaaaaatt gataattta aaaatacgag aacttctcgt    50340
ttcttgttct aagtaaaata acattccaat atagaattag ggtttagttg cctttggaaa    50400
attgctttgt aaaaagctag atattatgtt tcgtttagta tatctttgac tcatgatatt    50460
tgacatttga ttaaaaatca tgtttgcctt acatgcataa tatcttaaat gcttgtatca    50520
catgtctcta actaccacga aaacttttgt gtataaaaaa ttcaaatctt taatttttgg    50580
acgacaaatt cattagcgtt actaatttca ttgtacctat cagttttatg acgataataa    50640
```

```
tacaatttat ttcgtcccaa aaaaaataat atttatttat taagttaata ggaaaatagg  50700
tgtaaatata caaatatgta tatgtaatat gcaattagag aatatatgaa acaccactat  50760
actatcaaca ttaatattag taagatgaga aacataaatt agatgatttg agtcaatatt  50820
tttccctagt aatcttagta atagtttttt ttttctttta tttgcatagt tcatatacat  50880
atttgtatac atatatgttg tgcagatcta aaattttttgt ttaataccta ttttgcacct  50940
ctaccaaata aattgtgtta gaattttaaa aaattcataa tcacaacaaa atttctaaca  51000
ctatttaatt tgttgatcat aaaaaatctg aattttatg cacaaaacgt tcttaatag   51060 tcaaaactag tgatataaga agtgcaatgc caagaattat agagatttga agcgaaattt  51120
taaaatgaca tgattataca taacttttaa gttctaaact ataatcataa taaaaaaaat  51180
taagatatta aatagagcga acagacgttt aggttttttt cggatttacc atattcatca  51240
gattaatcca tgctggattg agaaaaagcc tcaagcttgg aacaactaca tgtaaatcat  51300
aacctcgaga tattttaagg ctttcaatgt cccaaagaaa gttatttggt gtcgaatcca  51360
tgagtgaaaa ttgagctttt cacatagaac aaagagggat atgaaatagt acaattttat  51420
gttttaaata aagaagataa aatgaaaggt aaatttatta ggtttagcca gcagagaaca  51480
aatgaaatga atgttttaag tttagacacc aagaacaaac ttagggttca agtctaagct  51540
tagtcatata cttctgaaca atattggact ttattgttca agtattaaac aaacattgaa  51600
atcttcttaa atcacttttc aaaatgcaac gaggatctat tcttttttt tttttcagaa  51660 gaagctacaa gaaagaacaa caagtttgga tatgaattat aaagttagta atccatgtaa  51720
gagacgctta tattaattaa tttatactgt taattatttc atccgtaatt tttattatta  51780
ttcaataaag tatttatttt actgaattaa aaaataataa ttatgggtgt ttggatattc  51840
ggtcgggtat tttgggtttg agtttttcgg gtttagaatt ttaagatccg ttcgagtaat  51900
tcaagattcc gggtcgggtt tggttcggtt tcgggtttag ttatatattg aaatatcaaa  51960
attttgtgtc cgaatctatt aaattatttg aaaatttcaa aaattcccta aacaacccga  52020
gtagttttgc ttgaatatat ttaaaaatac ataaaagtaa ctaaaatatc cgaaaaatca  52080
taatattgtc tatatgtaaa tataaatata aatatttag ttatatttat atttaagata   52140
tgtttgggta ccagttcggg ttcgggtttt tcaggttttg aagtttagat tcagtcggat  52200
atttgaaaat ttcaggttcg aatttagatt gggattttg gattgggatt tttggatcgg   52260
gttcagatcg gttttttcgg attcaggtat tatgtccaaa gtaaaaatgg taaacggtgg  52320
ttgttttgtt tgtatttgta aagcagaaga gagagagata tagagacact gaaagcaaag  52380
accaaaaaag aaaaattaaa aagagagaga ggaaaatgga gagcgacgaa gcagcagcag  52440
tgtctcctca agcaacgaca ccgagcgag gaaccggagc ttctgggccg aagaagagag   52500
gtcggaaacc taaaccaag gaagattctc agacgccgtc gtctcagcaa cagagcgatg   52560
ttaaaatgaa agaaagtggg aagaaaacgc agcagtcgcc gagtgttgac gagaagtact  52620
ctcagtggaa aggtctcgtc cccattctct acgactggct cgctaaccat aacctcgtct  52680
ggccttcact ctcttgcagg tctccccctt tctcctttcc tctccttcta gggtttcgtt  52740
tcgtaatcgt ttcttagctt tgaacattct catgtttgga atgaatttag taaaatctta  52800
cacatacatt ttctcgattt ctgggtttaa gtgagattgt tgcgattgtt ctagttaggg  52860
ttttggatgt ggctctgtct tcataccttg atatatctga tgttctattc atgaattgtt  52920
actattgatt accttgttgg ttactaatga ctaagaggaa ttttcagttt ctctgagtgt  52980
ttatatctga tgaagtcttt agttgttgtg ctaagagttt ccatttggtg aattgttgtt  53040
```

```
tgattttttt atagatgggg tccgcagctt gagcaagcaa cctacaagaa tcgccagcgt    53100
ctgtacctct cagagcaagt aagttttag ctttctcttg tatcttgttg tctcatcttc    53160
tttatatact tctcatcgta ttatttgtat ttttcttggt tgtgtcacca gactgatgga    53220
agtgtgccca atactttggt catagcaaat tgtgaagttg ttaagccaag ggttgctgca    53280
gcagagcaca tttctcaggt attatgtggt ttaatactaa gcttgtgtcc tttccatatc    53340
ctactccaca ctacaattgg tttcatgttt gacacttata tactatcttc tgaaaatgtg    53400
ttctcagttc aatgaagaag cacgttctcc atttgtgaag aagtacaaga ccatcattca    53460
ccctggagag gtgtgaattc tgcccactct tgagatattt ctgtattgac attgttcttt    53520
ttagttctat ttggtttgtt aattgtatct gcatccctgt ttcatctgtc catgaagtta    53580
ttcgtttggc acgttggtga aagtaaattt tgatgtgtat tcattactaa tttgcaattg    53640
caggttaaca gaatcaggga actcccacag aatagtaaga ttgttgctac tcacaccgac    53700
agtcctgatg tgagtgctgc ttctattttg ttatggtcat agcaacttga atatgtcgg    53760 tttcatattt ctgtatttgg cagtcaaaga gcatcctttg ttcggacata tgtccagttt    53820
cagagttatc taaatacaat atgttgattt caggttctca tttgggatgt tgaaacccaa    53880
ccaaaccgtc atgctgtgct tggagctgca aattcccgtc cagatttggt atgtccactt    53940
ctgagaatgt tgtttatgc tttattcttg tttgttctc atcattggaa gtgataaatc    54000
tctttgatat cttcttaaat agtgcttctt gtttgcatca tctgaatgaa ccattttca    54060 tgcagatact aactgggcac caagataatg ctgaatttgc tcttgccatg tgcccaacgg    54120 aacccttgt gctctccgga ggtttgtgtt tctgtaattt gtagagtcca atcctgtggt    54180
ttgccagttt ctcatacaaa agttcttctc ttaggcaagg acaagtcagt tgttttgtgg    54240
agtatccaag atcacatcac aacgattggg acagattcca aatcatctgg atctatcatc    54300
aaacagactg gtgaaggtac tgataagaat gagagtccta ctgttggccc acgaggtgta    54360
tatcatggcc atgaagatac agttgaagat gtggcattca gcccgacgag gtaacttctt    54420
agaacagact ccttctattg atatcgtgtt tgtttatgca tactgcagat attttcatga    54480
ttttctaata atacttctgg tgaacttta taccgtgaag tgcacaagaa ttctgcagtg    54540
ttggtgatga ttcttgcctt atactatggg atgcgagaac tggcacaaac cctgtcacga    54600
aggtactcta tcttttgaat cctatcaaaa gtttgaagat ttacctcctt ttgatattat    54660
atcttacttt tttgttttcc aggttgaaaa agcgcatgat gctgatcttc attgtgttga    54720
ttggaatcct catgacgaca atctgatcct gacagggtat ggagaaatac atacaaatag    54780
atgattaata catacttagt atctaattaa gaaattgatg aatatttcag gtcagcagac    54840
aacactgtcc ggttgtttga tcgtaggaag cttaccgcta atggagttgg ttcgcctatt    54900
tacaaatttg agggacacaa agctgctgtt ctttgtgttc aggtataatc aactttttt    54960 tttttttcc ttctttgtat gaagtatatc tcttaaccca ctgacactat cttgttattc    55020
aattcagtgg tctcctgata agtcatccgt ctttgggagc tctgcagaag atggtctctt    55080
gaacatctgg gattatgaca gggtgtgtac atagttcact cagatgtcta aaattaatct    55140
ttcttcacta tcatcactga aacatattca ttgtactcat gtttggtttg tttaattaac    55200
catcaggtca gtaagaagtc tgatcgtgca gctaaaagcc ccgctgggct cttcttccag    55260
catgctggtc acaggttctt aaagactat cttgattttt cttgattgct ttctcatttt    55320
acttgcttct aagttccctt gtttataaac catattaggg acaaagttgt tgatttccac    55380
tggaatgctt cagacccttg gactattgtc agtgtttctg atgactgtga gactactggt    55440
```

```
ggaggtggaa cattgcaggt aaccttgaaa tctttcttgg taccttgata agcaatttta    55500
ttgacatacc gttaaatgtt gtttatactt tcttctatgg cagatatggc ggatgagtga    55560
cttgatttac agaccagaag aagaagtcgt ggcagaattg gagaagttca agtcgcatgt    55620
tatgacttgt gcctccaagc cttaagagta aagaaaaccc attgtctatc tatctatcgc    55680
ctatggtaaa ctaatgcggg ttttagcgag gagtcttggt ttttgtaagg ctggtttgtc    55740
ttttgagata ttggtggtag cttttaggac ctttccatat cagttagggg tacatggttc    55800
tggttcatga tcctgtttca tcagactctt aggtgctgtt ttgttcaact gagatgttaa    55860
tcaaatcgga ccaactttat gtgttttggt ttaaggtttc aatacttggc ctgaacctaa    55920
tgattccttc tctgtaacta gtcgagacca acccggctac aaaaaaaata gttgcattga    55980
tgttcaaatg caaagcagaa ggggtcatta taaaacaata tagtaataag catcgcaaaa    56040
tttggaaact gggttcttga tgattcgtcg catcttaaat aatgtttgca ttgtcgtttt    56100
cattagaaaa aaactgttaa tcacgcttag cagtaggatt aggtgatttt caattcacag    56160
atttattcgt aggattttga agaaatttta agtattaaca gtcactaaac aatcagacca    56220
ttgcaaatca tacatagatc acctggtcat ttcataaaac taaactatat gataatgttt    56280
tactttattg ggcttaacgt taatggtcct cccgcttaat aggctttatg aagtctcttg    56340
atgagctaga gactttaaaa atccaatcac aaagcctaca tgagaccgtc aagatcagtc    56400
agagaagatc aaacgaagaa gttttttgttc caaaagatac taaagagaga aacatgaatc    56460
aatgtattgc ttgaggaata aggtagggaa gctaatcaat cacaagtaga cgaatcggag    56520
tatttcataa aattagggtt tttagaccta catttttcttt tcttttttccg acgatactta    56580 aattgctcga gaaactctat tagtgagaaa tcccccatcg gaatctcgat ggaatcatct    56640
ccttctggat ccgaacctcc gcagaaagtc gtttctaaac tgcagaaagt aggctggcga    56700
gctacgatga tcttcaatct cggttttgca ggttagagaa atcttcatta ctttcttagt    56760
aaggttttta gttttacgtc cgtaatgtgt tcgatgtaat gcctagctga gaaagttctt    56820
tcctttttct ttattaattt ttgagaatag aaaatacgaa ttcttctagc ggtcgtctga    56880
tatatatgat actacaattt atcccttgaa ctgttgttgt tgtccttgct ttgattctcg    56940
aagaaagctg attgcattac tctgagagtg tttgattctc cactctatta tcagatatta    57000
gaacatgctt attgaaagga catttttttgg atctgtatct ctcagtcact gttgatgttt    57060
tcagcgacat tgaattaagc aaatgtagta tctagaaact atctatatct ctgtgtgcgt    57120
gtgtgtatat atcttggcta agcattttg cgttgaatag aggattcaca caggttcttg    57180
taaattttct ggttcatgga catgattgca catcttatta tcttgtactc aatactttttc    57240 aaatgtttca gcatctcgat ttttagctgg cagaactaca agcttggtct aaatcagaat    57300
tgagaaaagc atgcttgctt gatttcttat gatatagcat tcatgataga caacttcaat    57360
gtttgctgat ttgatcattt ggttctgcag cttatatatt tgcgataaaa cgagaaaagg    57420
acattgatgc ggacgagaag aagaaagtta aaaagggcag cgaggctaga cataaaggtg    57480
tgaaaaaggg tgctgttaac accgaaatcg agaagaaagg tgcagaagaa actgataagg    57540
ctaaggaagc agaaactgca ataccggaga aggaagaaac caaactgatc cctgaactgg    57600
atccactgtt tgaatttaca gatgcaactg atcaatccat gtttcaaact gtggcaactg    57660
aacatgtaaa ggtagcaagg aaaccaattc cagaagatga gcaaaaggag cttttcaagt    57720
ggatattgga agagaaaagg aagatagaac caaaagacag aaaagaaaag aaacaaatcg    57780
atgaagagaa agctattctg aaacagttca ttcgtgctga gaggattcca aaacttctac    57840
```

```
ctgatgattc cgttgattct tcacttcgtg attgggacaa attcttctcc aagtagaacg   57900
aatacagaaa ctagtgtgta cttgtttttt gttagtacac caaatgacca ttgttggctt   57960
tttagtttta ctactctgat tgttactcta atcaacgaat agtttaaatg tgatttcttg   58020
ggggttgaga gtggcacttt tataaaactt tggggtaatg tttctatttc ttataatata   58080
aaggacttaa aatataaatt caataaaaat aagggtgttt ctgagaaaga gggtataaat   58140
agcttaaacc ctagagaaac tgaagaatcc taaattgatc atcgtcgtcc tttgagtaat   58200
ttagaaaatc aaaatgggtc gcaacgtcaa aaccaaggca agaggaaga acaaggtttg   58260
aacttttga atcccagctt tatcttgttt cgattctcca atctgatgtt ctcaaaccaa   58320
aacctaattg tgtgaattgg atttattttt gtttggtttt gaattataat agaagaaagc   58380
agaggcgtct tcttccgaga taccatcgat accaactagg gtttggcaac caggtgttga   58440
tacccttgaa gatggagaag aacttcagtg tgacccttct gcttataatt ctctccatgg   58500
cttccatgtt ggttggccct gtctgaggta atatcatttc tactcctata catgtgttca   58560
tgaagctgaa agcgtgagac ttaagggata attcaaatga gaagcttctt ctttgtttgt   58620
caacagtgta aagaaatgtg tttgcaagtt tacgattcat taagttaaga aaactactgt   58680
ttgtgaatga ttacagtgaa agttttggtg atttgatggc tttcaattat ttttctcagc   58740
tttgacattt taggtgataa gttgggtttg aaccgaactg agtttcctca cacactttat   58800
atggtggctg ggactcaggt aagttttgta ctttttatat cttcatatgt atttgtgctt   58860
ttagaatcct gtgtatacgt tttctttttt tctttaggct gagaaagcag ctcataactc   58920
catagggtta tttaaaatca ccaacgtatc tggtaagaga cgtgatgttg tgcctaagac   58980
atttggcaat ggtgaggatg aggatgagga tgacgaagat gacagtgaca gcgatgatga   59040
tgacggagat gaagcttcta aaactccaaa tattcaggta attcttgatt cgttttaact   59100
cttgtgttat tcattcatat ctcttgtctc ctaaggcggg agagtcctcg tggttgatat   59160
tttctctcaa aattttggta tacaggttcg aagggttgct caccatggat gtgttaaccg   59220
tatacgtgca atgccacaaa actctctata ctgtgtctct tgggcagatt ctggtcatgt   59280
acaggtaaga ttatattttt gtctactttc acagcttggg tgtctttttt tgtatgtgtc   59340
tttgttaatg tggattagct tttgtgtttc ttgacaggtc tgggacatga gctctcatct   59400
taatgcttta gccgaatcag aaacagaggg taaagatgga acttcaccgg ttcttaacca   59460
agcacccttg gttaacttt ctggtcacaa agatgaaggc tatgctatag actggagtcc   59520
tgcaaccgct ggaagacttc tttccggtat agttatctca gaaatttctg cgatactaaa   59580
taattacatg cttttcggca tggtcaatgt aattttttt tctccactgg ctagggact   59640
gcaagagtat gattcacctg tgggagccag cttctggttc atgggctgtt gatcctattc   59700
cgttcgctgg acacactgca agtgttgaag atttacaagt aaaactgcca ctttacagct   59760
aaataatatg tttgcttgta ccatttcctt ttggctgaac aatctgtttc tttattccag   59820
tggagtccag ccgaagaaaa cgtgtttgcc tcatgttctg tggatgggag tgttgcagtc   59880
tgggatattc gacttgggaa gtcccctgca ctatctttca aggcacataa cgcagatgtg   59940
aatgtcatct catggaacag gttcttgtcc cactatgctg tataacttaa ttctgtttgg   60000
ttttgtgctt cccacgaatg ttgtagtctt aattttctt cttcatgaa ggctggctag   60060
ttgcatgttg gcctcaggaa gtgatgacgg gacattctcc atccgtgatc ttagactgat   60120
caaagtaagt taaaaccgt agctatatat tttccttagc aatctcttaa caagattctg   60180
atatggtggc atataaatct tgaactaggg tggagatgct gtggtagcac attttgagta   60240
```

-continued

```
ccataagcat cctattacgt caattgaatg gagcgctcat gaagcttcga cacttgcagt   60300
cacttccggt gataaccagc tcacgtaagc aagaatacaa tacacaccga ttctctccag   60360
aaaaaccaaa actctgtctt aattgttttt ggctatctgt tgtatttaca ggatatggga   60420
tctatcctta gagaaggatg aagaagaaga ggcagagttc aatgcacaga ccaaggaact   60480
agtcaacaca cctcaagact tgcctcctca gcttctcttt gttcaccaag taacattctt   60540
acttcaacta tcattagctt ggtttatttg atctatgtat attttgtctg aaaacctcga   60600 ttatttttt ggggaaaacc agggacaaaa agatctgaag gaacttcact ggcacaacca   60660
gattccgggg atgatcatct caactgctgg tgatggtttc aacatcttaa tgccttacaa   60720
cattcagaac acgcttccgt ctgagctacc agcctgaaag acaaggtctt actctgaaaa   60780
ctcttgaagt attactcata gttttgtgtt gtcctctctc tgttctcttt ccttgtatca   60840
ttgatggcaa gttgcaagaa ttatacactc tttcacaagt ttcaagtttt catcatcagt   60900
ttatttactg atttcagttg tgacaaaatg tcaaattttg atttacattc tcctctccag   60960
taacagaagc cacaagccta ataatagttt aatccttaac aagtaaaaaa aaatcaagta   61020
gattaattgt tgaattctgc tcataacatt ctccaatttg aaaattacaa gtagtggata   61080
aactttgatt aaatgatcga aaacactcat gtagaatgta acaactatca tgacgatgat   61140
gagccatctc ccaaagacaa ctaacaaatt gtgttgttca acaatcgcag tcttggtaaa   61200
ctccaccgct atggaaacca attccttctg atgtttggtg taaccatgat tagctccttc   61260
cacaatctcc agcttatgat tcggtataac ctttgcaaac tccttagcat cttccccagg   61320
taccacggta tcatccgaac catgaactgt caaaactttg cattgtttat caatattgag   61380
acaagcttga tgcatatcag tgtttaacct atccattaaa gactcttgag taacacgaaa   61440
acaagatttg ccctctgtag catcaataaa cccctgttcc ttaatctttt ctatataacc   61500
atctccgaga cgcacatcat tcttaagatc aaaacgtcca gagatattga cgacattgcg   61560
gatataatcg ggaaacttgg aagcatagag aagaacgaca tcaccacctt tactatgacc   61620
aagaatgaca ggaactagac ggttcatgat gttagaggag gacaagtgtt gaataacgta   61680
atgcagatca tcctctgctt cactgttgaa gttaccataa tagaaagttc cttcactatc   61740
tccgttacca gagaaatcga acgaaaaga gctgatttt tctttctcca aagctgtagc   61800 cacgttttg agaatcttgt tggtcttgtc cgatctaaag ccatggcata agaccacaac   61860
ttcttttgat ccagtttcgt gaagcagacc cacgagcttc tcgttgcggc ggttcggaat   61920
cacgatcttc gttggcttca tcgtcttttt gcttcaggtg gtaatcgtag agaagaaaac   61980
aatgaggccc cctattgatg taaaagaat aaggtaatgg aagtatggaa ctggaactct   62040
cgccaaagat caaattgcat ttttctgtgg agatacgaat gagactcgta atcactttt   62100 cttttttttg ctaaactaaa actcgtaatc acttattctt ctcatgtcga tattcagtgg   62160
aaatttggac cttactcgta agtagactcc tcaaccatgg tgaaaactcc acagttttaa   62220
agtcacattt ctattgtaaa aacagttttt gttttttgtt tgaatgaatt ttacacacaa   62280
ttagaaaata aaagtgtttt gttgatacaa caaaaaaaat aacacgtgaa gacttatgag   62340
ctaacaggct tcccgtttag tttagggaaa ggatcttgct tgcttagaac taccactttg   62400
ctcttgtgag ctaaataacc tttcacaagg ttttgtata tcaatatcgt cattatacat   62460
tccacctgca aatacagtat tatttgaca actgtgagtt tatagaagat ttcaatttta   62520
gaagaagtca aaagcaatga atgggatggt attgtagaac aaacctcgtc cagatccatg   62580
tccatatcta gccatcttag tgctttggca atcccttcaa gcttcagctg gtgagctctc   62640
```

```
gctggatcac tcagcttctg gtttatataa ctgaaacatt gataataata agagttataa   62700
actcaagaat cttggatggt atcatagctt gtctttgctt acattttctt catgagtctc   62760
tggtagactt ggagctctag cttttccaag acaagataca cacccgacct caagaacctg   62820
tataaaagaa gagtattaga tcgagatatt aagttgttcg gtgatagaat caaaatactc   62880
atcatataga gacttgcaca actctactct cgacccaact gcaaatccta accctagac    62940 aaatccagaa catcccaact ctttctgccc caatttctt ttaacctgtt agctctctac    63000
ctaagaacca ggtgttactg acctgtcagc agagctatat aatccactac aagcagccta   63060
tactaattcc aatactcatg ctctagagta tccacaagga ctctatcatt tggattagat   63120
gagaaaagca agatatcgaa agaaatacat accgatcttc atgttcttga agagcatgcc   63180
ggagaagcct tagatcaccc tttctcagag cttgcacaat ctttgtgtac tggacacgta   63240
gagaaatagg attaagagag atatgatatc actcagcaga tgcgaaataa gttttgacat   63300
agattcgaag aaaattttat agaacaacag aaaagtcgtt acctcatgca gattataatt   63360
tcgcaggagc tcatcttttg gtataattcc taaagaaagc ttcaccggta ccaaatactt   63420
taatatcatc ctgattcaca taaggccaca ttagctgatt aagcaacgca atgcaagagt   63480
aaggtaatca cagagtaaaa ccagaatcag accttatatt tcgttctctt ttggggttgc   63540
aattttgcaa ggcatatgat agctttgtat cagcctgcaa gatccaaaaa aagagattaa   63600
atgttactat caatatttgg attgacacta cgaaatgaac tgtgatggta agaaaaaatc   63660
tcttagtgac tcacagcagg aaaattttcg ttgaagactt ctaatcggcc ggtataatac   63720
atgtatgtaa cctggtgttt gcgaagaata aacagaagat aataagtaac cgataagga    63780 ggccaaaaac taaaactgtt tgcagagaac tgcgccagac cttatctctt cttggaaact   63840
cctcaaagtc aaatatccga gcagtttcga tacttcttat tacacttcga caaagattga   63900
cggttccaag ctaaaataca aaattgggga tacctgttta gtactccatt taatggttaa   63960
atcataaata tcaaactgtt gccagaaagc atatcacctt aaagtaggtc ttgaacaatt   64020
ggcaagtcac atataatgct ccgactcgtt ttggacctt ccctatagt ttaaaactac      64080 ataaggagcc ggaaaaaata ttgaacacaa atataaacta atattcctga agatatatag   64140
atagatcaaa gggaaaactt acagcaagaa ctccaaaaac tttcatgaga agagacccag   64200
ctgcttttaa tttctctgga gactttccat tagaagttaa atcttatca gcctgcaatt    64260 ccatgtggaa aaatcatgct ttcagaactg actcctcgac acaatgaaac cagacaaggt   64320
taagattttg aaaagggat atacaaatga gatactacct tttccgcaag aactcgaatt    64380
tcataacaaa ctacatacag agcttccaat gcccaagcag attcccaatt acgaaactcc   64440
tgaacaaatg cactgcacat atagaatcca tcagatatca gacattgtga acagacaaaa   64500
aaaaaagctt atcaccctga aatcatatta gacatcaata gaggagcaga gaggaacaag   64560
aagactttac ttggcaaact tatcgaaagc aaggtatgct tcgactagat tcccaactcg   64620
gtaactttgt agagaacgaa acacatgagc cagaatctcg ccatattcag agaatctatc   64680
agactgtcta atcaaactgc tagaatcctg tatcagtcaa agaaaagaaa actcaaagga   64740
ttcagcactt tcacagctct ctacatataa ataaaaaccc taaatctaaa atccatactc   64800
ataaactcaa acatagacat agagtgttca ctacaacaac tcaataggag acactttcac   64860
ggcctaaatt catactcatt ggtgaagcag gaggacccaa ttggaaaatc atactcatta   64920
gtgaagtagg aggatcctag attgacattg attgaaccta aaagatacac actttgctaa   64980
cataaagata atgttcctag tgttttgagc cctaaattca gaaattcata ctcattggtg   65040
```

```
aagtaggagg acccaattag aaaatcatac tcttaaggat cttacattga atcgatttaa    65100
cctaaaagtt acaaactttg ctaacataaa aaccatgctc ctagtgttca caattcatac    65160
gagaacccaa tcggaacata tcagaagcat cctggatttg aaatcgaacc taactttacc    65220
aatttacaag gatcatgcca ctaatcacag gaacatactc caagctgcta atttgaatca    65280
tgggtctcga tttaacagag aatatatgta cctggaagac gttgagtgcg tcggcgagtg    65340
agagaagagg tggagaattg gaagagaaag agaggagacg gcaaagtgta gaagagtctt    65400
ggtacgaaac ggcgtcgcag aatcggttta ggtattcagt gattctccgg tgagcttcac    65460
ccatactaac gtacgccatt gtcaccttct tcgtctgcgt cttccttatt ctttgagaga    65520
gacacgaaat caaataagtc gccaggaaaa aaaggaaat  aacggagttg agaaaaacga    65580
cggcgtttgg taattaacta aattgttact acgtactagt cttttctggt attagactta    65640
ttgacatatg ttagttgggc catttaaggc ccatatgaaa tacaatcatt aaaatgtttg    65700
aaaatttatt tgtaaaggat ttgaaaatat cattagtgtt ggaaggattt taaagttcct    65760
gtaatcggtg gtactgatca tgaattttt  ttagagtttt taagttcata taatcgtttt    65820
atagatcatg attaatttgc tttaaggttt tttaagttca tgtaatcgtc cgtaatgttg    65880
acatctgtat gtaaatatgt cttcttagcc cgatggtgac gtgaggaact ttcttgaagg    65940
gacatgaaat caatttatac catgcatata actcaacaag ttgccaaaaa ctcgaagaaa    66000
tgaatataat caacttgtca aaagtaatta actgatcaaa taaatcactt gtttccaaat    66060
gtgatttata ctttcacact tctatatatt cccattgata ttccccttct ttcatagtta    66120
gcaaaggcct ctactacatg tacatgataa ataaataaat aaaaatcacg ctaatcatat    66180
aattatcaat atattttatt cttgaacaca caattaatag aaattttgag ttgagagaag    66240
tcaatccagg attagtattt atgtgtaatg ctaaaagttg aagataacga gaaacttgag    66300 aggttttaa  ggttcctact ttatttttgg tatgaaggtt cctactaaaa tatgctctta    66360
tatatcattt tatttaaaaa gcattccatt tgaaactaat ctaaaaatct ttagattcat    66420
tgttcaccac tcatagtaag agttgcatgt ggaccatctt atattctcta ctttctcata    66480
cttcgtattt ggaaccttta ttccaacaaa ttcaatgtgt aaagccatca ttacgttcat    66540
ttatttttgc cttttttgcgt acataaaaga aacatcataa cttgacatgt aaaaaaaaaa    66600
atcattgatt cgatttgaga cttttgaaaa ccttgtcaat tttataaaat ttggccgatt    66660
tgatctaatc cacataatcc atcccttata gacgaaatta aattttcaaa ggggatatta    66720
aaaaaaaata tcaaaaaatg gaaaaattta atatcaacaa ttttttttt  aacaatactc    66780 cataaacata ataattgtat taaatttaat tttttaatac aataaacatt tttaacaaat    66840
ttaaaaatat aaacttttct tattctctat gtgttatcca tcacatcaat ttcaacactt    66900 ttttttttt  cgtcaatttc aacactttta agaattaaaa agtctcattt tcttttttatt    66960 ccttttttt  taaaattcct ttattttttcg gataattaaa tgattctcta agcttcatag    67020
caatgaaaca ctttgaattc gcatttcggc gatatagtct ctaataacaa cctcgccgtg    67080
tgctcttgcc tcaccaccgc atcttctttc tccaccagaa ccgctccgac gatcctctcg    67140
tatcctcctc caccaccatt agccacataa tcaaccaacg ccgcctgtac tggtcccata    67200
ctaggattat acgccgccga ttccatatac caacctctgt acactttccc gtcacaatcc    67260
accagcgaaa ctcccgatgg acataaaacta tacggcgcgt acgatctatt cgccgccgct    67320
aaagccgttt gtttcaaatc ggcggatgaa tcggtgtttc cgttacaaat cgaatccaga    67380
tctgagattt tgagatggtt atcgtgagat tcgagaagaa gaggatgatc tttcccgaga    67440
```

```
agatcgtcgg gaccgaatct gtgtggcaag aagcttccga gacgtaagaa tccgtctgaa   67500
tcggcggcgg aatcggaatc ggcggagttg tttggatcgg tgataaggat tttgatttca   67560
ggtgcgtcgc gaatttcttg gaggaattga cggcaatggc cacatggtgc ggcggagacg   67620
gcgaagaaat tgagatgacg ttcaccgttg agtgtgagat tggtgacgag gaactgttcg   67680
gcgtggattg agtggtggag agggagattt gggaattcga cattgacgcc taagaagatc   67740
cgacctgatg atccgagtcc gacgactgcg acgttgaatt tcgaaatcgg agttcgagcg   67800
taggattgtg ctggtttgac tagcgacggg aggagctgaa tgacggaaac gccgagttgt   67860
ttcgcggcgg attctgcttc tttggattgg attacgaagc ttggcttatc cattgcgggt   67920
tgatccggtt tgggtcgcgt aaatgggtcg ggttatttt agatgggaga gatccgggaa   67980
atgaggaatt atgaaatgga tgctggacaa acaaactatt tatagataca acaacgtagg   68040
aaactacatt acgcaaatga agttttggtt cggtttcggt tatgtttcgg tttacgtttg   68100
gtacaaaata gaaaaattat atcagaattg aatttacaaa taatatgatt tcggtttgac   68160
taagccgcat ggaatcattg ttatgaaaac taccaaaaat gcaatagagt attagtgtaa   68220
cgtaatgtta aaatcgtggt ctaattaaga aaacacctag tagtttcatc aaccacgtta   68280
cgaaactaca ataatctccg gataatatta ttttagaggt cagaaatgaa ttaaactata   68340
gctaaaagac agcttagttt catataattt tgatagtatt aaacatttta attccggtgt   68400
tgtcaatttt aagttcccaa aaaatagtt aagaacaaag gtgatagtac tattgttgac   68460 aaagaaaac aaagattagg ttttgttctt atcgttggaa tcaacgtcac agaccaaaag   68520
agaagtcttt gttgataatt acgttttaac caacggttaa gttttctta atagaagaaa   68580 ctgagaaaac tctatgacaa caatcagttt tccaattagg gtcagttgtt tgtttacata   68640
gataagtgcc attttgtcga acataaactg ataaacatag aaacaaaatc cataaaaga   68700 aaaaaacctt ttccacacac aaagaaatca taatatgacg agctatttcc gaaaactcca   68760
atctcaacaa actacaaaca aatttataga cacaaacaca ttttagaccc aaccttgttt   68820
gtatttgcgg aagagatcct cagtctgagc attcctaaac gcgctacaag caataacata   68880
aacccatatg agaacaacga ctgtgatgat aagtatgaga tttgctttac gccattcttt   68940
tctaaggttt cccaataaac cagctttgca tgagttgcaa ttgtaacaaa gctggctttg   69000
gtcattgctc cataagtaac agtctgcgtc tgcagccata ttggttggat ttagccacag   69060
tgttgggttc acaaagttgt agccacatgc ggttggtggt ttgcagcagc cggactgtaa   69120
aacaacaaat gttcaagaaa ttgtcataat tagatttgac caaatatatg cttaaccatg   69180
ttttcaaata tgataatcat agtcttaaag atatttacac ttttttttta ttggtaaaaa   69240
atatttacac attgtaaaca caacgctac catttgcgtc tgcccttgt gtttacaaca   69300 aaaatttcat tttgcttaac atggttaata ttatgggttc atgtggagaa aaaaaagta   69360 tatactaaag gcaaacacaa acaatcaaga gttcaagagt caagacctaa acaatgaaa   69420 cactagtttt agtctgaaag ctataaaaat aaaacgacta caagaaacct aaaaaattgc   69480
ttgcttggta tgaaagtaca taaaaaaaat gaaaaaacat gttgaatctt atcacagaat   69540
aatcttcttt tacttatgag taaattttgg ttctgtctcg aggacgagaa attgtataac   69600
tctttcttag aaataaactt atttttttctt gagtcctaat ttatccaata agaaaaatta   69660
taatgtgagt ggggcaacat gggagggata taattatcta ttatgtttca tgatggagac   69720
aaagacttgt gatcgtaatt attgaatcaa atcattggtc caatatttaa taatgtctaa   69780
tgactaaaag attttaaaatt cagtcgagac ctcagcatct aggcttattt aattattagt   69840
```

```
ggttccaatc ttgttacagt gacaatggac taggatgaca acttgctata gaagttttag    69900
gaataaaatt atttaaatca cccttaatct ctccatgttt aaagcttaaa agacataaaa    69960
gacatgacaa tgaattttaa gagtgatttt aattaataaa attaaataga aaaagtagga    70020
aattttgtca agtttgagtt gtgatcacga aaaacactat ctaaagtgaa tgggatcatt    70080 gaatttatg agtgagatag tgacaaagga aaatataat taatacacag ataaaacata     70140
gtttatcatg taccatattg tgggtgcatg ggtgggtcct tatgatagtg tataattttg    70200
aaatctgact atcttactat ataatcttgt ggacttggtc tccagcaact tctacaccag    70260
tctactagga ataaatatgt gttcaataat ggtgattaca tatgcctaat ctatgagttt    70320
taccacaaaa tggcactaac tgcgaaacgt taagaaagct aatgtaggtt tctctccaac    70380
actagaaaac ataagattaa ttaagtcaga aaatatttt ttagttttt caaagatgag      70440 gaaatccaaa acgaaataac ttaaagctgc aaaacaaaaa aaagaatat agagaataag     70500 aacaattctc ttttggacat cttcacaaaa gctaaagaga aattttttaa cttttgatt     70560 taaaccaca tactttactt tttgaaagaa aaataaccct atctttctat ggcaagaaca     70620
aaccgtaggt ctcacataat ctagagattt tacaaaacat tctctttact tcgtatctta    70680
tctccattaa tcatctaata atatctaatt aaacccacaa tgattcgttg gcatagttgc    70740
ataaccgata tttagtctag atttacctct aaaccaaacc taaaccggaa actagaaatt    70800
tcggggttct ttttataaaa gagaataaaa gaagaaagaa catgcctgga gaggagtgat    70860
cttagaggag gagaagaact gatcggcggt gatgaattct tggttgagtt taggacaaac    70920
attagtatca gccaaacaag cccttagcct tccccagttc ttggaatcca caacgttctc    70980
cttaagccaa ttcgagaacc cttcaagcct atactcttta taacctctac ccggaacccg    71040
atacgatcca tcgggccggg tcacgacgaa tgcaaatata agaaccacca gcaaaagtcc    71100
gatcaatatc gccatacagc acaagtaaac cgccagtaga gtttccttgt acctgaaata    71160
tgagagctca aagtttacat ctttatgatt caatttgtgt ctatgttttc aaagtcttga    71220
agttctttga ttcttacttg taggcgccga tgaagcctgt ggcggagacg acgaggatga    71280
gaacgccgag gacgacaacg ggccaacgga ggagattgac acactcgttg tctggctttg    71340
aagctagcca tatacctgac gccgttattg gtatggaaca gagtaacgct agtaagttga    71400
gtatcgccgt taagttattc gctaacgcca ttaaattttc tctctctctc tctctttgtt    71460
cttgaagatt cgtgcttttt atggaaagaa aatgaaataa tgagagtgag aggagtgtct    71520
ctgtttttgt cttaatgact tatgaggtcg gtggttagag atgatgggat gtgtgaaacc    71580
agttactgct atttacagaa aacgatgttc ggtttggtcc ggtccggtta atcactgatt    71640
ttgctgattt ggattttcg acaacggtgg ttttaagaaa aaagaattag atattggatt     71700
aaagttaaca tgtgaatgtc agaataaaat atgtttagca atgaaaagtt aggttttgaa    71760
caagttttgg gttgtgatgt aataaagaga acttgttaat ctggtcggac cggcttttgg    71820
tttagaattt ggaatcttga acgggacacg tggatacgcg agatgccttt tgtgttaata    71880
ttcttccatt ctgcgagtta ccgaatgcat caaccagtga gaactatcca cgtggcaccg    71940
acgactttgg gtcatttgca ttgaacgtat gttactttcg acagagaatg caaaatggag    72000
taagttccat tgttcggaaa tcggaatttt cttcttttcc aagcattaga ggtttcggag    72060
caggatttgt cgttggctga tgagtgaaat gtcgggtaat ggtcaagaga taagcttttg    72120
ttttggttca gaggattggg attgcacaca agctgctcga tagaatgtgt gaaccaaaac    72180
atatggatga attttctca tctcgatttt attgcgattg gagaagaatt ttgagtcaat    72240
```

```
acacacttag ctttcagttt tagatgctga tatagaaatg ctatttgttt gattctagga    72300
attgggaagg aaatgagtca aatcagagag aatatgaaaa gagatgatgg cggagttgtg    72360
gattacgtta agagttgaat tacatcttat aaatcatgaa attgactgtc aatcttagag    72420
cttagattac aagctctttg tctaatctca agttcgacac agagcttgat gagactgctt    72480
cagtttggct ttggaacttt tcaagtggaa gtgaagaaag aagagtgaag tagtatagct    72540
gaatcagcaa gattctgaca tggctggtta tttaaattat aaggaaacac aagaagaaga    72600
caaagttttt atgatgtgag tacagaagcg tcaaattcca gatgcatcct aggctgaatc    72660
cgcatttccc attttcttca tggtctcaag tctggggcct ttgtctccaa acttggtagt    72720
tgaataaagc tttaggtagt cttgaaaacg gtagccactt ggatacaaga gctttggagc    72780
tggagatatt atggcatcac cagccggatt gtaaaacgta gcaatcgaca gtctacttcc    72840
atgcttcact gtcattacac ggtgaacaac actcttgtac ctcccattac tcagtatctc    72900
tagttgatca ccggtattga caaaaatggt attgttcttg gatggcggta taggaaccca    72960
cttcccatct ttaaagaact caagaccagg cacttgatca tcctgcagga gtaatatgat    73020
tcccccagca tccgtatgtt ctctcagccc tctcataagc tcaggacgtg ggcattctgg    73080
gtatttagcc acttttgttc caaaagctgg acctttggga ccagaaaagg cattcattat    73140
gtcttcctga tcaagaccaa gattctcaca catgagcttg gagagtctct ctgcaaactt    73200
gtgcagttga caaacatatt catccatcgt cttgctgcaa atatcaattt cacctctca     73260 cattgtttag ttaaataagc aaacaggtaa aaatggtaga gcctttggta ctattcaatt    73320
cttaattact ttacctgagt tcctctgaaa tgtttgggat ctgacagata tttgaagttg    73380
gtttatgtga gatgaagaaa ctgcttccc aatctgcatc tgaggttttg ccttcactca     73440
aagccttgac catctctgac tggtaaaact tctcttcaa atgctcctca tagtgagagt     73500
taatcatctt cttcactttc tccatcaact ctttatcaat tccatgatta tcaacctgaa    73560
aattcactaa ctctttaagg atatacagta gacatatctt agaaaacact gccttgtgca    73620
taaagatgtt atacatacca tgaagaatcc ccacttatca catgcatgat caagaagtga    73680
catggtcttg cttctcttct ctccatccaa ctctgcaaaa tcaataactg gaatctccat    73740
ctctctctct ttgatcaaaa ccatctcttt tttatttact ttttctcaca cacagatttg    73800
ttgaatgcaa tctagaaaga gtatttatag gcataagtga aaattaaatc tctgtttctc    73860
ttgtgtgtta ggaggcatag ttgcctactt ggaggcaaaa acaatagttt ctttcaacac    73920
tattctgtta actcattgaa tttgaagcat cattacgttt aatgaataaa aaattgtata    73980
agaatctgct ttggaaatgt aaaatgaaca ataggattga agaaaagtcc aagttcagtc    74040
catacaacca tgtgatcaca agttttgaa ttttcataa tttcttaatg gttttgggtc       74100
actcccattg tgtttccttg taacatcatt tatgtgaagt ttctttcttc ttcacaagga    74160
aagttttttt tttttttttt tttttttctt atccctactc atattcgatg gacctagcca    74220
tcatgtctaa ttgtgtatta tgttttctt ttcactgatt ttttttttct ttaaaacttc     74280
actaaactac ccatctaagc gtcattggcg tacttgtaaa atgtgttatt ctggtgtcac    74340
caaatttgga tatgcgtggt gttgtgttta gcaaggagct ctataacact catcaaatga    74400
taatatgacc ctttttggt atgaagaaat ctacttggcc taaagctaca gtatcgaatt     74460
gttacttgag aatagatttg tgaaaaggta cagtatcgaa ttgtttattt tgagattacc    74520
ggagtactac acaccatttg caatagaaaa agaaataatg tgggtctaag cggaattaag    74580
cgaaagaatt ggcccctcct atgggcgctc tcggttttga atatatattt ttgtgtgtca    74640
```

```
tattttataa caccttgtaa agaatttggg attgtgttta agaatgttta tcattttact    74700
ttttggggtc gaatatttcg gatatcgtta gttagtgtag ctctagtcta tataaatcag    74760
caccgacaaa tatattttt atgtggtgta aaattcaacc atgacggccc cttagagcgt    74820
aaacgggcca agacctaatc tacaaagact tttcagttat atataacttt gtttcgttta    74880
gtttgactgt ttgaggaaga aatggtaatg ttattgaatc ttttgttttg gtcatttggt    74940
gttgtaatat gttacataat tcgaaatgat ggtttatcgt taacacggac tttaaatatc    75000
attaacatgc gtgtatttga gattacaacg aattgattca acatttcaac ttttaacatg    75060
ttggagttaa ttattcaaaa agttaatacc ttgtcaagat atctaaacgt tttcaaattt    75120
catgctattg atattagtta gggtcataag acctctttag agtcttcata tattgtttta    75180
gtaaccccat taaaccttct gcttcaccaa gagcctttct ttccaattta ggtacatttt    75240
cttttaagta tgagaatttg gtaaacttaa actccaaact aaacaagcca aagagacca    75300 aacattacaa tgaaccctaa acaaaaatta taaaaatgtt aaagtgtaat acgcaatttg    75360
caaattcagc aactatcacc tttactttgt tcactttgtt gtataaatga ttttgttct    75420 cactccctga accacgcgct aacggtggcg cgtgttctta acacactttt tagtttccag    75480
aatcgatgga gactttaatt aacatttgc ccttaagcaa acaataaaca ataataaaaa     75540
aataaaatta atttccctct ctctctcaat ctttgtgctt tctcgttctc caaccaccgg    75600
aaagagagag agagagagat ctttgtgtgc ttcttctact tcttcttctt ctctctatcg    75660
ctccgccgcg ccacattcac tgagatgcgc cggtgtaaaa acaacactga caaattctct    75720
gtgataacga tgaggcttct aacgcttctt ctgatctgta ctttcttctt cttcttctcc    75780
tttgcttatt ccgccgagtc agataacgag actgactcag ttgttacacg tgagatcaat    75840
ggaaccgtcg ttgagtccaa tgccacgagt gcgaaaccta gggaagatag tttcgctgat    75900
atgatcgatc gagcacttga gaaagagttt cctgataatg accagaacga aggttcctcc    75960
tctctcacta gatagatctt catttcttct atttgttacc tgagctaggg tttctctagg    76020
gatttcaatt ttgttattat tgatccttct tctctaggga tttatcattg attagctgag    76080
tggtttagac tctctctttg tgcccacatt atagcaatta atgcttttgt gttgtttcga    76140
ttttgcagtt cctgatccag gaagcttcaa taatagtgtt gctgatcagc aggttggttg    76200
ttgcaagttt agatctttt ttaactactc tatgttttct ttcttttaa ttaaaggcat      76260 gtgttgtgct cattaggcgg ttctagagac tgttgcacga gttaagccaa agaaaaatga    76320
aaccaagacc aaggaggaga agtgagtttt tctgatgctt attttgccct gtttggctgt    76380 tttttttactt ttgtttcact ggttaaagca aactataaca tatgagtgat tttgttctag   76440
atccttcttt aatttggata acgagaatgg cgtagaggat actccaagac tgatagatag    76500
gaaggtaagc ttcgatcgtc ctaaattatt tgtactatat attgctgaag aatgtataat    76560
ctgttatgta cccatatgta aaggcattct cgtgatgtga atttgctgcg attttgatcc    76620
aggacaacgt ttttataatg tccaatccaa aatccaagta ccctgtactg cagctagatt    76680
taaggtgagt atagcattcg taagagaagt tcttcgttcg attatatttt ggaagtatct    76740
aacttacttt tttttgttgg gggcatctct cttaaatcgg tacatttgta ggctgatatc    76800
agatttggtc gtcgtcattg tttctgctac ttgtggtgga attgcctttg cttgtgcggg    76860
tcaaccggtt agcacacact tcctttgcaa agcttgtgac ttcaatatta ttttattagc    76920
attgagtatc cagctttccg gcattgtaga aatgattttg ctagctctta ctaatcaaac    76980
catgacagcg ttatttaatt tctacactac ttatggcagg tcattactgg gtatctattg    77040
```

```
gctggatcta tcattggacc gggcgggtta agctttgtta gtgaaatggt gcaggtagct    77100
tacatcagct ttagtacttc aaagttcatc tttttttttt tcttcatata cgtttgtatg    77160
ttttcatgac taccagattg cctgggacaa gggcttgatt tataattttt ttgtgtagca    77220
caggtcgaaa cagtagctca gtttggtgtt atctttctcc ttttttgcttt aggattagaa    77280 ttttctgcag cgaaggtttg catgttttca ctctcttata tttgtctggt ttctttgtca    77340
atgcgattga aacttttgag tcagttattg tactgcgtgg ttgcagcttc gtgtggttcg    77400
tgcagtagct attccaggag gtcttcttca gatattttg ttcatgtgct tgagtggaat    77460
aacagcctcg gtatgttcta aaagtgtagc aatcgagtta agaatgagtt attaggcatt    77520
tgtggtatga catgtatgta gagtgcatta ggttgactta gctgtttctt cattgcagtt    77580
atgtggcggt aaactaacag aaggaatatt cgtaggcgca tttctatcga tgtcatcaac    77640
agcagtggta tattctaatt tcctatgtgt acttcaatta atattttgat cttgttctac    77700
actgtttgaa tatttcccta ctctcactta tttttctcttt tctttactgt gccagttata    77760
ttttcctaaa gtattcttta gacttgattg tcatatgtta tccttacctc cccatgattc    77820
ttgtaccagg ttttgaaatt tttaatgaaa agaaatagca taagtgctct acatggccag    77880
ataactgtag gaactcttat tcttcaggta tctctacctg ataactctca aaactatagc    77940
ttctctatta tcattttcac acgtttttttt gttttccta ttattctaaa actgcatatc    78000
cttttgatcc gaaatatgat tcaaatccaa ttccaatagg tagtatgttg catgcagcaa    78060
gtacttttgt tagaaacttta atttactgtt tcatgaatca ccaggattgt gctgtgggct    78120
tgctgtttgc tctcctgcca gttcttggtg gcacatctgg tgtccttcaa ggagtgttgt    78180
ccatggcgaa atcgtatgta ttttttctctt ccacgaattt ctatgaaact atcgacaata    78240
ccctgcttcc attgttcact tgttacaata aaacctagtt tttggttaca ctttctttt    78300 gactgggttt taatatcttt ccaggttggc tattttgatt gcgttttttgg gagctttgtt    78360 tgtattatcc cgtacctggg taccttggtt tctaaaactt atgacaagcc tttcttctca    78420
ggtatagaca catttcttac ctgctccagt tttggtcttt aaattgttta tcaactcaag    78480 cgttttcaa tctttgacag actaatgagc tctatcagtt ggccgctgta gcattttgtt    78540
tacttgtcgc ttgggttagt ctgatccctt tgttcttctt agctattggc tgtttgcaca    78600
tttgtgactc tcgaatttc atttcttaaa tccagtatcg ttttggcttc ttcagtgtag    78660
tgacaagctc ggtctaagtc tggagttggg ttcctttgcg gcaggagtga tgatctcaac    78720
aactgatctc gctcagcata ctcttgaaca ggcaagaagt caagtttgac tgtttcgaac    78780
tagagggtct ctacccatat attttggcca ctctcttatt ttgaaagtgt ctttcttgct    78840
tatatactat cttggtttcc tgatgaaata cgtttccttt ctttggcaca ttctaccaaa    78900 gttttttcata taaacctgtt ctgatcgctt ctgtttcctt gcaggtggaa cccatccgca    78960 attttttgc agcactgttc cttgctagta tcggcatgtt gatacatatg cacttcttgt    79020
ggaaccatgt tgacattctg ctagcagctg tgttactggt gatagtgata aagacggtgg    79080
tagttgctat cgttgttaaa gtcttttggat acaataacaa aactgcagta cttgtaagaa    79140
gcgaaccctt ttttttttcc ttctttctca tcattcgaaa gaagccttaa ggttttcttg    79200
tctgtaggtt ggtatgtccc ttgcacagat tggggaattt gcttttgttc tgctaagtcg    79260
agcatctaat cttcacctaa ttgaggtaag ctctctatga ttattgatgc ttagttatat    79320
tatatgttag catatatctt tgaaaccgtg tgtgaccata atagatttct cataatttgc    79380
ttttggtgga gcgataagta acaatgaagg ggttttgtgt ttatttgcag agcaaattgt    79440
```

```
acctcctgct tctgggaaca actgctttaa gcctggtatg gtctatttcc tcatcatatt    79500
tataataagt tcatattcaa aaacgaataa acgaatattg acacggacgt tgctttatca    79560
atgaataaca gtagaattta catactccag tatcaatatt gtataattac taaacaaatt    79620
aaatgatgta acaggtaaca acaccattgc tattcaagtt gataccagca gttgtacatt    79680
taggagtgct cttacggtgg ttctctcccg acagctcaac cgaggtaaat acaaatcatc    79740
gtcgtgtgtg tctctctcaa tgactttggc tcaaactcaa ctatgaacta taatcttcat    79800
ctgtacagat tggtttcaaa ggagagttgt atcactcaga gagtgcaaag cgtatatcac    79860
tgatgatcca aggttctctt cacgactctt gaagtgttga tggtatgttc acagcataac    79920
acgcaacatg aagccacatt tggtctcaag gtaggcaaag gcaatgaatg ggagcttccg    79980
aatgtataga tgctttgaga tatcagaaga gaacccccag aggaacctgt ataaaatctc    80040
tctacacgaa gataattaca gagacttgta acttcacttc aattttttgt tttgggattc    80100
ttttttgagt aaaaaggtag gaagaggtta tattttagtt tgtttacttt cttctcatgt    80160
gctctgaaac aaaataagaa acatctccaa cgtattgtag tgattaccaa ccgataaaaa    80220
gctaaagaat ttttgagtta gtcgattaca aagtataaac acaaatttga attgatacac    80280
caaagatttc tttaacattt cgtgggaggc cgagtattat ttggctttag cttcgaacca    80340
agactctctg gagatagaag ctctggctaa atacatgacg gactgagagg actacggggg    80400
ctatcttaat ttccttttat atgaattttt ctatgttaat ttaactttt agatattgat     80460 ttccattgta attaaaacgc tgtttgtcct aattttattt tatatatata ttgtataggt    80520
tccattaacc ctacgatcaa aacagtttca tacaaactcg cctcatcttg ttctctaaga    80580
tcaacgtgtc tgatcaagct tgatctgctt ctctttttt tttgtttttg taattattct     80640
tgcttgattc gatcaacgtg tctgagcttt gattcaagtg ggggtttgga ggtatgtgag    80700
cgtcaaatct tcaagtttta attctggaat taggtttctc ttagtgggtt ttttttttgt    80760
atcatccgag tgttgttgtt tgaatataaa tataaatcca accactagaa catgtttttac   80820 ttactttggt tttgttttac ctccagatat ataccgccat cgccatggat aatcacttgg    80880
aattagcgat aaaggatgca atcaccgcgg atgatcttaa acgtgtggat caagaaactc    80940
aacacccttt gttagctcag gagcttgatc ttgattcctt ggagaatcct cctcgggcca    81000
caactcatac atatcggtta tactccaagg gtttggtgag tgaagagctt attaaggatg    81060
atacgatgct ggtcgttggt ctaggtttgt ccctctgtga ctcgcacgat tacacgaaac    81120
aggagattaa taaagctctg agaaaccaaa agctggcggc acacccagaa gctgcggaac    81180
tggctgccat cattcacggc ttgaaatggg ccttggaact tggtatcgaa cgtatccaat    81240
tcttctgtga cgactccaat atcttggcct acgtatgttt ctctctcttt cttcttttac    81300
cctgaatcca gtatcctgtt tgtacacctc tcatgttgtt tttacaggtt actcgtaaag    81360
ctgcacctaa cgagtccatt gtagcaaaac ttttggagca tgtgtctctt cttcagacaa    81420
gattcacgtc atgtcaggca cttgcaactg taagcagaga cgacatcgtt tctgtcatta    81480
agctagcaaa agatgctata gcttcccaaa ctagatggtg tgaaggcgac accgagtatg    81540
agagttgtcc agtctgctac gcttacgttt cacctaatga taagtttgag gtgcaaggct    81600
gcttccaccg catctgcgtt acgtgcatga ggaagccctt ctcatccgaa caaatactac    81660
gagggaacac agcaatctgc ccttacccgg attgcgagaa tgatcttgtg ccagaggatt    81720
gtagagcttt tgctgatgct gatgctatta ctccttatgat ccagcgcaag aaggagaagg    81780
ctatccccgt taaagacaga gtctattgtc ccaacccatc ttgttctttt ctgatgtcgg    81840
```

```
acctcgacct cattaggcac ataagcaaaa atcctcggca ctcagaagaa gcacggaagt   81900
gcatggagtg cggcttgtct ttctgcaaaa aatgccatgt tccgtggcac tacaagaaga   81960
catgcgatga gttcaagaag tcggagtctt acctgaaatc tgacgcggcg attttggagt   82020
cttttgtgaa gacacaagga tggaaaaagt gttcccagtg tcagagcatc gttcaacatg   82080
gtggcggctg ccaacaaatg acttgcaggt attggacatt tgttatttat tgagcctact   82140
tttatattat ttgactttaa ctatctgtct ttttgttcct ggcagacatt gcaaacacga   82200
gttctgttac acatgtggcg ctccgtgtaa aaagaagaaa ctgacatgta aatgctcgcg   82260
ttcagggaaa taaacatcca aggtttcact atacagatca ttccaaatag tttcttatat   82320
aacttgtttt gatggtgttg aagatattag tctcttctca tgttttctga acaacatta    82380 gagacatacc aaccgagaaa cgctaaaact atctcttata aataaagagt ttttgagtta   82440
atcgattaca aagtacaaac acgaatttaa taaaagaata tttgaattga taaaccaaat   82500
atgagaggaa gaatacaatg aatcaacgtg tgtggtggct ttaacatttc gtgggaaccc   82560 gagttttat tggctttaac ttcaaaccaa gactctctgg tgatagaagc tctggcgaaa    82620
tacatgacgg acttagtgga ctccgggggc tatcgctaac ccgaccaggc cgatacaatc   82680
caaaccccat gaaaagaac tccattggta tcaacattgc atgtggttgc tcttctgtca    82740
ccattgatcc acaagcttgc acctgcaatt ctaaaaacat caaagcatgt tccacgaatc   82800
taaaagcctg aatctttagt ctcggagaga agttaagagc taccagagct gttttacat    82860 taaccgcat acctcaacca aggcgctgta cttttctgtcc aatgctgtca ccatgtgaag    82920
agtttcagag tggaaggag attggtcgcc aacaaagatg agtgtacggc atttcaaact    82980
cttcaatcca tcagttaagt catgtctcct gttaactgct tctagaaacc gcataagact   83040
actaccgtgt ctttcaccta gcagctgtat aaacatgtcg tatcaacaac gtaatcaagg   83100
tggtgaaaag cagtaaaatc atctggaaat aactactagg tttaggcgtt tagcactcac   83160
tcttctgcat tcatgtacca catcccgctc tggaacttca gagctaccac gagcttcctg   83220
tcgtaattta agaacaagat taatcggtaa ctattaagta tatacggatc tcattcagaa   83280
atcacaagaa agattacctt actgaagtac ctctgaagga aaatatcttt taacagtcca   83340
gacatgccat agtagtacaa taagtttgac acaacctgca ggaagtttta acatcggttt   83400
atgcgaaaga acctttgtta cagtcatatg aactactatg ggaaggtgaa aaaagaaac    83460 cttgtaataa aaccattcag accatgaggg tgctttgcat agaggcgata taagaatcaa   83520
acccaaaact cgttctttat gtttaatctg caacctcaaa acaatcactg ataagtaatg   83580
agttacatta ttgtataatg ttctgagaat gcagctacaa ataaatcctc aagaggcctc   83640
aatgagtaca tacagcaaac aaggaaagga tgtaggcacc agctgtgatt cccatgcaca   83700
ttactgcctc gaggctgcaa gagacataga tagttagagg ataatagcgg aaattactct   83760
tgttatgata gcccaaattt agagtgagag ttagtcgaaa catgattcaa gatttaccta   83820
aagaagttca atacttcaag aatctggtcc gcgaggtctt caacagaagg tgacggatca   83880
ttggaacaaa ctggagcagc tccaaactgc aaaaactctt gtggaaacga tggaacccaa   83940
cacaacgtga gcaaacagca agggagatac aaagaaaata atgaattgtt tcaagacaat   84000
caattctgca aacctcatgt cctggaggac taatatggta gatgcagaaa ttatggagca   84060
gtaaggacac tgcttcaggg catagaaaca atccttggaa acaagacata tctagcagcc   84120
ataaaaacat acaagaatct aaaatcagat taccaaatga tgttaaaatg aaaacaaatc   84180
atgtaccaaa tgtatattcg ccactcttac agtttagtgc tacatctgga taagtgatca   84240
```

```
atgctggttt ctcttgatct ccatatacta caactgaaac tgaaccatgg caagttttga    84300
catgatgctc ctgcaagaga taagaaaata agcaagaaac gaatcagtct acatccaaat    84360
taagagaaaa atataaacaa taccacatgc ttcattctca tatcctcacc attagtgttc    84420
atccaaaatc aactcaacat ttttaatttg tgttctttaa atcggataca gctaagaaaa    84480
ggaacattcc aactttgttc cagacaacaa aaaatattaa ggacctcaag agattctccc    84540
atgtgcaatg actcagaaaa atcagtacga agagataact tatggctaaa aaagtcaga    84600 cattatatat caatcatgga gccaataaaa gataccattt tcaagggaat ctcttggacc    84660
ttttaggcaa gaagaacaaa gaatcaaact aaaagaaaca cccaacttgt aaatttcaga    84720
tgacaaagtg aaacaacttt tcggtatcaa tgaagtagta ttaatctccc aactagtaag    84780
taaattaagc atacaaacta aaatcaagaa cacaatagac aaaattgatt tcaatcacga    84840
aactgaagct agattttaga aatcagggag ctaattagat gctatttcgg gaaagtaata    84900
acccagaagg aagaaaacga aatgtgactg ttcttagtgc ctaagagtga agacaaaagg    84960
agaaaaggaa gaaaatttgg tagctcaaag cgtaaacaaa ccttgccacc attgcagatc    85020
tcttcaatgt cgagtgagac ggcgttgttt aaacccacca tgacccgaga aaccccccaaa   85080 gactgcgcct ttcttgctct ttctatcttg aaactgaaat tgaaagagat agcaacaata    85140
ataaagtctt aagctttatt gtgggtactg ccttagattg tacgcttcaa cggctctttt    85200
gggtttcact ttgtcttctt cttcgatgga atggaccact actacttatc tctctctctc    85260
tctctgtctc gatgtctgag tcttataagc aaagccgcgt tgcgtttaat tgtccagcgg    85320
ttaatcaaat cattcccacc gacgccgatg agtcttcttc aatttgattt gcaccgatct    85380
ttaaacggcg ccgtttctgt aatcatttc tcattttatt catactataa ttcatttat     85440 tttatctcta ctaatttggt agctgaagtt ttgattggtc acttgcggat cttcgtagtt    85500
tttataagtt acagtataac ttctataaat taatacttaa taaattaata attttttataa    85560 attaatattt gggaccaaac caatataaaa attaacacaa atcgataaat aataagataa    85620
taattttttt gaaagttcta tgtaaatata tggttccatc aatatcatta attaataatt    85680
acataaatgt atcaattata tatatatttt atatgtaaga aatttctttg aaatatattt    85740
ctaatatttt ttttccataaa tttgtattta ttttattta aatttagtt ttaatattat    85800 actgtatcaa aaacatttga tgttgttttc taaatatgat atgattttta cttattattg    85860
attttagaac aatatttct ataatgaaaa aaaatttata gaatttttt aaaagttatt    85920 aaattaggaa aatctctcta taaaataatg aatattaatt tatcgataaa ttaaaacctc    85980
tctaaattaa taaattttgc agtcccaata ttattaattt atagagattt tacggtatat    86040
tatatcgttt tgtcaatttt atggctaaga agaaacaaat tgtattgttt ccaagtaaat    86100
tttatgttag attaataact tttaccattt ttatgctttt tgacgatttt tatattatat    86160
cattaatagt taatcaagaa aattttgata tcatactaaa aaaaaataga acatactgtt    86220 tttattagg atcaatcaat cacattcttt ctttcataca attctcttga acttgaaatc    86280
tttaacgatt taatagtttc tcaatatatt ttttcaaaca aaacaaaaat ctcataaaaa    86340
aactcagtcc aacgaggatg atgaatcatg atccaaactg agttttctta tgagattcat    86400
catcttctag aacccacatt ttaatactca taagaaactc agtccgacga ggtgatatta    86460
ttttgggact cagttttctt tttttgagtt tctgaaaaca aaaatgtcat aagaaagtca    86520
atccagcatt ataaatattg ttctaagatc agagaggaat agatgagaac caagatccaa    86580
actagttcta ttacaaagag ctaggtgtca acttaaaaag tcctaattaa aagaattgca    86640
```

```
ttagcttcac atcctctaca tgatccagaa aggtgtaaac attactctct ttaaatgctt     86700
ccattccttg catttcaacc tttttgattg tgtttctttc gatattgtag tagaaaacgt     86760
agaaacgcat accttttatc gaccagaaga caaattcctt tgtctgagtc attccaacac     86820
aacgtaaatc tgtggttttc attatatcat gcattgcagg caatatgtat gtatgctcag     86880
accattcttg ccttttggca tcttcaagaa cccacaattt aatacttctt attactccat     86940
taaaacggga ataaactgtt gacggcagat acaaacttag tttcccattg tagtttatga     87000
gagatccatg atgcagtgct ccgataataa atctaaactc ctcagacctg acgtcaaagc     87060
aaactatcac aatatcattg ttgttgaccc cagcataata atatataaga ccatcaatgc     87120
atatccctcc atcgaaagaa cgatgtggta tgcaacattg gatcgttctc catgacatgt     87180
ttccacttcc taaggtcaaa atatgatgca tatgataatt gacgactaca ggagacgact     87240
tcttatgatc atcatcagga ttttgaagct gaggtgacga taaaaataaa taatcgctac     87300
cttttctgta ggcgaacaat agcttcgggc gagccaaaga tctagtcaag aacaactcgg     87360
tgaaatatgg acggctaagt gtggaggccc attgcttcga tacgcaacga catctcgcta     87420
tagaattcac cgacaacctc aagaatatct cgataatgag atcaattggg atctgcaagg     87480
agtttttagt tccatcctct aagcgcagag acgttttcat ggccgaaata aataaaccct     87540
aagagagaga gactccttgt agaagaagaa accaatgcgg taaaacaaag gcaagtaaaa     87600
gccaaaaaaa agttaatcac aatggtaaaa acatggactg agagaaagcc cgtatagccc     87660
aaagtttcca agcttgtata aggcccaacc aaataaccta acgagtttaa agttcaaacg     87720
tgatgaaacg ttaccgtttt agcgtttctc atgtttcttc catataaata gttttagttt     87780
tgtagaaaac cctaatcgac gacggccatt atgataaatg acggcggagc taaaccggag     87840
acgctgctta gggttgcaga atcggtggaa gaggaagga gtttggtggc ggcacagtct     87900
cttcgtgctg acaagttat cctcagagag tctcctctcc ttctctactc tgcttttcca     87960
tttctctcct cctctgtttc tccttactgc gaccattgtt tccgtttgtt agcttcatcg     88020
gcgcatcaga aatgtcaatc ttgctctctc gtctccttt gtagccctaa ttgcttcgcc     88080
tctcatactc cttggctctg cgaatctctt cgccggcttc accaatcatc ctcctctgca     88140
ttctccgatc aaccttctga tcgtcaagtc caagctcgtt tcctcctctc tgcttacaat     88200
ctcgccgctg cttctccttc tgatttccag attttgctct ctctccaagg tagtggcagc     88260
agcaatggag atccttcttg ttctgcgggt gattctgcag ctgctgggtt tcttcattct     88320
cttttatctt ccgtgtgtcc atctcttccg gtgtctatct cgccggatct cacggcggct     88380
ttactgtcaa aggataaagt taacgccttt ggtctgatgg aaccgtgctc tgtttcgaat     88440
gagaaaagat ctgtgcgagc ttatgggatt tatccaaaga cttcgttttt caatcatgat     88500
tgtcttccta atgcttgtag attcgattat gttgactctg cttctgatgg taatactgat     88560
atcatcatta ggatgattca tgatgttcct gaaggtagaa aagtttgttt aagctacttc     88620
cctgtgaaca tgaactattc gagtagacaa aagagattgc ttgaggatta cggttttaag     88680
tgtgactgtg atcggtgcaa agtggaattt agttggtctg aaggtgagga agatgagaat     88740
gagattatgg aagagatgga ggatcaagat gaacaagaag agatggaaga ttcagtaggt     88800
gagaatgaag aagaagtttg tggaaatggt gtggatgatg aatctaattt tcctcatgct     88860
tacttttttg tgagatatat gtgtgagaag gagaattgtt ttggcactct agctccgctt     88920
cccccgaaga ctcatgatgc ttcgagagtt cttgaatgta atgtttgtgg aagcgttaag     88980
gaggatgaag ttggcgtaaa tcaatgagga aggttagctt aaagaattga tcagccgaaa     89040
```

```
atctcaagct tgtttgatgc agccagaccc aaacaacaag agacttgtct tggaccacat   89100
cgttaatcaa tgttgtttgt tgtttgatgt ttactttttt tttttactc agttttgaaa    89160 attcgataag tattctagct ctagaattcc atatctaggt tttttgtttt ctcctagata    89220
gtctgaagaa tcaattgtaa tggtctgtgg aattacacgg aaacagtttt gttgtaataa    89280
tggagcatca gttttctttg gttgaatgaa aaatcataat ttttttgact ttttaagttg    89340
aaaactgcag aattacatgg cttgatgatg tttgcattgt taatctctat tactcttcag    89400
tgtgctcagt gcctgaaacc atagcttcct tgatagggat caatgtattg gtaaaccaaa    89460
ttgtgtaata gttttttccat aaaatagatt caatagaacc agtgtaacaa aaaattatta   89520
gggggctctg ttttaaggtc gcaacatgac ggtgacacaa acattttta gtgattaact     89580 tgttctcatt ctgttccaag ttcaacaaca caaactgagt tttttggctt ctctatcaga    89640
gaactaatgt gattctacaa cacaacctgc tctgactgac ttactctgct atgttctgtt    89700
ttgctctgct ctgttctcac ttccacgtct ctgtttttgt cattgacatt tcgacttgta    89760
ggaacttaaa catttagtgg attgactggc aagattgatc caaccttttc caatcttaca    89820
tccataaata agttgatatt ttttctggtt tttatttggc aaaacactaat gcaccctagg   89880 gttcaatgag atatatatat attacactaa cacaagtaca caaccaaatg ttattgtagg    89940
gacttgtaat aatttaacag acccagattc ctcacaaatt ctaccaaatt tgcgagtcat    90000
tcaagctagc aaacattatc atctataaat aaatagtttt ctaaacatag taagaacat     90060 aattttaaaa ttcgaaacgt tcctgataaa ttttcttctc acattctaaa gaacaaaagt    90120
atagatcagc tccgtcctcg ggaagcgtac gaacgaaagg gagcttgcat cgagagttgc    90180
acacgcagca aagtggtcta caaatagagt ggttggatac aaatgttcct atccatgtta    90240
acgctcctgg catggaatat gcgtaagtat ctataacgca ggaaatatgc aatgtgatcc    90300
cacactcatt gcatgtatag aaccattttt ctggttcac agttgtttcg catgcttcac     90360
accaatattt gccagccacg cccatttcgc cataagataa gaagagagga tgatcgtcgt    90420
acctatgcct cattaccttt tgcggtaaaa tagcacactt gaagcacaaa ccaaattcac    90480
aatcatcgca actcaatttc ccgtctccat cacactcact acaacgtttg gagtgatctg    90540
tagagtagtg taaaggatgt tgatggcttt tgtgctcaaa tggttctgta actgtagcgc    90600
accgtacatc tatccttaat tccttagatt cataggagaa accggtgaac agttgacggc    90660
aaatactaca cctatgtaac aagtaggtgc cataatttgg ggatagttcg agtggctggt    90720
tgtggcacac atgacgtttc tttaaaggaa gcttggcaca ttttttcgtgg attatgaaat   90780 cgcatctctt tctcgcgcaa gcgtagaacg gttctgaaca aatctggaag acacatgcgg    90840
tacaaactac actttctggt agattccagc cacggtaaat tcgtaagtta tgcttatggc    90900
cgtaatggtc tatcgtgttg tcatcaatca ccttgaatgg cgcagtttcc tcttcttcgg    90960
gtgtcccttc cagttcgatc atgtcccata catccctcct ggttgcgcat cttgaatgaa    91020 caaataatc aaaacatttg gagcaagaat aagccccgta gaacccatcc acatttttac     91080
gacaaactct gcatttcccg tctccatgtc cgaggcgagg ggtgtaagag atgcggtggt    91140
cgtggcggtt gatgtttatg acgcgaggta gatcgataca ttcccgatga atcatgaaat    91200
tgcactgaag acagaaataa gggctacggt cacctagcgt cccacaagca ttgcaagtga    91260
agtcaatgcg tcttggaaca aggtgaagtt gatgttcatg ggtcctcggg cttttaacaa    91320
gaaccggtgg tgggttttc atacatgatc tgcatatgct aaaattacaa acaccacagt     91380
ggtgaagctg gcgatggatt ccatcaaact cctcgcggca aagaagacat tcttgtcgg     91440
```

```
cgtaaccagg gacttcatat ctaagtgact tgagtgggtg ttgggggtga gaagtgtggt    91500
atgcttctgg actattatga tcgatacaat ccagactgat gaaaaactcg cattgatgac    91560
atgtgtagaa atgttccag ctattatgtt gatggccaca cccttttgcaa tctctgagtg     91620 tttcgtgcgc ttcatgggag agttggagtg gatgctcgtg taggtaggag ttttcagcaa    91680
gaacaagtag ggctggtctc ctcgcgcaaa tcaaatccaa ctggaaatca catttgttac    91740
agcgataacc gacactgaaa aattctccac agaaactaca attagaaact ctggtatgta    91800
ggaggatcag cttgagagga tggactggat ggtaagggtg gtcgatttct ggtaacggct    91860
tggcgcactc ttcatggaac acaacatcac atcccggctc attgcatcgg tgtcctccgt    91920
aaatgtaact gcaaccggga tgtttggaaa tgaagcttgt attatcttca tcggtcgagt    91980
agcatccttt acacttggtg aactcgaagc gtgtaaaagg tatcaacgga tgctcatgaa    92040
atggtaacaa ttttcaagg cgggatgctt cttcgtccat gccttcatta aacaaagcta     92100
gaaagttttc catggtgatg ttttcttact tccaccaaaa cacaaagctc ttctcttctg    92160
cactagtttc agacttggtt tcttgttttt ctctctttct tttctttcag atttttttt     92220 caagtggttt atcattttca gactttgcaa atagttaata tgaattcgca ccacagaaat    92280 gattctttc attactgaga ttgagaccac atgtgttggc ttcatccttg cattattaa      92340 ttaactcaga ccacatatgt tgactctgca actattgtgt ccggccaaaa cataaataat    92400
tgaatgaata caaaaaggt ttttcttgc attaaatgga atagaagttt atggatagaa      92460
tagtttagaa tttaaatgga tggaactgta cattttgtgg aaaaaacagt ttgaagtctg    92520
aaccacacaa ctccttggcc aagtagcttt ggaggtagac tttgctgcat tcaagtctct    92580
gaaaccaaag ttttattatt gtattgcatc cactaacttt tatgtaattt cagaccaaaa    92640
gatttgtatt tttgtcttta agaccaggat tgggccaatc tttgtttttt aattttata    92700 cagccaaaag taagttctat t                                             92721
```

```
<210> SEQ ID NO 38
<211> LENGTH: 3
<212> TYPE: PRT
<213> ORGANISM: Artificial Sequence
<220> FEATURE:
<223> OTHER INFORMATION: GHS motif of cytokinin oxidase

<400> SEQUENCE: 38

Gly His Ser
  1

<210> SEQ ID NO 39
<211> LENGTH: 7
<212> TYPE: PRT
<213> ORGANISM: Artificial Sequence
<220> FEATURE:
<223> OTHER INFORMATION: FAD binding domain motif of cytokinin oxidase

<400> SEQUENCE: 39

Val Gly Gly Thr Leu Ser Asn
  1               5

<210> SEQ ID NO 40
<211> LENGTH: 9
<212> TYPE: PRT
<213> ORGANISM: Artificial Sequence
<220> FEATURE:
<223> OTHER INFORMATION: FAD binding domain motif of cytokinin oxidase

<400> SEQUENCE: 40
```

```
Val Leu Gly Gly Leu Gly Gln Phe Cys
  1               5
```

```
<210> SEQ ID NO 41
<211> LENGTH: 6
<212> TYPE: PRT
<213> ORGANISM: Artificial Sequence
<220> FEATURE:
<223> OTHER INFORMATION: FAD binding domain motif of cytokinin oxidase

<400> SEQUENCE: 41

Ile Thr Arg Ala Arg Ile
  1               5
```

```
<210> SEQ ID NO 42
<211> LENGTH: 534
<212> TYPE: PRT
<213> ORGANISM: Zea mays

<400> SEQUENCE: 42

Met Ala Val Val Tyr Tyr Leu Leu Ala Gly Leu Ile Ala Cys Ser
  1               5                  10                  15

His Ala Leu Ala Ala Gly Thr Pro Ala Leu Gly Asp Asp Arg Gly Arg
                 20                  25                  30

Pro Trp Pro Ala Ser Leu Ala Ala Leu Ala Leu Asp Gly Lys Leu Arg
                 35                  40                  45

Thr Asp Ser Asn Ala Thr Ala Ala Ser Thr Asp Phe Gly Asn Ile
 50                  55                  60

Thr Ser Ala Leu Pro Ala Ala Val Leu Tyr Pro Ser Thr Gly Asp
 65                  70                  75                  80

Leu Val Ala Leu Leu Ser Ala Ala Asn Ser Thr Pro Gly Trp Pro Tyr
                 85                  90                  95

Thr Ile Ala Phe Arg Gly Arg Gly His Ser Leu Met Gly Gln Ala Phe
                100                 105                 110

Ala Pro Gly Gly Val Val Asn Met Ala Ser Leu Gly Asp Ala Ala
                115                 120                 125

Ala Pro Pro Arg Ile Asn Val Ser Ala Asp Gly Arg Tyr Val Asp Ala
                130                 135                 140

Gly Gly Glu Gln Val Trp Ile Asp Val Leu Arg Ala Ser Leu Ala Arg
145                 150                 155                 160

Gly Val Ala Pro Arg Ser Trp Asn Asp Tyr Leu Tyr Leu Thr Val Gly
                165                 170                 175

Gly Thr Leu Ser Asn Ala Gly Ile Ser Gly Gln Ala Phe Arg His Gly
                180                 185                 190

Pro Gln Ile Ser Asn Val Leu Glu Met Asp Val Ile Thr Gly His Gly
                195                 200                 205

Glu Met Val Thr Cys Ser Lys Gln Leu Asn Ala Asp Leu Phe Asp Ala
            210                 215                 220

Val Leu Gly Gly Leu Gly Gln Phe Gly Val Ile Thr Arg Ala Arg Ile
225                 230                 235                 240

Ala Val Glu Pro Ala Pro Ala Arg Ala Arg Trp Val Arg Phe Val Tyr
                245                 250                 255

Thr Asp Phe Ala Ala Phe Ser Ala Asp Gln Glu Arg Leu Thr Ala Pro
                260                 265                 270

Arg Pro Gly Gly Gly Gly Ala Ser Phe Gly Pro Met Ser Tyr Val Glu
            275                 280                 285

Gly Ser Val Phe Val Asn Gln Ser Leu Ala Thr Asp Leu Ala Asn Thr
290                 295                 300
```

-continued

```
Gly Phe Phe Thr Asp Ala Asp Val Ala Arg Ile Val Ala Leu Ala Gly
305                 310                 315                 320

Glu Arg Asn Ala Thr Thr Val Tyr Ser Ile Glu Ala Thr Leu Asn Tyr
                325                 330                 335

Asp Asn Ala Thr Ala Ala Ala Ala Val Asp Gln Glu Leu Ala Ser
            340                 345                 350

Val Leu Gly Thr Leu Ser Tyr Val Glu Gly Phe Ala Phe Gln Arg Asp
        355                 360                 365

Val Ala Tyr Ala Ala Phe Leu Asp Arg Val His Gly Glu Glu Val Ala
        370                 375                 380

Leu Asn Lys Leu Gly Leu Trp Arg Val Pro His Pro Trp Leu Asn Met
385                 390                 395                 400

Phe Val Pro Arg Ser Arg Ile Ala Asp Phe Asp Arg Gly Val Phe Lys
                405                 410                 415

Gly Ile Leu Gln Gly Thr Asp Ile Val Gly Pro Leu Ile Val Tyr Pro
                420                 425                 430

Leu Asn Lys Ser Met Trp Asp Asp Gly Met Ser Ala Ala Thr Pro Ser
            435                 440                 445

Glu Asp Val Phe Tyr Ala Val Ser Leu Leu Phe Ser Ser Val Ala Pro
    450                 455                 460

Asn Asp Leu Ala Arg Leu Gln Glu Gln Asn Arg Arg Ile Leu Arg Phe
465                 470                 475                 480

Cys Asp Leu Ala Gly Ile Gln Tyr Lys Thr Tyr Leu Ala Arg His Thr
                485                 490                 495

Asp Arg Ser Asp Trp Val Arg His Phe Gly Ala Ala Lys Trp Asn Arg
            500                 505                 510

Phe Val Glu Met Lys Asn Lys Tyr Asp Pro Lys Arg Leu Leu Ser Pro
            515                 520                 525

Gly Gln Asp Ile Phe Asn
        530
```

METHOD FOR MODIFYING PLANT MORPHOLOGY, BIOCHEMISTRY AND PHYSIOLOGY

This application is a continuation of U.S. application Ser. No. 11/801,018, now U.S. Pat. No. 7,807,879, filed May 8, 2007, which is a divisional of co-pending U.S. application Ser. No. 10/014,101, now U.S. Pat. No. 7,259,296, filed Dec. 10, 2001, which is a continuation-in-part application of PCT/EP01/06833, having an international filing date of Jun. 18, 2001, which claims priority of U.S. Provisional application No. 60/258,415, filed Dec. 27, 2000.

FIELD OF THE INVENTION

The present invention generally relates to methods for modifying plant morphological, biochemical and physiological properties or characteristics, such as one or more developmental processes and/or environmental adaptive processes, including but not limited to the modification of initiation or stimulation or enhancement of root growth, and/or adventitious root formation, and/or lateral root formation, and/or root geotropism, and/or shoot growth, and/or apical dominance, and/or branching, and/or timing of senescence, and/or timing of flowering, and/or flower formation, and/or seed development, and/or seed yield. Methods for increasing seed size and/or weight, increasing embryo size and/or weight, and increasing cotyledon size and/or weight are also provided. The methods comprise expressing a cytokinin degradation control protein, in particular cytokinin oxidase, in the plant, operably under the control of a regulatable promoter sequence such as a cell-specific promoter, tissue-specific promoter, or organ-specific promoter sequence. Preferably, the characteristics modified by the present invention are cytokinin-mediated and/or auxin-mediated characteristics. The present invention extends to genetic constructs which are useful for performing the inventive method and to transgenic plants produced therewith having altered morphological and/or biochemical and/or physiological properties compared to their otherwise isogenic counterparts.

BACKGROUND OF THE INVENTION

Roots are an important organ of higher plants. Their main functions are anchoring of the plant in the soil and uptake of water and nutrients (N-nutrition, minerals, etc.). Thus, root growth has a direct or indirect influence on growth and yield of aerial organs, particularly under conditions of nutrient limitation. Roots are also relevant for the production of secondary plant products, such as defense compounds and plant hormones.

Roots are also storage organs in a number of important staple crops. Sugar beet is the most important plant for sugar production in Europe (260 Mill t/year, 38% of world production). Manioc (cassava), yams and sweet potato (batate) are important starch producers (app. 150 Mill t/year each). Their content in starch can be twice as high as that of potato. Roots are also the relevant organ for consumption in a number of vegetables (e.g. carrots, radish), herbs (e.g. ginger, kukuma) and medicinal plants (e.g. ginseng). In addition, some of the secondary plant products found in roots are of economic importance for the chemical and pharmaceutical industry. An example is yams, which contain basic molecules for the synthesis of steroid hormones. Another example is shikonin, which is produced by the roots of *Lithospermum erythrorhizon* in hairy root cultures. Shikonin is used for its anti-inflammatory, anti-tumor and wound-healing properties.

Moreover, improved root growth of crop plants will also enhance competitiveness with weedy plants and will improve growth in arid areas, by increasing water accessibility and uptake.

Improved root growth is also relevant for ecological purposes, such as bioremediation and prevention/arrest of soil erosion.

Root architecture is an area that has remained largely unexplored through classical breeding, because of difficulties with assessing this trait in the field. Thus, biotechnology could have significant impact on the improvement of this trait, because it does not rely on large-scale screenings in the field. Rather, biotechnological approaches require a basic understanding of the molecular components that determine a specific characteristic of the plant. Today, this knowledge is only fragmentary, and as a consequence, biotechnology was so far unable to realize a break-through in this area.

A well-established regulator of root growth is auxin. Application of indole-3-acetic acid (IAA) to growing plants stimulates lateral root development and lateral root elongation (Torrey, Am J Bot 37: 257-264, 1950; Blakely et al., Bot Gaz 143: 341-352, 1982; Muday and Haworth, Plant Physiol Biochem 32: 193-203, 1994). Roots exposed to a range of concentrations of IAA initiated increasing numbers of lateral roots (Kerk et al., Plant Physiol, 122: 925-932, 2000). Furthermore, when roots that had produced laterals in response to a particular concentration of exogenous auxin were subsequently exposed to a higher concentration of IAA, numerous supernumerary lateral roots spaced between existing ones were formed (Kerk et al., Plant Physiol, 122: 925-932, 2000). Conversely, growth of roots on agar containing auxin-transport inhibitors, including NPA, decreases the number of lateral roots (Muday and Haworth, Plant Physiol Biochem 32: 193-203, 1994).

*Arabidopsis* mutants containing increased levels of endogenous IAA have been isolated (Boerjan et al., Plant Cell 7: 1405-141, 1995; Celenza et al., Gene Dev 9: 2131-2142, 1995; King et al., Plant Cell 7: 2023-2037, 1995; Lehman et al., Cell 85: 183-194, 1996). They are now known to be alleles of a single locus located on chromosome 2. These mutant seedlings have excess adventitious and lateral roots, which is in accordance with the above-described effects of external auxin application.

The stimulatory effect of auxins on adventitious and lateral root formation suggests that overproduction of auxins in transgenic plants is a valid strategy for increasing root growth. Yet, it is also questionable whether this would yield a commercial product with improved characteristics. Apart from its stimulatory effect on adventitious and lateral root formation, auxin overproduction triggers other effects, such as reduction in leaf number, abnormal leaf morphology (narrow, curled leaves), aborted inflorescences, increased apical dominance, adventitious root formation on the stem, most of which are undesirable from an agronomic perspective (Klee et al., Genes Devel 1: 86-96, 1987; Kares et al., Plant Mol Biol 15: 225-236, 1990). Therefore, the major problem with approaches that rely on increased auxin synthesis is a problem of containment, namely to confine the effects of auxin to the root. This problem of containment is not likely overcome by using tissue-specific promoters: auxins are transported in the plant and their action is consequently not confined to the site of synthesis. Another issue is whether auxins will always enhance the total root biomass. For agar-grown plants, it has been noticed that increasing concentrations progressively stimulated lateral root formation but concurrently inhibited the outgrowth of these roots (Kerk et al., Plant Physiol, 122: 925-932, 2000).

Seeds are the reproduction unit of higher plants. Plant seeds contain reserve compounds to ensure nutrition of the embryo after germination. These storage organs contribute significantly to human nutrition as well as cattle feeding. Seeds consist of three major parts, namely the embryo, the endosperm and the seed coat. Reserve compounds are deposited in the storage organ which is either the endosperm (resulting form double fertilisation; e.g. in all cereals), the so-called perisperm (derived from the nucellus tissue) or the cotyledons (e.g. bean varieties). Storage compounds are lipids (oil seed rape), proteins (e.g. in the aleuron of cereals) or carbohydrates (starch, oligosaccharides like raffinose).

Starch is the storage compound in the seeds of cereals. The most important species are maize (yearly production ca. 570 mio t; according to FAO 1995), rice (540 mio t p.a.) and wheat (530 mio t p.a.). Protein rich seeds are different kinds of beans (*Phaseolus* spec., *Vicia faba*, *Vigna* spec.; ca. 20 mio t p.a.), pea (*Pisum sativum;* 14 mio t p.a.) and soybean (*Glycine max;* 136 mio t p.a.). Soybean seeds are also an important source of lipids. Lipid rich seeds are as well those of different *Brassica* species (app. 30 mio t p.a.), cotton, oriental sesame, flax, poppy, castor bean, sunflower, peanut, coconut, oilpalm and some other plants of less economic importance.

After fertilization, the developing seed becomes a sink organ that attracts nutritional compounds from source organs of the plant and uses them to produce the reserve compounds in the storage organ. Increases in seed size and weight, are desirable for many different crop species. In addition to increased starch, protein and lipid reserves and hence enhanced nutrition upon ingestion, increases in seed size and/or weight and cotyledon size and/or weight are correlated with faster growth upon germination (early vigor) and enhanced stress tolerance. Cytokinins are an important factor in determining sink strength. The common concept predicts that cytokinins are a positive regulator of sink strength.

Numerous reports ascribe a stimulatory or inhibitory function to cytokinins in different developmental processes such as root growth and branching, control of apical dominance in the shoot, chloroplast development, and leaf senescence (Mok M. C. (1994) in *Cytokines: Chemistry, Activity and Function*, eds., Mok, D. W. S. & Mok, M. C. (CRC Boca Raton, Fla.), pp. 155-166). Conclusions about the biological functions of cytokinins have mainly been derived from studies on the consequences of exogenous cytokinin application or endogenously enhanced cytokinin levels (Klee, H. J. & Lanehon, M. B. (1995) in *Plant Hormones: Physiology, Biochemistry and Molecular Biology*, ed. Davies, P. J. (Kluwer, Dordrdrocht, the Netherlands), pp. 340-353, Smulling, T., Rupp, H. M. Frank, M & Schafer, S. (1999) in *Advances in Regulation of Plant Growth and Development*, eds. Sumad, M. Pac P. & Beck, E. (Peres, Prague), pp. 85-96). Up to now, it has not been possible to address the reverse question: what are the consequences for plant growth and development if the endogenous cytokinin concentration is decreased? Plants with a reduced cytokinin content are expected to yield more precise information about processes cytokinins limit and, therefore, might regulate. Unlike other plant hormones such as abscisic acid, gibberellins, and ethylene, no cytokinin biosynthetic mutants have been isolated (Hooykens, P. J. J., Hall, M. A. & Libbeuga, K. R., eds. (1999) *Biochemistry and Molecular Biology of Plant Hormones* (Elsevier, Amsterdam).

The catabolic enzyme cytokinin oxidase (CKX) plays a principal role in controlling cytokinin levels in plant tissues. CKX activity has been found in a great number of higher plants and in different plant tissues. The enzyme is a FAD-containing oxidoreductase that catalyzes the degradation of cytokinins bearing unsaturated isoprenoid side chains. The free bases iP and Z, and their respective ribosides are the preferred substrates. The reaction products of iP catabolism are adenine and the unsaturated aldehyde 3-methyl-2-butonal (Armstrong, D. J. (1994) in *Cytokinins: Chemistry, Activity and Functions*, eds. Mok. D. W. S & Mok, M. C. (CRC Boca Raton, Fla.), pp. 139-154). Recently, a cytokinin oxidase gene from *Zea mays* has been isolated (Morris, R. O., Bilyeu, K. D., Laskey, J. G. & Cherich, N. N. (1999) *Biochem. Biophys. Res. Commun.* 255, 328-333, Houba-Heria, N., Pethe, C. d'Alayer, J & Lelouc, M. (1999) *Plant J.* 17:615-626). The manipulation of CKX gene expression could partially overcome the lack of cytokinin biosynthetic mutants and can be used as a powerful tool to study the relevance of iP- and Z-type cytokinins during the whole life cycle of higher plants.

The present invention overcomes problems related to containment of auxin effects, maintenance of root outgrowth, and promotion of increased seed, embryo, and cotyledon size and/or weight through reduction of endogenous cytokinin concentration.

SUMMARY OF THE INVENTION

The present invention provides plant cytokinin oxidase proteins, nucleic acid sequences encoding such proteins, and vectors, host cells and transgenic plant cells, plants, and plant parts comprising the proteins, nucleic acid sequences, and vectors. For example, the present invention relates to a genetic construct comprising a gene encoding a protein with cytokinin oxidase activity from *Arabidopsis thaliana*. This gene may be expressed under control of a regulated promoter. This promoter may be regulated by endogenous tissue-specific or environment-specific factors or, alternatively, it may be induced by application of specific chemicals.

The present invention also relates to a method to modify root architecture and biomass by expression of a cytokinin oxidase gene or expression of a nucleic acid encoding a protein that reduces the level of active cytokinins in plants or plant parts. Preferably, expression is under control of a promoter that is specific to the root or to certain tissues or cell types of the root.

Additionally, the present invention relates to methods of increasing seed size and/or weight, embryo size and/or weight, and cotyledon size and/or weight. The methods involve expression of a cytokinin oxidase gene or expression of a nucleic acid encoding a protein that reduces the level of active cytokinins in plants or plant parts. Preferably, expression is under control of a promoter directs expression preferentially in the seed, embryo, or cotyledon.

Figure 1:
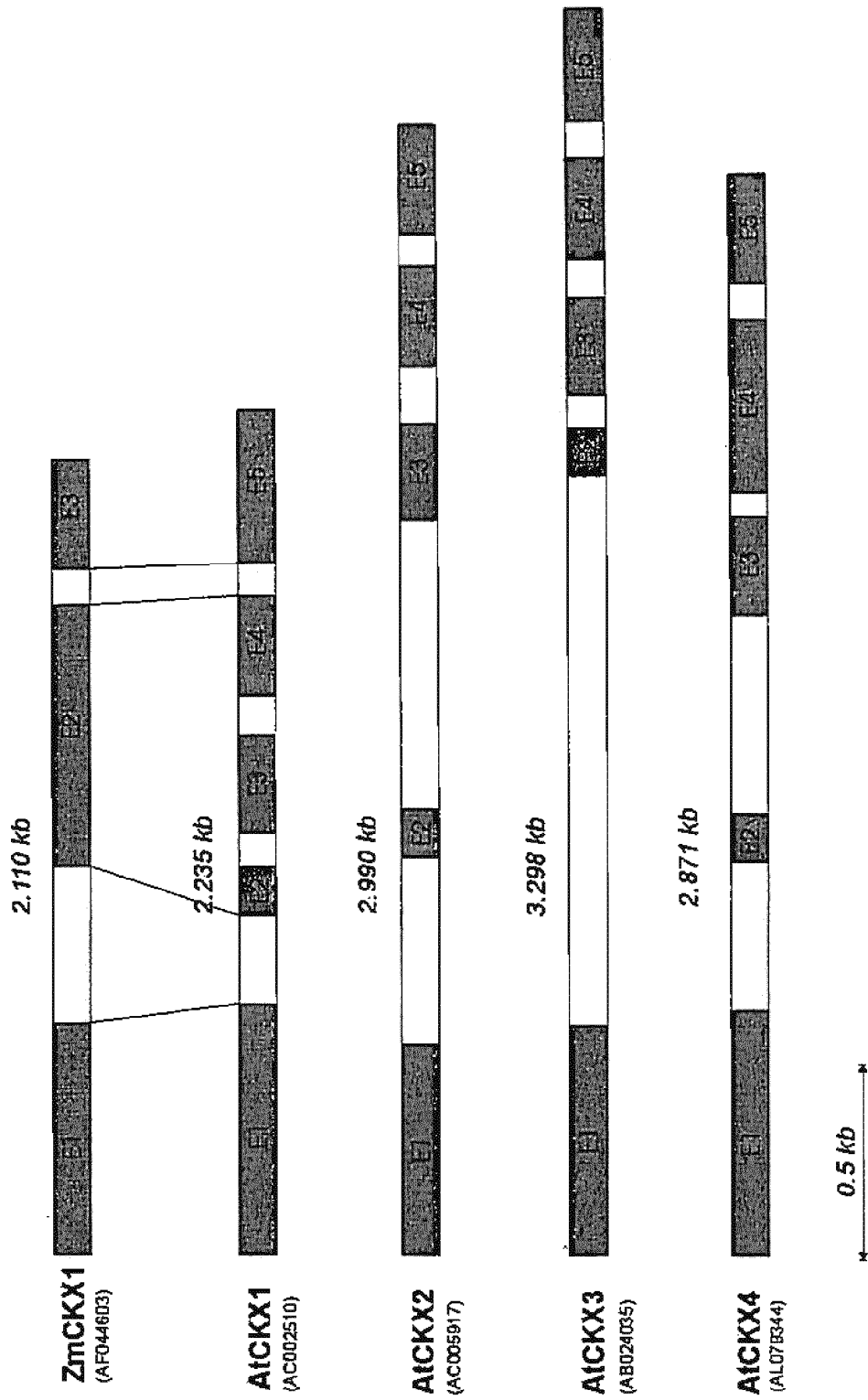
FIG. 1. Schematic representation of plant cytokinin oxidase genes.

Shown are the structures of different cytokinin oxidase genes isolated from maize (ZmCKX1, accession number AF044603, Biochem. Biophys. Res. Com. 255:328-333, 1999) and *Arabidopsis* (AtCKX1 to AtCKX4). Exons are denominated with 'E' and represented by shaded boxes. Introns are represented by white boxes. Further indicated are the gene sizes (in kb, on top of each structure), the gene accession numbers (under the names) and a size bar representing 0.5 kb.

Figure 2:
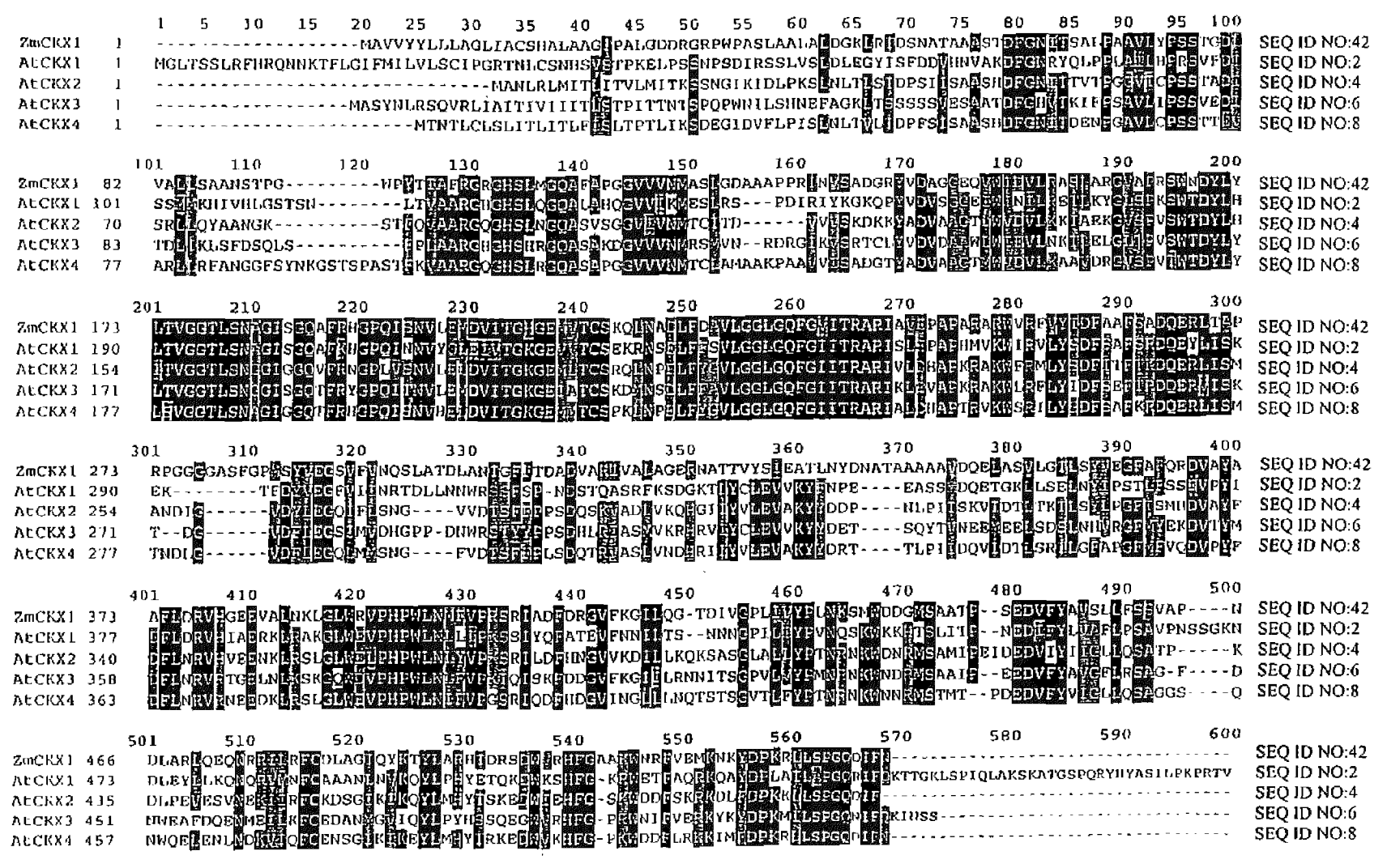

FIG. 2. Alignment of plant cytokinin oxidase amino acid sequences.

The amino acid sequences from cytokinin oxidases from maize (ZmCKX1) and *Arabidopsis* (AtCKX1 to AtCKX4)

are aligned. Identical amino acid residues are marked by a black box, similar amino acid residues are in a grey box. Amino acid similarity groups: (M,I,L,V), (F,W,Y), (G,A), (S,T), (R,K,H), (E,D), (N,Q), FIG. 3. Northern blot analysis of AtCKX1-expressing tobacco and *Arabidopsis* plants.

(A) Northern blot analysis of constitutively expressing tobacco plants (lanes 1-8) compared to wild type SNN tobacco (lane 9)

(B) Comparison of tetracycline-induced gene expression in leaves after 12 h of induction with a constitutively expressing clone. Lanes 2-9, leaves of four different AtCKX1-W38TetR clones (+, -, with or without tetracycline treatment), lane 1, constitutively expressing 35S::AtCKX1 clone.

(C) Northern blot analysis of *Arabidopsis* plants constitutively expressing AtCKX1 gene. Lanes 2-4, three different constitutively expressing 35S::AtCKX1 clones compared to wild type *Arabidopsis* plant (lane 1).

Figure 4:
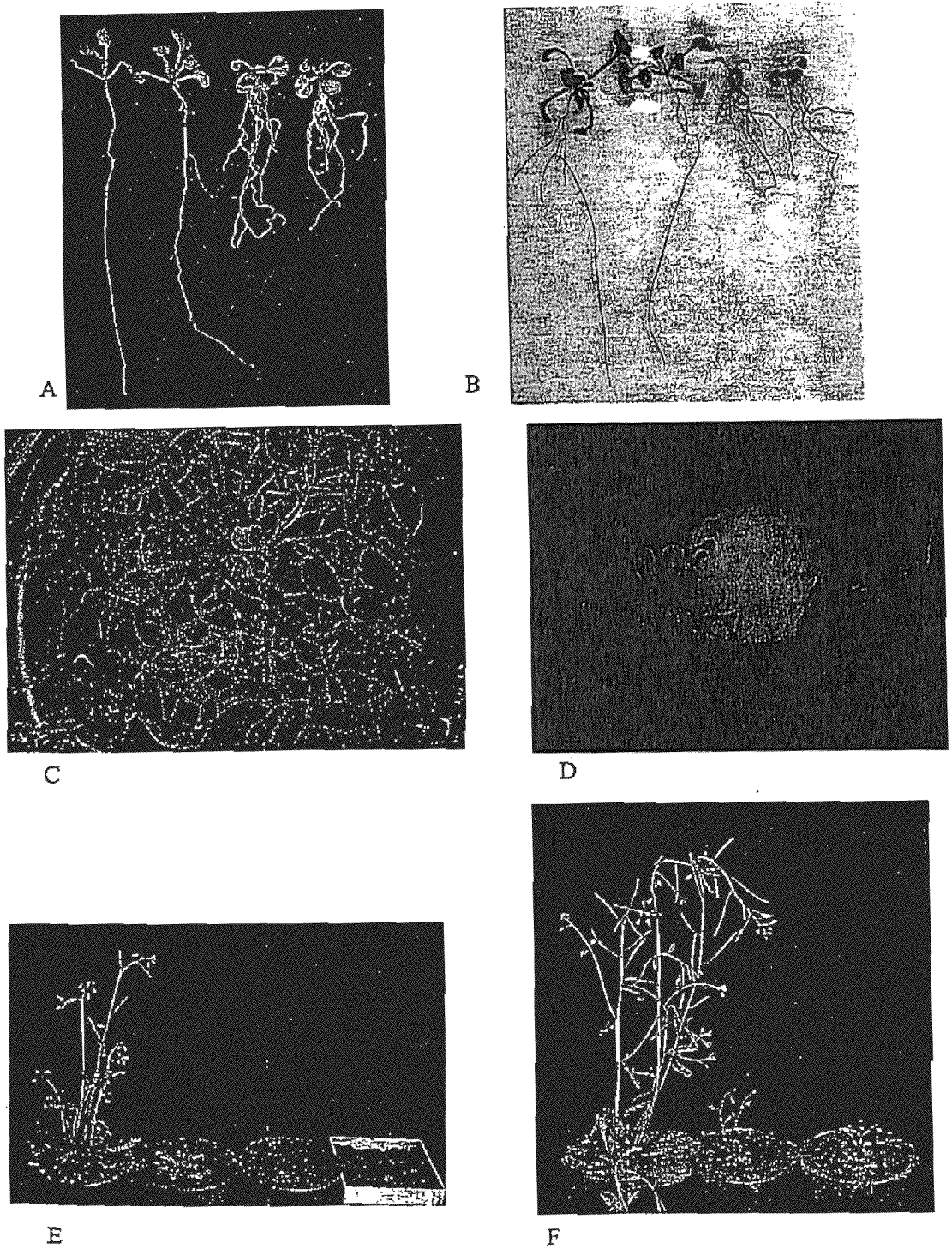

FIG. 4: Growth characteristics of 35S::AtCKX1 transgenic *Arabidopsis* plants.

(A) Two wild type seedlings (left) compared to two 35S::AtCKX1 expressing seedlings (right). Note the increased formation of adventitious roots and increased root branching in the transgenic seedlings. Pictures were taken 14 days after germination. Plants were grown in vitro on MS medium in petri dishes in a vertical position.

(B) Like A, but roots stained with toluidine blue.

(C) Top view of a petri dish with 35S::AtCKX1 transgenic seedlings three weeks after germination.

(D) A 35S::AtCKX1 transgenic plants grown in liquid culture. Roots of wild type seedlings grow poorly under these conditions (not shown).

(E) Transformants (T0) that express the 35S::AtCKX1 gene (three plants on the right), a wild type plant is shown on the left.

(F) Phenotype of T1 plants grown in soil. Wild type plant (left) compared to two 35S::AtCKX1 transgenic plants.

Figure 5:
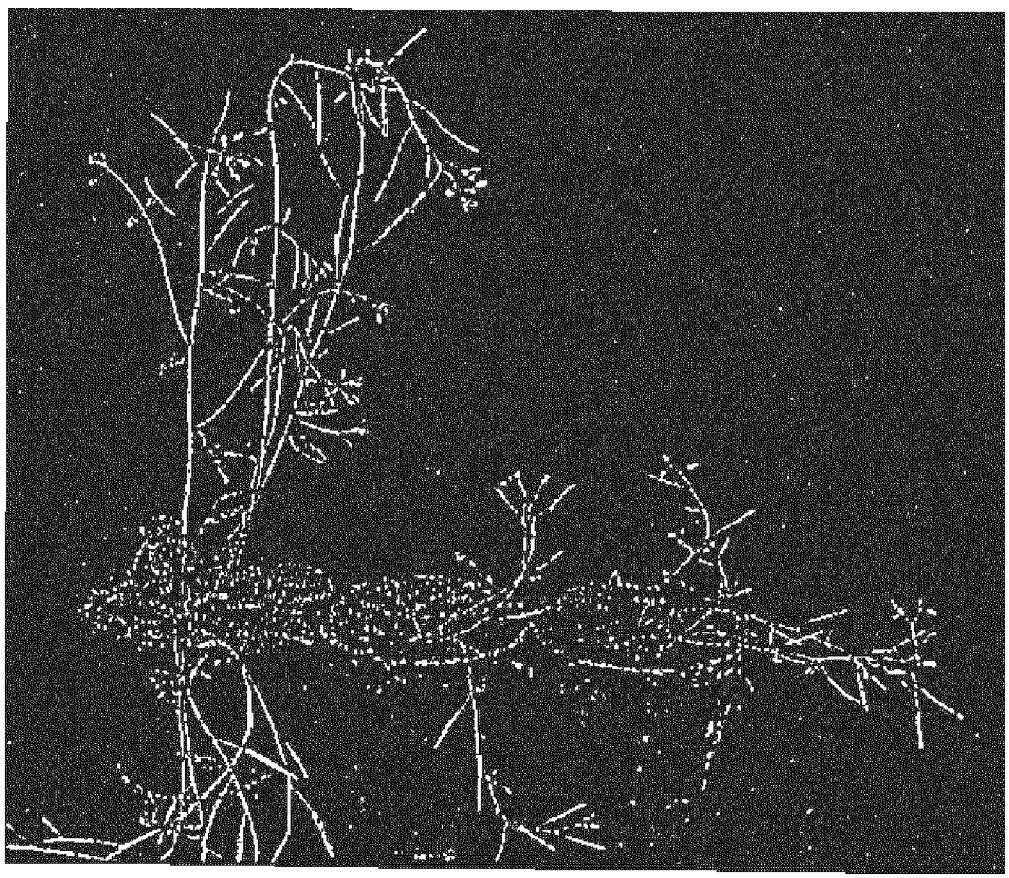

FIG. 5: Phenotype of AtCKX2 overexpressing *Arabidopsis* plants.

T1 generation of 35S::AtCKX2 expressing *Arabidopsis* plants (two plants on the right) compared to wild type (plant on the left).

Figure 6:
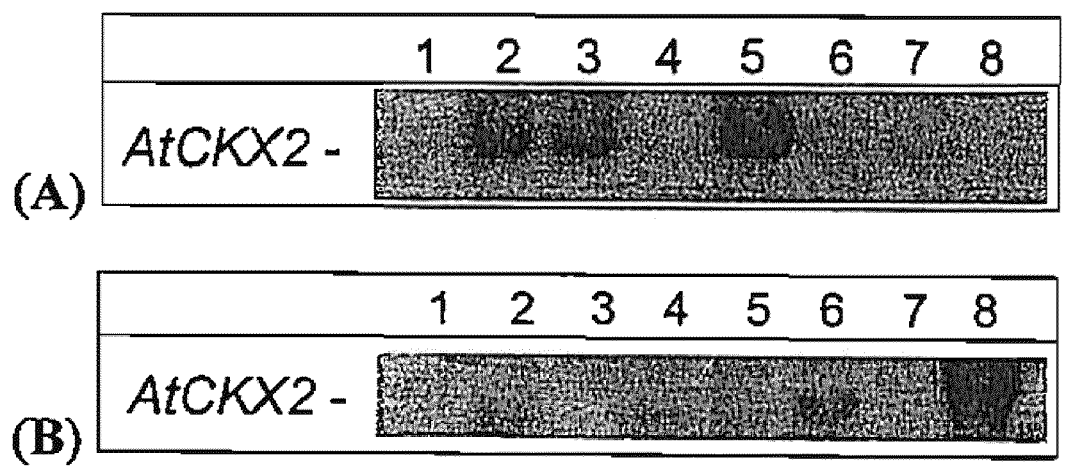

FIG. 6. Northern blot analysis of AtCKX2-expressing tobacco and *Arabidopsis* plants.

(A) Northern blot analysis of constitutively expressing tobacco plants (lanes 1-7) compared to wild type SNN tobacco (lane 8)

(B) Northern blot analysis of *Arabidopsis* plants constitutively expressing AtCKX2 gene. Lanes 2-8, seven different constitutively expressing 35S::AtCKX2 clones compared to wild type *Arabidopsis* plant (lane 1).

Figure 7:
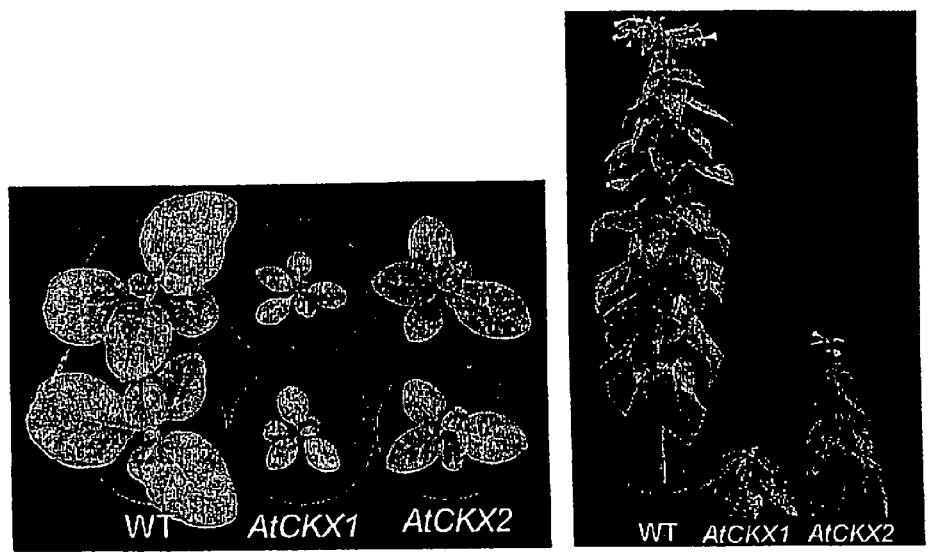
Figure 7:
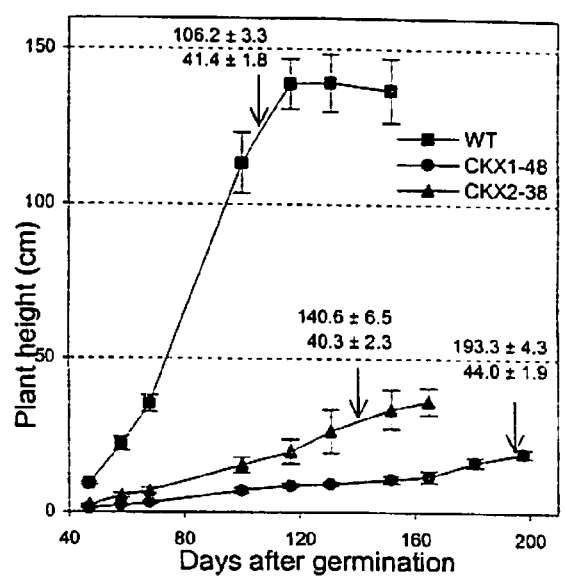
Figure 7:
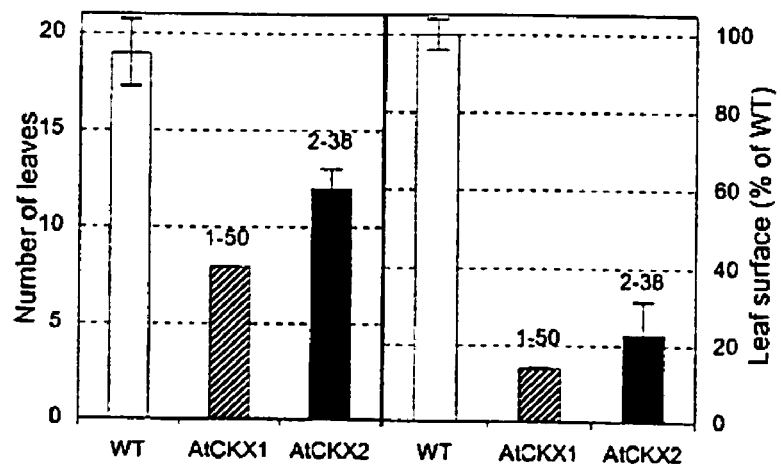
Figure 7:
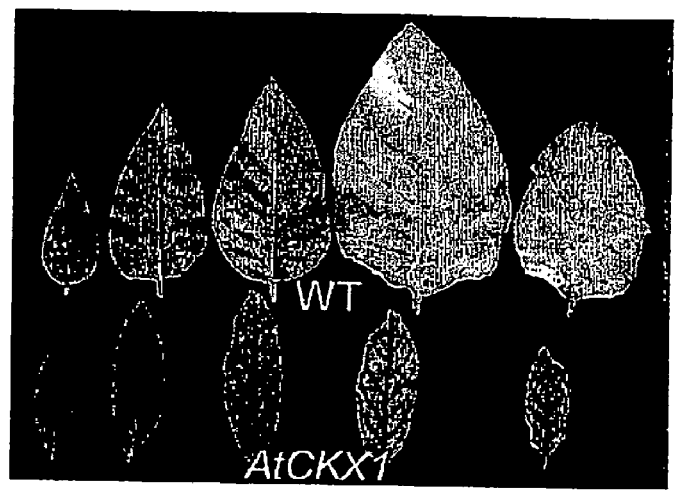

FIG. 7. Shoot phenotype of AtCKX1 and AtCKX2 expressing tobacco plants.

(A) Top view of six week old plants.

(B) Tobacco plants at the flowering stage.

(C) Kinetics of stem elongation. Arrows mark the onset of flowering. Age of plants (days after germination) and leaf number at that stage are indicated above the arrows. Bars indicate SD; n=12.

(D) Number of leaves (n=12) formed between day 68 and day 100 after germination and final surface area of these leaves (100% of wild type is 3646±144 cm$^2$; n=3).

(E) Comparison of leaf size and senescence. Leaves were from nodes number 4, 9, 12, 16 and 20 from the top (from left to right).

Figure 8:
Figure 8:
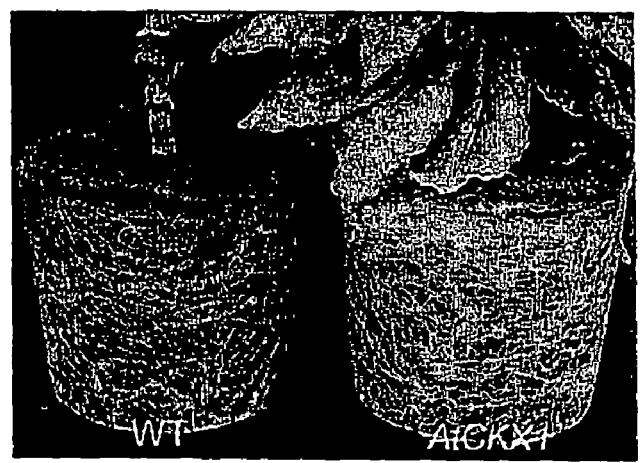
Figure 8:
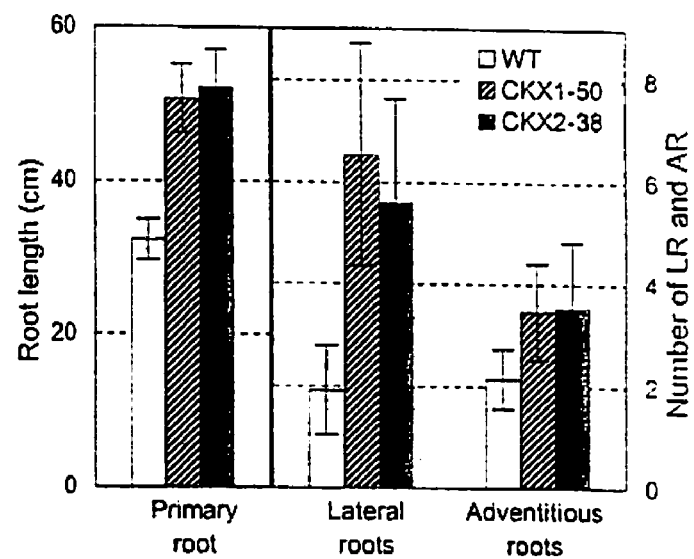
Figure 8:
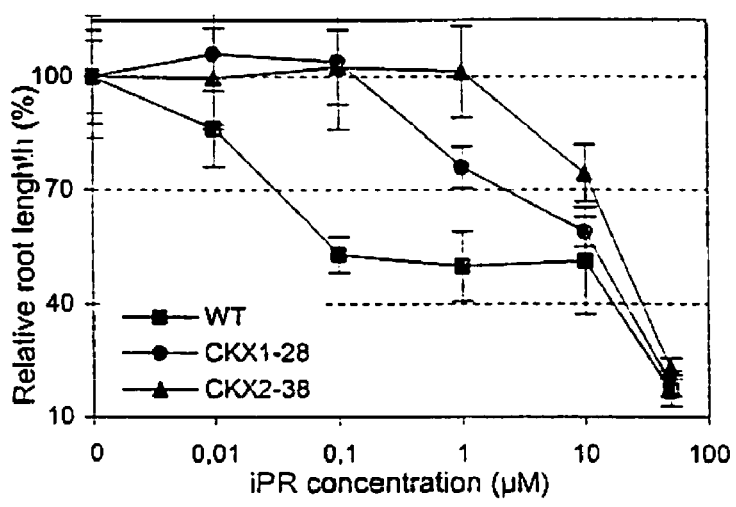

FIG. 8. Root phenotype of AtCKX expressing transgenic tobacco plants.

(A) Seedlings 17 days after germination.

(B) Root system of soil grown plants at the flowering stage.

(C) Root length, number of lateral roots (LR) and adventitious roots (AR) on day 10 after germination.

(D) Dose-response curve of root growth inhibition by exogenous cytokinin. Bars indicate ±SD; n=30.

Figure 9:

FIG. 9: Growth of axillary shoot meristems in 35S::AtCKX1 expressing tobacco plants.

Figure 10:
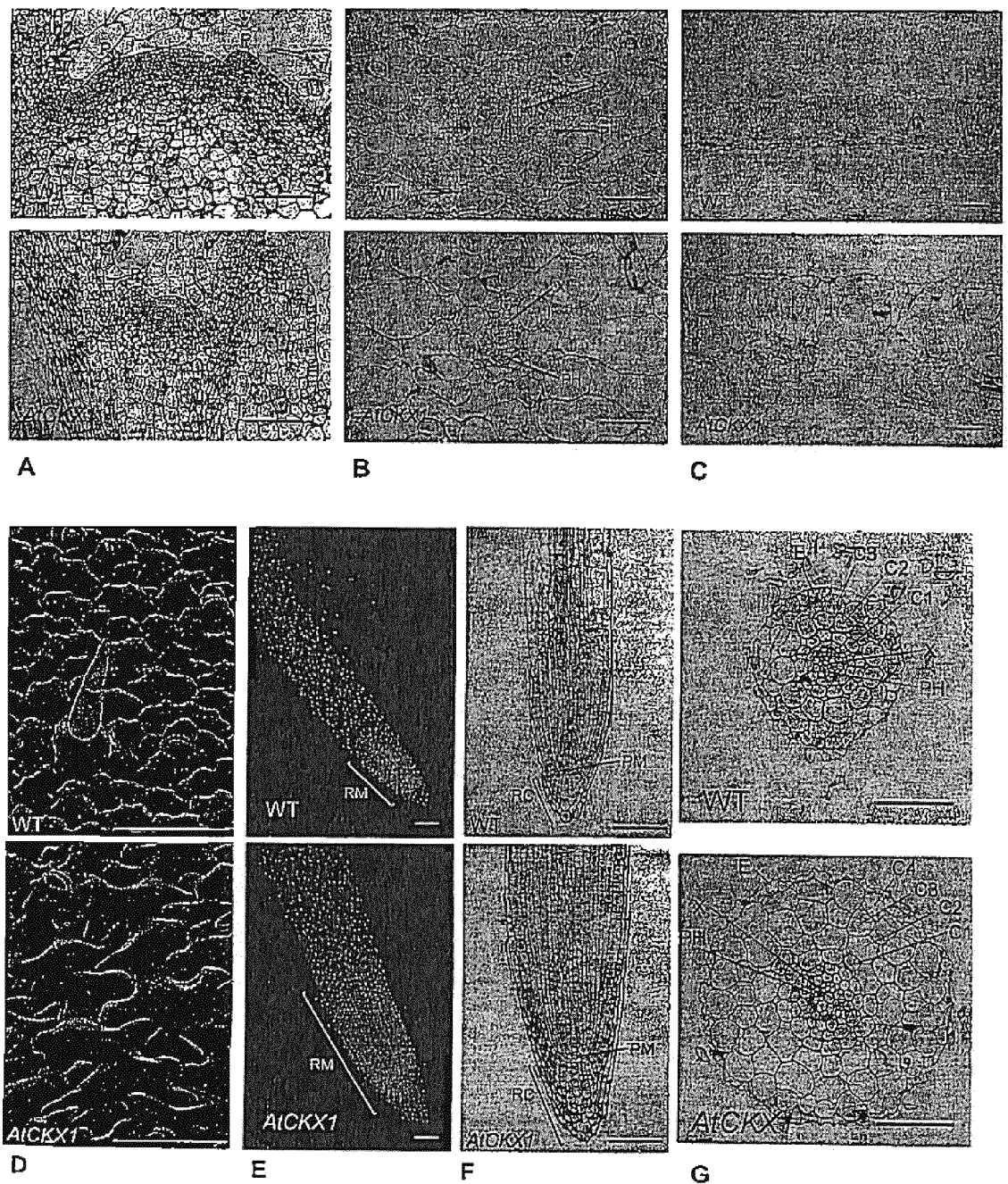

FIG. 10: Histology of shoot meristems, leaves and root meristems of AtCKX1 overexpressing tobacco plants versus wild type (WT) tobacco.

(A) Longitudinal median section through the vegetative shoot apical meristem. P, leaf primordia.

(B) Vascular tissue in second order veins of leaves. X, xylem, PH, a phloem bundle.

(C) Cross sections of fully developed leaves.

(D) Scanning electron microscopy of the upper leaf epidermis.

(E) Root apices stained with DAPI. RM, root meristem.

(F) Longitudinal median sections of root meristems ten days after germination. RC, root cap; PM, promeristem.

(G) Transverse root sections 10 mm from the apex. E, epidermis, C1-C4, cortical cell layer, X, xylem, PH, phloem. Bars are 100 µm.

Figure 11:
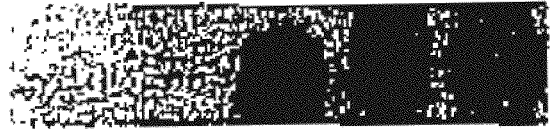
Figure 11:
Figure 11:
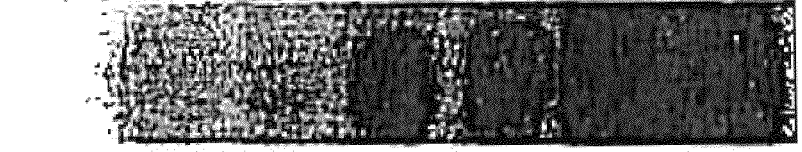
Figure 11:
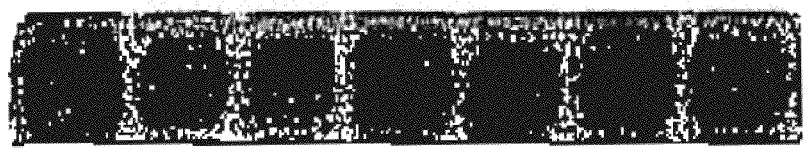

FIG. 11: Northern blot analysis of AtCKX3 and AtCKX4-expressing tobacco plants.

(A) Northern blot analysis of constitutively expressing AtCKX3 tobacco plants. Lane designations indicate individual transgenic plant numbers, WT is wild type SNN tobacco. The blot on top was probed with a AtCKX3 specific probe, the lower blot with a probe specific for the 25S rRNA and serves as a control for RNA loading.

(B) Northern blot analysis of constitutively expressing AtCKX4 tobacco plants. Lane designations indicate individual transgenic plant numbers, WT is wild type SNN tobacco. The blot on top was probed with an AtCKX4 specific probe, the lower blot with a probe specific for the 25S rRNA and serves as a control for RNA loading.

Figure 12:
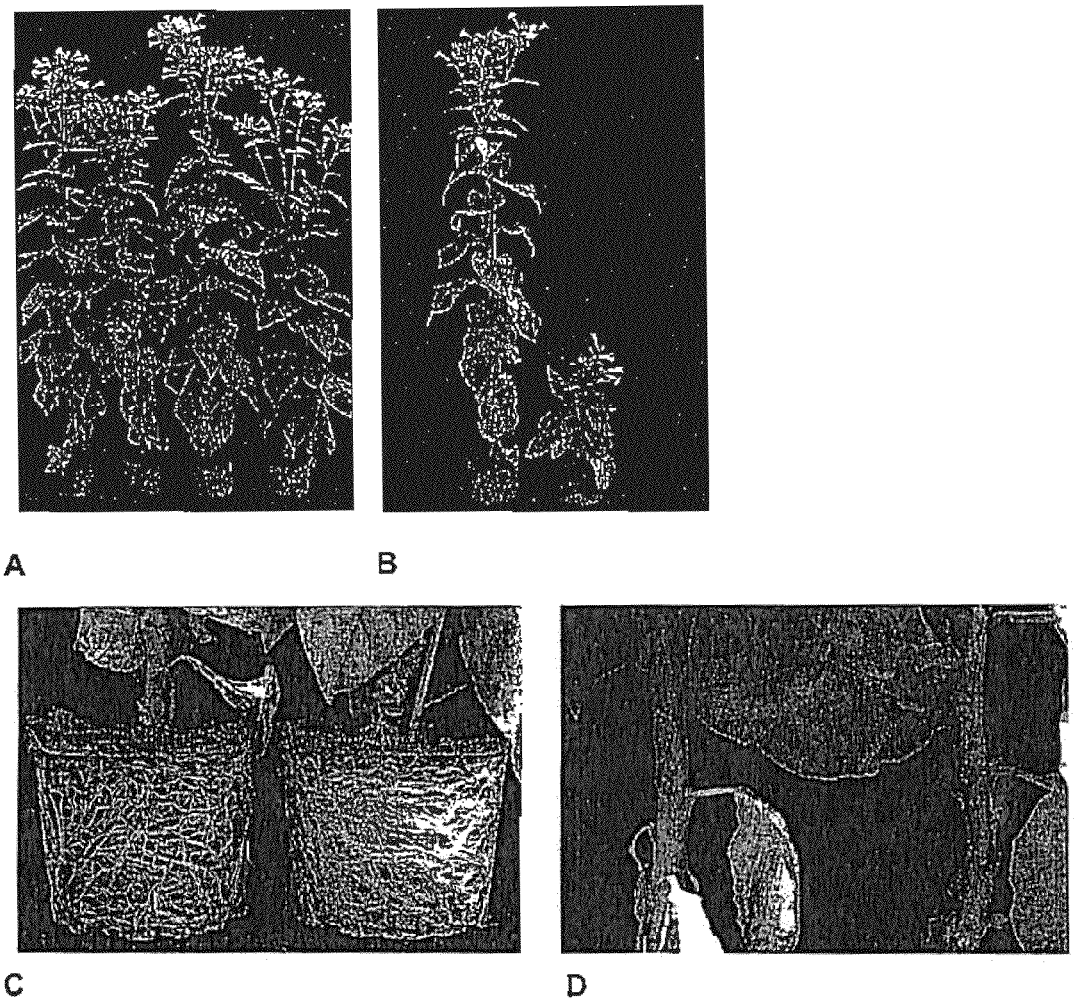

FIG. 12: Reciprocal grafts of AtCKX2 transgenic tobacco plants and wild type plants.

(A) Two plants on the left: Control (WT scion grafted on a WT rootstock).

Two plants on the right: WT scion grafted on a AtCKX2-38 transgenic rootstock.

(B) Left: Control (WT scion grafted on a WT rootstock).

Right: Scion of AtCKX2-38 plant grafted on WT rootstock.

(C) Magnification of root area.

Left: Control (WT scion grafted on a WT rootstock).

Right: WT scion grafted on an AtCKX2-38 transgenic rootstock.

(D) Formation of adventitious roots.

Left: Control (WT scion grafted on an WT rootstock).

Right: WT scion grafted on an AtCKX2-38 transgenic rootstock.

Figure 13A:
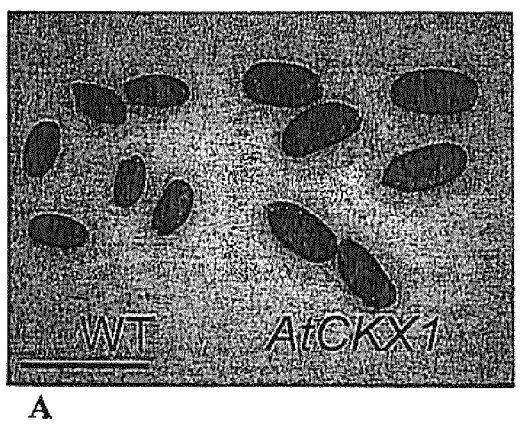
Figure 13B:
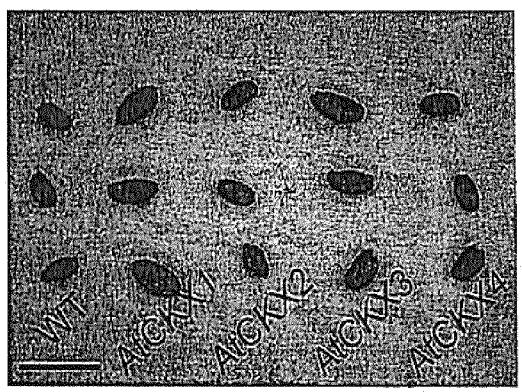
Figure 13C:

FIG. 13: Phenotype of *Arabidopsis* seeds, embryos and seedlings.

(A) Seeds of an AtCKX1 transgenic line and wild type seeds. Bar size 1 mm.

(B) Seeds of AtCKX1, AtCKX2, AtCKX3 and AtCKX4 transgenic lines and wild type seeds. Bar size 1 mm.

(C) Mature embryos of AtCKX1 transgenic *Arabidopsis* and of a wild type plant. Bar size 200 µm. Embryos were obtained from mature seeds that had been imbibed for 12 hours in 20% EtOH, squeezed out from the seed coat, cleared with chloralhydrate and photographed using Nomarski optics.

(D) Wild type (top) and AtCKX1 expressing *Arabidopsis* seedlings 4 days after germination.

(E) Close-up of D.

Figure 14:
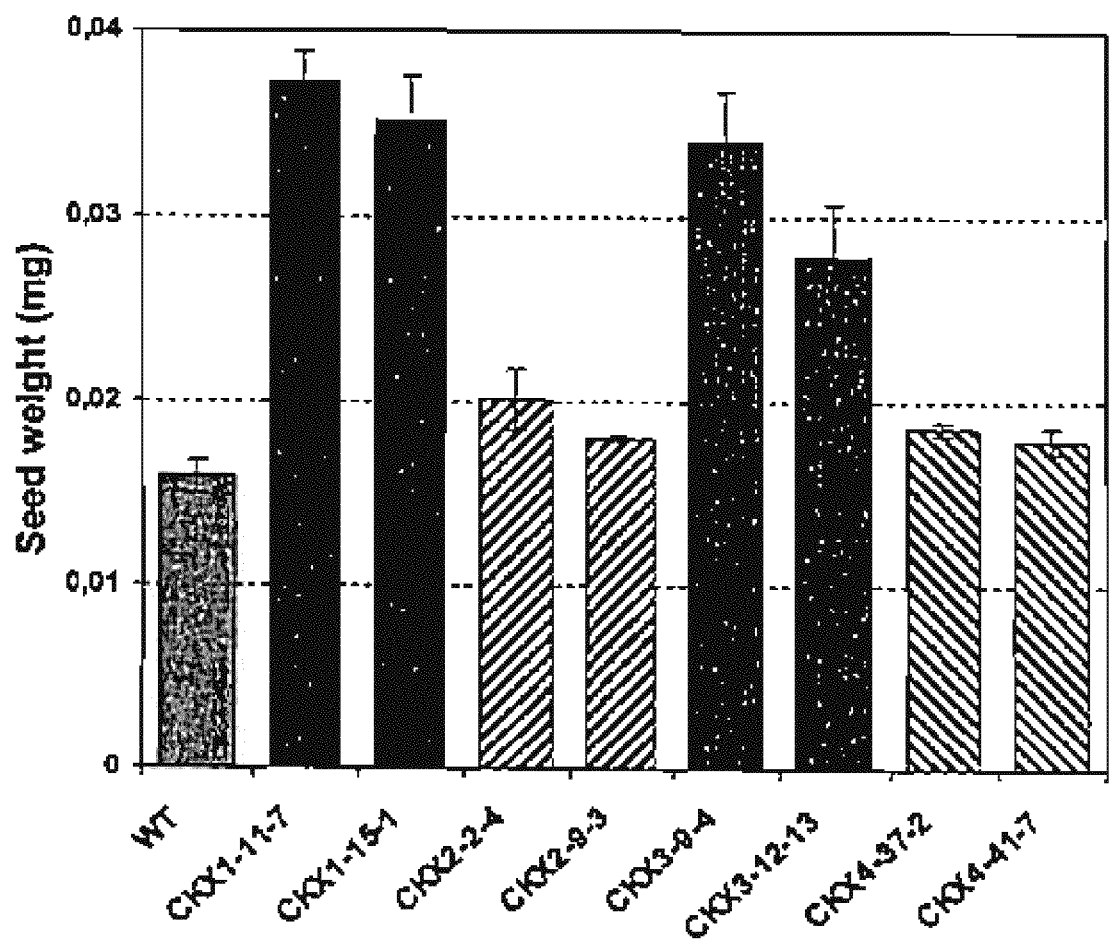

FIG. 14: Seed weight of wild type and two independent clones for each of the four investigated AtCKX genes. Average weight obtained by analysing five different batches of 200 seeds for each clone.

DETAILED DESCRIPTION OF THE INVENTION

To by-pass above-mentioned problems associated with increasing auxin biosynthesis, it was decided to follow an alternative approach. We reasoned that down-regulation of biological antagonists of auxins could evoke similar or even superior effects on root growth as compared to increasing auxin levels. Hormone actions and interactions are extremely complex, but we hypothesized that cytokinins could function as auxin antagonists with respect to root growth. Hormone studies on plant tissue cultures have shown that the ratio of auxin versus cytokinin is more important for organogenesis than the absolute levels of each of these hormones, which indeed indicates that these hormones function as antagonists—at least in certain biological processes. Furthermore, lateral root formation is inhibited by exogenous application of cytokinins. Interestingly, also root elongation is negatively affected by cytokinin treatment, which suggests that cytokinins control both root branching and root outgrowth.

Together, current literature data indicate that increasing cytokinin levels negatively affects root growth, but the mechanisms underlying this process are not understood. The sites of cytokinin synthesis in the plant are root tips and young tissues of the shoot. Endogenous concentrations of cytokinins are in the nM range. However, as their quantification is difficult, rather large tissue amounts need to be extracted and actual local concentrations are not known. Also the subcellular compartmentation of cytokinins is not known. It is generally thought that the free base and ribosides are localized in the cytoplasm and nucleus, while glucosides are localized in the vacuole. There exist also different cytokinins with slightly different chemical structure. As a consequence, it is not known whether the effects of exogenous cytokinins should be ascribed to a raise in total cytokinin concentration or rather to the competing out of other forms of plant-borne cytokinins (which differ either in structure, cellular or subcellular location) for receptors, translocators, transporters, and modifying enzymes.

In order to test the hypothesis that cytokinin levels in the root indeed exceed the level optimal for root growth, novel genes encoding cytokinin oxidases (which are cytokinin metabolizing enzymes) were cloned from *Arabidopsis thaliana* (designated AtCKX) and were subsequently expressed under a strong constitutive promoter in transgenic tobacco and *Arabidopsis*. Transformants showing AtCKX mRNA expression and increased cytokinin oxidase activity also manifested enhanced formation and growth of roots. Negative effects on shoot growth were also observed. The latter is in accordance with the constitutive expression of the cytokinin oxidase gene in these plants, illustrating the importance of confined expression of the cytokinin oxidase gene for general plant growth properties. Containment of cytokinin oxidase activity can be achieved by using cell-, tissue- or organ-specific promoters, since cytokinin degradation is a process limited to the tissues or cells that express the CKX protein, this in contrast to approaches relying on hormone synthesis, as explained above.

The observed negative effects of cytokinin oxidase expression on shoot growth demonstrate that cytokinin oxidases are interesting targets for the design of or screening for growth-promoting chemicals. Such chemicals should inhibit cytokinin oxidase activity, should preferably not be transported to the root and should be rapidly degraded in soil, so that application of these chemicals will not inhibit root growth. Cytokinins also delay leaf senescence, which means that positive effects will include both growth and maintenance of photosynthetic tissues. In addition, the observation that cytokinins delay senescence, enhance greening (chlorophyll content) of leaves and reduce shoot apical dominance shows that strategies based on suppressing CKX activity (such as antisense, ribozyme, and cosuppression technology) in the aerial parts of the plant could result in delayed senescence, enhanced leaf greening and increased branching.

Similarly, the observed positive effects of cytokinin oxidase expression on root growth demonstrate that cytokinin oxidases are interesting targets for the design of or screening for herbicides. Such herbicides should inhibit cytokinin oxidase activity, should preferably not be transported to the shoot, and should be soluble and relatively stable in a solvent that can be administered to the root through the soil.

These effects of cytokinin oxidase overexpression on plant development and architecture were hitherto unknown and, as a consequence, the presented invention and its embodiments could not be envisaged.

The observed negative effects on shoot growth demonstrate that manipulation of cytokinin oxidases can also be used for obtaining dwarfing phenotypes. Dwarfing phenotypes are particularly useful in commercial crops such as cereals and fruit trees for example.

In accordance with the present invention, it has also been surprisingly discovered that transgenic plants overexpressing a cytokinin oxidase gene develop seeds (including embryos) and cotyledons of increased size and/or weight. These results are surprising as a reduced cytokinin content would have been expected to be associated with a reduced organ growth.

Preferable embodiments of the invention relate to the positive effect of cytokinin oxidase expression on plant growth and architecture, and in particular on root growth and architecture, seed size and weight, embryo size and weight, and cotyledon size and weight. The cytokinin oxidase gene family contains at least six members in *Arabidopsis* (see examples below) and the present inventors have shown that there are quantitative differences in the effects achieved with some of these genes in transgenic plants. It is anticipated that functional homologs of the described *Arabidopsis* cytokinin oxidases can be isolated from other organisms, given the evidence for the presence of cytokinin oxidase activity in many green plants (Hare and van Staden, Physiol Plant 91:128-136, 1994; Jones and Schreiber, Plant Growth Reg 23:123-134, 1997), as well as in other organisms (Armstrong, in Cytokinins: Chemistry, Activity and Function. Eds Mok and Mok, CRC Press, pp 139-154, 1994). Therefore, the sequence of the cytokinin oxidase, functional in the invention, need not to be identical to those described herein. This invention is particularly useful for cereal crops and monocot crops in general and cytokinin oxidase genes from for example wheat or maize may be used as well (Morris et al., 1999; Rinaldi and Comandini, 1999). It is envisaged that other genes with cytokinin oxidase activity or with any other cytokinin metabolizing activity (see Zažimalová et al., Biochemistry and Molecular Biology of Plant Hormones, Hooykaas, Hall and Libbenga (Eds.), Elsevier Science, pp 141-160, 1997) can also be used for the purpose of this invention. Similarly, genes encoding proteins that would increase endogenous cytokinin metabolizing activity can also be used for the purpose of this invention. In principle, similar phenotypes could also be obtained by interfering with genes that function downstream of cytokinin such as receptors or proteins involved in signal transduction pathways of cytokinin.

For the purpose of this invention, it should be understood that the term 'root growth' encompasses all aspects of growth of the different parts that make up the root system at different stages of its development, both in monocotyledonous and dicotyledonous plants. It is to be understood that enhanced growth of the root can result from enhanced growth of one or more of its parts including the primary root, lateral roots, adventitious roots, etc. all of which fall within the scope of this invention.

For purposes of this invention, it should also be understood that increases in seed weight or seed size can include increases in the size of one or more of the embryo, the endosperm, aleurone, and seed coat. Moreover, increases in embryo size and/or weight can include increases in different organs associated therewith such as e.g., cotyledons, hypocotyl, and roots.

According to a first embodiment, the present invention relates to a method for stimulating root growth and/or enhancing the formation of lateral and/or adventitious roots and/or altering root geotropism comprising expression of a plant cytokinin oxidase or comprising expression of another protein that reduces the level of active cytokinins in plants or plant parts.

In another embodiment, the present invention relates to a method for increasing plant seed size and/or weight, by increasing the level or activity of a cytokinin oxidase in the plant or by expression, of another protein that reduces the level of active cytokinins in a plant or plant part. Preferably, the increased level or activity of a cytokinin oxidase or expression of another protein that reduces the level of active cytokinins in a plant or plant part is localized in the seed including different tissues or cell types of the seed.

In another embodiment, the present invention relates to a method for increasing plant embryo size and/or weight, by increasing the level or activity of a cytokinin oxidase in the plant or by expression of another protein that reduces the level of active cytokinins in a plant or plant part. Preferably, the increased level or activity of a cytokinin oxidase or expression of another protein that reduces the level of active cytokinins in a plant or plant part is localized in the seed. Even more preferably, the increased level or activity of a cytokinin oxidase or expression of another protein that reduces the level of active cytokinins in a plant or plant part is localized in the embryo.

In yet another embodiment, the present invention relates to a method for increasing plant cotyledon size and/or weight, by increasing the level or activity of a cytokinin oxidase in the plant or by expression of another protein that reduces the level of active cytokinins in a plant or plant part. Preferably, the increased level or activity of a cytokinin oxidase or expression of another protein that reduces the level of active cytokinins in a plant or plant part is localized in the cotyledon.

In the context of the present invention it should be understood that the term "expression" and/or 'overexpression' are used interchangeably and both relate to an "enhanced and/or ectopic expression" of a plant cytokinin oxidase or any other protein that reduces the level of active cytokinins in plants. It should be clear that herewith an enhanced expression of the plant cytokinin oxidase as well as "de novo" expression of plant cytokinin oxidases or of said other proteins is meant. Alternatively, said other protein enhances the cytokinin metabolizing activity of a plant cytokinin oxidase.

It further should be understood that in the context of the present invention the expression "lateral and/or adventitious roots" can mean "lateral and adventitious roots" but also "lateral or adventitious roots". The enhancement can exist in the formation of lateral roots or in the formation of adventitious roots as well as in the formation of both types of non-primary roots, but not necessarily.

In addition, as used herein, "increasing seed size and/or weight," can mean increasing seed size and weight, but also size or weight. Thus, the enhancement can exist in an increase in the size of the seed or the weight of the seed or both. Similar interpretations should be applied to "increasing embryo size and/or weight" and "increasing cotyledon size and/or weight."

The terms "plant" and "plant part" are used interchangeably with the terms "plants" and "plant parts."

According to a further embodiment, the present invention relates to a method for stimulating root growth and/or enhancing the formation of lateral or adventitious roots and/or altering root geotropism and/or increasing yield and/or enhancing early vigor and/or modifying root/shoot ratio and/or improving resistance to lodging and/or increasing drought tolerance and/or promoting in vitro propagation of explants, comprising expression of a plant cytokinin oxidase or comprising expression of another protein that reduces the level of active cytokinins in plants or plant parts.

According to a preferred embodiment, the present invention relates to a method for stimulating root growth resulting in an increase of root mass by overexpression of a cytokinin oxidase, preferably a cytokinin oxidase according to the invention, or another protein that reduces the level of active cytokinins in plants or plant parts, preferably in roots.

Higher root biomass production due to overexpression of growth promoting sequences has a direct effect on the yield and an indirect effect of production of compounds produced by root cells or transgenic root cells or cell cultures of said transgenic root cells. One example of an interesting compound produced in root cultures is shikonin, the yield of which can be advantageously enhanced by said methods.

According to a more specific embodiment, the present invention relates to methods for stimulating root growth or for enhancing the formation of lateral and/or adventitious roots or for altering root geotropism or for increasing seed size and/or weight, or for increasing embryo size and/or weight, or for increasing cotyledon size and/or weight. The methods comprise expression of a nucleic acid encoding a plant cytokinin oxidase selected from the group consisting of:

(a) nucleic acids comprising a DNA sequence as given in any of SEQ ID NOs: 27, 1, 3, 5, 7, 9, 11, 25, 26, 28 to 31, 33 or 34, or the complement thereof, (b) nucleic acids comprising the RNA sequences corresponding to any of SEQ ID NOs: 27, 1, 3, 5, 7, 9, 11, 25, 26, 28 to 31, 33 or 34, or the complement thereof, (c) nucleic acids specifically hybridizing to any of SEQ ID NOs: 27, 1, 3, 5, 7, 9, 11, 25, 26, 28 to 31, 33 or 34, or to the complement thereof, (d) nucleic acids encoding a protein comprising the amino acid sequence as given in any of SEQ ID NOs: 2, 4, 6, 8, 10, 12, 32 or 35, or the complement thereof, (e) nucleic acids as defined in any of (a) to (d) characterized in that said nucleic acid is DNA, genomic DNA, cDNA, synthetic DNA or RNA wherein T is replaced by U, (f) nucleic acids which are degenerated to a nucleic acid as given in any of SEQ ID NOs: 27, 1, 3, 5, 7, 9, 11, 25, 26, 28 to 31, 33 or 34, or which are degenerated to a nucleic acid as defined in any of (a) to (e) as a result of the genetic code, (g) nucleic acids which are diverging from a nucleic acid encoding a protein as given in any of SEQ ID NOs: 2, 4, 6, 8, 10, 12 or 35 or which are diverging from a nucleic acid as defined in any of (a) to (e), due to the differences in codon usage between the organisms, (h) nucleic acids encoding a protein as given in SEQ ID NOs: 2, 4, 6, 8, 10, 12 or 35 or nucleic acids as defined in (a) to (e) which are diverging due to the differences between alleles, (i) nucleic acids encoding a protein as given in any of SEQ ID NOs: 2, 4, 6, 8, 10, 12 or 35, (j) functional fragments of nucleic acids as defined in any of (a) to (i) having the biological activity of a cytokinin oxidase, and (k) nucleic acids encoding a plant cytokinin oxidase, or comprise expression, preferably in roots, or in seeds (including parts of seeds such as embryo, endosperm, seed coat or aleurone) or in cotyledons, of a nucleic acid encoding a protein that reduces the level of active cytokinins in plants or plant parts.

In the present invention, nucleic acids encoding novel *Arabidopsis thaliana* cytokinin oxidases have been isolated and for the first time, the present inventors have surprisingly shown that the expression of cytokinin oxidases in transgenic plants or in transgenic plant parts resulted in the above-mentioned root and seed-related features. In order that root-related features be effected, the expression of the cytokinin oxidase(s) should take place in roots, preferably under the control of a root-specific promoter. In order that seed-related features be effected (including the embryo), expression of the cytokinin oxidase(s) should take place in seeds, preferably under the control of a seed-specific promoter. One example of such a root-specific promoter is provided in SEQ ID NO: 36. Examples of seed-specific promoters include but are not limited to those listed in Table 4.

In order that cotyledon-related features be effected, the expression of the cytokinin oxidase(s) should take place in the cotyledons, preferably under the control of a promoter which preferentially expresses in cotyledon.

It should be clear that, although the invention is supported in the examples section by several new AtCKX genes and proteins, the inventive concept also relates to the use of other cytokinin oxidases isolated from and expressed in other plants, preferably in the roots and/or seeds and/or cotyledons of said other plants to obtain similar effects in plants as described in the examples section.

Therefore, the present invention more generally relates to the use of a nucleic acid encoding a plant cytokinin oxidase or encoding a protein that reduces the level of active cytokinins in plants or plant parts for stimulating root growth or for enhancing the formation of lateral or adventitious roots or for altering root geotropism. The present invention also relates to the use of a nucleic acid encoding a plant cytokinin oxidase or encoding a protein that reduces the level of active cytokinins in plants or plant parts for increasing seed size and/or weight, or for increasing embryo size and/or weight, or for increasing plant cotyledon size and/or weight. Preferred cytokinin oxidases to be used are encoded by the nucleic acids encoding the cytokinin oxidases as defined above and are encoded by the novel nucleic acids of the invention as defined hereunder.

The invention relates to an isolated nucleic acid encoding a novel plant protein having cytokinin oxidase activity selected from the group consisting of:

(a) a nucleic acid comprising a DNA sequence as given in any of SEQ ID NOs: 29, 3, 5, 9, 26, 27, 31, 33 or 34, or the complement thereof, (b) a nucleic acid comprising the RNA sequences corresponding to any of SEQ ID NOs: 29, 3, 5, 9, 26, 27, 31, 33 or 34, or the complement thereof, (c) a nucleic acid specifically hybridizing to a nucleic acid as given in any of SEQ ID NOs: 29, 3, 5, 9, 26, 27, 31, 33 or 34, or the complement thereof, (d) a nucleic acid encoding a protein with an amino acid sequence comprising the polypeptide as given in SEQ ID NO: 32 and which is at least 70% similar, preferably at least 75%, 80% or 85%, more preferably at least 90% or 95%, most preferably at least 99% similar to the amino acid sequence as given in SEQ ID NO: 4, (e) a nucleic acid encoding a protein with an amino acid sequence which is at least 35% similar, preferably 37%, 40%, 45%, 47% or 50%, similar, more preferably 55%, 60%, 65%, 70%, 75% or 80% similar, most preferably 85%, 90% or 95% similar to the amino acid sequence as given in SEQ ID NO: 6, (f) a nucleic acid encoding a protein with an amino acid sequence which is at least 35% similar, preferably 37%, 40%, 45%, 47% or 50%, similar, more preferably 55%, 60%, 65%, 70%, 75% or 80% similar, most preferably 85%, 90% or 95% similar to the amino acid sequence as given in SEQ ID NO: 10 or 35, (g) a nucleic acid encoding a protein comprising the amino acid sequence as given in any of SEQ ID NOs: 4, 6, 10, 32 or 35, (h) a nucleic acid which is degenerated to a nucleic acid as given in any of SEQ ID NOs: 29, 3, 5, 9, 26, 27, 33 or 34 or which is degenerated to a nucleic acid as defined in any of (a) to (g) as a result of the genetic code, (i) a nucleic acid which is diverging from a nucleic acid encoding a protein as given in any of SEQ ID NOs: 4, 6, 10 or 35 or which is diverging from a nucleic acid as defined in any of (a) to (g) due to the differences in codon usage between the organisms, (j) a nucleic acid encoding a protein as given in SEQ ID NOs: 4, 6, 10 or 35, or a nucleic acid as defined in (a) to (g) which is diverging due to the differences between alleles, (k) a nucleic acid encoding an immunologically active fragment of a cytokinin oxidase encoded by a nucleic acid as given in any of SEQ ID NOs: 29, 3, 5, 9, 26, 27, 31, 33 or 34, or an immunologically active fragment of a nucleic acid as defined in any of (a) to (j), (l) a nucleic acid encoding a functional fragment of a cytokinin oxidase encoded by a nucleic acid as given in any of SEQ ID NOs: 29, 3, 5, 9, 26, 27, 31, 33 or 34, or a functional fragment of a nucleic acid as defined in any of (a) to (j), wherein said fragment has the biological activity of a cytokinin oxidase, and (m) a nucleic acid encoding a protein as defined in SEQ ID NOs: 4, 6, 10 or 35, provided that said nucleic acid is not the nucleic acid as deposited under any of the following Genbank accession numbers: AC005917, AB024035, and AC023754

The invention also relates to an isolated nucleic acid of the invention which is DNA, cDNA, genomic DNA or synthetic DNA, or RNA wherein T is replaced by U.

The invention also relates to a nucleic acid molecule of at least 15 nucleotides in length hybridizing specifically with or specifically amplifying a nucleic acid of the invention.

Different cytokinin forms may have differing roles to play in the various developmental processes. Thus, differential effects of CKX1, CKX2, CKX 3 and CKX4 may relate to distinct effects on the pools of different cytokinins. For example, CKX1 and CKX3 mostly promote root elongation and branching, while CKX2 and CKX4 primarily stimulate the formation of adventitious roots. In addition, CKX1 and CKX3 increase seed size and weight to a greater degree than CKX2 and CKX4. Without being bound to a particular mode of action, this differential effect on cytokine pools may result from some differences in substrate specificity or from differential compartmentation of cytokinin oxidases in the cell (predicted to be mitochondrial for CKX1 and CKX3, while extracellular for CKX 2, CKX4, CKX5, and CKX6).

According to another embodiment, the invention also relates to a vector comprising a nucleic acid of the invention. In a preferred embodiment, said vector is an expression vector wherein the nucleic acid is operably linked to one or more control sequences allowing the expression of said sequence in prokaryotic and/or eukaryotic host cells.

It should be understood that for expression of the cytokinin oxidase genes of the invention in monocots, a nucleic acid sequence corresponding to the cDNA sequence should be used to avoid mis-splicing of introns in monocots. Preferred cDNA sequences to be expressed in monocots have a nucleic acid sequence as represented in any of SEQ ID NOs: 25 to 30 and 34.

The invention also relates to a host cell containing any of the nucleic acid molecules or vectors of the invention. Said host cell is chosen from the group comprising bacterial, insect, fungal, plant or animal cells.

Another embodiment of the invention relates to an isolated polypeptide encodable by a nucleic acid of the invention, or a homologue or a derivative thereof, or an immunologically active or a functional fragment thereof. Preferred polypeptides of the invention comprise the amino acid sequences as represented in any of SEQ ID NOs: 2, 4, 6, 8, 10; 12, 32 and 35, or a homologue or a derivative thereof, or an immunologically active and/or functional fragment thereof. In an even more preferred embodiment, the invention relates to a polypeptide which has an amino acid sequence as given in SEQ ID: NO 2, 4, 6, 8, 10, 12 or 35, or a homologue or a derivative thereof, or an immunologically active and/or functional fragment thereof. Preferred functional fragments thereof are those fragments which are devoid of their signal peptide.

According to yet another embodiment, the invention relates to a method for producing a polypeptide of the invention comprising culturing a host cell of the invention under conditions allowing the expression of the polypeptide and recovering the produced polypeptide from the culture.

The invention also relates to an antibody specifically recognizing a polypeptide of the invention or a specific epitope thereof.

The invention further relates to a method for the production of transgenic plants, plant cells or plant tissues comprising the introduction of a nucleic acid molecule of the invention in an expressible format or a vector of the invention in said plant, plant cell or plant tissue.

The invention also relates to a method for the production of altered plants, plant cells or plant tissues comprising the introduction of a polypeptide of the invention directly into a cell, a tissue or an organ of said plant.

According to another embodiment, the invention relates to a method for effecting the expression of a polypeptide of the invention comprising the introduction of a nucleic acid molecule of the invention operably linked to one or more control sequences or a vector of the invention stably into the genome of a plant cell. The invention further relates to the method as described above further comprising regenerating a plant from said plant cell.

The invention also relates to a transgenic plant cell comprising a nucleic acid sequence of the invention which is operably linked to regulatory elements allowing transcription and/or expression of said nucleic acid in plant cells or obtainable by a method as explained above.

According to another preferred embodiment, the invention relates to a transgenic plant cell as described hereinabove wherein the nucleic acid of the invention is stably integrated into the genome of said plant cell.

The invention further relates to a transgenic plant or plant tissue comprising plant cells as herein described and also to a harvestable part of said transgenic plant, preferably selected from the group consisting of seeds, leaves, fruits, stem cultures, roots, tubers, rhizomes and bulbs. The invention also relates to the progeny derived from any of said transgenic plants or plant parts.

According to another embodiment, the invention relates to a method for stimulating root growth comprising expression of a nucleic acid of the invention or comprising expression of another protein that reduces the level of active cytokinins in plants or plant parts.

In another aspect of the invention, there is provided a method of increasing seed size and/or weight. The method comprises increasing the level or activity of a cytokinin oxidase in a plant or increasing the level or activity of a protein that reduces the level of active cytokinins in a plant or plant part, preferably seeds.

Various parts (organs) of the seed may also be increased in size and/or weight such as e.g., embryo, endosperm, seed coat, or aleurone. For example, in accordance with the present invention, there is provided a method of increasing embryo size and/or weight. The method comprises increasing the level or activity of a cytokinin oxidase in a plant or increasing the level or activity of a protein that reduces the level of active cytokinins in a plant or plant part, preferably embryos.

In still another aspect of the invention, there is provided a method of increasing cotyledon size and/or weight. The method comprises increasing the level or activity of a cytokinin oxidase in a plant or increasing the level or activity of a protein that reduces the level of active cytokinins in a plant or plant part, preferably cotyledons.

In accordance with the methods of increasing seed size and/or weight, there is a resultant increase in the speed of growth of seedlings or an increase in early vigor. Increases in yield are also obtained. Similarly, in accordance with the methods of increasing embryo size and/or weight, or cotyledon size and/or weight, there is a resultant increase in speed of growth of seedlings or an increase in early vigor. In many cases, increases in yield are also obtained. Increases in growth of seedlings or early vigor is often associated with increased stress tolerance. For example, faster development of seedlings, including the root systems of seedlings upon germination is critical for survival particularly under adverse conditions such as drought.

Any nucleotide sequence encoding a polypeptide with cytokinin oxidase activity may be used in the methods of the invention. For example, any of the various sequences provided herein encoding a polypeptide with cytokinin oxidase activity may be used in the methods of increasing seed, embryo, or cotyledon size and/or weight.

Preferably, transgenic plants are produced which express a nucleic acid as set forth in any of SEQ ID NOs: 1, 5, 25, or 27 or an ortholog of said nucleic acid. Preferably, the ortholog is derived from a related species of the transgenic plant. Even more preferably, the ortholog is specific (native or endogenous) to the species of the transgenic plant.

As described above, promoters which control expression specifically, or preferentially may be used in the methods of the invention. Thus, where increases in seed size or weight are desired, a seed-specific promoter may be used. Where increases in embryo size or weight are desired, an embryo-specific promoter may be used. Where increases in cotyledon size or weight is desired, a promoter which controls expression in cotyledons is preferred. Such promoters are well known, widely available and listed herein in e.g., Table 4.

In another embodiment, the invention relates to a method for increasing seed size or seed weight, or both, said method comprising expression of a nucleic acid of the invention or comprising expression of another protein that reduces the level of active cytokinins in plants or plant parts In yet another embodiment, the invention relates to a method for increasing embryo size or weight, or both, said method comprising expression of a nucleic acid of the invention or comprising expression of another protein that reduces the level of active cytokinins in plants or plant parts.

In still another embodiment, the invention relates to a method for increasing cotyledon size comprising expression of a nucleic acid of the invention or comprising expression of another protein that reduces the level of active cytokinins in plants or plant parts. Localized expression of a subject cytokinin oxidase gene or part thereof, or of another protein that reduces the level of active cytokinins in plants or plant parts leads to enhanced growth of cotyledons. In species having cotyledons as storage organs, such enhanced growth of cotyledons leads to enhanced yields and/or to enhanced growth performance of seedlings. Further in this regard, carbohydrates, lipids and proteins are all stored within seeds and are metabolized during germination in order to provide energy and metabolites during early growth of the plant. Seed size is often associated with early vigor, since larger seeds contain more carbohydrates, lipids and proteins and thus confer faster growth. Thus, the methods of the present invention lead to faster growth of seedlings. Such early vigor is associated with enhanced stress tolerance. For example, faster development of a plant's root system is critical for survival, particularly under adverse conditions, such as drought. Early vigor is also related to enhanced yield and shortened time to flowering.

A plant cell or tissue culture is an artificially produced culture of plants cells or plant tissues that is grown in a special medium, either liquid or solid, which provides these plant cells or tissues with all requirements necessary for growth and/or production of certain compounds. Plant cell and/or tissue cultures can be used for the rapid propagation of plants and for the production of transgenic plant to name a few examples. Root formation can be difficult for some explants or under some conditions in said cultures and expression of a cytokinin oxidase gene in said cultured plant cells or tissue(s) can be used to enhance root formation. Plant cell and/or tissue culture can also be used for the industrial production of valuable compounds. Possible production compounds are pharmaceuticals, pesticides, pigments, cosmetics, perfumes, food additives, etc. An example of such a product is shikonin, which is produced by the roots of the plant *Lithospermum erythrorhizon*. An example of a plant tissue culture is a hairy root culture, which is an artificially produced mass of hairy roots. Roots of *L. erythrorhizon* are difficult to collect in large numbers and by preparing hairy root cultures, the end product shikonin could be industrially prepared at a faster rate than would normally occur. As disclosed herein, expression of cytokinin oxidases enhances root growth and development and can therefore be used advantageously in said plant cell and tissue culture procedures. Therefore, according to another embodiment of this invention, a method is provided for stimulating root growth and development comprising expression of a nucleic acid encoding a plant cytokinin oxidase, preferably a cytokinin oxidase of the invention, in a transgenic plant cell or tissue culture comprising said transgenic plant cells.

The invention further relates to a method for enhancing the formation of lateral or adventitious roots comprising expression of a nucleic acid of the invention or comprising expression of another protein that reduces the level of active cytokinins in plants or plant parts.

The invention also relates to method for altering root geotropism comprising altering the expression of a nucleic acid of the invention or comprising expression of another protein that that reduces the level of active cytokinins in plants or plant parts.

The invention also relates to methods for enhancing early vigor and/or for modifying root/shoot ratio and/or for improving resistance to lodging and/or for increasing drought tolerance and/or for promoting in vitro propagation of explants comprising expression of a nucleic acid of the invention comprising expression of another protein that reduces the level of active cytokinins in plants or plant parts.

The invention further relates to methods for increasing the root size or the size of the root meristem comprising expression of a nucleic acid of the invention or comprising expression of another protein that reduces the level of active cytokinins in plants or plant parts, preferably in roots.

According to yet another embodiment, the invention relates to a method for increasing the size of the shoot meristem comprising downregulation of expression of a nucleic acid of the invention, preferably in shoots.

According to a preferred embodiment the invention relates to a method for delaying leaf senescence comprising downregulation of expression of any of the cytokinin oxidases of the invention in leaves, preferably in senescing leaves. Also the invention relates to a method for altering leaf senescence comprising expression of one of the cytokinin oxidases in senescing leaves.

The invention also relates to methods for increasing leaf thickness comprising expression of a nucleic acid of the invention or comprising expression of another protein that reduces the level of active cytokinins in plants or plant parts, preferably in leaves.

The invention also relates to a method for reducing the vessel size comprising expression of a nucleic acid of the invention or comprising expression of another protein that reduces the level of active cytokinins in plants or plant parts, preferably in vessels.

The invention further relates to a method for increasing the vessel size comprising downregulation of expression of a nucleic acid of the invention in plants or plant parts.

According to another embodiment, the invention relates to a method for improving standability of seedlings comprising expression of a nucleic acid of the invention or comprising expression of another protein that reduces the level of active cytokinins in seedlings.

Furthermore, the invention relates to any of the above described methods, said method leading to an increase in yield.

The invention further relates to any of the methods of the invention wherein said expression of said nucleic acid occurs under the control of a strong constitutive promoter. With respect to those aspects of the invention having effects on plant roots such as e.g., methods for stimulating root growth, enhancing the formation of lateral or adventitious roots, or for altering root geotropism, preferably, expression of a subject nucleic acid preferably occurs under the control of a promoter that is preferentially expressed in roots. In Table 5 a non-exhaustive list of root specific promoters is included. A preferred promoter to be used in the methods of the invention is the root clavata homolog promoter, having a sequence as given in SEQ ID NO: 36.

With respect to those aspect of the invention having effects on plant seeds such as e.g., methods for increasing seed size or weight, embryo size or weight, or having effects on plant cotyledons such as methods for increasing cotyledon size of weight, expression of a subject nucleic acid occurs under the control of a promoter that is preferentially expressed in seeds. A seed specific promoter may be one which is expressed in all seed organs or one which shows a preference in expression to one or more organs or tissue such as the embryo, endosperm, or aleurone. Examples of such promoters are set forth herein at Table 4.

According to yet another embodiment, the invention relates to a method for modifying cell fate and/or modifying plant development and/or modifying plant morphology and/or modifying plant biochemistry and/or modifying plant physiology and/or modifying the cell cycle progression rate comprising the modification of expression in particular cells, tissues or organs of a plant, of a nucleic acid of the invention.

The invention also relates to a method for obtaining enhanced growth, and/or increased yield and/or altered senescence of a plant cell, tissue and/or organ and/or increased frequency of formation of lateral organs in a plant, comprising the ectopic expression of a nucleic acid of the invention.

The invention also relates to a method for promoting and extending cell division activity in cells in adverse growth conditions and/or in stress, comprising the ectopic expression of a nucleic acid sequence of the invention.

According to yet another embodiment, the invention relates to a method for identifying and obtaining proteins interacting with a polypeptide of the invention comprising a screening assay wherein a polypeptide of the invention is used.

In a more preferred embodiment, the invention relates to a method for identifying and obtaining proteins interacting with a polypeptide of the invention comprising a two-hybrid screening assay wherein a polypeptide of the invention as a bait and a cDNA library as prey are used.

The invention further relates to a method for modulating the interaction between a polypeptide of the invention and interacting protein partners obtainable by a method as described above.

In a further embodiment, the invention relates to a method for identifying and obtaining compounds interacting with a polypeptide of the invention comprising the steps of:
 (a) providing a two-hybrid system wherein a polypeptide of the invention and an interacting protein partner obtainable by a method as described above,
 (b) interacting said compound with the complex formed by the expressed polypeptides as defined in a), and,
 (c) performing (real-time) measurement of interaction of said compound with said polypeptide or the complex formed by the expressed polypeptides as defined in a).

The invention further relates to a method for identifying compounds or mixtures of compounds which specifically bind to a polypeptide of the invention, comprising:
 (a) combining a polypeptide of the invention with said compound or mixtures of compounds under conditions suitable to allow complex formation, and,
 (b) detecting complex formation, wherein the presence of a complex identifies a compound or mixture which specifically binds said polypeptide.

The invention also relates to a method as described above wherein said compound or mixture inhibits the activity of said polypeptide of the invention and can be used for the rational design of chemicals.

According to another embodiment, the invention relates to the use of a compound or mixture identified by means of a method as described above as a plant growth regulator or herbicide.

The invention also relates to a method for production of a plant growth regulator or herbicide composition comprising the steps of the compound screening methods described above and formulating the compounds obtained from said steps in a suitable form for the application in agriculture or plant cell or tissue culture.

The invention also relates to a method for increasing branching comprising expression of a nucleic acid of the invention in plants or plant parts, preferably in stems or axillary buds.

The invention also relates to a method for improving lodging resistance comprising expression of a nucleic acid of the invention in plants or plant parts, preferably in stems or axillary buds.

The invention also relates to a method for the design of or screening for growth-promoting chemicals or herbicides comprising the use of a nucleic acid of the invention or a vector of the invention.

According to another embodiment, the invention relates to the use of a nucleic acid molecule of the invention, a vector of the invention or a polypeptide of the invention for increasing yield.

The invention also relates to the use of a nucleic acid molecule of the invention, a vector of the invention or a polypeptide of the invention for stimulating root growth.

The invention also relates to the use of a nucleic acid molecule of the invention, a vector of the invention or a polypeptide of the invention for enhancing the formation of lateral or adventitious roots.

The invention also relates to the use of a nucleic acid molecule of the invention, a vector of the invention or a polypeptide of the invention for altering root geotropism.

The invention also relates to the use of a nucleic acid molecule of the invention, a vector of the invention or a polypeptide of the invention for increasing at least one of seed size, seed weight, embryo size, embryo weight, cotyledon size, and cotyledon weight.

The invention further relates to the use of a nucleic acid molecule of the invention, a vector of the invention or a polypeptide of the invention for enhancing early vigor and/or for modifying root/shoot ratio and/or for improving resistance to lodging and/or for increasing drought tolerance and/or for promoting in vitro propagation of explants.

The invention also relates to the use of a nucleic acid molecule of the invention, a recombinant vector of the invention or a polypeptide of the invention for modifying plant development and/or for modifying plant morphology and/or for modifying plant biochemistry and/or for modifying plant physiology.

According to yet another embodiment, the invention relates to a diagnostic composition comprising at least a nucleic acid molecule of the invention, a vector of the invention, a polypeptide of the invention or an antibody of the invention.

Another embodiment of the current invention relates to the use of a transgenic rootstock that has an enhanced root growth and development due to expression of a cytokinin oxidase in grafting procedures with a scion to produce a plant or tree with improved agricultural or horticultural characteristics. The scion may be transgenic or non-transgenic. Specific characteristics envisaged by this embodiment are those conferred by root systems and include improved anchoring of the plant/tree in the soil and/or improved uptake of water resulting for example in improved drought tolerance, and/or improved nutrient uptake from the soil and/or improved transport of organic substances throughout the plant and/or enhanced secretion of substances into the soil such as for example phytosiderophores, and/or improved respiration and/or improved disease resistance and/or enhanced yield. An advantage of using AtCKX transformed rootstocks for grafting, in addition to their enhanced root system, is the delayed senescence of leaves on the graft, as disclosed herein (see FIG. 12 A). Preferred plants or trees for this particular embodiment include plants or trees that do not grow well on their own roots and are grafted in cultivated settings such as commercially profitable varieties of grapevines, citrus, apricot, almond, plum, peach, apple, pear, cherry, walnut, fig, hazel and loquat.

As mentioned supra, auxins and cytokinins act as antagonists in certain biological processes. For example, the cytokinin/auxin ratio regulates the production of roots and shoots with a high concentration of auxin resulting in organized roots and a high concentration of cytokinins resulting in shoot production. As disclosed in this invention, expression of cytokinin oxidases in tobacco and *Arabidopsis* results in enhanced root development consistent with enhanced auxin effects. Auxins are also involved in the development of fruit. Treatment of female flower parts with auxin results in the development of parthenocarpic fruit in some plant species. Parthenocarpic fruit development has been genetically engineered in several horticultural crop plants through increased biosynthesis of auxins in the female reproductive organs (WO0105985).

Therefore, according to another embodiment, this invention relates to a method for inducing the parthenocarpic trait in plants, said method consisting of downregulating the expression of one or more cytokinin oxidases or of another protein that reduces the level of active cytokinins in plants or plant parts, preferably in the female reproductive organs such as the placenta, ovules and tissues derived therefrom. The DefH9 promoter region from *Antirrhinum majus* or one of its homologues, which confer high expression specificity in placenta and ovules, can be used for this purpose.

Those skilled in the art will be aware that the invention described herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any or more of said steps or features.

The present invention is applicable to any plant, in particular a monocotyledonous plants and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis, Albizia amara, Alsophila tricolor, Andropogon* spp., *Arachis* spp, *Areca catechu, Astelia fragrans, Astragalus cicer, Baikiaea plurijuga, Betula* spp., *Brassica* spp., *Bruguiera gymnorrhiza, Burkea africana, Butea frondosa, Cadaba farinosa, Calliandra* spp, *Camellia sinensis, Canna indica, Capsicum* spp., *Cassia* spp., *Centroema pubescens, Chaenomeles* spp., *Cinnamomum cassia, Coffee arabica, Colophospermum mopane, Coronillia varia, Cotoneaster serotina, Crataegus* spp., *Cucumis* spp., *Cupressus* spp., *Cyathea dealbata, Cydonia oblonga, Cryptomeria japonica, Cymbopogon* spp., *Cynthea dealbata, Cydonia oblonga, Dalbergia monetaria, Davallia divaricata, Desmodium* spp., *Dicksonia squarrosa, Diheteropogon amplectens, Dioclea* spp, *Dolichos* spp., *Dorycnium rectum, Echinochloa pyramidalis, Ehrarlia* spp., *Eleusine coracana, Eragrestis* spp., *Erythrina* spp., *Eucalyptus* spp., *Euclea schimperi, Eulalia villosa, Fagopyrum* spp., *Feijoa sellowiana, Fragaria* spp., *Flemingia* spp, *Freycinetia banksii, Geranium thunbergii, Ginkgo biloba, Glycine javanica, Gliricidia* spp, *Gossypium hirsutum, Grevillea* spp., *Guibourtia coleosperma, Hedysarum* spp., *Hemarthia altissima, Heteropogon contortus, Hordeum vulgare, Hyparrhenia rufa, Hypericum erectum, Hyperthelia dissoluta, Indigo incarnata, Iris* spp., *Leptarrhena pyrolifolia, Lespediza* spp., *Leituca* spp., *Leucaena leucocephala, Loudetia simplex, Lotonus bainesii, Lotus* spp., *Macrotyloma axillare, Malus* spp., *Manihot esculenta, Medicago sativa, Metasequoia glyptostroboides, Musa sapientum, Nicolianum* spp., *Onobrychis* spp., *Ornithopus* spp., *Oryza* spp., *Peltophorum africanum, Pennisetum* spp., *Persea gratissima, Petunia* spp., *Phaseolus* spp., *Phoenix canariensis, Phormium cookianum, Photinia* spp., *Picea glauca, Pinus* spp., *Pisum sativum, Podocarpus totara, Pogonarthria Pogonarthria squarrosa, Populus* spp., *Prosopis cineraria, Pseudotsuga menziesii, Pterolobium stellatum, Pyrus communis, Quercus* spp., *Rhaphiolepsis umbellata, Rhopalostylis sapida, Rhus natalensis, Ribes grossularia, Ribes* spp., *Robinia pseudoacacia, Rosa* spp., *Rubus* spp., *Salix* spp., *Schyzachyrium sanguineum, Sciadopitys verticillata, Sequoia sempervirens, Sequoiadendron giganteum, Sorghum bicolor, Spinacia* spp., *Sporobolus fimbriatus, Stiburus alopecuroides, Stylosanthos humilis, Tadehagi* spp, *Taxodium distichum, Themeda triandra, Trifolium* spp., *Triticum* spp., *Tsuga heterophylla, Vaccinium* spp., *Vicia* spp. *Vitis vinifera, Watsonia pyramidata, Zantedeschia aethiopica, Zea mays*, amaranth, artichoke, asparagus, broccoli, brussel sprout, cabbage, canola, carrot, cauliflower, celery, collard greens, flax, kale, lentil, oilseed rape, okra, onion, potato, rice, soybean, straw, sugarbeet, sugar cane, sunflower, tomato, squash, and tea, amongst others, or the seeds of any plant specifically named above or a tissue, cell or organ culture of any of the above species.

Throughout this specification, unless the context requires otherwise the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source.

The terms "protein(s)", "peptide(s)" or "oligopeptide(s)", when used herein refer to amino acids in a polymeric form of any length. Said terms also include known amino acid modifications such as disulphide bond formation, cysteinylation, oxidation, glutathionylation, methylation, acetylation, farnesylation, biotinylation, stearoylation, formylation, lipoic acid addition, phosphorylation, sulphation, ubiquitination, myristoylation, palmitoylation, geranylgeranylation, cyclization (e.g. pyroglutamic acid formation), oxidation, deamidation, dehydration, glycosylation (e.g. pentoses, hexosamines, N-acetylhexosamines, deoxyhexoses, hexoses, sialic acid etc.) and acylation as well as non-naturally occurring amino acid residues, L-amino acid residues and D-amino acid residues.

"Homologues" of a protein of the invention are those peptides, oligopeptides, polypeptides, proteins and enzymes which contain amino acid substitutions, deletions and/or additions relative to the said protein with respect to which they are a homologue, without altering one or more of its functional properties, in particular without reducing the activity of the resulting. For example, a homologue of said protein will consist of a bioactive amino acid sequence variant of said protein. To produce such homologues, amino acids present in the said protein can be replaced by other amino acids having similar properties, for example hydrophobicity, hydrophilicity, hydrophobic moment, antigenicity, propensity to form or break α-helical structures or β-sheet structures, and so on. An overview of physical and chemical properties of amino acids is given in Table 1.

Substitutional variants of a protein of the invention are those in which at least one residue in said protein amino acid sequence has been removed and a different residue inserted in its place. Amino acid substitutions are typically of single residues, but may be clustered depending upon functional constraints placed upon the polypeptide; insertions will usually be of the order of about 1-10 amino acid residues and deletions will range from about 1-20 residues. Preferably, amino acid substitutions will comprise conservative amino acid substitutions, such as those described supra.

TABLE 1

Properties of naturally occurring amino acids.

| Charge properties/<br>hydrophobicity | Side group | Amino Acid |
| --- | --- | --- |
| Nonpolar<br>hydrophobic | Aliphatic<br>aliphatic, S-containing<br>aromatic<br>imino | ala, ile, leu, val<br>met<br>phe, trp<br>pro |
| polar uncharged | Aliphatic<br>Amide<br>Aromatic<br>Hydroxyl<br>Sulfhydryl | gly<br>asn, gln<br>tyr<br>ser, thr<br>cys |
| Positively charged | Basic | arg, his, lys |
| Negatively charged | Acidic | asp, glu |

Insertional amino acid sequence variants of a protein of the invention are those in which one or more amino acid residues are introduced into a predetermined site in said protein. Insertions can comprise amino-terminal and/or carboxy-terminal fusions as well as intra-sequence insertions of single or multiple amino acids. Generally, insertions within the amino acid sequence will be smaller than amino or carboxyl terminal fusions, of the order of about 1 to 10 residues. Examples of amino- or carboxy-terminal fusion proteins or peptides include the binding domain or activation domain of a transcriptional activator as used in a two-hybrid system, phage coat proteins, (histidine)$_6$-tag, glutathione S-transferase, protein A, maltose-binding protein, dihydrofolate reductase, Tag•100 epitope (EETARFQPGYRS), c-myc epitope (EQKLISEEDL), FLAG®-epitope (DYKDDDK), lacZ, CMP (calmodulin-binding peptide), HA epitope (YPYDVPDYA), protein C epitope (EDQVDPRLIDGK) and VSV epitope (YTDIEMNRLGK).

Deletional variants of a protein of the invention are characterized by the removal of one or more amino acids from the amino acid sequence of said protein.

Amino acid variants of a protein of the invention may readily be made using peptide synthetic techniques well known in the art, such as solid phase peptide synthesis and the like, or by recombinant DNA manipulations. The manipulation of DNA sequences to produce variant proteins which manifest as substitutional, insertional or deletional variants are well known in the art. For example, techniques for making substitution mutations at predetermined sites in DNA having known sequence are well known to those skilled in the art, such as by M13 mutagenesis, T7-Gen in vitro mutagenesis kit (USB, Cleveland, Ohio), QuickChange Site Directed mutagenesis kit (Stratagene, San Diego, Calif.), PCR-mediated site-directed mutagenesis or other site-directed mutagenesis protocols.

In the current invention "identity" and/or "similarity" percentages between DNA sequences and/or proteins are calculated using computer programs known in the art such as the DNAstar/MegAlign programs in combination with the Clustal method.

"Derivatives" of a protein of the invention are those peptides, oligopeptides, polypeptides, proteins and enzymes which comprise at least about five contiguous amino acid residues of said polypeptide but which retain the biological activity of said protein. A "derivative" may further comprise additional naturally-occurring, altered glycosylated, acylated or non-naturally occurring amino acid residues compared to the amino acid sequence of a naturally-occurring form of said polypeptide. Alternatively or in addition, a derivative may comprise one or more non-amino acid substituents compared to the amino acid sequence of a naturally-occurring form of said polypeptide, for example a reporter molecule or other ligand, covalently or non-covalently bound to the amino acid sequence such as, for example, a reporter molecule which is bound thereto to facilitate its detection.

With "immunologically active" is meant that a molecule or specific fragments thereof such as specific epitopes or haptens are recognized by, i.e. bind to antibodies. Specific epitopes may be determined using, for example, peptide scanning techniques as described in Geysen et al. (1996) (Geysen, H. M., Rodda, S. J. and Mason, T. J. (1986). A priori delineation of a peptide which mimics a discontinuous antigenic determinant. *Mol. Immunol.* 23, 709-715).

The term "fragment of a sequence" or "part of a sequence" means a truncated sequence of the original sequence referred to. The truncated sequence (nucleic acid or protein sequence) can vary widely in length; the minimum size being a sequence of sufficient size to provide a sequence with at least a comparable function and/or activity or the original sequence referred to (e.g. "functional fragment"), while the maximum size is not critical. In some applications, the maximum size usually is not substantially greater than that required to provide the desired activity and/or function(s) of the original sequence. Typically, the truncated amino acid sequence will range from about 5 to about 60 amino acids in length. More typically, however, the sequence will be a maximum of about 50 amino acids in length, preferably a maximum of about 60 amino acids. It is usually desirable to select sequences of at least about 10, 12 or 15 amino acids, up to a maximum of about 20 or 25 amino acids.

Functional fragments can also include those comprising an epitope which is specific for the proteins according to the invention. Preferred functional fragments have a length of at least, for example, 5, 10, 25, 100, 150 or 200 amino acids.

It should thus be understood that functional fragments can also be immunologically active fragments or not.

In the context of the current invention are embodied homologues, derivatives and/or immunologically active and/or functional fragments of the cytokinin oxidases as defined supra. Particularly preferred homologues, derivatives and/or immunologically active and/or functional fragments of the cytokinin oxidase proteins which are contemplated for use in the current invention are derived from plants, more specifically from *Arabidopsis thaliana*, even more specifically said cytokinin oxidases are the *Arabidopsis thaliana* (At)CKX, or are capable of being expressed therein. The present invention clearly contemplates the use of functional homologues or derivatives and/or immunologically active fragments of the AtCKX proteins and is not to be limited in application to the use of a nucleotide sequence encoding one of said AtCKX proteins.

Any of said proteins, polypeptides, peptides and fragments thereof can be produced in a biological system, e.g. a cell culture. Alternatively any of said proteins, polypeptides, peptides and fragments thereof can be chemically manufactured e.g. by solid phase peptide synthesis. Said proteins or fragments thereof can be part of a fusion protein as is the case in e.g. a two-hybrid assay which enables e.g. the identification of proteins interacting with a cytokinin oxidase according to the invention.

The proteins or fragments thereof are furthermore useful e.g. to modulate the interaction between a cytokinin oxidase according to the invention and interacting protein partners obtained by a method of the invention. Chemically synthesized peptides are particularly useful e.g. as a source of antigens for the production of antisera and/or antibodies.

"Antibodies" include monoclonal, polyclonal, synthetic or heavy chain camel antibodies as well as fragments of antibodies such as Fab, Fv or scFv fragments. Monoclonal antibodies can be prepared by the techniques as described in e.g. Liddle and Cryer (1991) which comprise the fusion of mouse myeloma cells to spleen cells derived from immunized animals. Furthermore, antibodies or fragments thereof to a molecule or fragments thereof can be obtained by using methods as described in e.g. Harlow and Lane (1988). In the case of antibodies directed against small peptides such as fragments of a protein of the invention, said peptides are generally coupled to a carrier protein before immunization of animals. Such protein carriers include keyhole limpet hemocyanin (KLH), bovine serum albumin (BSA), ovalbumin and Tetanus toxoid. The carrier protein enhances the immune response of the animal and provides epitopes for T-cell receptor binding sites. The term "antibodies" furthermore includes derivatives thereof such as labeled antibodies. Antibody labels include alkaline phosphatase, PKH2, PKH26, PKH67, fluorescein (FITC), Hoechst 33258, R-phycoerythrin (PE), rhodamine (TRITC), Quantum Red, Texas Red, Cy3, biotin, agarose, peroxidase and gold spheres. Tools in molecular biology relying on antibodies against a protein include protein gel blot analysis, screening of expression libraries allowing gene identification, protein quantitative methods including ELISA and RIA, immunoaffinity purification of proteins, immunoprecipitation of proteins (see e.g. Example 6) and immunolocalization. Other uses of antibodies and especially of peptide antibodies include the study of proteolytic processing (Loffler et al. 1994, Woulfe et al. 1994), determination of protein active sites (Lerner 1982), the study of precursor and post-translational processing (Baron and Baltimore 1982, Lerner et al. 1981, Semier et al. 1982), identification of protein domains involved in protein-protein interactions (Murakami et al. 1992) and the study of exon usage in gene expression (Tamura et al. 1991).

Embodied in the current invention are antibodies specifically recognizing a cytokinin oxidase or homologue, derivative or fragment thereof as defined supra. Preferably said cytokinin oxidase is a plant cytokinin oxidase, more specifically one of the *Arabidopsis thaliana* cytokinin oxidases (AtCKX).

The terms "gene(s)", "polynucleotide(s)", "nucleic acid(s)", "nucleic acid sequence(s)", "nucleotide sequence(s)", or "nucleic acid molecule(s)", when used herein refer to nucleotides, either ribonucleotides or deoxyribonucleotides or a combination of both, in a polymeric form of any length. Said terms furthermore include double-stranded and single-stranded DNA and RNA. Said terms also include known nucleotide modifications such as methylation, cyclization and 'caps' and substitution of one or more of the naturally occurring nucleotides with an analog such as inosine. Modifications of nucleotides include the addition of acridine, amine, biotin, cascade blue, cholesterol, Cy3®, Cy5®, Cy5.5® Dabcyl, digoxigenin, dinitrophenyl, Edans, 6-FAM, fluorescein, 3'-glyceryl, HEX, IRD-700, IRD-800, JOE, phosphate psoralen, rhodamine, ROX, thiol (SH), spacers, TAMRA, TET, AMCA-S®, SE, BODIPY®, Marina Blue®, Pacific Blue®, Oregon Green®, Rhodamine Green®, Rhodamine Red®, Rhodol Green® and Texas Red®. Polynucleotide backbone modifications include methylphosphonate, 2'-OMe-methylphosphonate RNA, phosphorothioate, RNA, 2'-OMeRNA. Base modifications include 2-amino-dA, 2-aminopurine, 3'-(ddA), 3' dA (cordycepin), deaza-dA, 8-Br-dA, 8-oxo-dA, $N^6$-Me-dA, abasic site (dSpacer), biotin dT, 2'-OMe-5Me-C, 2'-OMe-propynyl-C, 3'-(S-Me-dC), 3'-(ddC), 5-Br-dC, 5-I-dC, 5-Me-dC, 5-F-dC, carboxy-dT, convertible dA, convertible dC, convertible dG, convertible dT, convertible dU, 7-deaza-dG, 8-Br-dG, 8-oxo-dG, $O^6$-Me-dG, S6-DNP-dG, 4-methyl-indole, 5-nitroindole, 5-OMe-inosine, 2'-dI, $O^6$-phenyl-dI, 4-methyl-indole, 2'-deoxynebularine, 5-nitroindole, 2-aminopurine, dP (purine analogue), dK (pyrimidine analogue), 3-nitropyrrole, 2-thio-dT, 4-thio-dT, biotin-dT, carboxy-dT, $O^4$-Me-dT, $O^4$-triazol dT, 2'-OMe-propynyl-U, 5-Br-dU, 2'-dU, 5-F-dU, 5-I-dU, $O^4$-triazol dU. Said terms also encompass peptide nucleic acids (PNAs), a DNA analogue in which the backbone is a pseudopeptide consisting of N-(2-aminoethyl)-glycine units rather than a sugar. PNAs mimic the behavior of DNA and bind complementary nucleic acid strands. The neutral backbone of PNA results in stronger binding and greater specificity than normally achieved. In addition, the unique chemical, physical and biological properties of PNA have been exploited to produce powerful biomolecular tools, antisense and antigene agents, molecular probes and biosensors.

The present invention also advantageously provides nucleic acid sequences of at least approximately 15 contiguous nucleotides of a nucleic acid according to the invention and preferably from 15 to 50 nucleotides. These sequences may, advantageously be used as probes to specifically hybridize to sequences of the invention as defined above or primers to initiate specific amplification or replication of sequences of the invention as defined above, or the like. Such nucleic acid sequences may be produced according to techniques well known in the art, such as by recombinant or synthetic means. They may also be used in diagnostic kits or the like for detecting the presence of a nucleic acid according to the invention. These tests generally comprise contacting the probe with the sample under hybridising conditions and detecting the presence of any duplex or triplex formation between the probe and any nucleic acid in the sample.

Advantageously, the nucleic acid sequences, according to the invention may be produced using such recombinant or synthetic means, such as for example using PCR cloning mechanisms which generally involve making a pair of primers, which may be from approximately 15 to 50 nucleotides to a region of the gene which is desired to be cloned, bringing the primers into contact with mRNA, cDNA or genomic DNA from a cell, performing a polymerase chain reaction under conditions which bring about amplification of the desired region, isolating the amplified region or fragment and recovering the amplified DNA. Generally, such techniques as defined herein are well known in the art, such as described in Sambrook et al. (Molecular Cloning: a Laboratory Manual, 1989).

A "coding sequence" or "open reading frame" or "ORF" is defined as a nucleotide sequence that can be transcribed into mRNA and/or translated into a polypeptide when placed under the control of appropriate control sequences or regulatory sequences, i.e. when said coding sequence or ORF is present in an expressible format. Said coding sequence of ORF is bounded by a 5' translation start codon and a 3' translation stop codon. A coding sequence or ORF can include, but is not limited to RNA, mRNA, cDNA, recombinant nucleotide sequences, synthetically manufactured nucleotide sequences or genomic DNA. Said coding sequence or ORF can be interrupted by intervening nucleic acid sequences.

Genes and coding sequences essentially encoding the same protein but isolated from different sources can consist of substantially divergent nucleic acid sequences. Reciprocally, substantially divergent nucleic acid sequences can be designed to effect expression of essentially the same protein. Said nucleic acid sequences are the result of e.g. the existence of different alleles of a given gene, of the degeneracy of the genetic code or of differences in codon usage. Thus, as indicated in Table 2, amino acids such as methionine and tryptophan are encoded by a single codon whereas other amino acids such as arginine, leucine and serine can each be translated from up to six different codons. Differences in preferred codon usage are illustrated in Table 3 for *Agrobacterium tumefaciens* (a bacterium), *A. thaliana*, *M. sativa* (two dicotyledonous plants) and *Oryza sativa* (a monocotyledonous plant). To extract one example, the codon GGC (for glycine) is the most frequently used codon in *A. tumefaciens* (36.2‰), is the second most frequently used codon in *O. sativa* but is used at much lower frequencies in *A. thaliana* and *M. sativa* (9‰ and 8.4‰, respectively). Of the four possible codons encoding glycine (see Table 2), said GGC codon is most preferably used in *A. tumefaciens* and *O. sativa*. However, in *A. thaliana* this is the GGA (and GGU) codon whereas in *M. sativa* this is the GGU (and GGA) codon.

DNA sequences as defined in the current invention can be interrupted by intervening sequences. With "intervening sequences" is meant any nucleic acid sequence which disrupts a coding sequence comprising said inventive DNA sequence or which disrupts the expressible format of a DNA sequence comprising said inventive DNA sequence. Removal of the intervening sequence restores said coding sequence or said expressible format. Examples of intervening sequences include introns and mobilizable DNA sequences such as transposons. With "mobilizable DNA sequence" is meant any DNA sequence that can be mobilized as the result of a recombination event.

TABLE 2

Degeneracy of the genetic code.

| Amino Acid | Three-letter code | One-letter code | Possible codons | | | | | |
|---|---|---|---|---|---|---|---|---|
| Alanine | Ala | A | GCA | GCC | GCG | GCU | | |
| Arginine | Arg | R | AGA | AGG | CGA | CGC | CGG | CGU |
| Asparagine | Asn | N | AAC | AAU | | | | |
| Aspartic Acid | Asp | D | GAC | GAU | | | | |
| Cysteine | Cys | C | UGC | UGU | | | | |
| Glutamic Acid | Glu | E | GAA | GAG | | | | |
| Glutamine | Gln | Q | CAA | CAG | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Leucine | Leu | L | UUA | UUG | CUA | CUC | CUG | CUU |
| Lysine | Lys | K | AAA | AAG | | | | |
| Methionine | Met | M | AUG | | | | | |
| Phenylalanine | Phe | F | UUC | UUU | | | | |
| Proline | Pro | P | CCA | CCC | CCG | CCU | | |
| Serine | Ser | S | AGC | AGU | UCA | UCC | UCG | UCU |
| Threonine | Thr | T | ACA | ACC | ACG | ACU | | |
| Tryptophan | Trp | W | UGG | | | | | |
| Tyrosine | Tyr | Y | UAC | UAU | | | | |
| Valine | Val | V | GUA | GUC | GUG | GUU | | |
| Possible "STOP" codons | | | UAA | UAG | UGA | | | |

TABLE 3

Usage of the indicated codons in the different organisms given as frequency per thousand codons (kazusa.or.ip/codon).

| Codon | Agrobacterium tumefaciens | Arabidopsis thaliana | Medicago sativa | Oryza sativa |
|---|---|---|---|---|
| UUU | 13.9 | 22.5 | 24.1 | 11.3 |
| UUC | 24.3 | 20.7 | 16.9 | 26.3 |
| UUA | 3.5 | 12.9 | 10.4 | 4.7 |
| UUG | 13.2 | 21.0 | 22.4 | 11.8 |
| UCU | 7.0 | 24.6 | 19.8 | 10.1 |
| UCC | 14.8 | 10.8 | 7.7 | 16.9 |
| UCA | 7.4 | 17.8 | 17.2 | 9.7 |
| UCG | 18.2 | 8.9 | 3.2 | 10.8 |
| UAU | 12.3 | 15.2 | 16.6 | 9.2 |
| UAC | 10.3 | 13.7 | 14.0 | 20.6 |
| UAA | 0.9 | 0.9 | 1.2 | 0.9 |
| UAG | 0.6 | 0.5 | 0.8 | 0.8 |

TABLE 3-continued

Usage of the indicated codons in the different organisms given as frequency per thousand codons (kazusa.or.ip/codon).

| Codon | Agrobacterium tumefaciens | Arabidopsis thaliana | Medicago sativa | Oryza sativa |
|---|---|---|---|---|
| UGU | 3.0 | 10.8 | 10.6 | 5.0 |
| UGC | 7.4 | 7.2 | 5.8 | 14.3 |
| UGA | 1.8 | 1.0 | 0.8 | 1.3 |
| UGG | 12.2 | 12.7 | 10.0 | 12.8 |
| CUU | 19.1 | 24.3 | 28.3 | 14.6 |
| CUC | 25.7 | 15.9 | 12.0 | 28.0 |
| CUA | 5.2 | 10.0 | 8.8 | 5.7 |
| CUG | 31.6 | 9.9 | 8.5 | 22.1 |
| CCU | 7.7 | 18.3 | 23.2 | 11.8 |
| CCC | 10.6 | 5.3 | 5.3 | 12.5 |
| CCA | 8.9 | 16.1 | 22.6 | 12.2 |
| CCG | 20.7 | 8.3 | 3.6 | 16.7 |
| CAU | 10.6 | 14.0 | 14.6 | 9.2 |
| CAC | 9.1 | 8.7 | 9.1 | 14.6 |
| CAA | 11.2 | 19.7 | 23.2 | 11.9 |
| CAG | 24.9 | 15.2 | 12.3 | 24.6 |
| CGU | 12.2 | 8.9 | 10.1 | 6.8 |
| CGC | 25.5 | 3.7 | 4.2 | 15.9 |
| CGA | 8.2 | 6.2 | 4.2 | 4.2 |
| CGG | 13.2 | 4.8 | 1.8 | 9.7 |
| AUU | 15.4 | 22.0 | 29.4 | 13.8 |
| AUC | 36.9 | 18.5 | 14.7 | 25.5 |
| AUA | 6.2 | 12.9 | 11.7 | 7.2 |
| AUG | 24.7 | 24.5 | 21.7 | 24.4 |
| ACU | 6.4 | 17.8 | 20.8 | 10.3 |
| ACC | 20.9 | 10.3 | 11.7 | 18.6 |
| ACA | 9.1 | 15.9 | 18.9 | 10.0 |
| ACG | 18.8 | 7.6 | 2.8 | 10.8 |
| AAU | 13.5 | 22.7 | 25.0 | 12.9 |
| AAC | 18.7 | 20.9 | 18.7 | 25.1 |
| AAA | 13.6 | 31.0 | 32.2 | 12.0 |
| AAG | 24.4 | 32.6 | 35.1 | 39.4 |
| AGU | 5.7 | 14.0 | 12.6 | 7.3 |
| AGC | 15.8 | 11.1 | 8.8 | 16.9 |
| AGA | 5.3 | 18.7 | 13.6 | 7.7 |
| AGG | 6.5 | 10.9 | 11.7 | 14.9 |
| GUU | 16.6 | 27.3 | 34.7 | 15.0 |
| GUC | 29.3 | 12.7 | 9.9 | 22.8 |
| GUA | 6.1 | 10.1 | 10.0 | 5.7 |
| GUG | 19.7 | 17.5 | 16.5 | 25.0 |
| GCU | 17.4 | 28.0 | 34.6 | 19.8 |
| GCC | 35.8 | 10.3 | 11.4 | 33.2 |
| GCA | 19.5 | 17.6 | 25.9 | 15.6 |
| GCG | 31.7 | 8.8 | 3.4 | 25.3 |
| GAU | 25.8 | 36.8 | 40.0 | 21.5 |
| GAC | 28.0 | 17.3 | 15.5 | 31.6 |
| GAA | 29.9 | 34.4 | 35.9 | 17.1 |
| GAG | 26.3 | 32.2 | 27.4 | 41.1 |
| GGU | 16.5 | 22.2 | 28.7 | 16.3 |
| GGC | 36.2 | 9.0 | 8.4 | 34.7 |
| GGA | 12.5 | 23.9 | 27.3 | 15.0 |
| GGG | 11.3 | 10.2 | 7.4 | 16.6 |

"Hybridization" is the process wherein substantially homologous complementary nucleotide sequences anneal to each other. The hybridization process can occur entirely in solution, i.e. both complementary nucleic acids are in solution. Tools in molecular biology relying on such a process include PCR, subtractive hybridization and DNA sequence determination. The hybridization process can also occur with one of the complementary nucleic acids immobilized to a matrix such as magnetic beads, Sepharose beads or any other resin. Tools in molecular biology relying on such a process include the isolation of poly (A+) mRNA. The hybridization process can furthermore occur with one of the complementary nucleic acids immobilized to a solid support such as a nitrocellulose or nylon membrane or immobilized by e.g. photolithography to e.g. a silicious glass support (the latter known as nucleic acid arrays or microarrays or as nucleic acid chips). Tools in molecular biology relying on such a process include RNA and DNA gel blot analysis, colony hybridization, plaque hybridization and microarray hybridization. In order to allow hybridization to occur, the nucleic acid molecules are generally thermally or chemically (e.g. by NaOH) denatured to melt a double strand into two single strands and/or to remove hairpins or other secondary structures from single stranded nucleic acids. The stringency of hybridization is influenced by conditions such as temperature, salt concentration and hybridization buffer composition. High stringency conditions for hybridization include high temperature and/or low salt concentration (salts include NaCl and Na3-citrate) and/or the inclusion of formamide in the hybridization buffer and/or lowering the concentration of compounds such as SDS (detergent) in the hybridization buffer and/or exclusion of compounds such as dextran sulfate or polyethylene glycol (promoting molecular crowding) from the hybridization buffer. Conventional hybridization conditions are described in e.g. Sambrook et al. (1989) but the skilled craftsman will appreciate that numerous different hybridization conditions can be designed in function of the known or the expected homology and/or length of the nucleic acid sequence. Sufficiently low stringency hybridization conditions are particularly preferred to isolate nucleic acids heterologous to the DNA sequences of the invention defined supra. Elements contributing to said heterology include allelism, degeneration of the genetic code and differences in preferred codon usage as discussed supra.

The term "specifically hybridizing" or "hybridizing specifically" refers to the binding, duplexing, or hybridizing of a molecule to a particular nucleotide sequence under medium to stringent conditions when that sequence is presented in a complex mixture e.g., total cellular DNA or RNA.

"Stringent hybridization conditions" and "stringent hybridization wash conditions" in the context of nucleic acid hybridization experiments such as Southern and Northern hybridizations are sequence dependent and are different under different environmental parameters. For example, longer sequences hybridize specifically at higher temperatures. The $T_m$ is the temperature under defined ionic strength and pH, at which 50% of the target sequence hybridizes to a perfectly matched probe. Specificity is typically the function of post-hybridization washes. Critical factors of such washes include the ionic strength and temperature of the final wash solution.

Generally, stringent conditions are selected to be about 50° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. The $T_m$ is dependent upon the solution conditions and the base composition of the probe, and may be calculated using the following equation:

$T_m = 79.8° C. + (18.5 \times Log [Na+])$ $+ (58.4° C. \times \%[G+C])$ $- (820/\# bp\ in\ duplex)$ $- (0.5 \times \%\ formamide)$ More preferred stringent conditions are when the temperature is 20° C. below $T_m$, and the most preferred stringent conditions are when the temperature is 10° C. below $T_m$. Nonspecific binding may also be controlled using any one of a number of known techniques such as, for example, blocking the membrane with protein-containing solutions, addition of heterologous RNA, DNA, and SDS to the hybridization buffer, and treatment with RNase.

Wash conditions are typically performed at or below stringency. Generally, suitable stringent conditions for nucleic acid hybridization assays or gene amplification detection procedures are as set forth above. More or less stringent conditions may also be selected.

For the purposes of defining the level of stringency, reference can conveniently be made to Sambrook, J., E. F. Fritsch, et al. 1989 "Molecular Cloning: a Laboratory Manual, $2^{nd}$ Edition, Cold Spring Harbor, N.Y., Cold Spring Harbor Laboratory Press, at 11.45. An example of low stringency conditions is 4-6×SSC/0.1-0.5% w/v SDS at 37°-45° C. for 2-3 hours. Depending on the source and concentration of the nucleic acid involved in the hybridization, alternative conditions of stringency may be employed such as medium stringent conditions. Examples of medium stringent conditions include 1-4×SSC/0.25% w/v SDS at ≧45° C. for 2-3 hours. An example of high stringency conditions includes 0.1-1× SSC/0.1% w/v SDS at 60 C for 1-3 hours. The skilled artisan is aware of various parameters which may be altered during hybridization and washing and which will either maintain or change the stringency conditions. For example, another stringent hybridization condition is hybridization at 4×SSC at 65° C., followed by a washing in 0.1×SSC at 65° C. for about one hour. Alternatively, an exemplary stringent hybridization condition is in 50% formamide, 4×SSC, at 42° C. Still another example of stringent conditions include hybridization at 62° C. in 6×SSC, 0.05×BLOTTO, and washing at 2×SSC, 0.1% SDS at 62° C.

Clearly, the current invention embodies the use of the inventive DNA sequences encoding a cytokinin oxidase, homologue, derivative or immunologically active and/or functional fragment thereof as defined higher in any method of hybridization. The current invention furthermore also relates to DNA sequences hybridizing to said inventive DNA sequences. Preferably said cytokinin oxidase is a plant cytokinin oxidase, more specifically the *Arabidopsis thaliana* (At)CKX.

To effect expression of a protein in a cell, tissue or organ, preferably of plant origin, either the protein may be introduced directly to said cell, such as by microinjection or ballistic means or alternatively, an isolated nucleic acid molecule encoding said protein may be introduced into said cell, tissue or organ in an expressible format.

Preferably, the DNA sequence of the invention comprises a coding sequence or open reading frame (ORF) encoding a cytokinin oxidase protein or a homologue or derivative thereof or an immunologically active and/or functional fragment thereof as defined supra. The preferred protein of the invention comprises the amino acid sequence of said cytokinin oxidase. Preferably said cytokinin oxidase is a plant cytokinin oxidase and more specifically a *Arabidopsis thaliana* (At)CKX.

With "vector" or "vector sequence" is meant a DNA sequence which can be introduced in an organism by transformation and can be stably maintained in said organism. Vector maintenance is possible in e.g. cultures of *Escherichia coli, A. tumefaciens, Saccharomyces cerevisiae* or *Schizosaccharomyces pombe*. Other vectors such as phagemids and cosmid vectors can be maintained and multiplied in bacteria and/or viruses. Vector sequences generally comprise a set of unique sites recognized by restriction enzymes, the multiple cloning site (MCS), wherein one or more non-vector sequence(s) can be inserted.

With "non-vector sequence" is accordingly meant a DNA sequence which is integrated in one or more of the sites of the MCS comprised within a vector.

"Expression vectors" form a subset of vectors which, by virtue of comprising the appropriate regulatory or control sequences enable the creation of an expressible format for the inserted non-vector sequence(s), thus allowing expression of the protein encoded by said non-vector sequence(s). Expression vectors are known in the art enabling protein expression in organisms including bacteria (e.g. *E. coli*), fungi (e.g. *S. cerevisiae, S. pombe, Pichia pastoris*), insect cells (e.g. baculoviral expression vectors), animal cells (e.g. COS or CHO cells) and plant cells (e.g. potato virus X-based expression vectors).

The current invention clearly includes any cytokinin oxidase, homologue, derivative and/or immunologically active and/or functional fragment thereof as defined supra. Preferably said cytokinin oxidase is a plant cytokinin oxidase, more specifically a *Arabidopsis thaliana* (At)CKX.

As an alternative to expression vector-mediated protein production in biological systems, chemical protein synthesis can be applied. Synthetic peptides can be manufactured in solution phase or in solid phase. Solid phase peptide synthesis (Merrifield 1963) is, however, the most common way and involves the sequential addition of amino acids to create a linear peptide chain. Solid phase peptide synthesis includes cycles consisting of three steps: (i) immobilization of the carboxy-terminal amino acid of the growing peptide chain to a solid support or resin; (ii) chain assembly, a process consisting of activation, coupling and deprotection of the amino acid to be added to the growing peptide chain; and (iii) cleavage involving removal of the completed peptide chain from the resin and removal of the protecting groups from the amino acid side chains. Common approaches in solid phase peptide synthesis include Fmoc/tBu (9-fluorenylmethyloxycarbonyl/ t-butyl) and Boc (t-butyloxycarbonyl) as the amino-terminal protecting groups of amino acids. Amino acid side chain protecting groups include methyl (Me), formyl (CHO), ethyl (Et), acetyl (Ac), t-butyl (t-Bu), anisyl, benzyl (Bzl), trifluoroacetyl (Tfa), N-hydroxysuccinimide (ONSu, OSu), benzoyl (Bz), 4-methylbenzyl (Meb), thioanizyl, thiocresyl, benzyloxymethyl (Bom), 4-nitrophenyl (ONp), benzyloxycarbonyl (Z), 2-nitrobenzoyl (NBz), 2-nitrophenylsulphenyl (Nps), 4-toluenesulphonyl (Tosyl, Tos), pentafluorophenyl (Pfp), diphenylmethyl (Dpm), 2-chlorobenzyloxycarbonyl (Cl—Z), 2,4,5-trichlorophenyl, 2-bromobenzyloxycarbonyl (Br—Z), tripheylmethyl (Trityl, Trt), and 2,5,7,8-pentamethyl-chroman-6-sulphonyl (Pine). During chain assembly, Fmoc or Boc are removed resulting in an activated amino-terminus of the amino acid residue bound to the growing chain. The carboxy-terminus of the incoming amino acid is activated by conversion into a highly reactive ester, e.g. by HBTU. With current technologies (e.g. PerSeptive Biosystems 9050 synthesizer, Applied Biosystems Model 431A Peptide Synthesizer), linear peptides of up to 50 residues can be manufactured. A number of guidelines is available to produce peptides that are suitable for use in biological systems including (i) limiting the use of difficult amino acids such as cys, met, trp (easily oxidized and/or degraded during peptide synthesis) or arg; (ii) minimize hydrophobic amino acids (can impair peptide solubility); and (iii) prevent an amino-terminal glutamic acid (can cyclize to pyroglutamate).

By "expressible format" is meant that the isolated nucleic acid molecule is in a form suitable for being transcribed into mRNA and/or translated to produce a protein, either constitutively or following induction by an intracellular or extracellular signal, such as an environmental stimulus or stress (mitogens, anoxia, hypoxia, temperature, salt, light, dehydration, etc) or a chemical compound such as IPTG (isopropyl-β-D-thiogalactopyranoside) or such as an antibiotic (tetracycline, ampicillin, rifampicin, kanamycin), hormone (e.g. gibberellin, auxin, cytokinin, glucocorticoid, brassinosteroid, ethylene, abscisic acid etc), hormone analogue (indoleacetic acid (IAA), 2,4-D, etc), metal (zinc, copper, iron, etc), or dexamethasone, amongst others. As will be known to those skilled in the art, expression of a functional protein may also require one or more post-translational modifications, such as glycosylation, phosphorylation, dephosphorylation, or one or more protein-protein interactions, amongst others. All such processes are included within the scope of the term "expressible format".

Preferably, expression of a protein in a specific cell, tissue, or organ, preferably of plant origin, is effected by introducing and expressing an isolated nucleic acid molecule encoding said protein, such as a cDNA molecule, genomic gene, synthetic oligonucleotide molecule, mRNA molecule or open reading frame, to said cell, tissue or organ, wherein said nucleic acid molecule is placed operably in connection with suitable regulatory or control sequences including a promoter, preferably a plant-expressible promoter, and a terminator sequence.

Reference herein to a "promoter" is to be taken in its broadest context and includes the transcriptional regulatory sequences derived from a classical eukaryotic genomic gene, including the TATA box which is required for accurate transcription initiation, with or without a CCAAT box sequence and additional regulatory or control elements (i.e. upstream activating sequences, enhancers and silencers) which alter gene expression in response to developmental and/or external stimuli, or in a tissue-specific manner.

The term "promoter" also includes the transcriptional regulatory sequences of a classical prokaryotic gene, in which case it may include a −35 box sequence and/or a −10 box transcriptional regulatory sequences.

The term "promoter" is also used to describe a synthetic or fusion molecule, or derivative which confers, activates or enhances expression of a nucleic acid molecule in a cell, tissue or organ.

Promoters may contain additional copies of one or more specific regulatory elements, to further enhance expression and/or to alter the spatial expression and/or temporal expression of a nucleic acid molecule to which it is operably connected. Such regulatory elements may be placed adjacent to a heterologous promoter sequence to drive expression of a nucleic acid molecule in response to e.g. copper, glucocorticoids, dexamethasone, tetracycline, gibberellin, cAMP, abscisic acid, auxin, wounding, ethylene, jasmonate or salicylic acid or to confer expression of a nucleic acid molecule to specific cells, tissues or organs such as meristems, leaves, roots, embryo, flowers, seeds or fruits.

In the context of the present invention, the promoter preferably is a plant-expressible promoter sequence. Promoters that also function or solely function in non-plant cells such as bacteria, yeast cells, insect cells and animal cells are not excluded from the invention. By "plant-expressible" is meant that the promoter sequence, including any additional regulatory elements added thereto or contained therein, is at least capable of inducing, conferring, activating or enhancing expression in a plant cell, tissue or organ, preferably a monocotyledonous or dicotyledonous plant cell, tissue, or organ.

The terms "plant-operable" and "operable in a plant" when used herein, in respect of a promoter sequence, shall be taken to be equivalent to a plant-expressible promoter sequence.

Regulatable promoters as part of a binary viral plant expression system are also known to the skilled artisan (Yadav 1999—WO9922003; Yadav 2000—WO0017365).

In the present context, a "regulatable promoter sequence" is a promoter that is capable of conferring expression on a structural gene in a particular cell, tissue, or organ or group of cells, tissues or organs of a plant, optionally under specific conditions, however does generally not confer expression throughout the plant under all conditions. Accordingly, a regulatable promoter sequence may be a promoter sequence that confers expression on a gene to which it is operably connected in a particular location within the plant or alternatively, throughout the plant under a specific set of conditions, such as following induction of gene expression by a chemical compound or other elicitor.

Preferably, the regulatable promoter used in the performance of the present invention confers expression in a specific location within the plant, either constitutively or following induction, however not in the whole plant under any circumstances. Included within the scope of such promoters are cell-specific promoter sequences, tissue-specific promoter sequences, organ-specific promoter sequences, cell cycle specific gene promoter sequences, inducible promoter sequences and constitutive promoter sequences that have been modified to confer expression in a particular part of the plant at any one time, such as by integration of said constitutive promoter within a transposable genetic element (Ac, Ds, Spm, En, or other transposon).

Similarly, the term "tissue-specific" shall be taken to indicate that expression is predominantly in a particular tissue or tissue-type, preferably of plant origin, albeit not necessarily exclusively in said tissue or tissue-type.

Similarly, the term "organ-specific" shall be taken to indicate that expression is predominantly in a particular organ, preferably of plant origin, albeit not necessarily exclusively in said organ.

Similarly, the term "cell cycle specific" shall be taken to indicate that expression is predominantly cyclic and occurring in one or more, not necessarily consecutive phases of the cell cycle albeit not necessarily exclusively in cycling cells, preferably of plant origin.

Those skilled in the art will be aware that an "inducible promoter" is a promoter the transcriptional activity of which is increased or induced in response to a developmental, chemical, environmental, or physical stimulus. Similarly, the skilled craftsman will understand that a "constitutive promoter" is a promoter that is transcriptionally active throughout most, but not necessarily all parts of an organism, preferably a plant, during most, but not necessarily all phases of its growth and development.

Those skilled in the art will readily be capable of selecting appropriate promoter sequences for use in regulating appropriate expression of the cytokinin oxidase protein from publicly-available or readily-available sources, without undue experimentation.

Placing a nucleic acid molecule under the regulatory control of a promoter sequence, or in operable connection with a promoter sequence, means positioning said nucleic acid molecule such that expression is controlled by the promoter sequence. A promoter is usually, but not necessarily, positioned upstream, or at the 5'-end, and within 2 kb of the start site of transcription, of the nucleic acid molecule which it regulates. In the construction of heterologous promoter/structural gene combinations it is generally preferred to position the promoter at a distance from the gene transcription start site that is approximately the same as the distance between that promoter and the gene it controls in its natural setting (i.e., the gene from which the promoter is derived). As is known in the art, some variation in this distance can be accommodated without loss of promoter function. Similarly, the preferred positioning of a regulatory sequence element with respect to a heterologous gene to be placed under its control is defined by the positioning of the element in its natural setting (i.e., the gene from which it is derived). Again, as is known in the art, some variation in this distance can also occur.

Examples of promoters suitable for use in gene constructs of the present invention include those listed in Table 4, amongst others. The promoters listed in Table 4 are provided for the purposes of exemplification only and the present invention is not to be limited by the list provided therein. Those skilled in the art will readily be in a position to provide additional promoters that are useful in performing the present invention.

In the case of constitutive promoters or promoters that induce expression throughout the entire plant, it is preferred that such sequences are modified by the addition of nucleotide sequences derived from one or more of the tissue-specific promoters listed in Table 4, or alternatively, nucleotide sequences derived from one or more of the above-mentioned tissue-specific inducible promoters, to confer tissue-specificity thereon. For example, the CaMV 35S promoter may be modified by the addition of maize Adh1 promoter sequence, to confer anaerobically-regulated root-specific expression thereon, as described previously (Ellis et al., 1987). Another example describes conferring root specific or root abundant gene expression by fusing the CaMV35S promoter to elements of the maize glycine-rich protein GRP3 gene (Feix and Wulff 2000—WO0015662). Such modifications can be achieved by routine experimentation by those skilled in the art.

The term "terminator" refers to a DNA sequence at the end of a transcriptional unit which signals termination of transcription. Terminators are 3'-non-translated DNA sequences containing a polyadenylation signal, which facilitates the addition of polyadenylate sequences to the 3'-end of a primary transcript. Terminators active in cells derived from viruses, yeasts, molds, bacteria, insects, birds, mammals and plants are known and described in the literature. They may be isolated from bacteria, fungi, viruses, animals and/or plants.

TABLE 4

Exemplary plant-expressible promoters for use in the performance of the present invention

I: CELL-SPECIFIC, TISSUE-SPECIFIC, AND ORGAN-SPECIFIC PROMOTERS

| GENE SOURCE | EXPRESSION PATTERN | REFERENCE |
| --- | --- | --- |
| α-amylase (Amy32b) | aleurone | Lanahan, M. B., et al., Plant Cell 4: 203-211, 1992; Skriver, K., et al. Proc. Natl. Acad. Sci. (USA) 88: 7266-7270, 1991 |
| cathepsin β-like gene | aleurone | Cejudo, F. J., et al. Plant Molecular Biology 20: 849-856, 1992. |
| *Agrobacterium rhizogenes* rolB | cambium | Nilsson et al., Physiol. Plant. 100: 456-462, 1997 |
| AtPRP4 | flowers | salus.medium.edu/mmg/tierney/html |
| chalcone synthase (chsA) | flowers | Van der Meer, et al., Plant Mol. Biol. 15, 95-109, 1990. |
| LAT52 | Anther | Twell et al Mol. Gen Genet. 217: 240-245 (1989) |
| apetala-3 | flowers | |

TABLE 4-continued

Exemplary plant-expressible promoters for use in the performance of the present invention

| | | |
|---|---|---|
| Chitinase | fruit (berries, grapes, etc) | Thomas et al. CSIRO Plant Industry, Urrbrae, South Australia, Australia; winetitles.com.au/gwrdc/csh95-1.html |
| rbcs-3A | green tissue (eg leaf) | Lam, E. et al., The Plant Cell 2: 857-866, 1990.; Tucker et al., Plant Physiol. 113: 1303-1308, 1992. |
| leaf-specific genes | Leaf | Baszczynski, et al., Nucl. Acid Res. 16: 4732, 1988. |
| AtPRP4 | Leaf | http://salus.medium.edu/mmg/tierney/html |
| *chlorella* virus adenine methyltransferase gene promoter | Leaf | Mitra and Higgins, 1994, Plant Molecular Biology 26: 85-93 |
| aldP gene promoter from rice | Leaf | Kagaya et al., 1995, Molecular and General Genetics 248: 668-674 |
| rbcs promoter from rice or tomato | Leaf | Kyozuka et al., 1993, Plant Physiology 102: 991-1000 |
| *Pinus* cab-6 | Leaf | Yamamoto et al., Plant Cell Physiol. 35: 773-778, 1994. |
| rubisco promoter | Leaf | |
| cab (chlorophyll a/b/binding protein | Leaf | |
| SAM22 | senescent leaf | Crowell, et al., Plant Mol. Biol. 18: 459-466, 1992. |
| ltp gene (lipid transfer gene) | | Fleming, et al, Plant J. 2, 855-862. |
| *R. japonicum* nif gene | Nodule | U.S. Pat. No. 4,803,165 |
| *B. japonicum* nifH gene | Nodule | U.S. Pat. No. 5,008,194 |
| GmENOD40 | Nodule | Yang, et al., The Plant J. 3: 573-585. |
| PEP carboxylase (PEPC) | Nodule | Pathirana, et al., Plant Mol. Biol. 20: 437-450, 1992. |
| Leghaemoglobin (Lb) | Nodule | Gordon, et al., J. Exp. Bot. 44: 1453-1465, 1993. |
| *Tungro bacilliform* virus gene | phloem | Bhattacharyya-Pakrasi, et al, The Plant J. 4: 71-79, 1992. |
| pollen-specific genes | Pollen; microspore | Albani, et al., Plant Mol. Biol. 15: 605, 1990; Albani, et al., Plant Mol. Biol. 16: 501, 1991) |
| Zm13 | Pollen | Guerrero et al Mol. Gen. Genet. 224: 161-168 (1993) |
| apg gene | microspore | Twell et al Sex. Plant Reprod. 6: 217-224 (1993) |
| maize pollen-specific gene | Pollen | Hamilton, et al., Plant Mol. Biol. 18: 211-218, 1992. |
| sunflower pollen-expressed gene | Pollen | Baltz, et al., The Plant J. 2: 713-721, 1992. |
| *B. napus* pollen-specific gene | pollen; anther; tapetum | Arnoldo, et al., J. Cell. Biochem., Abstract No. Y101, 204, 1992. |
| root-expressible genes | Roots | Tingey, et al., EMBO J. 6: 1, 1987. |
| tobacco auxin-inducible gene | Root tip | Van der Zaal, et al., Plant Mol. Biol. 16, 983, 1991. |
| β-tubulin | Root | Oppenheimer, et al., Gene 63: 87, 1988. |
| tobacco root-specific genes | Root | Conkling, et al., Plant Physiol. 93: 1203, 1990. |
| *B. napus* G1-3b gene | Root | U.S. Pat. No. 5,401,836 |
| SbPRP1 | Roots | Suzuki et al., Plant Mol. Biol. 21: 109-119, 1993. |
| AtPRP1; AtPRP3 | roots; root hairs | medium.edu/mmg/tierney/html |
| RD2 gene | root cortex | cnsu.edu/ncsu/research |
| TobRB7 gene | root vasculature | cnsu.edu/ncsu/research |
| AtPRP4 | leaves; flowers; lateral root primordia | medium.edu/mmg/tierney/html |
| seed-specific genes | Seed | Simon, et al., Plant Mol. Biol. 5: 191, 1985; Scofield, et al., J. Biol. Chem. 262: 12202, 1987.; Baszczynski, et al., Plant Mol. Biol. 14: 633, 1990. |
| Brazil Nut albumin | Seed | Pearson, et al., Plant Mol. Biol. 18: 235-245, 1992. |
| Legumin | Seed | Ellis, et al., Plant Mol. Biol. 10: 203-214, 1988. |
| glutelin (rice) | Seed | Takaiwa, et al., Mol. Gen. Genet. 208: 15-22, 1986; Takaiwa, et al., FEBS Letts. 221: 43-47, 1987. |
| Zein | Seed | Matzke et al Plant Mol Biol, 14(3): 323-32 1990 |
| NapA | Seed | Stalberg, et al, Planta 199: 515-519, 1996. |

TABLE 4-continued

Exemplary plant-expressible promoters for use in the performance of the present invention

| | | |
|---|---|---|
| wheat LMW and HMW glutenin-1 | Endosperm | Mol Gen Genet 216: 81-90, 1989; NAR 17: 461-2, 1989 |
| wheat SPA | Seed | Albani et al, Plant Cell, 9: 171-184, 1997 |
| wheat α, β, γ-gliadins | Endosperm | EMBO 3: 1409-15, 1984 |
| barley Itr1 promoter | Endosperm | |
| barley B1, C, D, hordein | Endosperm | Theor Appl Gen 98: 1253-62, 1999; Plant J 4: 343-55, 1993; Mol Gen Genet 250: 750-60, 1996 |
| barley DOF | Endosperm | Mena et al, The Plant Journal, 116(1): 53-62, 1998 |
| blz2 | Endosperm | EP99106056.7 |
| synthetic promoter | Endosperm | Vicente-Carbajosa et al., Plant J. 13: 629-640, 1998. |
| rice prolamin NRP33 | Endosperm | Wu et al, Plant Cell Physiology 39(8) 885-889, 1998 |
| rice α-globulin Glb-1 | Endosperm | Wu et al, Plant Cell Physiology 39(8) 885-889, 1998 |
| rice OSH1 | Embryo | Sato et al, Proc. Natl. Acad. Sci. USA, 93: 8117-8122, 1996 |
| rice α-globulin REB/OHP-1 | Endosperm | Nakase et al. Plant Mol. Biol. 33: 513-522, 1997 |
| rice ADP-glucose PP | Endosperm | Trans Res 6: 157-68, 1997 |
| maize ESR gene family | Endosperm | Plant J 12: 235-46, 1997 |
| sorgum γ-kafirin | Endosperm | PMB 32: 1029-35, 1996 |
| KNOX | Embryo | Postma-Haarsma et al, Plant Mol. Biol. 39: 257-71, 1999 |
| rice oleosin | embryo and aleuron | Wu et at, J. Biochem., 123: 386, 1998 |
| sunflower oleosin | seed (embryo and dry seed) | Cummins, et al., Plant Mol. Biol. 19: 873-876, 1992 |
| LEAFY | shoot meristem | Weigel et al., Cell 69: 843-859, 1992. |
| *Arabidopsis thaliana* knat1 | shoot meristem | Accession number AJ131822 |
| *Malus domestica* kn1 | shoot meristem | Accession number Z71981 |
| CLAVATA1 | shoot meristem | Accession number AF049870 |
| stigma-specific genes | Stigma | Nasrallah, et al., Proc. Natl. Acad. Sci. USA 85: 5551, 1988; Trick, et al., Plant Mol. Biol. 15: 203, 1990. |
| class I patatin gene | Tuber | Liu et al., Plant Mol. Biol. 153: 386-395, 1991. |
| PCNA rice | Meristem | Kosugi et al, Nucleic Acids Research 19: 1571-1576, 1991; Kosugi S. and Ohashi Y, Plant Cell 9: 1607-1619, 1997. |
| Pea TubA1 tubulin | Dividing cells | Stotz and Long, Plant Mol. Biol. 41, 601-614. 1999 |
| *Arabidopsis* cdc2a | cycling cells | Chung and Parish, FEBS Lett, 3; 362(2): 215-9, 1995 |
| *Arabidopsis* Rop1A | Anthers; mature pollen + pollen tubes | Li et al. 1998 Plant Physiol 118, 407-417. |
| *Arabidopsis* AtDMC1 | Meiosis-associated | Klimyuk and Jones 1997 Plant J. 11, 1-14. |
| Pea PS-IAA4/5 and PS-IAA6 | Auxin-inducible | Wong et al. 1996 Plant J. 9, 587-599. |
| Pea farnesyltransferase | Meristematic tissues; phloem near growing tissues; light- and sugar-repressed | Zhou et al. 1997 Plant J. 12, 921-930 |
| Tobacco (*N. sylvestris*) cyclin B1; 1 | Dividing cells/ meristematic tissue | Trehin et al. 1997 Plant Mol. Biol. 35, 667-672. |
| Mitotic cyclins CYS (A-type) and CYM (B-type) | Dividing cells/ meristematic tissue | Ito et al. 1997 Plant J. 11, 983-992 |
| *Arabidopsis* cyc1 At (=cyc B1; 1) and cyc3aAt (A-type) | Dividing cells/ meristematic tissue | Shaul et al. 1996 Proc. Natl. Acad. Sci. U.S.A 93, 4868-4872. |
| *Arabidopsis* tef1 promoter box | Dividing cells/ meristematic tissue | Regad et al. 1995 Mol. Gen. Genet. 248, 703-711. |
| *Catharanthus roseus* cyc07 | Dividing cells/ meristematic tissue | Ito et al. 1994 Plant Mol. Biol. 24, 863-878. |

TABLE 4-continued

Exemplary plant-expressible promoters for use
in the performance of the present invention

II: EXEMPLARY CONSTITUTIVE PROMOTERS

| GENE SOURCE | EXPRESSION PATTERN | REFERENCE |
|---|---|---|
| Actin | Constitutive | McElroy et al, Plant Cell, 2: 163-171, 1990 |
| CAMV 35S | Constitutive | Odell et al, Nature, 313: 810-812, 1985 |
| CaMV 19S | Constitutive | Nilsson et al., Physiol. Plant. 100: 456-462, 1997 |
| GOS2 | Constitutive | de Pater et al, Plant J. 2: 837-844, 1992 |
| Ubiquitin | Constitutive | Christensen et al, Plant Mol. Biol. 18: 675-689, 1992 |
| rice cyclophilin | Constitutive | Buchholz et al, Plant Mol Biol. 25: 837-843, 1994 |
| maize histone H3 | Constitutive | Lepetit et al, Mol. Gen. Genet. 231: 276-285, 1992 |
| alfalfa histone H3 | Constitutive | Wu et al., Nucleic Acids Res. 17: 3057-3063, 1989; Wu et al., Plant Mol. Biol. 11: 641-649, 1988 |
| actin 2 | Constitutive | An et al, Plant J. 10(1); 107-121, 1996 |

III: EXEMPLARY STRESS-INDUCIBLE PROMOTERS

| NAME | STRESS | REFERENCE |
|---|---|---|
| P5CS (delta(1)-pyrroline-5-carboxylate syntase) | salt, water | Zhang et al. Plant Science. 129: 81-89, 1997 |
| cor15a | Cold | Hajela et al., Plant Physiol. 93: 1246-1252, 1990 |
| cor15b | Cold | Wlihelm et al., Plant Mol Biol. 23: 1073-1077, 1993 |
| cor15a (−305 to +78 nt) | cold, drought | Baker et al., Plant Mol Biol. 24: 701-713, 1994 |
| rd29 | salt, drought, cold | Kasuga et al., Nature Biotechnology 18: 287-291, 1999 |
| heat shock proteins, including artificial promoters containing the heat shock element (HSE) | Heat | Barros et al., Plant Mol Biol 19: 665-75, 1992. Marrs et al., Dev Genet. 14: 27-41, 1993. Schoffl et al., Mol Gen Gent, 217: 246-53, 1989. |
| smHSP (small heat shock proteins) | heat | Waters et al, J Experimental Botany 47: 325-338, 1996 |
| wcs120 | Cold | Ouellet et al., FEBS Lett. 423: 324-328, 1998 |
| ci7 | Cold | Kirch et al., Plant Mol Biol 33: 897-909, 1997 |
| Adh | Cold, drought, hypoxia | Dolferus et al., Plant Physiol 105: 1075-87, 1994 |
| pwsi18 | water: salt and drought | Joshee et al., Plant Cell Physiol 39: 64-72, 1998 |
| ci21A | Cold | Schneider et al., Plant Physiol 113: 335-45, 1997 |
| Trg-31 | Drought | Chaudhary et al., Plant Mol Biol 30: 1247-57, 1996 |
| Osmotin | Osmotic | Raghothama et al., Plant Mol Biol 23: 1117-28, 1993 |
| Rab17 | osmotic, ABA | Vilardell et al., Plant Mol Biol 17: 985-93, 1991 |
| LapA | wounding, enviromental | WO99/03977 University of California/INRA |

IV: EXEMPLARY PATHOGEN-INDUCIBLE PROMOTERS

| NAME | PATHOGEN | REFERENCE |
|---|---|---|
| RB7 | Root-knot nematodes (*Meloidogyne* spp.) | U.S. Pat. No. 5760386 - North Carolina State University; Opperman et al (1994) Science 263: 221-23. |
| PR-1, 2, 3, 4, 5, 8, 11 | fungal, viral, bacterial | Ward et al (1991) Plant Cell 3: 1085-1094; Reiss et al 1996; Lebel et al (1998), Plant J, 16(2): 223-33; Melchers et al (1994), Plant J, |

TABLE 4-continued

Exemplary plant-expressible promoters for use
in the performance of the present invention

| | | |
|---|---|---|
| HMG2 | Nematodes | 5(4): 469-80; Lawton et al (1992), Plant Mol Biol, 19(5): 735-43. WO9503690 - Virginia Tech Intellectual Properties Inc. |
| Abi3 | Cyst nematodes (*Heterodera* spp.) | Unpublished |
| ARM1 | Nematodes | Barthels et al., (1997) The Plant Cell 9, 2119-2134. WO 98/31822 - Plant Genetic Systems |
| Att0728 | Nematodes | Barthels et al., (1997) The Plant Cell 9, 2119-2134. PCT/EP98/07761 |
| Att1712 | Nematodes | Barthels et al., (1997) The Plant Cell 9, 2119-2134. PCT/EP98/07761 |
| Gst1 | Different types of pathogens | Strittmatter et al (1996) Mol. Plant-Microbe Interact. 9, 68-73. |
| LEMMI | Nematodes | WO 92/21757 - Plant Genetic Systems |
| CLE | Geminivirus | PCT/EP99/03445 - CINESTAV |
| PDF1.2 | Fungal including *Alternaria brassicicola* and *Botrytis cinerea* | Manners et al (1998), Plant Mol Biol, 38(6): 1071-80. |
| Thi2.1 | Fungal - *Fusarium oxysporum* f sp. Matthiolae | Vignutelli et al (1998) Plant J; 14(3): 285-95 |
| DB#226 | nematodes | Bird and Wilson (1994) Mol. Plant-Microbe Interact., 7, 419-42 WO 95.322888 |
| DB#280 | nematodes | Bird and Wilson (1994) Mol. Plant-Microbe Interact., 7, 419-42 WO 95.322888 |
| Cat2 | nematodes | Niebel et al (1995) Mol Plant Microbe Interact 1995 May-June; 8(3): 371-8 |
| ☐Tub | nematodes | Aristizabal et al (1996), 8$^{th}$ International Congress on Plant-Microbe Interaction, Knoxville US B-29 |
| SHSP | nematodes | Fenoll et al (1997) In: Cellular and molecular aspects of plant-nematode interactions. Kluwer Academic, C. Fenoll, F. M. W. Grundler and S. A. Ohl (Eds.), |
| Tsw12 | nematodes | Fenoll et al (1997) In: Cellular and molecular aspects of plant-nematode interactions. Kluwer Academic, C. Fenoll, F. M. W. Grundler and S. A. Ohl (Eds.) |
| Hs1(pro1) | nematodes | WO 98/122335 - Jung |
| NsLTP | viral, fungal, bacterial | Molina & García-Olmedo (1993) FEBS Lett, 316(2): 119-22 |
| RIP | viral, fungal | Turner et al (1997) Proc Natl Acad Sci USA, 94(8): 3866-71 |

Examples of terminators particularly suitable for use in the gene constructs of the present invention include the *Agrobacterium tumefaciens* nopaline synthase (NOS) gene terminator, the *Agrobacterium tumefaciens* octopine synthase (OCS) gene terminator sequence, the Cauliflower mosaic virus (CaMV) 35S gene terminator sequence, the *Oryza sativa* ADP-glucose pyrophosphorylase terminator sequence (t3'Bt2), the *Zea mays* zein gene terminator sequence, the rbcs-1A gene terminator, and the rbcs-3A gene terminator sequences, amongst others.

Preferred promoter sequences of the invention include root specific promoters and seed-specific promoters such as but not limited to the ones listed in Table 5, Table 4, and as outlined in the Examples.

TABLE 5

Exemplary of root specific promoters for use
in the performance of the present invention

| NAME | ORIGIN | REFERENCE |
|---|---|---|
| SbPRP1 | Soybean | Suzuki et al., Plant Mol Biol, 21: 109-119, 1993 |
| 636 bp fragment of TobRB7 | Tobacco | Yamamoto et al., Plant Cell 3: 371-382, 1991 |
| GGPS3 | *Arabidopsis* | Okada et al., Plant Physiol 122: 1045-1056, 2000 |
| 580 bp fragment of prxEa | *Arabidopsis* | Wanapu and Shinmyo, Ann NY Acad Sci 782: 107-114, 1996 |
| Ids2 promoter | Barley | Okumura et al., Plant Mol Biol 25: 705-719, 1994 |
| AtPRP3 | *Arabidopsis* | Fowler et al., Plant Physiol 121: 1081-1092, 1999 |

Those skilled in the art will be aware of additional promoter sequences and terminator sequences which may be suitable for use in performing the invention. Such sequences may readily be used without any undue experimentation.

In the context of the current invention, "ectopic expression" or "ectopic overexpression" of a gene or a protein are conferring to expression patterns and/or expression levels of said gene or protein normally not occurring under natural conditions, more specifically is meant increased expression and/or increased expression levels. Ectopic expression can be achieved in a number of ways including operably linking of a coding sequence encoding said protein to an isolated homologous or heterologous promoter in order to create a chimeric gene and/or operably linking said coding sequence to its own isolated promoter (i.e. the unisolated promoter naturally driving expression of said protein) in order to create a recombinant gene duplication or gene multiplication effect. With "ectopic co-expression" is meant the ectopic expression or ectopic overexpression of two or more genes or proteins. The same or, more preferably, different promoters are used to confer ectopic expression of said genes or proteins.

Preferably, the promoter sequence used in the context of the present invention is operably linked to a coding sequence or open reading frame (ORF) encoding a cytokinin oxidase protein or a homologue, derivative or an immunologically active and/or functional fragment thereof as defined supra.

"Downregulation of expression" as used herein means lowering levels of gene expression and/or levels of active gene product and/or levels of gene product activity. Decreases in expression may be accomplished by e.g. the addition of coding sequences or parts thereof in a sense orientation (if resulting in co-suppression) or in an antisense orientation relative to a promoter sequence and furthermore by e.g. insertion mutagenesis (e.g. T-DNA insertion or transposon insertion) or by gene silencing strategies as described by e.g. Angell and Baulcombe (1998—WO9836083), Lowe et al. (1989—WO9853083), Lederer et al. (1999—WO9915682) or Wang et al. (1999—WO9953050). Genetic constructs aimed at silencing gene expression may have the nucleotide sequence of said gene (or one or more parts thereof) contained therein in a sense and/or antisense orientation relative to the promoter sequence. Another method to down-regulate gene expression comprises the use of ribozymes.

Modulating, including lowering, the level of active gene products or of gene product activity can be achieved by administering or exposing cells, tissues, organs or organisms to said gene product, a homologue, derivative and/or immunologically active fragment thereof. Immunomodulation is another example of a technique capable of downregulation levels of active gene product and/or of gene product activity and comprises administration of or exposing to or expressing antibodies to said gene product to or in cells, tissues, organs or organisms wherein levels of said gene product and/or gene product activity are to be modulated. Such antibodies comprise "plantibodies", single chain antibodies, IgG antibodies and heavy chain camel antibodies as well as fragments thereof.

Modulating, including lowering, the level of active gene products or of gene product activity can furthermore be achieved by administering or exposing cells, tissues, organs or organisms to an agonist of said gene product or the activity thereof. Such agonists include proteins (comprising e.g. kinases and proteinases) and chemical compounds identified according to the current invention as described supra.

In the context of the current invention is envisaged the downregulation of the expression of a cytokinin oxidase gene as defined earlier. Preferably said cytokinin oxidase gene is a plant cytokinin oxidase gene, more specifically an AtCKX. The invention further comprises downregulation of levels of a cytokinin oxidase protein or of a cytokinin oxidase activity whereby said cytokinin oxidase protein has been defined supra. Preferably said cytokinin oxidase protein is a plant cytokinin oxidase, more specifically an AtCKX.

By "modifying cell fate and/or plant development and/or plant morphology and/or biochemistry and/or physiology" is meant that one or more developmental and/or morphological and/or biochemical and/or physiological characteristics of a plant is altered by the performance of one or more steps pertaining to the invention described herein.

"Cell fate" refers to the cell-type or cellular characteristics of a particular cell that are produced during plant development or a cellular process therefor, in particular during the cell cycle or as a consequence of a cell cycle process.

"Plant development" or the term "plant developmental characteristic" or similar term shall, when used herein, be taken to mean any cellular process of a plant that is involved in determining the developmental fate of a plant cell, in particular the specific tissue or organ type into which a progenitor cell will develop. Cellular processes relevant to plant development will be known to those skilled in the art. Such processes include, for example, morphogenesis, photomorphogenesis, shoot development, root development, vegetative development, reproductive development, stem elongation, flowering, and regulatory mechanisms involved in determining cell fate, in particular a process or regulatory process involving the cell cycle.

"Plant morphology" or the term "plant morphological characteristic" or similar term will, when used herein, be understood by those skilled in the art to refer to the external appearance of a plant, including any one or more structural features or combination of structural features thereof. Such structural features include the shape, size, number, position, color, texture, arrangement, and patternation of any cell, tissue or organ or groups of cells, tissues or organs of a plant, including the root, stem, leaf, shoot, petiole, trichome, flower, petal, stigma, style, stamen, pollen, ovule, seed, embryo, endosperm, seed coat, aleurone, fiber, fruit, cambium, wood, heartwood, parenchyma, aerenchyma, sieve element, phloem or vascular tissue, amongst others.

"Plant biochemistry" or the term "plant biochemical characteristic" or similar term will, when used herein, be understood by those skilled in the art to refer to the metabolic and catalytic processes of a plant, including primary and secondary metabolism and the products thereof, including any small molecules, macromolecules or chemical compounds, such as but not limited to starches, sugars, proteins, peptides, enzymes, hormones, growth factors, nucleic acid molecules, celluloses, hemicelluloses, calloses, lectins, fibers, pigments such as anthocyanins, vitamins, minerals, micronutrients, or macronutrients, that are produced by plants.

"Plant physiology" or the term "plant physiological characteristic" or similar term will, when used herein, be understood to refer to the functional processes of a plant, including developmental processes such as growth, expansion and differentiation, sexual development, sexual reproduction, seed set, seed development, grain filling, asexual reproduction, cell division, dormancy, germination, light adaptation, photosynthesis, leaf expansion, fiber production, secondary growth or wood production, amongst others; responses of a plant to externally-applied factors such as metals, chemicals, hormones, growth factors, environment and environmental stress factors (e.g. anoxia, hypoxia, high temperature, low temperature, dehydration, light, daylength, flooding, salt, heavy metals, amongst others), including adaptive responses of plants to said externally-applied factors.

Means for introducing recombinant DNA into plant tissue or cells include, but are not limited to, transformation using $CaCl_2$ and variations thereof, in particular the method described by Hanahan (1983), direct DNA uptake into protoplasts (Krens et al., 1982; Paszkowski et al, 1984), PEG-mediated uptake to protoplasts (Armstrong et al, 1990) microparticle bombardment, electroporation (Fromm et al., 1985), microinjection of DNA (Crossway et al., 1986), microparticle bombardment of tissue explants or cells (Christou et al, 1988; Sanford, 1988), vacuum-infiltration of tissue with nucleic acid, or in the case of plants, T-DNA-mediated transfer from *Agrobacterium* to the plant tissue as described essentially by An et al. (1985), Dodds et al., (1985), Herrera-Estrella et al., (1983a, 1983b, 1985). Methods for transformation of monocotyledonous plants are well known in the art and include *Agrobacterium*-mediated transformation (Cheng et al., 1997—WO9748814; Hansen 1998—WO9854961; Hiei et al., 1994—WO9400977; Hiei et al., 1998—WO9817813; Rikiishi et al., 1999—WO9904618; Saito et al., 1995—WO9506722), microprojectile bombardment (Adams et al., 1999—U.S. Pat. No. 5,969,213; Bowen et al., 1998—U.S. Pat. No. 5,736,369; Chang et al., 1994—WO9413822; Lundquist et al., 1999—U.S. Pat. No. 5,874,265/U.S. Pat. No. 5,990,390; Vasil and Vasil, 1995—U.S. Pat. No. 5,405,765. Walker et al., 1999—U.S. Pat. No. 5,955,362), DNA uptake (Eyal et al., 1993—WO9318168), microinjection of *Agrobacterium* cells (von Holt, 1994—DE4309203) and sonication (Finer et al., 1997—U.S. Pat. No. 5,693,512).

For microparticle bombardment of cells, a microparticle is propelled into a cell to produce a transformed cell. Any suitable ballistic cell transformation methodology and apparatus can be used in performing the present invention. Exemplary apparatus and procedures are disclosed by Stomp et al. (U.S. Pat. No. 5,122,466) and Sanford and Wolf (U.S. Pat. No. 4,945,050). When using ballistic transformation procedures, the gene construct may incorporate a plasmid capable of replicating in the cell to be transformed. Examples of microparticles suitable for use in such systems include 1 to 5 μm gold spheres. The DNA construct may be deposited on the microparticle by any suitable technique, such as by precipitation.

A whole plant may be regenerated from the transformed or transfected cell, in accordance with procedures well known in the art. Plant tissue capable of subsequent clonal propagation, whether by organogenesis or embryogenesis, may be transformed with a gene construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem).

The term "organogenesis", as used herein, means a process by which shoots and roots are developed sequentially from meristematic centers.

The term "embryogenesis", as used herein, means a process by which shoots and roots develop together in a concerted fashion (not sequentially), whether from somatic cells or gametes.

Preferably, the plant is produced according to the inventive method is transfected or transformed with a genetic sequence, or amenable to the introduction of a protein, by any art-recognized means, such as microprojectile bombardment, microinjection, *Agrobacterium*-mediated transformation (including in planta transformation), protoplast fusion, or electroporation, amongst others. Most preferably said plant is produced by *Agrobacterium*-mediated transformation.

*Agrobacterium*-mediated transformation or agrolistic transformation of plants, yeast, molds or filamentous fungi is based on the transfer of part of the transformation vector sequences, called the T-DNA, to the nucleus and on integration of said T-DNA in the genome of said eukaryote.

With "*Agrobacterium*" is meant a member of the Agrobacteriaceae, more preferably *Agrobacterium* or *Rhizobacterium* and most preferably *Agrobacterium tumefaciens*.

With "T-DNA", or transferred DNA, is meant that part of the transformation vector flanked by T-DNA borders which is, after activation of the *Agrobacterium* vir genes, nicked at the T-DNA borders and is transferred as a single stranded DNA to the nucleus of an eukaryotic cell.

When used herein, with "T-DNA borders", "T-DNA border region", or "border region" are meant either right T-DNA border (RB) or left T-DNA border (LB). Such a border comprises a core sequence flanked by a border inner region as part of the T-DNA flanking the border and/or a border outer region as part of the vector backbone flanking the border. The core sequences comprise 22 bp in case of octopine-type vectors and 25 bp in case of nopaline-type vectors. The core sequences in the right border region and left border region form imperfect repeats. Border core sequences are indispensable for recognition and processing by the *Agrobacterium* nicking complex consisting of at least VirD1 and VirD2. Core sequences flanking a T-DNA are sufficient to promote transfer of said T-DNA. However, efficiency of transformation using transformation vectors carrying said T-DNA solely flanked by said core sequences is low. Border, inner and outer regions are known to modulate efficiency of T-DNA transfer (Wang et al. 1987). One element enhancing T-DNA transfer has been characterized and resides in the right border outer region and is called overdrive (Peralta et al. 1986, van Haaren et al. 1987).

With "T-DNA transformation vector" or "T-DNA vector" is meant any vector encompassing a T-DNA sequence flanked by a right and left T-DNA border consisting of at least the right and left border core sequences, respectively, and used for transformation of any eukaryotic cell.

With "T-DNA vector backbone sequence" or "T-DNA vector backbone sequences" is meant all DNA of a T-DNA containing vector that lies outside of the T-DNA borders and, more specifically, outside the nicking sites of the border core imperfect repeats.

The current invention includes optimized T-DNA vectors such that vector backbone integration in the genome of a eukaryotic cell is minimized or absent. With "optimized T-DNA vector" is meant a T-DNA vector designed either to decrease or abolish transfer of vector backbone sequences to the genome of a eukaryotic cell. Such T-DNA vectors are known to the one familiar with the art and include those described by Hanson et al. (1999) and by Stuiver et al. (1999—WO9901563).

The current invention clearly considers the inclusion of a DNA sequence encoding a cytokinin oxidase, homologue, derivative or immunologically active and/or functional fragment thereof as defined supra, in any T-DNA vector comprising binary transformation vectors, super-binary transformation vectors, co-integrate transformation vectors, Ri-derived transformation vectors as well as in T-DNA carrying vectors used in agrolistic transformation. Preferably, said cytokinin oxidase is a plant cytokinin oxidase, more specifically an *Arabidopsis thaliana* (At)CKX.

With "binary transformation vector" is meant a T-DNA transformation vector comprising:

(a) a T-DNA region comprising at least one gene of interest and/or at least one selectable marker active in the eukaryotic cell to be transformed; and (b) a vector backbone region comprising at least origins of replication active in *E. coli* and *Agrobacterium* and markers for selection in *E. coli* and *Agrobacterium*.

The T-DNA borders of a binary transformation vector can be derived from octopine-type or nopaline-type Ti plasmids or from both. The T-DNA of a binary vector is only transferred to a eukaryotic cell in conjunction with a helper plasmid.

With "helper plasmid" is meant a plasmid that is stably maintained in *Agrobacterium* and is at least carrying the set of vir genes necessary for enabling transfer of the T-DNA. Said set of vir genes can be derived from either octopine-type or nopaline-type Ti plasmids or from both.

With "super-binary transformation vector" is meant a binary transformation vector additionally carrying in the vector backbone region a vir region of the Ti plasmid pTiBo542 of the super-virulent *A. tumefaciens* strain A281 (EP0604662, EP0687730). Super-binary transformation vectors are used in conjunction with a helper plasmid.

With "co-integrate transformation vector" is meant a T-DNA vector at least comprising:

(a) a T-DNA region comprising at least one gene of interest and/or at least one selectable marker active in plants; and (b) a vector backbone region comprising at least origins of replication active in *Escherichia coli* and *Agrobacterium*, and markers for selection in *E. coli* and *Agrobacterium*, and a set of vir genes necessary for enabling transfer of the T-DNA.

The T-DNA borders and said set of vir genes of a said T-DNA vector can be derived from either octopine-type or nopaline-type Ti plasmids or from both.

With "Ri-derived plant transformation vector" is meant a binary transformation vector in which the T-DNA borders are derived from a Ti plasmid and said binary transformation vector being used in conjunction with a 'helper' Ri-plasmid carrying the necessary set of vir genes.

As used herein, the term "selectable marker gene" or "selectable marker" or "marker for selection" includes any gene which confers a phenotype on a cell in which it is expressed to facilitate the identification and/or selection of cells which are transfected or transformed with a gene construct of the invention or a derivative thereof. Suitable selectable marker genes contemplated herein include the ampicillin resistance (Amp$^r$), tetracycline resistance gene (Tc$^r$) bacterial kanamycin resistance gene (Kan$^r$), phosphinothricin resistance gene, neomycin phosphotransferase gene (nptII), hygromycin resistance gene, β-glucuronidase (GUS) gene, chloramphenicol acetyltransferase (CAT) gene, green fluorescent protein (gfp) gene (Haseloff et al, 1997), and luciferase gene, amongst others.

With "agrolistics", "agrolistic transformation" or "agrolistic transfer" is meant here a transformation method combining features of *Agrobacterium*-mediated transformation and of biolistic DNA delivery. As such, a T-DNA containing target plasmid is co-delivered with DNA/RNA enabling in planta production of VirD1 and VirD2 with or without VirE2 (Hansen and Chilton 1996; Hansen et al. 1997; Hansen and Chilton 1997—WO9712046).

With "foreign DNA" is meant any DNA sequence that is introduced in the host's genome by recombinant techniques. Said foreign DNA includes e.g. a T-DNA sequence or a part thereof such as the T-DNA sequence comprising the selectable marker in an expressible format. Foreign DNA furthermore include intervening DNA sequences as defined supra.

With "recombination event" is meant either a site-specific recombination event or a recombination event effected by transposon 'jumping'.

With "recombinase" is meant either a site-specific recombinase or a transposase.

With "recombination site" is meant either site-specific recombination sites or transposon border sequences.

With "site specific recombination event" is meant an event catalyzed by a system generally consisting of three elements: a pair of DNA sequences (the site-specific recombination sequences or sites) and a specific enzyme (the site-specific recombinase). The site-specific recombinase catalyzes a recombination reaction only between two site-specific recombination sequences depending on the orientation of the site-specific recombination sequences. Sequences intervening between two site-specific recombination sites will be inverted in the presence of the site-specific recombinase when the site-specific recombination sequences are oriented in opposite directions relative to one another (i.e. inverted repeats). If the site-specific recombination sequences are oriented in the same direction relative to one another (i.e. direct repeats), then any intervening sequences will be deleted upon interaction with the site-specific recombinase. Thus, if the site-specific recombination sequences are present as direct repeats at both ends of a foreign DNA sequence integrated into a eukaryotic genome, such integration of said sequences can subsequently be reversed by interaction of the site-specific recombination sequences with the corresponding site specific recombinase.

A number of different site specific recombinase systems can be used including but not limited to the Cre/lox system of bacteriophage P1, the FLP/FRT system of yeast, the Gin recombinase of phage Mu, the Pin recombinase of *E. coli*, the PinB, PinD and PinF from *Shigella*, and the R/RS system of the pSR1 plasmid. Recombinases generally are integrases, resolvases or flippases. Also dual-specific recombinases can be used in conjunction with direct or indirect repeats of two different site-specific recombination sites corresponding to the dual-specific recombinase (WO99/25840). The two preferred site-specific recombinase systems are the bacteriophage P1 Cre/lox and the yeast FLP/FRT systems. In these systems a recombinase (Cre or FLP) interact specifically with its respective site-specific recombination sequence (lox or FRT respectively) to invert or excise the intervening sequences. The site-specific recombination sequences for each of these two systems are relatively short (34 bp for lox and 47 bp for FRT). Some of these systems have already been used with high efficiency in plants such as tobacco (Dale et al. 1990) and *Arabidopsis* (Osborne et al. 1995). Site-specific recombination systems have many applications in plant molecular biology including methods for control of homologous recombination (e.g. U.S. Pat. No. 5,527,695), for targeted insertion, gene stacking, etc. (WO99/25821) and for resolution of complex T-DNA integration patterns or for excision of a selectable marker (WO99/23202).

Although the site-specific recombination sequences must be linked to the ends of the DNA to be excised or to be inverted, the gene encoding the site specific recombinase may be located elsewhere. For example, the recombinase gene could already be present in the eukaryote's DNA or could be supplied by a later introduced DNA fragment either introduced directly into cells, through crossing or through cross-pollination. Alternatively, a substantially purified recombinase protein could be introduced directly into the eukaryotic cell, e.g. by micro-injection or particle bombardment. Typically, the site-specific recombinase coding region will be operably linked to regulatory sequences enabling expression of the site-specific recombinase in the eukaryotic cell.

With "recombination event effected by transposon jumping" or "transposase-mediated recombination" is meant a recombination event catalyzed by a system consisting of three elements: a pair of DNA sequences (the transposon border sequences) and a specific enzyme (the transposase). The transposase catalyzes a recombination reaction only between two transposon border sequences which are arranged as inverted repeats.

A number of different transposon/transposase systems can be used including but not limited to the Ds/Ac system, the Spm system and the Mu system. These systems originate from corn but it has been shown that at least the Ds/Ac and the Spm system also function in other plants (Fedoroff et al. 1993, Schlappi et al. 1993, Van Sluys et al. 1987), Preferred are the Ds- and the Spm-type transposons which are delineated by 11 bp- and 13 bp-border sequences, respectively.

Although the transposon border sequences must be linked to the ends of the DNA to be excised, the gene encoding the transposase may be located elsewhere. For example, the recombinase gene could already be present in the eukaryote's DNA or could be supplied by a later introduced DNA fragment either introduced directly into cells, through crossing or through cross-pollination. Alternatively, a substantially purified transposase protein could be introduced directly into cells, e.g. by microinjection or by particle bombardment.

As part of the current invention, transposon border sequences are included in a foreign DNA sequence such that they lie outside said DNA sequence and transform said DNA into a transposon-like entity that can move by the action of a transposase.

As transposons often reintegrate at another locus of the host's genome, segregation of the progeny of the hosts in which the transposase was allowed to act might be necessary to separate transformed hosts containing e.g. only the transposon footprint and transformed hosts still containing the foreign DNA.

In performing the present invention, the genetic element is preferably induced to mobilize, such as, for example, by the expression of a recombinase protein in the cell which contacts the integration site of the genetic element and facilitates a recombination event therein, excising the genetic element completely, or alternatively, leaving a "footprint", generally of about 20 nucleotides in length or greater, at the original integration site. Those hosts and host parts that have been produced according to the inventive method can be identified by standard nucleic acid hybridization and/or amplification techniques to detect the presence of the mobilizable genetic element or a gene construct comprising the same. Alternatively, in the case of transformed host cells, tissues, and hosts wherein the mobilizable genetic element has been excised, it is possible to detect a footprint in the genome of the host which has been left following the excision event, using such techniques. As used herein, the term "footprint" shall be taken to refer to any derivative of a mobilizable genetic element or gene construct comprising the same as described herein which is produced by excision, deletion or other removal of the mobilizable genetic element from the genome of a cell transformed previously with said gene construct. A footprint generally comprises at least a single copy of the recombination loci or transposon used to promote excision. However, a footprint may comprise additional sequences derived from the gene construct, for example nucleotide sequences derived from the left border sequence, right border sequence, origin of replication, recombinase-encoding or transposase-encoding sequence if used, or other vector-derived nucleotide sequences. Accordingly, a footprint is identifiable according to the nucleotide sequence of the recombination locus or transposon of the gene construct used, such as, for example, a sequence of nucleotides corresponding or complementary to a lox site or frt site.

The term "cell cycle" means the cyclic biochemical and structural events associated with growth and with division of cells, and in particular with the regulation of the replication of DNA and mitosis. Cell cycle includes phases called: G0, Gap1 (G1), DNA synthesis (S), Gap2 (G2), and mitosis (M). Normally these four phases occur sequentially, however, the cell cycle also includes modified cycles wherein one or more phases are absent resulting in modified cell cycle such as endomitosis, acytokinesis, polyploidy, polyteny, and endoreduplication.

The term "cell cycle progression" refers to the process of passing through the different cell cycle phases. The term "cell cycle progression rate" accordingly refers to the speed at which said cell cycle phases are run through or the time spans required to complete said cell cycle phases.

With "two-hybrid assay" is meant an assay that is based on the observation that many eukaryotic transcription factors comprise two domains, a DNA-binding domain (DB) and an activation domain (AD) which, when physically separated (i.e. disruption of the covalent linkage) do not effectuate target gene expression. Two proteins able to interact physically with one of said proteins fused to DB and the other of said proteins fused to AD will re-unite the DB and AD domains of the transcription factor resulting in target gene expression. The target gene in the yeast two-hybrid assay is usually a reporter gene such as the β-galactosidase gene. Interaction between protein partners in the yeast two-hybrid assay can thus be quantified by measuring the activity of the reporter gene product (Bartel and Fields 1997). Alternatively, a mammalian two-hybrid system can be used which includes e.g. a chimeric green fluorescent protein encoding reporter gene (Shioda et al., 2000).

Furthermore, folding simulations and computer redesign of structural motifs of the protein of the invention can be performed using appropriate computer programs (Olszewski, Proteins 25 (1996), 286-299; Hoffman, Comput. Appl. Biosci. 1 (1995), 675-679). Computer modeling of protein folding can be used for the conformational and energetic analysis of detailed peptide and protein models (Monge, J. Mol. Biol. 247 (1995), 995-1012; Renouf, Adv. Exp. Med. Biol. 376 (1995), 37-45). In particular, the appropriate programs can be used for the identification of interactive sites of the cytokinin oxidases, its ligands or other interacting proteins by computer assistant searches for complementary peptide sequences (Fassina, Immunomethods 5 (1994), 114-120). Further appropriate computer systems for the design of protein and peptides are described in the prior art, for example in Berry, Biochem. Soc. Trans. 22 (1994), 1033-1036; Wodak, Ann, N.Y. Acac. Sci. 501 (1987), 1-13; Pabo, Biochemistry 25 (1986), 5987-5991. The results obtained form the above-described computer analysis can be used for, e.g. the preparation of peptidomimetics of the protein of the invention or fragments thereof. Such pseudopeptide analogues of the natural amino acid sequence of the protein may very efficiently mimic the parent protein (Benkirane, J. Biol. Chem. 271 (1996), 33218-33224). For example, incorporation of easily available achiral Ω-amino acid residues into a protein of the invention or a fragment thereof results in the substitution of amino bonds by polymethylene units of an aliphatic chain, thereby providing a convenient strategy for constructing a peptidomimetic (Banerjee, Biopolymers 39 (1996), 769-777). Superactive peptidomimetic analogues of small peptide hormones in other systems are described in the prior art (Zhang, Biochem. Biophys. Res. Commun. 224 (1996), 327-331). Appropriate peptidomimetics of the protein of the present invention can also be identified by the synthesis of peptidomimetic combinatorial libraries through successive amine alkylation and testing the resulting compounds, e.g., for their binding, kinase inhibitory and/or immunological properties. Methods for the generation and use of peptidomimetic combinatorial libraries are described in the prior art, for example in Ostresh, Methods in Enzymology 267 (1996), 220-234 and Darner, Bioorg. Med. Chem. 4 (1996), 709-715.

Furthermore, a three-dimensional and/or crystallographic structure of the protein of the invention can be used for the design of peptidomimetic inhibitors of the biological activity of the protein of the invention (Rose, Biochemistry 35 (1996), 12933-12944; Ruterber, Bioorg. Med. Chem. 4 (1996), 1545-1558).

The compounds to be obtained or identified in the methods of the invention can be compounds that are able to bind to any of the nucleic acids, peptides or proteins of the invention. Other interesting compounds to be identified are compounds that modulate the expression of the genes or the proteins of the invention in such a way that either the expression of said gene or protein is enhanced or decreased by the action of said compound. Alternatively the compound can exert his action by enhancing or decreasing the activity of any of the proteins of the invention. Herein, preferred proteins are novel cytokinin oxidases.

Said compound or plurality of compounds may be comprised in, for example, samples, e.g., cell extracts from, e.g., plants, animals or microorganisms. Furthermore, said compound(s) may be known in the art but hitherto not known to be capable of suppressing or activating cytokinin oxidase interacting proteins. The reaction mixture may be a cell free extract of may comprise a cell or tissue culture. Suitable set ups for the method of the invention are known to the person skilled in the art and are, for example, generally described in Alberts et al., Molecular Biology of the Cell, third edition (1994), in particular Chapter 17. The plurality of compounds may be, e.g., added to the reaction mixture, culture medium or injected into the cell.

If a sample containing a compound or a plurality of compounds is identified in the method of the invention, then it is either possible to isolate the compound form the original sample identified as containing the compound capable of acting as an agonist, or one can further subdivide the original sample, for example, if it consists of a plurality of different compounds, so as to reduce the number of different substances per sample and repeat the method with the subdivisions of the original sample. Depending on the complexity of the samples, the steps described above can be performed several times, preferably until the sample identified according to the method of the invention only comprises a limited number of or only one substance(s). Preferably said sample comprises substances or similar chemical and/or physical properties, and most preferably said substances are identical. Preferably, the compound identified according to the above-described method or its derivative is further formulated in a form suitable for the application in plant breeding or plant cell and tissue culture.

The term "early vigor" refers to the ability of a plant to grow rapidly during early development, and relates to the successful establishment, after germination, of a well-developed root system and a well-developed photosynthetic apparatus.

The term "resistance to lodging" or "standability" refers to the ability of a plant to fix itself to the soil. For plants with an erect or semi-erect growth habit this term also refers to the ability to maintain an upright position under adverse (environmental) conditions. This trait relates to the size, depth and morphology of the root system.

The term 'grafting' as used herein, refers to the joining together of the parts of two different plants so that they bind together and the sap can flow, thus forming a single new plant that can grow and develop. A graft therefore consists of two parts: (i) the lower part is the rootstock as referred to herein and essentially consists of the root system and a portion of the stem, and (ii) the upper part, the scion or graft, which gives rise to the aerial parts of the plant.

As used herein, tblastn refers to an alignment tool that is part of the BLAST (Basic Local Alignment Search Tool) family of programs (.ncbi.nlm.nih.gov/BLAST/). BLAST aims to identify regions of optimal local alignment, i.e. the alignment of some portion of two nucleic acid or protein sequences, to detect relationships among sequences which share only isolated regions of similarity (Altschul et al., 1990). In the present invention, tblastn of the BLAST 2.0 suite of programs was used to compare the maize cytokinin oxidase protein sequence against a nucleotide sequence database dynamically translated in all reading frames (Altschul et al., Nucleic Acids Res. 25: 3389-3402 (1997)).

The following examples are given by means of illustration of the present invention and are in no way limiting. The contents of all references included in this application are incorporated by reference herein as if fully set forth.

EXAMPLES

Example 1

Brief Description of the Sequences of the Invention

| SEQ ID NO: | DESCRIPTION |
| --- | --- |
| 1 | AtCKX1 genomic |
| 2 | AtCKX1 protein |
| 3 | AtCKX2 genomic |
| 4 | AtCKX2 protein |
| 5 | AtCKX3 genomic |
| 6 | AtCKX3 protein |
| 7 | AtCKX4 genomic |
| 8 | AtCKX4 protein |
| 9 | AtCKX5 genomic (short version) |
| 10 | AtCKX5 protein (short version) |
| 11 | AtCKX6 genomic |
| 12 | AtCKX6 protein |
| 13 | 5'primer AtCKX1 |
| 14 | 3'primer AtCKX1 |
| 15 | 5'primer AtCKX2 |
| 16 | 3'primer AtCKX2 |
| 17 | 5'primer AtCKX3 |
| 18 | 3'primer AtCKX3 |
| 19 | 5'primer AtCKX4 |
| 20 | 3'primer AtCKX4 |
| 21 | 5'primer AtCKX5 |
| 22 | 3'primer AtCKX5 |
| 23 | 5'primer AtCKX6 |
| 24 | 3'primer AtCKX6 |
| 25 | AtCKX1 cDNA |
| 26 | AtCKX2 cDNA |
| 27 | AtCKX3 cDNA |
| 28 | AtCKX4 cDNA |
| 29 | AtCKX5 cDNA (short version) |
| 30 | AtCKX6 cDNA |

| SEQ ID NO: | DESCRIPTION |
|---|---|
| 31 | AtCKX2 cDNA fragment |
| 32 | AtCKX2 peptide fragment |
| 33 | AtCKX5 genomic (long version) |
| 34 | AtCKX5 cDNA (long version) |
| 35 | AtCKX5 protein (long version) |
| 36 | root clavata homolog promoter |

Example 2

Identification of Candidate Cytokinin Oxidase Encoding Genes from *Arabidopsis thaliana*

Six different genes were identified from *Arabidopsis thaliana* that bear sequence similarity to a cytokinin oxidase gene from maize (Morris et al., Biochem Biophys Res Comm 255:328-333, 1999; Houda-Herin et al., Plant J 17:615-626; WO 99/06571). These genes were found by screening 6-frame translations of nucleotide sequences from public genomic databases with the maize protein sequence, employing tblastn program. These sequences were designated as *Arabidopsis thaliana* cytokinin oxidase-like genes or AtCKX. They were arbitrarily numbered as AtCKX1 to AtCKX6. The below list summarizes the information on these genes. The predicted ORF borders and protein sequences are indicative, in order to illustrate by approximation the protein sequence divergence between the *Arabidopsis* and maize cytokinin oxidases, as well as amongst the different *Arabidopsis* cytokinin oxidases. The ORF borders and protein sequences shown should not be taken as conclusive evidence for the mode of action of these AtCKX genes. For DNA and protein sequence comparisons the program MegAlign from DNAstar was used. This program uses the Clustal method for alignments. For multiple alignments of protein and cDNA sequences the gap penalty and gap length penalty was set at 10 each. For pairwise alignments of proteins the parameters were as follows: Ktuple at 1; Gap penalty at 3; window at 5; diagonals saved at 5. For pairwise alignments of cDNA's the parameters were as follows: Ktuple at 2; Gap penalty at 5; window at 4; diagonals saved at 4. The similarity groups for protein alignments was: (M,I,L,V), (F,W,Y), (G,A), (S,T), (R,K,H), (E,D), (N,Q). The values that are indicated amongst the *Arabidopsis* cDNA, and protein sequences represent the lowest and highest values found with all combinations.

A. Gene name: AtCKX1 (*Arabidopsis thaliana* cytokinin oxidase-like protein 1, SEQ ID NO: 1)
Location in database (accession number, location on bac): AC002510, *Arabidopsis thaliana* chromosome II section 225 of 255 of the complete sequence. Sequence from clones T32G6.
ORF predicted in the database:
15517 . . . 16183, 16415 . . . 16542, 16631 . . . 16891, 16995 . . . 17257, 17344 . . . 17752 The AtCKX1 cDNA sequence is listed as SEQ ID NO: 25
Predicted protein sequence: SEQ ID NO: 2:
Homologies
% identity with *Z. mays* cDNA:
  31.5% (Dnastar/MegAlign—Clustal method)
% similarity with *Z. mays* protein:
  32.2% (Dnastar/MegAlign—Clustal method)
% identity with other *Arabidopsis* cDNA's (range):
  38.2% (AtCKX2)-54.1% (AtCKX6) (Dnastar/MegAlign—Clustal method)
% similarity with other *Arabidopsis* proteins (range):
  37.1% (AtCKX2)-58.1% (AtCKX6) (Dnastar/MegAlign—Clustal method)

B. Gene name: AtCKX2 (*Arabidopsis thaliana* cytokinin oxidase-like protein 2, SEQ ID NO: 3)
Location in database (accession number, location on bac): AC005917, *Arabidopsis thaliana* chromosome II section 113 of 255 of the complete sequence. Sequence from clones F27F23, F3P11.
ORF predicted in the database:
complement, 40721 . . . 41012, 41054 . . . 41364, 41513 . . . 41770, 42535 . . . 42662, 43153 . . . 43711
Please note: The cDNA sequence identified by the inventor using the gene prediction program NetPlantGene (.cbs.dtu.dk/services/NetGene2/) was different than the one annotated in the database. Based on the new cDNA sequence the ORF predicted in the database was revised:
complement, 40721 . . . 41012, 41095 . . . 41364, 41513 . . . 41770, 42535 . . . 42662, 43153 . . . 43711
The protein sequence encoded by this cDNA is listed as SEQ ID NO: 4. The cDNA of AtCKX2 was cloned by RT-PCR from total RNA of AtCKX2 transgenic plant tissue with the one-step RT-PCR kit (Qiagen, Hilden, Germany) and sequenced using an ABI PRISM Big Dye Terminator cycle sequencing reaction kit (Perkin Elmer Applied Biosystems Division). This confirmed that the cDNA sequence identified and predicted by the inventor was correct. The new AtCKX2 cDNA sequence is listed as SEQ ID NO: 26. An 84-bp fragment corresponding to nucleotides 1171 through 1254 of the AtCKX2 cDNA is listed as SEQ ID NO: 31. The corresponding peptide sequence of this 84-bp cDNA sequence is listed as SEQ ID NO: 32.
Homologies
% identity with *Z. mays* cDNA:
  38.4% (Dnastar/MegAlign—Clustal method)
% similarity with *Z. mays* protein:
  37.5% (Dnastar/MegAlign—Clustal method)
% identity with other *Arabidopsis* cDNA's (range):
  34.9% (AtCKX6)-64.5% (AtCKX4) (Dnastar/MegAlign—Clustal method)
% similarity with other *Arabidopsis* proteins (range):
  36.5% (AtCKX6)-66.1% (AtCKX4) (Dnastar/MegAlign—Clustal method)

C. Gene name: AtCKX3 (*Arabidopsis thaliana* cytokinin oxidase-like protein 3, SEQ ID NO: 5)
Location in database (accession number, location on bac): AB024035, *Arabidopsis thaliana* genomic DNA, chromosome 5, P1 clone: MHM17, complete sequence.
No prediction of the ORF in the database.
The gene was identified by the inventor using several gene prediction programs including GRAIL (arthur.epm.oml.gov/pub/xgrail), Genscan (CCR-081.mit.edu/GENSCAN html) and NetPlantGene (.cbs.dtu.dk/services/NetGene2/):
complement, 29415 . . . 29718, 29813 . . . 30081, 30183 . . . 30443, 30529 . . . 30656, 32107 . . . 32716
The new AtCKX3 cDNA sequence identified by the inventor is listed as SEQ ID NO: 27
Predicted protein sequence, based on own ORF prediction: SEQ ID NO: 6
Homologies
% identity with *Z. mays* cDNA:
  38.7% (Dnastar/MegAlign—Clustal method)
% similarity with *Z. mays* protein:
  39.2% (Dnastar/MegAlign—Clustal method)
% identity with other *Arabidopsis* cDNA's (range):
  38.8% (AtCKX6)-51.0% (AtCKX2) (Dnastar/MegAlign—Clustal method)

% similarity with other *Arabidopsis* proteins (range):
39.9% (AtCKX6)-46.7% (AtCKX2) (Dnastar/MegAlign—Clustal method)

D. Gene name: AtCKX4 (*Arabidopsis thaliana* cytokinin oxidase-like protein 4, SEQ ID NO: 7)
Location in database (accession number, location on bac):
1) AL079344, *Arabidopsis thaliana* DNA chromosome 4, BAC clone T16L4 (ESSA project)
2) AL161575, *Arabidopsis thaliana* DNA chromosome 4, contig fragment No. 71.
ORF predicted in the database:
1) 76187 . . . 76814, 77189 . . . 77316, 77821 . . . 78080, 78318 . . . 78586, 78677 . . . 78968
2) 101002 . . . 101629, 102004 . . . 102131, 102638 . . . 102895, 103133 . . . 103401, 103492 . . . 103783

The AtCKX4 cDNA sequence is listed as SEQ ID NO: 28
Predicted protein sequence: SEQ ID NO: 8
Homologies
% identity with *Z. mays* cDNA:
41.0% (Dnastar/MegAlign—Clustal method)
% similarity with *Z. mays* protein:
41.0% (Dnastar/MegAlign—Clustal method)
% identity with other *Arabidopsis* cDNA's (range):
35.2% (AtCKX6)-64.5% (AtCKX2) (Dnastar/MegAlign—Clustal method)
% similarity with other *Arabidopsis* proteins (range):
35.1% (AtCKX6)-66.1% (AtCKX2) (Dnastar/MegAlign—Clustal method)

E. Gene name: AtCKX5 (*Arabidopsis thaliana* cytokinin oxidase-like protein 5, SEQ ID NO: 9)
Location in database (accession number, location on bac):
AC023754, F1B16, complete sequence, chromosome 1
No prediction of the ORF in the database.

The gene was identified by the inventors using several gene prediction programs including GRAIL (ftp://arthur.epm.oml.gov/pub/xgrail), Genscan (http://CCR-081.mit.edu/GEN_SCAN.html) and NetPlantGene (http://www.cbs.d-tu.dk/services/NetGene2/).
43756 . . . 44347, 44435 . . . 44562, 44700 . . . 44966, 45493 . . . 45755, 46200 . . . 46560

The new AtCKX5 cDNA sequence identified and predicted by the inventor is listed as SEQ ID NO: 29. The predicted protein sequence for this cDNA is listed as SEQ ID NO: 10. A second potential ATG start codon is present 9 nucleotides more upstream in the genomic sequence. It is unclear which of these 2 start codons encodes the first amino acid of the protein. Therefore, a second potential AtCKX5 cDNA starting at this upstream start codon is also listed in this invention as SEQ ID NO: 34. The corresponding genomic sequence is listed as SEQ ID NO: 33 and the encoded protein as SEQ ID NO: 35.
Homologies
% identity with *Z. mays* cDNA:
39.1% (Dnastar/MegAlign—Clustal method)
% similarity with *Z. mays* protein:
36.6% (Dnastar/MegAlign—Clustal method)
% identity with other *Arabidopsis* cDNA's (range):
40.1% (AtCKX2)-44.0% (AtCKX3) (Dnastar/MegAlign—Clustal method)
% similarity with other *Arabidopsis* proteins (range):
41.6% (AtCKX4)-46.4% (AtCKX6) (Dnastar/MegAlign—Clustal method)

F. Gene name: AtCKX6 (*Arabidopsis thaliana* cytokinin oxidase-like protein 6, SEQ ID NO: 11)
Location in database (accession number, location on bac): AL163818, *Arabidopsis thaliana* DNA chromosome 3, P1 clone MAA21 (ESSA project).

ORF predicted in the database:
46630 . . . 47215, 47343 . . . 47470, 47591 . . . 47806, 47899 . . . 48161, 48244 . . . 48565

The AtCKX6 cDNA sequence is listed as SEQ ID NO: 30
Predicted protein sequence: SEQ ID NO: 12
Homologies
% identity with *Z. mays* cDNA:
37.3% (Dnastar/MegAlign—Clustal method)
% similarity with *Z. mays* protein:
36.1% (Dnastar/MegAlign—Clustal method)
% identity with other *Arabidopsis* cDNA's (range):
34.9% (AtCKX2)-54.1% (AtCKX1) (Dnastar/MegAlign—Clustal method)
% similarity with other *Arabidopsis* proteins (range):
35.1% (AtCKX4)-58.1% (AtCKX1) (Dnastar/MegAlign—Clustal method)

Genes AtCKX3 and AtCKX5 were not annotated as putative cytokinin oxidases in the database and ORFs for these genes were not given. Furthermore, the ORF (and consequently the protein structures) predicted for AtCKX2 was different from our own prediction and our prediction was confirmed by sequencing the AtCKX2 cDNA.

A comparison of the gene structure of the *Arabidopsis* AtCKX genes 1 to 4 and the maize CKX gene is shown in FIG. 1.

The predicted proteins encoded by the *Arabidopsis* AtCKX genes show between 32% and 41% sequence similarity with the maize protein, while they show between 35% and 66% sequence similarity to each other. Because of this reduced sequence conservation, it is not clear a priori whether the *Arabidopsis* AtCKX genes encode proteins with cytokinin oxidase activity. An alignment of the *Arabidopsis* AtCKX predicted proteins 1 to 4 and the maize CKX gene is shown in FIG. 2.

Example 3

Transgenic Plants Overexpressing AtCKX1 Showed Increased Cytokinin Oxidase Activity and Altered Plant Morphology 1. Description of the Cloning Process The following primers were used to PCR amplify the AtCKX1 gene from *Arabidopsis thaliana*, accession Columbia (non-homologous sequences used for cloning are in lower case):

```
Sequence of 5' primer:
                                   (SEQ ID NO: 13)
cggtcgacATGGGATTGACCTCATCCTTACG Sequence of 3' primer:
                                   (SEQ ID NO: 14)
gcgtcgacTTATACAGTTCTAGGTTTCGGCAGTAT
```

A 2235-bp PCR fragment, amplified by these primers, was inserted in the Sal I site of pUC19. The insert was sequenced and confirmed that the PCR amplification product did not contain any mutations. The SalI/SalI fragment of this vector was subcloned in the SalI site downstream of a modified CaMV 35S promoter (carrying three tetracycline operator sequences) in the binary vector pBinHyg-Tx (Gatz et al., 1992). The resulting construct was introduced into tobacco and *Arabidopsis thaliana* through *Agrobacterium*-mediated transformation, using standard transformation protocols.

2. Molecular Analysis of the Transgenic Lines

Figure 3:
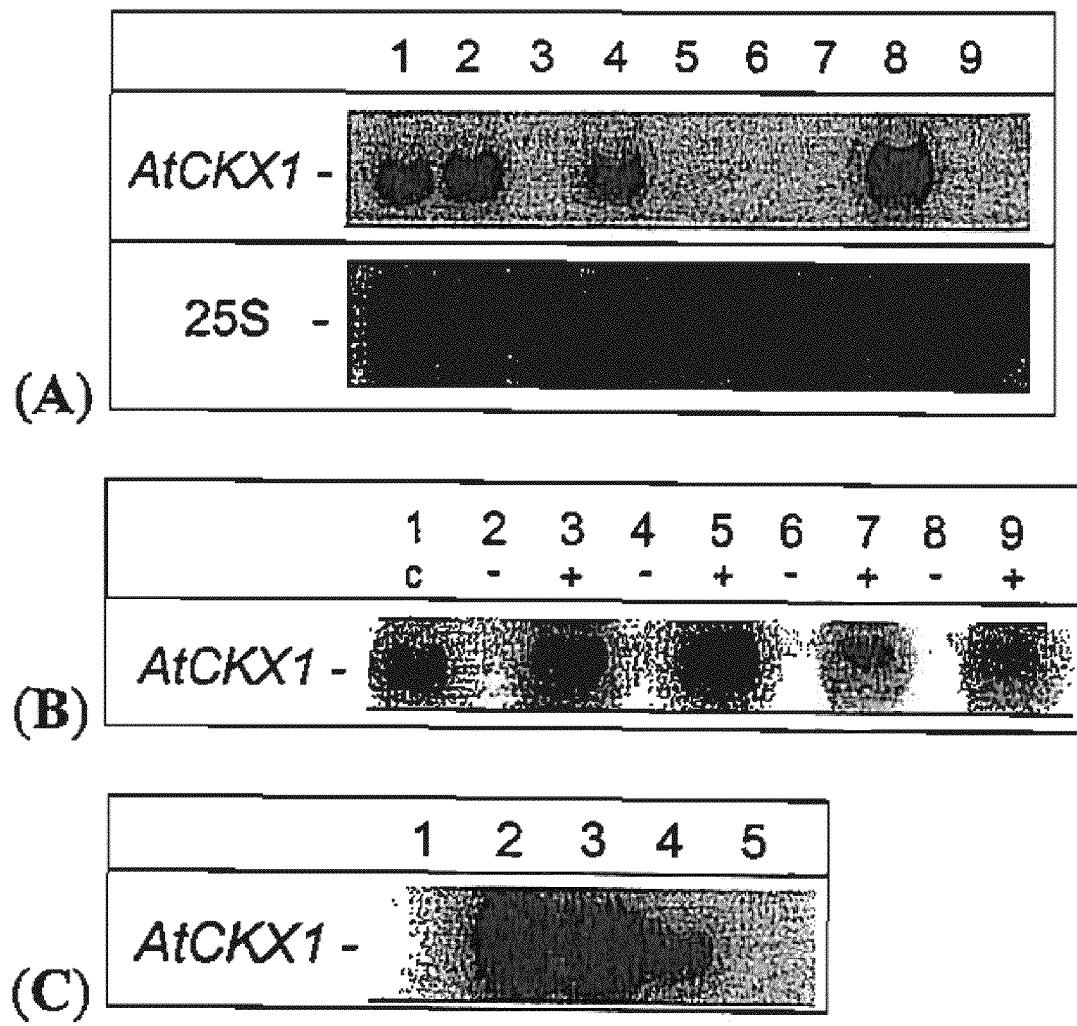

Several transgenic lines were identified that synthesize the AtCKX1 transcript at high levels (FIG. 3). Transgenic lines expressing AtCKX1 transcript also showed increased cytokinin oxidase activity as determined by a standard assay for cytokinin oxidase activity based on conversion of [2-$^3$H]iP to adenine as described (Motyka et al., 1996). This is exemplified for 2 tobacco and 2 *Arabidopsis* lines in Table 6. This result proves that the AtCKX1 gene encodes a protein with cytokinin oxidase activity.

TABLE 6

Cytokinin oxidase activity in AtCKX1 transgenic plant tissues

| Plant species | Leaf sample Plant line | Cytokinin oxidase activity (nmol Ade/mg protein.h) |
|---|---|---|
| *Arabidopsis* | Col-0 wild-type | 0.009 |
|  | CKX1-11 | 0.024 |
|  | CKX1-22 | 0.026 |
|  | CKX1-22 | 0.027 |
| Tobacco | SNN wild-type | 0.004 |
|  | CKX1-SNN-8 | 0.016 |
|  | CKX1-SNN-28 | 0.021 |

3. Phenotypic Description of the Transgenic Lines

3.1 In Tobacco:

The plants had a dwarfed phenotype with reduced apical dominance (FIGS. 7 A, B and C) and increased root production (FIG. 8).

Five categories of phenotype:
1) strong—2 clones
2) intermediate—3 clones
3) weak—4 clones
4) tall plants (as WT) with large inflorescence—5 clones
5) similar to WT, 9 clones Height (see FIGS. 7 B and C)
  WT: between 100-150 cm
  weak: approximately 75 cm
  intermediate: appr. 40-45 cm (main stem app. 25 cm but overgrown by side branches.
  strong: appr. 10 cm The transgenics AtCKX1-48 and AtCKX1-50 displayed a strong phenotype. Below are measurements for stem elongation as compared to WT plants:

| Line Days after germination | Wild-type Height (cm) | AtCKX1-48 Height (cm) | AtCKX1-50 Height (cm) |
|---|---|---|---|
| 47 | 9.5 ± 0.5 | 1.3 ± 0.3 | 1.2 ± 0.2 |
| 58 | 22.4 ± 2.3 | 2.2 ± 0.3 | 2.3 ± 0.3 |
| 68 | 35.3 ± 2.6 | 3.1 ± 0.5 | 2.6 ± 0.5 |
| 100 | 113.3 ± 9.8 | 7.1 ± 0.8 | 4.8 ± 0.9 |
| 117 | 138.6 ± 8.1 | 8.7 ± 0.7 | 6.6 ± 0.9 |
| 131 | 139.0 ± 9.3 | 9.3 ± 0.7 | 8.6 ± 1.0 |
| 152 | 136.6 ± 10.4 | 10.9 ± 1.1 | 10.0 ± 1.0 |
| 165 |  | 11.8 ± 1.9 | 11.4 ± 1.4 |
| 181 |  | 16.5 ± 1.7 | 14.9 ± 1.2 |
| 198 |  | 19.5 ± 1.5 | 18.1 ± 1.3 |

Experimental: Plants were grown in soil in a greenhouse.
Data were collected from at least ten plants per line.
Leaves (see FIGS. 7 D and E)
The shape of leaves of AtCKX1 transgenic expressors was lanceolate (longer and narrow): the width-to-length ratio of mature leaves was reduced from 1:2 in wild type plants to 1:3 in AtCKX1 transgenics (FIG. 7 E). The number of leaves and leaf surface was reduced compared to WT (see FIG. 7 D). A prominent difference was also noted for progression of leaf senescence. In WT tobacco, leaf senescence starts in the most basal leaves and leads to a uniform reduction of leaf pigment (FIG. 7 E). By contrast, ageing leaves of strongly expressing AtCKX1 plants stayed green along the leaf veins and turned yellow in the intercostal regions, indicating altered leaf senescence. The texture of older leaves was more rigid.

Roots

In vitro grown plants highly expressing the gene were easily distinguishable from the WT by their ability to form more roots which are thicker (stronger) (FIG. 8 A), as well as by forming aerial roots along the stem.

The primary root was longer and the number of lateral and adventitious roots was higher as illustrated in FIG. 8 C for AtCKX1-50 overexpressing seedlings (see also Example 9).

The dose-response curve of root growth inhibition by exogenous cytokinin showed that roots of transgenic seedlings are more cytokinin resistant than WT roots (FIG. 8 D). The resistance of AtCKX1 transgenics to iPR was less marked than for AtCKX2, which is consistent with the smaller changes in iP-type cytokinins in the latter (see Table 10).

A large increase in root biomass was observed for adult plants grown in soil (see FIG. 8 B for a plant grown in soil for 4 to 5 months) despite the fact that growth of the aerial plant parts was highly reduced.

Internode Distance intermediate phenotype: the $5^{th}$ internode below inflorescence is about 2.5 cm long and $9^{th}$ internode was about 0.5 cm long compared to 5 cm and 2 cm for the length of the $5^{th}$ and $9^{th}$ internode respectively, in WT plants.

strong phenotype: plant AtCKX1-50 The length of the $20^{th}$ internode from the bottom measured at day 131 after germination was 1.3±0.4 mm compared to 39.2±3.8 mm for WT Apical Dominance and Branching More side branches were formed indicating reduced apical dominance compared to WT plants during vegetative growth (see FIG. 9). The side branches overgrew the main stem, reaching a height of 40-45 cm for intermediate AtCKX1 expressors. Even secondary branches appeared. However, the buds were not completely released from apical dominance, i.e. lateral shoots did not really continue to develop. The reduced apical dominance might be due to reduced auxin production by the smaller shoot apical meristem (see Example 10).

Reproductive Development

The onset of flowering in AtCKX1 transgenics was delayed, the number of flowers and the seed yield per capsule was reduced. The size of flowers was not altered in transgenic plants and the weight of the individual seeds was comparable to the weight of seeds from wild type plants. Data for two representative AtCKX1 transgenics is summarized below:

A. Onset of Flowering

| Line | Wild-type | AtCKX1-48 | AtCKX1-50 |
|---|---|---|---|
| Flowering time (DAG) | 106.2 ± 3.3 | 193.3 ± 4.3 | 191.8 ± 3.8 |

Experimental: Data collected for at least ten plants per line. The full elongation of the first flower was defined as onset of flowering. DAG=days after germination.

B. Number of Seed Capsules Per Plant

| Line | Wild-type | AtCKX1-48 | AtCKX1-50 |
| --- | --- | --- | --- |
| Number of capsules | 83.33 ± 5.13 | 2.00 ± 1.00 | 2.60 ± 1.67 |

Experimental: Number of seed capsules was determined at least from 5 different plants. Please note that these plants were grown under greenhouse conditions during winter time. This affects negatively the number of flowers that are formed, in particular in the transgenic clones. However, the general picture that they form a reduced number of flowers is correct. n.d., not determined C. Seed Yield/Capsule (mg)

| Line | Wild-type | AtCKX1-48 | AtCKX1-50 |
| --- | --- | --- | --- |
| Seed/capsule (mg) | 87.41 ± 28.75 | 23.83 ± 13.36 | 61.8 ± 40.66 |

Experimental: Seed yield was determined for at least 12 seed capsules. The size of seed capsules was very variable, hence the large standard deviations. n.d., not determined D. Weight of 100 Seeds (mg)

| Line | Wild-type | AtCKX1-48 | AtCKXI-50 |
| --- | --- | --- | --- |
| Seeds weight (mg) | 9.73 ± 0.44 | 10.70 ± 1.60 | 9.54 ± 0.94 |

Experimental: The seed biomass was determined as the weight of 100 seed from at least 5 different seed capsules. n.d., not determined 3.2 In *Arabidopsis*

- onset of germination was same as for WT
- the total root system was enlarged and the number of side roots and adventitious roots was enhanced (see FIGS. 4 A through D)
- the growth of aerial organs was reduced resulting in a dwarfed phenotype (see FIGS. 4 E and F) and the leaf biomass was reduced. Leaf and flower formation is delayed.
- the life cycle was longer compared to WT and the seed yield was lower compared to WT The following morphometric data illustrate these phenotypes:

Root Development

A. Total Length of the Root System

| Line | Wild-type | AtCKX1-11 | AtCKX1-15 |
| --- | --- | --- | --- |
| Length (mm) | 32.5 | 76.5 | 68.4 |

B. Primary Root Length

| Line | Wild-type | AtCKX1-11 | AtCKX1-15 |
| --- | --- | --- | --- |
| Length (mm) | 32.3 ± 3.8 | 52.3 ± 4.8 | 39.9 ± 4.2 |

C. Lateral Roots (LR) Length

| Line | Wild-type | AtCKX1-11 | AtCKX1-15 |
| --- | --- | --- | --- |
| Length (mm) | 0.2 ± 0.4 | 15.6 ± 11.0 | 10.4 ± 7.6 |

D. Adventitious Roots Length

| Line | Wild-type | AtCKX1-11 | AtCKX1-15 |
| --- | --- | --- | --- |
| Length (mm) | 0.03 ± 0.18 | 8.6 ± 8.5 | 19.1 ± 11.0 |

E. Number of Lateral Roots (LR)

| Line | Wild-type | AtCKX1-11 | AtCKX1-15 |
| --- | --- | --- | --- |
| Number of LR | 0.3 ± 0.5 | 10.4 ± 5.4 | 2.6 ± 1.1 |

F. Number of Adventitious Roots (AR)

| Line | Wild-type | AtCKX1-11 | AtCKX1-15 |
| --- | --- | --- | --- |
| Number of AR | 0.03 ± 0.18 | 1.6 ± 1.1 | 2.6 ± 1.1 |

Experimental: Measurements were carried out on plants 8 days after germination in vitro on MS medium. At least 17 plants per line were scored.

Shoot Development

A. Leaf Surface

| Line | Wild-type | AtCKX1-11-7 T3 homozygous plants | AtCKX1-11-12 T3 homozygous plants | AtCKX1-15-1 T3 homozygous plants |
| --- | --- | --- | --- | --- |
| Leaf surface (cm$^2$) | 21.16 ± 1.73 | 2.28 ± 0.58 | 2.62 ± 0.28 | 1.66 ± 0.22 |

Experimental: Leaf surface area of main rosette leaves formed after 30 days after germination was measured. 3 plants per clone were analyzed.

Reproductive Development

Onset of Flowering

| Line | Wild-type | AtCKX1-11 T3 heterozygous plants | AtCKX2-2 T2 heterozygous plants | AtCKX2-5 T2 heterozygous plants |
|---|---|---|---|---|
| Flowering time (DAG) | 43.6 ± 5.8 | 69.7 ± 9.4 | 51.2 ± 4.1 | 45.1 ± 6.9 |

Experimental: Plants were grown under greenhouse condition. At least 13 plants per clone were analyzed. DAG=days after germination Conclusion: The analysis of AtCKX1 transgenic *Arabidopsis* plants confirmed largely the results obtained from tobacco and indicates the general nature of the consequences of a reduced cytokinin content. The total root system was enlarged (the total root length was increased app. 110-140% in AtCKX1 transgenics), the shoot developed more slowly (retarded flowering) and the leaf biomass was reduced. The seed yield was lower in the transgenics as well.

Example 4

Transgenic Plants Overexpressing AtCKX2 Showed Increased Cytokinin Oxidase Activity and Altered Plant Morphology 1. Description of the Cloning Process The following primers were used to PCR amplify the AtCKX2 gene from *Arabidopsis thaliana*, accession Columbia (non-homologous sequences used for cloning are in lower case):

```
Sequence of 5' primer:
                                        (SEQ ID NO: 15)
gcggtaccAGAGAGAGAAACATAAACAAATGGC Sequence of 3' primer:
                                        (SEQ ID NO: 16)
gcggtaccCAATTTTACTTCCACCAAAATGC
```

A 3104-bp PCR fragment, amplified by these primers, was inserted in the KpnI site of pUC19. The insert was sequenced to check that no differences to the published sequence were introduced by the PCR procedure. The KpnI/KpnI fragment of this vector was subcloned in the KpnI site downstream of a modified CaMV 35S promoter (carrying three tetracycline operator sequences) in the binary vector pBinHyg-Tx (Getz et al., 1992). The resulting construct was introduced into tobacco and *Arabidopsis thaliana* through *Agrobacterium*-mediated transformation, using standard transformation protocols.

2. Molecular Analysis of the Transgenic Lines

Several transgenic lines were identified that synthesize the AtCKX2 transcript at high levels (FIG. 6). Transgenic lines expressing AtCKX2 transcript also showed increased cytokinin oxidase activity. This is exemplified for 2 tobacco and 3 *Arabidopsis* line's in Table 7. This result proves that the AtCKX2 gene encodes a protein with cytokinin oxidase activity.

TABLE 7

Cytokinin oxidase activity in AtCKX2 transgenic plant tissues

| Sample | | Cytokinin oxidase activity |
|---|---|---|
| Plant species and tissue | Plant line | (nmol Ade/mg protein.h) |
| *Arabidopsis* callus | Col-0 wild-type | 0.037 |
| | CKX2-15 | 0.351 |
| | CKX2-17 | 0.380 |
| | CKX2-55 | 0.265 |
| Tobacco leaves | SNN wild-type | 0.009 |
| | CKX2-SNN-18 | 0.091 |
| | CKX2-SNN-19 | 0.091 |

3. Phenotypic Description of the Transgenic Lines 3.1 In Tobacco (see FIG. 7 to 10):

Three categories of phenotype:

1) strong—15 clones (similar to intermediate phenotype of AtCKX1)

2) weak—6 clones 3) others—similar to WT plants, 7 clones

Aerial Plant Parts

The observations concerning plant height, internode distance, branching, leaf form and yellowing were similar as for AtCKX1 transgenics with some generally minor quantitative differences in that the dwarfing characteristics were more severe in AtCKX1 transgenics than in AtCKX2 transgenics (compare AtCKX1 plants with AtCKX2 plants in FIGS. 7 A and B). This is illustrated below for stem elongation and internode distance measurements of clones with a strong phenotype AtCKX2-38 and AtCKX2-40:

Stem Elongation

| Line Days after germination | Wild-type Height (cm) | AtCKX2-38 Height (cm) | AtCKX2-40 Height (cm) |
|---|---|---|---|
| 47 | 9.5 ± 0.5 | 2.4 ± 0.1 | 2.6 ± 0.2 |
| 58 | 22.4 ± 2.3 | 5.5 ± 0.7 | 5.3 ± 0.5 |
| 68 | 35.3 ± 2.6 | 7.1 ± 0.8 | 7.0 ± 0.7 |
| 100 | 113.3 ± 9.8 | 15.5 ± 2.5 | 20.3 ± 6.4 |
| 117 | 138.6 ± 8.1 | 19.8 ± 3.8 | 29.5 ± 6.0 |
| 131 | 139.0 ± 9.3 | 26.5 ± 7.0 | 33.4 ± 5.8 |
| 152 | 136.6 ± 10.4 | 33.7 ± 6.3 | 33.9 ± 6.4 |
| 165 | | 36.2 ± 4.3 | |

Experimental: Plants were grown in soil in a green house. Data were collected from at least ten plants per line.

Internode Distance

| Line | Wild-type | AtCKX2-38 |
|---|---|---|
| Internode distance (mm) | 39.2 ± 3.8 | 7.2 ± 1.6 |

Experimental: The length of the 20$^{th}$ internode from the bottom was measured at day 131 after germination.

Roots

In vitro grown plants highly expressing the gene were easily distinguishable from WT plants by their ability to form more roots which are thicker (stronger) as well as by forming aerial roots along the stem.

The primary root was longer and the number of lateral and adventitious roots was higher as illustrated in FIG. 8 C for AtCKX2-38 overexpressing seedlings (see also Example 9).

The dose-response curve of root growth inhibition by exogenous cytokinin showed that roots of transgenic seedlings were more cytokinin resistant than WT roots (FIG. 8 D). The resistance of AtCKX1-28 transgenics to iPR was less marked than for AtCKX2-38, which is consistent with the smaller changes in iP-type cytokinins in the latter (see Table 10).

An increase in fresh and dry weight of the root biomass of T0 lines of AtCKX2 transgenic plants compared to WT was observed for plant grown in soil, as illustrated in the following table:

| Line | Wild-type | AtCKX2 (T0) |
|---|---|---|
| Fresh weight (g) | 45.2 ± 15.4 | 77.1 ± 21.3 |
| Dry weight (g) | 6.3 ± 1.9 | 8.6 ± 2.2 |

Experimental: Six WT plants and six independent T0 lines of 35S::AtCKX2 clone were grown on soil. After flowering the root system was washed with water, the soil was removed as far as possible and the fresh weight and dry weight was measured.

An increase in fresh and dry weight of the root biomass was also observed for F1 progeny of AtCKX2 transgenics grown in hydroponics as compared to WT, as illustrated in the following table:

| Line | Wild-type | AtCKX2-38 | AtCKX2-40 |
|---|---|---|---|
| Fresh weight ROOT (g) | 19.76 ± 6.79 | 33.38 ± 7.76 | 50.04 ± 15.59 |
| Dry weight ROOT (g) | 2.36 ± 0.43 | 2.61 ± 0.39 | 3.52 ± 1.06 |
| Fresh weight SHOOT (g) | 159.8 ± 44.53 | 33.66 ± 2.67 | 48.84 ± 11.83 |
| Fresh weight SHOOT/ROOT ratio | 8.24 ± 0.63 | 1.04 ± 0.18 | 1.08 ± 0.51 |

Experimental: Soil grown plants were transferred 60 days after germination to a hydroponic system (Hoagland's solution) and grown for additional 60 days. The hydroponic solution was aerated continuously and replaced by fresh solution every third day.

In summary, transgenic plants grown in hydroponic solution formed approximately 65-150% more root biomass (fresh weight) than wild type plants. The increase in dry weight was 10-50%. This difference is possibly in part due to the larger cell volume of the transgenics. This reduces the relative portion of cell walls, which forms the bulk of dry matter material. The shoot biomass was reduced to 20%-70% of wild type shoots. The difference in fresh weight leads to a shift in the shoot/root ratio, which was approximately 8 in wild type but approximately 1 in the transgenic clones.

Conclusion:

An increase in root growth and biomass was observed for AtCKX2 transgenic seedlings and adult plants grown under different conditions compared to WT controls despite the fact that growth of the aerial plant parts is reduced. Quantitative differences were observed between different transgenic plants: higher increases in root biomass were observed for the strongest expressing clones.

Reproductive Development

The onset of flowering in AtCKX2 transgenics was delayed, the number of flowers and the seed yield per capsule was reduced. These effects were very similar to those observed in the AtCKX1 transgenic plants but they were less prominent in the AtCKX2 transgenics, as indicated in the tables below. The size of flowers was not altered in transgenic plants and the weight of the individual seeds was comparable to the weight of seeds from wild type plants.

A. Onset of Flowering

| Line | Wild-type | AtCKX1-48 | AtCKX1-50 | AtCKX2-38 | AtCKX2-40 |
|---|---|---|---|---|---|
| Flowering time (DAG) | 106.2 ± 3.3 | 193.3 ± 4.3 | 191.8 ± 3.8 | 140.6 ± 6.5 | 121.9 ± 9.8 |

Experimental: Data collected for at least ten plants per line. The full elongation of the first flower was defined as onset of flowering. DAG=days after germination.

B. Number of Seed Capsules Per Plant

| Line | Wild-type | AtCKX1-48 | AtCKX1-50 | AtCKX2-38 | AtCKX2-40 |
|---|---|---|---|---|---|
| Number of capsules | 83.33 ± 5.13 | 2.00 ± 1.00 | 2.60 ± 1.67 | 4.30 ± 2.58 | n.d. |

Experimental: Number of seed capsules was determined at least from 5 different plants. Please note that these plants were grown under green house conditions during winter time. This affects negatively the number of flowers that are formed, in particular in the transgenic clones. However, the general picture that they form a reduced number of flowers is correct. n.d., not determined C. Seed Yield/Capsule (mg)

| Line | Wild-type | AtCKX1-48 | AtCKX1-50 | AtCKX2-38 | AtCKX2-40 |
|---|---|---|---|---|---|
| Seed/capsule (mg) | 87.41 ± 28.75 | 23.83 ± 13.36 | 61.8 ± 40.66 | 46.98 ± 29.30 | n.d. |

Experimental: Seed yield was determined for at least 12 seed capsules. The size of seed capsules was very variable, hence the large standard deviations. n.d., not determined D. Weight of 100 Seeds (mg)

| Line | Wild-type | AtCKX1-48 | AtCKX1-50 | AtCKX2-38 | AtCKX2-40 |
|---|---|---|---|---|---|
| Seeds weight (mg) | 9.73 ± 0.44 | 10.70 ± 1.60 | 9.54 ± 0.94 | 10.16 ± 0.47 | n.d. |

Experimental: The seed biomass was determined as the weight of 100 seed from at least 5 different seed capsules. n.d., not determined 3.2 In *Arabidopsis*:

The following morphometric data were obtained for AtCKX2 transgenics:

Root Development

A. Total Length of the Root System

| Line | Wild-type | AtCKX2-2 | AtCKX2-5 |
|---|---|---|---|
| Length (mm) | 32.5 | 50.6 | 48.5 |

B. Primary Root Length

| Line | Wild-type | AtCKX2-2 | AtCKX2-5 |
|---|---|---|---|
| Length (mm) | 32.3 ± 3.8 | 30.7 ± 4.8 | 31.6 ± 6.8 |

C. Lateral Roots Length

| Line | Wild-type | AtCKX2-2 | AtCKX2-5 |
|---|---|---|---|
| Length (mm) | 0.2 ± 0.4 | 5.5 ± 9.0 | 1.9 ± 2.5 |

D. Adventitious Roots Length

| Line | Wild-type | AtCKX2-2 | AtCKX2-5 |
|---|---|---|---|
| Length (mm) | 0.03 ± 0.18 | 14.4 ± 10.2 | 14.9 ± 9.1 |

E. Number of Lateral Roots(LR)

| Line | Wild-type | AtCKX2-2 | AtCKX2-5 |
|---|---|---|---|
| Number of LR | 0.3 ± 0.5 | 2.9 ± 2.3 | 1.9 ± 1.0 |

F. Number of Adventitious Roots (AR)

| Line | Wild-type | AtCKX2-2 | AtCKX2-5 |
|---|---|---|---|
| Number of AR | 0.03 ± 0.18 | 1.8 ± 0.9 | 1.8 ± 1.0 |

Experimental: Measurements were carried out on plants 8 d.a.g. in vitro on MS medium. At least 17 plants per line were scored.

Shoot Development
Leaf Surface

| Line | Wild-type | AtCKX2-2 T2 heterozygous plants | AtCKX2-5 T2 heterozygous plants | AtCKX2-9 T2 heterozygous plants |
|---|---|---|---|---|
| Leaf surface (cm²) | 21.16 ± 1.73 | 8.20 ± 2.35 | 8.22 ± 0.55 | 7.72 ± 0.85 |

Experimental: Leaf surface area of main rosette leaves formed after 30 days after germination was measured. 3 plants per clone were analyzed.

Reproductive Development
Onset of Flowering

| Line | Wild-type | AtCKX1-11 T3 heterozygous plants | AtCKX2-2 T2 heterozygous plants | AtCKX2-5 T2 heterozygous plants |
|---|---|---|---|---|
| Flowering time (DAG) | 43.6 ± 5.8 | 69.7 ± 9.4 | 51.2 ± 4.1 | 45.1 ± 6.9 |

Experimental: Plants were grown under greenhouse condition. At least 13 plants per clone were analyzed. DAG=days after germination.

Conclusion: *Arabidopsis* AtCKX2 transgenics had reduced leaf biomass and a dwarfing phenotype similar to AtCKX1 transgenics (compare FIG. 5 with FIG. 4 F). The total root system was also enlarged in AtCKX2 transgenic *Arabidopsis*. The total root length is increased approximately 50% in AtCKX2 transgenics. The AtCKX1 transgenics have longer primary roots, more side roots and form more adventitious roots. AtCKX2 transgenics lack the enhanced growth of the primary root but form more side roots and lateral roots than WT.

Summary:

The phenotypes observed for AtCKX2 transgenics were very similar but not identical to the AtCKX1 transgenics, which in turn were very similar but not identical to the results obtained for the tobacco transgenics. This confirms the general nature of the consequences of a reduced cytokinin content in these two plant species and therefore, similar phenotypes can be expected in other plant species as well. The main difference between tobacco and *Arabidopsis* is the lack of enhanced primary root growth in AtCKX2 overexpressing plants.

Example 5

Transgenic Plants Overexpressing AtCKX3 Showed Increased Cytokinin Oxidase Activity and Altered Plant Morphology 1. Description of the Cloning Process The following primers were used to PCR amplify the AtCKX3 gene from *Arabidopsis thaliana*, accession Columbia (non-homologous sequences used for cloning are in lower case):

```
Sequence of 5' primer:
                                   (SEQ ID NO: 17)
gcggtaccTTCATTGATAAGAATCAAGCTATTCA Sequence of 3' primer:
                                   (SEQ ID NO: 18)
gcggtaccCAAAGTGGTGAGAACGACTAACA
```

A 3397-bp PCR fragment, produced by this PCR amplification, was inserted in the KpnI site of pBluescript. The insert was sequenced to confirm that the PCR product has no sequence changes as compared to the gene. The KpnI/KpnI fragment of this vector was subcloned in the KpnI site downstream of a modified CaMV 35S promoter (carrying three tetracycline operator sequences) in the binary vector pBin-Hyg-Tx (Gatz et al., 1992). The resulting construct was introduced into tobacco and *Arabidopsis thaliana* through *Agrobacterium*-mediated transformation, using standard transformation protocols.

2. Molecular Analysis of the Transgenic Lines

Several transgenic tobacco lines were identified that synthesize the AtCKX3 transcript at high levels (FIG. 11 A). Transgenic tobacco lines expressing AtCKX3 transcript also showed increased cytokinin oxidase activity. This is exemplified for three plants in Table 8. This proves that the AtCKX3 gene encodes a protein with cytokinin oxidase activity.

TABLE 8

Cytokinin oxidase activity in AtCKX4 transgenic plant tissues

| Sample | | |
|---|---|---|
| Plant species and tissue | Plant line | Cytokinin oxidase activity (nmol Ade/mg protein.h) |
| tobacco leaves | SNN wild-type | 0.011 |
| | CKX3-SNN-3 | 0.049 |
| | CKX3-SNN-6 | 0.053 |
| | CKX3-SNN-21 | 0.05 |

3. Plant Phenotypic Analysis

The phenotypes generated by overexpression of the AtCKX3 gene in tobacco and *Arabidopsis* were basically similar as those of AtCKX1 and AtCKX2 expressing plants, i.e. enhanced rooting and dwarfing. However, overexpression of the AtCKX3 gene in tobacco resulted in a stronger phenotype compared to AtCKX2. In this sense AtCKX3 overexpression was more similar to AtCKX1 overexpression.

Example 6

Transgenic Plants Overexpressing AtCKX4 Showed Increased Cytokinin Oxidase Activity and Altered Plant Morphology 1. Description of the Cloning Process The following primers were used to PCR amplify the AtCKX4 gene from *Arabidopsis thaliana*, accession Columbia (non-homologous sequences used for cloning are in lower case):

```
Sequence of 5' primer:
                                          (SEQ ID NO: 19)
gcggtaccCCCATTAACCTACCCGTTTG Sequence of 3' primer:
                                          (SEQ ID NO: 20)
gcggtaccAGACGATGAACGTACTTGTCTGTA
```

A 2890-bp PCR fragment, produced by this PCR amplification, was inserted in the KpnI site of pBluescript. The insert was sequenced to confirm that the PCR product has no sequence changes as compared to the gene. The KpnI/KpnI fragment of this vector was subcloned in the KpnI site downstream of a modified CaMV 35S promoter (carrying three tetracycline operator sequences) in the binary vector pBin-Hyg-Tx (Gatz et al., 1992). The resulting construct was introduced into tobacco and *Arabidopsis thaliana* through *Agrobacterium*-mediated transformation, using standard transformation protocols.

2. Molecular Analysis of the Transgenic Lines

Several transgenic tobacco lines synthesized the AtCKX4 transcript at high levels (FIG. 11 B). Transgenic lines expressing AtCKX4 transcript also showed increased cytokinin oxidase activity. This is exemplified for 3 *Arabidopsis* and 3 tobacco lines in Table 9. This result proves that the AtCKX4 gene encodes a protein with cytokinin oxidase activity.

TABLE 9

Cytokinin oxidase activity in AtCKX4 transgenic plant tissues

| Sample | | |
|---|---|---|
| Plant species and tissue | Plant line | Cytokinin oxidase activity (nmol Ade/mg protein.h) |
| *Arabidopsis callus* | Col-0 wild-type | 0.037 |
|  | CKX4-37 | 0.244 |
|  | CKX4-40 | 0.258 |
|  | CKX4-41 | 0.320 |
| tobacco leaves | SNN wild-type | 0.011 |
|  | CKX4-SNN-3 | 0.089 |
|  | CKX4-SNN-18 | 0.085 |
|  | CKX4-SNN-27 | 0.096 |

Overall, the data showed that the apparent $K_m$ values for the four cytokinin oxidases were in the range of 0.2 to 9.5 µM with iP as substrate, which further demonstrates that the proteins encoded by AtCKX1 through 4 are indeed cytokinin oxidase enzymes as disclosed herein.

3. Plant Phenotypic Analysis

The phenotypes generated by overexpression of the AtCKX4 gene in tobacco and *Arabidopsis* were basically similar as those of AtCKX1 and AtCKX2 expressing plants, i.e. enhanced rooting, reduced apical dominance, dwarfing and yellowing of intercostal regions in older leaves of tobacco. An additional phenotype in tobacco was lanceolate leaves (altered length-to-width ratio).

General Observations of AtCKX Overexpressing Tobacco Plants

Overall, the phenotypic analysis demonstrated that AtCKX gene overexpression caused drastic developmental alterations in the plant shoot and mot system in tobacco, including enhanced development of the root system and dwarfing of the aerial plant part. Other effects such as altered leaf senescence, formation of adventitious root on stems, and others were also observed as disclosed herein. The alterations were very similar, but not identical, for the different genes. In tobacco, AtCKX1 and AtCKX3 overexpressors were alike as were AtCKX2 and AtCKX4. Generally, the two former showed higher expression of the traits, particularly in the shoot. Therefore, a particular cytokinin oxidase gene may be preferred for achieving the phenotypes that are described in the embodiments of this invention.

Example 7

Cloning of the AtCKX5 Gene

The following primers were used to PCR amplify the AtCKX5 gene from *Arabidopsis thaliana*, accession Columbia (non-homologous sequences used for cloning are in lower case):

```
Sequence of 5' primer:
ggggtaccTTGATGAATCGTGAAATGAC            (SEQ ID NO: 21)

Sequence of 3' primer:
ggggtaccCTTTCCTCTTGGTTTTGTCCTGT         (SEQ ID NO: 22)
```

The sequence of the 5' primer includes the two potential start codons of the AtCKX5 protein, the most 5' start codon is underlined and a second ATG is indicated in italics.

A 2843-bp PCR fragment, produced by this PCR amplification, was inserted as a blunt-end product in pCR-Blunt II-TOPO cloning vector (Invitrogen).

Example 8

Cloning of the AtCKX6 Gene

The following primers were used to PCR amplify the AtCKX6 gene from *Arabidopsis thaliana*, accession Columbia (non-homologous sequences used for cloning are in lower case):

```
Sequence of 5' primer:
gctctagaTCAGGAAAAGAACCATGCTTATAG        (SEQ ID NO: 23)

Sequence of 3' primer:
gctctagaTCATGAGTATGAGACTGCCTTTTG        (SEQ ID NO: 24)
```

A 1949-bp PCR fragment, produced by this PCR amplification, was inserted as a blunt-end product in pCR-Blunt II-TOPO cloning vector (Invitrogen).

Example 9

Tobacco Seedling Growth Test Demonstrated Early Vigor of AtCKX Transgenics

Seeds of AtCKX1-50 and AtCKX2-38 overexpressing transgenics and WT tobacco were sown in vitro on MS medium, brought to culture room 4 days after cold treatment and germinated after 6 days. Observations on seedling growth were made 10 days after germination (see also FIG. 8C) and are summarized below. At least 20 individuals were scored per clone. Similar data have been obtained in two other experiments.

A. Total Length of the Root System

| Line | Wild-type | AtCKX1-50 | AtCKX2-38 |
|---|---|---|---|
| Length (mm) | 61.1 | 122.0 | 106.5 |

B. Primary Root Length

| Line | Wild-type | AtCKXI-50 | AtCKX2-38 |
|---|---|---|---|
| Length (mm) | 32.3 ± 2.6 | 50.8 ± 4.5 | 52.4 ± 4.8 |

C. Lateral Roots Length

| Line | Wild-type | AtCKX1-50 | AtCKX2-38 |
|---|---|---|---|
| Length (mm) | 9.8 ± 5.5 | 18.0 ± 8.1 | 13.0 ± 6.0 |

D. Adventitious Roots Length

| Line | Wild-type | AtCKX1-50 | AtCKX2-38 |
|---|---|---|---|
| Length (mm) | 19.0 ± 5.0 | 53.0 ± 12.0 | 42.0 ± 9.8 |

E. Number of Lateral Roots (LR)

| Line | Wild-type | AtCKX1-50 | AtCKX2-38 |
|---|---|---|---|
| Number of LR | 1.9 ± 0.9 | 6.5 ± 2.2 | 5.6 ± 2.0 |

F. Number of Adventitious Roots (AR)

| Line | Wild-type | AtCKX1-50 | AtCKX2-38 |
|---|---|---|---|
| Number of AR | 2.2 ± 0.6 | 3.5 ± 0.9 | 3.6 ± 1.3 |

AtCKX1 and AtCKX2 Plants, General Observations:

Seedlings of AtCKX1 and AtCKX2 overexpressing tobacco plants had 60% more adventitious roots and three times more lateral roots than untransformed control plants 10 days after germination. The length of the primary root was increased by about 70%. This—together with more and longer side roots and secondary roots—resulted in a 70-100% increase in total root length. These results showed that overexpression of cytokinin oxidase enhances the growth and development of both the main root and the adventitious roots, resulting in early vigor.

Example 10

Histological Analysis of Altered Plant Morphology in AtCKX1 Overexpressing Tobacco Plants Microscopic analysis of different tissues revealed that the morphological changes in AtCKX transgenics are reflected by distinct changes in cell number and rate of cell formation (see FIG. 10). The shoot apical meristem (SAM) of AtCKX1 transgenics was smaller than in wild type and fewer cells occupy the space between the central zone and the peripheral zone of lateral organ formation, but the cells were of the same size (FIG. 10 A). The reduced cell number and size of the SAM as a consequence of a reduced cytokinin content indicates that cytokinins have a role in the control of SAM proliferation. No obvious changes in the differentiation pattern occurred, suggesting that the spatial organization of the differentiation zones in the SAM is largely independent from cell number and from the local cytokinin concentration. The overall tissue pattern of leaves in cytokinin oxidase overexpressors was unchanged. However, the size of the phloem and xylem was significantly reduced (FIG. 10 B). By contrast, the average cell size of leaf parenchyma and epidermal cells was increased four- to fivefold (FIG. 10 C, D). New cells of AtCKX1 transgenics are formed at 3-4% of the rate of wild type leaves and final leaf cell number was estimated to be in the range of 5-6% of wild type. This indicates an absolute requirement for cytokinins in leaves to maintain the cell division cycle. Neither cell size nor cell form of floral organs was altered and seed yield per capsule was similar in wild type and AtCKX transgenic plants. The cell population of root meristems of AtCKX1 transgenic plants was enlarged approximately 4-fold and the cell numbers in both the central and lateral columnella were enhanced (FIG. 10 E, F). The final root diameter was increased by 60% due to an increased diameter of all types of root cells. The radial root patterns was identical in wild type and transgenics, with the exception that frequently a fourth layer of cortex cells was noted in transgenic roots (FIG. 10 G). The increased cell number and the slightly reduced cell length indicates that the enhanced root growth is due to an increased number of cycling cells rather than increased cell growth. In the presence of lowered cytokinin content, root meristem cells must undergo additional rounds of mitosis before they leave the meristem and start to elongate. The exit from the meristem is therefore regulated by a mechanism that is sensitive to cytokinins. Apparently, cytokinins have a negative regulatory role in the root meristem and wild type cytokinin concentrations are inhibitory to the development of a maximal root system. Therefore, reducing the level of active cytokinins by overexpressing cytokinin oxidases stimulates root development, which results in an increase in the size of the root with more lateral and adventitious roots as compared to WT plants.

Example 11

AtCKX1 and AtCKX2-Overexpressing Tobacco Plants had a Reduced Cytokinin Content

Among the 16 different cytokinin metabolites that were measured, the greatest change occurred in the iP-type cytokinins in AtCKX2 overexpressers (Table 10): the overall decrease in the content of iP-type cytokinins is more pronounced in AtCKX2 expressing plants than in AtCKX1 transgenics. AtCKX1 transgenics showed a stronger phenotype in the shoot. It is not known which cytokinin metabolite is relevant for the different traits that were analysed. It may be that different cytokinin forms play different roles in the various development processes. Smaller alterations were noted for Z-type cytokinins, which could be due to a different accessibility of the substrate or a lower substrate specificity of the protein. The total content of iP and Z metabolites in individual transgenic clones was between 31% and 63% of wild type. The cytokinin reserve pool of O-glucosides was also lowered in the transgenics (Table 10). The concentration of N-glucosides and DHZ-type cytokinins was very low and was not or only marginally, altered in transgenic seedlings (data not shown).

transgenic shoot (FIG. 12 C). Interestingly, the WT scions grafted on the transgenic rootstocks looked healthier and were better developed. Notably, senescence of the basal leaves was retarded in these plants (see FIG. 12 A); (ii) the transgenic scion grafted on the WT rootstock looked similar to the aerial part of the transgenic plant from which it was derived, i.e. the shoot dwarfing phenotype is also autonomous and not dependent on the improved root growth (see FIG. 12 B).

In addition to the above-mentioned better appearance of WT shoots grafted on a transgenic rootstock, the formation of

TABLE 10

Cytokinin content of AtCKX transgenic plants.

| Line | | AtCKX1-2 | | AtCKX1-28 | | AtCKX2-38 | | AtCKX2-40 | |
| --- | --- | --- | --- | --- | --- | --- | --- | --- | --- |
| Cytokinin meta-bolite | WT Concentration | Concentration | % of WT | Concentration | % of WT | Concentration | % of WT | Concentration | % of WT |
| iP   | 5.90 ± 1.80 | 4.76 ± 0.82 | 81  | 4.94 ± 2.62 | 84 | 1.82 ± 0.44 | 31 | 2.85 ± 0.62 | 48 |
| iPR  | 2.36 ± 0.74 | 1.53 ± 0.14 | 65  | 0.75 ± 0.27 | 32 | 0.55 ± 0.39 | 23 | 0.89 ± 0.07 | 38 |
| iPRP | 3.32 ± 0.73 | 0.87 ± 0.26 | 26  | 1.12 ± 0.13 | 34 | 0.80 ± 0.48 | 24 | 1.68 ± 0.45 | 51 |
| Z    | 0.24 ± 0.06 | 0.17 ± 0.02 | 71  | 0.22 ± 0.03 | 92 | 0.21 ± 0.06 | 88 | 0.22 ± 0.02 | 92 |
| ZR   | 0.60 ± 0.13 | 0.32 ± 0.12 | 53  | 0.34 ± 0.03 | 57 | 0.34 ± 0.15 | 57 | 0.32 ± 0.05 | 53 |
| ZRP  | 0.39 ± 0.17 | 0.42 ± 0.11 | 107 | 0.28 ± 0.15 | 72 | 0.06 ± 0.01 | 15 | 0.17 ± 0.06 | 44 |
| ZOG  | 0.46 ± 0.20 | 0.32 ± 0.09 | 70  | 0.26 ± 0.13 | 57 | 0.20 ± 0.07 | 43 | 0.12 ± 0.02 | 26 |
| ZROG | 0.48 ± 0.17 | 0.30 ± 0.06 | 63  | 0.47 ± 0.02 | 98 | 0.23 ± 0.05 | 48 | 0.30 ± 0.13 | 63 |
| Total | 13.75 | 8.69 | 63 | 8.38 | 61 | 4.21 | 31 | 6.55 | 48 |

Cytokinin extraction, immunopurification, HPLC separation and quantification by ELISA methods was carried out as described by Faiss et al., 1997. Three independently pooled samples of approximately 100 two week old seedlings (2.5 g per sample) were analysed for each clone. Concentrations are in pmol x g fresh weight$^{-1}$.
Abbreviations:
iP, $N^6$-($\Delta^2$isopentenyl)adenine;
iPR, $N^6$-($\Delta^2$isopentenyl)adenine riboside;
iPRP, $N^6$-($\Delta^2$isopentenyl)adenine riboside 5'-monophosphate;
Z, trans-zeatin;
ZR, zeatin riboside;
ZRP, zeatin riboside 5'-monophosphate;
ZOG, zeatin O-glucoside;
ZROG, zeatin riboside O-glucoside.

Example 12

Grafting Experiments Showed that Dwarfing and Enhanced Root Development Due to AtCKX Overexpression is Confined to Transgenic Tissues To investigate which phenotypic effects of cytokinin oxidase overexpression are restricted to expressing tissues, i.e. are cell- or organ-autonomous traits, grafting experiments were performed. Reciprocal grafts were made between an AtCKX2 transgenic tobacco plant and a WT tobacco. The transgenic plant used in this experiment was AtCKX2-38, which displayed a strong phenotype characterized by enhanced root growth and reduced development of the aerial plant parts. As described in Example 3 through 6, these were two important phenotypes that resulted from cytokinin oxidase overexpression in tobacco and *arabidopsis*.

Plants were about 15 cm tall when grafted and the graft junction was about 10 cm above the soil. FIG. 12 shows plants 15 weeks after grafting. The main results were that: (i) the aerial phenotype of a WT scion grafted on a transgenic rootstock was similar to the WT control graft (=WT scion on WT rootstock). Importantly, this showed that overexpression of the AtCKX2 transgene in the rootstock did not induce dwarfing of the non-transgenic aerial parts of the plant (see FIG. 12 A). Improved root growth of the transgenic rootstock was maintained, indicating that improved root growth of AtCKX transgenics is autonomous and does not depend on an AtCKX adventitious roots on the basal part of WT shoots was noted (FIG. 12 D, right plant). Formation of adventitious roots also occurred on the stem of AtCKX transgenics but not on stems of WT control grafts (FIG. 12 D, left plant) and therefore seems to be a non-autonomous trait.

In summary, it is disclosed in this invention that enhanced root formation and dwarfing of the shoot in AtCKX overexpressing tobacco are autonomous traits and can be uncoupled by grafting procedures. Surprisingly, grafting of a WT scion on an AtCKX transgenic rootstock resulted in more vigorously growing plants and retardation of leaf senescence.

As an alternative to grafting, tissue-specific promoters could be used for uncoupling the autonomous phenotypic effects of cytokinin overexpression. Therefore, it is disclosed in this invention that cytokinin oxidase overexpression in a tissue specific manner can be used to alter the morphology of a plant such as the shoot or root system.

Example 13

Expression of an AtCKX Gene Under a Root-Specific Promoter in Transgenic Plants Leads to Increased Root Production An AtCKX gene (see example 4) is cloned under control of the root clavata homolog promoter of *Arabidopsis* (SEQ ID NO: 36), which is a promoter that drives root-specific expression. Other root-specific promoters may also be used for the purpose of this invention. See Table 5 for exemplary root-specific promoters.

Transgenic plants expressing the AtCKX gene specifically in the roots show increased root production without negatively affecting growth and development of the aerial parts of the plant. Positive effects on leaf senescence and growth of aerial plant parts are observed.

Example 14

Suppression of an AtCKX Gene Under a Senescence-Induced Promoter in Transgenic Plants Leads to Delayed Leaf Senescence and Enhanced Seed Yield A chimeric gene construct derived from an AtCKX gene and designed to suppress expression of endogenous cytokinin oxidase gene(s) is cloned under control of a senescence-induced promoter. For example, promoters derived from senescence-associated genes (SAG) such as the SAG12 promoter can be used (Quirino et al., 2000). Transgenic plants suppressing endogenous cytokinin oxidase gene(s) specifically in senescing leaves show delayed leaf senescence and higher seed yield without negatively affecting the morphology and growth and development of the plant.

type. Gain of weight for seeds of AtCKX2 and AtCKX4 expressing lines was in the range of 10-25% (Table 11 and FIG. 14).

The increases in size and weight for seeds, embryos, and cotyledons are unexpected as a reduced cytokinin content would have been expected to be associated with a reduced organ growth. One possible reason for the increases in seed, embryo, and cotyledon size is a previously unknown negative regulatory function of cytokinins in these storage organs. A negative regulatory functions of cytokinins in the control of organ growth is so far only known from roots (Werner et al. 2001). We propose, therefore, that localized expression of cytokinin oxidase genes in tissues where growth is negatively regulated by cytokinins leads to enhanced growth of this tissue. For example, localized expression of CKX genes during cotyledon development likely leads to enhanced growth of cotyledons and in species with cotyledons as storage organs, to enhanced yield and to an enhanced growth performance of seedlings. Total number of seeds is lowered in AtCKX1 and AtCKX3 expressers. There have been no previous reports however, of lower seed number in *Arabidopsis* being linked to an increase in size.

TABLE 11

|  | WT | CKX1-11-7 | CKX1-15-1 | CKX2-2-4 | CKX2-9-3 | CKX3-9-4 | CKX3-12-13 | CKX4-37-2 | CKX4-41-7 |
| --- | --- | --- | --- | --- | --- | --- | --- | --- | --- |
| Seed Weight | 0.0158 ± 0.0009 | 0.0372 ± 0.0015 | 0.0352 ± 0.0023 | 0.0201 ± 0.0017 | 0.0180 ± 0.0001 | 0.0340 ± 0.0027 | 0.0280 ± 0.0027 | 0.0185 ± 0.0004 | 0.0179 ± 0.0007 |
| % of WT | 100 | 235.5 | 222.6 | 126.7 | 113.7 | 215.0 | 176.7 | 116.8 | 112.7 |

Example 15

Overexpression of an AtCKX Gene in the Female Reproductive Organs Leads to Parthenocarpic Fruit Development The open reading frame of an AtCKX gene is cloned under control of a promoter that confers overexpression in the female reproductive organs such as for example the DefH9 promoter from *Antirrhinum majus* or one of its homologues, which have high expression specificity in the placenta and ovules. Transgenic plants with enhanced cytokinin oxidase activity in these tissues show parthenocarpic fruit development.

Example 16

Overexpression of AtCKX Genes Result in Increased Seed and Cotyledon Size

Transgenic *Arabidopsis thaliana* plants that overexpress cytokinin oxidase (AtCKX) genes under control of the 35S promoter as described supra. Transgenic plants, in particular those expressing the AtCKX1 and AtCKX3 genes, developed seeds with increased size which was almost entirely due to an enlarged embryo. Details of the seed, embryo and early postembryonic phenotypes are shown in FIGS. 13A through 13E. Table 11 shows seed weight of wild type and two independent clones for each of the four investigated AtCKX genes. Average weight was obtained by analysing five different batches of 200 seeds for each clone. A quantitative evaluation showed that the seed weight of AtCKX1 and AtCKX3 expressing clones was app. 1.8-2.3-fold higher than in wild

REFERENCES

WO0105985. Method to modulate the expression of genes inducing the parthenocarpic trait in plants.

Alberts, B., Bray, D., Lewis, J., Raff, M., Roberts, K., and Watson, J. D. (1994). "Molecular Biology of the Cell." Garland Publishing Inc.

Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." *Nucl. Acids Res.* 25, 3389-3402.

Armstrong, D. J. (1994) in *Cytokinins: Chemistry, Activity and Functions*, eds. Mok. D. W. S & Mok, M. C. (CRC Boca Raton, Fla.), pp. 139-154.

An, G., Watson, B. D., Stachel, S., Gordon, M. P., and Nester, E. W. (1985). New cloning vehicles for transformation of higher plants. *EMBO J.* 4, 277-284.

Armstrong, C. L., Petersen, W. P., Buchholz, W. G., Bowen, B. A., and Sulc, S. L. (1990). Factors affecting PEG-mediated stable transformation of maize protoplasts. *Plant Cell Reports* 9, 335-339.

Banerjee, A., Pramanik, A., Bhattacharjya, S., and Balaram, P. (1996). Omega amino acids in peptide design: incorporation into helices. *Biopolymers* 39, 769-777.

Baron, M. H. and Baltimore, D. (1982). Antibodies against the chemically synthesized genome-linked protein of poliovirus react with native virus-specific proteins. *Cell* 28, 395-404.

Bartel, P. L. and Fields, S. (1997). "The Yeast Two-Hybrid System." Oxford University Press.

Benkirane, N., Guichard, G., Briand, J. P., and Muller, S. (1996). Exploration of requirements for peptidomimetic immune recognition. Antigenic and immunogenic properties of reduced peptide bond pseudopeptide analogues of a historic hexapeptide. *J. Biol Chem.* 271, 33218-33224.

Berry, A. and Brenner, S. E. (1994). A prototype computer system for de novo protein design. *Biochem. Soc. Trans.* 22, 1033-1036.

Christou, P., McCabe, D. E., and Swain, W. F. (1988). Stable transformation of soybean callus by DNA-coated gold particles. *Plant Physiol.* 87, 671-674.

Crossway, A., Oakes, J. V., Irvine, J. M., Ward, B., Knauf, V. C., and Shewmaker, C. K. (1986). Integration of foreign DNA following microinjection of tobacco mesophyll protoplasts. *Mol. Gen. Genet.* 202, 179-185.

Dale, E. C. and Ow, D. W. (1990). Intra- and intermolecular site-specific recombination in plant cells mediated by bacteriophage P1 recombinase. *Gene* 91, 79-85.

Dodds, J. H. (1985). "Plant genetic engineering." Cambridge University Press.

Doerner, P., Jorgensen, J. E., You, R., Steppuhn, J., and Lamb, C. (1996). Control of root growth and development by cyclin expression. *Nature* 380, 520-523.

Dorner, B., Husar, G. M., Ostresh, J. M., and Houghten, R. A. (1996). The synthesis of peptidomimetic combinatorial libraries through successive amide alkylations. *Bioorg. Med. Chem.* 4, 709-715.

Ellis, J. G., Llewellyn, D. J., Dennis, E. S., and Peacock, W. J. (1987). Maize Adh-1 promoter sequences control anaerobic regulation: addition of upstream promoter elements from constitutive genes is necessary for expression in tobacco. *EMBO J.* 6, 11-16.

Faiss, M., Zalubilová, J., Strnad, M., Schmülling, T. (1997). Conditional transgenic expression of the ipt gene indicates a function for cytokinins in paracrine signaling in whole tobacco plants. *Plant J.* 12, 401-415.

Fassina, G. and Melli, M. (1994). Identification of interactive sites of proteins and protein receptors by computer-assisted searches for complementary peptide sequences. *Immunomethods.* 5, 114-120.

Fedoroff, N. V. and Smith, D. L. (1993). A versatile system for detecting transposition in *Arabidopsis*. *Plant J.* 3, 273-289.

Hanahan, D. (1983). Studies on transformation of *Escherichia coli* with plasmids. *J. Mol. Biol* 166, 557-580.

Hansen, G. and Chilton, M. D. (1996). "Agrolistic" transformation of plant cells: integration of T-strands generated in planta. *Proc. Natl. Acad. Sci. U.S.A* 93, 14978-14983.

Hansen, G., Shillito, R. D., and Chilton, M. D. (1997). T-strand integration in maize protoplasts after codelivery of a T-DNA substrate and virulence genes. *Proc. Natl. Acad. Sci. U.S.A* 94, 11726-11730.

Hanson, B., Engler, D., Moy, Y., Newman, B., Ralston, E., and Gutterson, N. (1999). A simple method to enrich an *Agrobacterium*-transformed population for plants containing only T-DNA sequences. *Plant J.* 19, 727-734.

Harlow, E. and Lane, D. (1988). "Antibodies: A Laboratory Manual." Cold Spring Harbor Laboratory Press.

Herrera-Estrella, L., De Block, M., Messens, E. H. J. P., Van Montagu, M., and Schell, J. (1983). Chimeric genes as dominant selectable markers in plant cells. *EMBO J.* 2, 987-995.

Hoffman, D. L., Laiter, S., Singh, R. K., Vaisman, I. I., and Tropsha, A. (1995). Rapid protein structure classification using one-dimensional structure profiles on the bioSCAN parallel computer. *Comput. Appl. Biosci.* 11, 675-679.

Hooykens, P. J. J., Hall, M. A. & Libbeuga, K. R., eds. (1999) *Biochemistry and Molecular Biology of Plant Hormones* (Elsevier, Amsterdam).

Houba-Heria, N., Pethe, C. d'Alayer, J & Lelouc, M. (1999) *Plant J.* 17:615-626.

Klee, H. J. & Lanehon, M. B. (1995) in *Plant Hormones: Physiology, Biochemistry and Molecular Biology*, ed. Davies, P. J. (Kluwer, Dordrdrocht, the Netherlands), pp. 340-353.

Krens, F. A., Molendijk, L., Wullems, G. J., and Schilperoort, R. A. (1982). In vitro transformation of plant protoplasts with Ti-plasmid DNA. *Nature* 296, 72-74.

Lerner, R. A. (1982). Tapping the immunological repertoire to produce antibodies of predetermined specificity. *Nature* 299, 593-596.

Lerner, R. A., Green, N., Alexander, H., Liu, F. T., Sutcliffe, J. G., and Shinnick, T. M. (1981). Chemically synthesized peptides predicted from the nucleotide sequence of the hepatitis B virus genome elicit antibodies reactive with the native envelope protein of Dane particles. *Proc. Natl. Acad. Sci. U.S.A* 78, 3403-3407.

Liddle, J. E. and Cryer, A. (1991). "A Practical Guide to Monoclonal Antibodies." Wiley New York.

Loffler, J., Langui, D., Probst, A., and Huber, G. (1994). Accumulation of a 50 kDa N-terminal fragment of beta-APP695 in Alzheimer's disease hippocampus and neocortex. *Neurochem. Int.* 24, 281-288.

Mok M. C. (1994) in *Cytokines: Chemistry, Activity and Function*, eds., Mok, D. W. S. & Mok, M. C. (CRC Boca Raton, Fla.), pp. 155-166.

Monge, A., Lathrop, E. J., Gunn, J. R., Shenkin, P. S., and Friesner, R. A. (1995). Computer modeling of protein folding: conformational and energetic analysis of reduced and detailed protein models. *J. Mol. Biol* 247, 995-1012.

Morris, R. O. et al. (1999). Isolation of a gene encoding a glycosylated cytokinin oxidase from maize. Bioechem. *Biophys. Res. Commun.* 255, 328-333

Motyka, V., Faiss, M., Strnad, M., Kaminek, M. and Schmuelling, T. (1996). Changes in cytokinin content and cytokinin oxidase activity in response to derepression of ipt gene transcription in transgenic tobacco calli and plants. *Plant Physiol.* 112, 1035-1043.

Murakami, T., Simonds, W. F., and Spiegel, A. M. (1992). Site-specific antibodies directed against G protein beta and gamma subunits: effects on alpha and beta gamma subunit interaction. *Biochemistry* 31, 2905-2911.

Olszewski, K. A., Kolinski, A., and Skolnick, J. (1996). Folding simulations and computer redesign of protein A three-helix bundle motifs. *Proteins* 25, 286-299.

Osborne, B. I., Wirtz, U., and Baker, B. (1995). A system for insertional mutagenesis and chromosomal rearrangement using the Ds transposon and Cre-lox. *Plant J.* 7, 687-701.

Ostresh, J. M., Blondelle, S. E., Dorner, B., and Houghten, R. A. (1996). Generation and use of nonsupport-bound peptide and peptidomimetic combinatorial libraries. *Methods Enzymol.* 267, 220-234.

Pabo, C. O. and Suchanek, E. G. (1986). Computer-aided model-building strategies for protein design. *Biochemistry* 25, 5987-5991.

Paszkowski, J., Shillito, R. D., Saul, M., Mandak, V., and Hohn, T. H. B. P. I. (1984). Direct gene transfer to plants. *EMBO J.* 3, 2717-2722.

Peralta, E. G., Hellmiss, R., and Ream, W. (1986). Overdrive, a T-DNA transmission enhancer on the *A. tumefaciens* tumour-inducing plasmid. *EMBO J.* 5, 1137-1142.

Quirino, B. F., Noh, Y.-S., Himelbau, E., and Amasino, R. M. (2000). Molecular aspects of leaf senescence. *Trends in Plant Science* 5, 278-282.

Renouf, D. V. and Hounsell, E. F. (1995). Molecular modelling of glycoproteins by homology with non-glycosylated protein domains, computer simulated glycosylation and molecular dynamics. *Adv. Exp. Med. Biol* 376, 37-45.

Rinaldi, A. C. and Comandini, O. (1999). Cytokinin oxidase strikes again. *Trends in Plant Sc.* 4, 300.

Rose, R. B., Craik, C. S., Douglas, N. L., and Stroud, R. M. (1996). Three-dimensional structures of HIV-1 and SIV protease product complexes. *Biochemistry* 35, 12933-12944.

Rutenber, E. E., McPhee, F., Kaplan, A. P., Gallion, S. L., Hogan, J. C., Jr., Craik, C. S., and Stroud, R. M. (1996). A new class of HIV-1 protease inhibitor: the crystallographic structure, inhibition and chemical synthesis of an aminimide peptide isostere. *Bioorg. Med. Chem.* 4, 1545-1558.

Sambrook, J., Fritsch, E. F., and Maniatis, T. (1989). "Molecular Cloning: A Laboratory Manual." Cold Spring Harbor Laboratory Press.

Schlappi, M., Smith, D., and Fedoroff, N. (1993). TnpA transactivates methylated maize Suppressor-mutator transposable elements in transgenic tobacco. *Genetics* 133, 1009-1021.

Shioda, T., Andriole, S., Yahata, T., and Isselbacher, K. J. (2000). A green fluorescent protein-reporter mammalian two-hybrid system with extrachromosomal maintenance of a prey expression plasmid: Application to interaction screening. *Proc. Natl. Acad. Sci. U.S.A* 97, 5220-5224.

Smulling, T., Rupp, H. M. Frank, M & Schafer, S. (1999) in *Advances in Regulation of Plant Growth and Development*, eds. Surnad, M. Pac P. & Beck, E. (Peres, Prague), pp. 85-96.

Tamura, R. N., Cooper, H. M., Collo, G., and Quaranta, V. (1991). Cell type-specific integrin variants with alternative alpha chain cytoplasmic domains. *Proc. Natl. Acad. U.S.A* 88, 10183-10187.

Werner, T., Vadau Motyka, Miroslav Strnad, and Thomas Schmülling (2001) Regulation of plant growth by cytokinin. *Proc. Nat. Acad. Sci.* 58 (18) 10487-10492.

Van Haaren, M. J., Sedee, N. J., Schilperoort, R. A., and Hooykaas, P. J. (1987). Overdrive is a T-region transfer enhancer which stimulates T-strand production in *Agrobacterium tumefaciens*. *Nucleic Acids Res.* 15, 8983-8997.

Van Sluys, M. A., Tempe, J., and Fedoroff, N. (1987). Studies on the introduction and mobility of the maize Activator element in *Arabidopsis thaliana* and *Daucus carota*. *EMBO J.* 6, 3881-3889.

Wang, K., Genetello, C., Van Montagu, M., and Zambryski, P. C. (1987). Sequence context of the T-DNA border repeat element determines its relative activity during T-DNA transfer to plant cells. *Mol. Gen. Genet.* 210, 338-346.

Woulfe, J., Lafortune, L., de Nadai, F., Kitabgi, P., and Beaudet, A. (1994). Post-translational processing of the neurotensin/neuromedin N precursor in the central nervous system of the rat—II. Immunohistochemical localization of maturation products. *Neuroscience* 60, 167-181.

Zhang, Y. L., Dawe, A. L., Jiang, Y., Becker, J. M., and Naider, F. (1996). A superactive peptidomimetic analog of a farnesylated dodecapeptide yeast pheromone. *Biochem. Biophys. Res. Commun.* 224, 327-331.

What is claimed is:

1. A method for increasing seed size or weight said method comprising introducing into a plant a nucleic acid molecule encoding a plant cytokinin oxidase selected from the group consisting of:
   (a) an isolated nucleic acid molecule comprising the DNA sequence as set forth in SEQ ID NO:11 or 30, or the complement thereof,
   (b) an isolated nucleic acid molecule comprising the RNA sequence encoding the amino acid sequence of SEQ ID NO:12, or the complement thereof,
   (c) an isolated nucleic acid molecule encoding the protein comprising the amino acid sequence as set forth in SEQ ID NO: 12, or the complement thereof, and
   (d) an isolated nucleic acid molecule as defined in any of (a) to (c) characterized in that said nucleic acid molecule is DNA, genomic DNA, cDNA, synthetic DNA or RNA wherein T is replaced by U, wherein the isolated nucleic acid molecule is preferentially expressed in the seed of the plant and wherein said expression increases seed size or weight.

2. A method for increasing embryo size or weight said method comprising introducing into a plant a nucleic acid molecule encoding a plant cytokinin oxidase selected from the group consisting of:
   (a) an isolated nucleic acid molecule comprising the DNA sequence as set forth in SEQ ID NO:11 or 30 or the complement thereof,
   (b) an isolated nucleic acid molecule comprising the RNA sequence encoding the amino acid sequence of SEQ ID NO:12, or the complement thereof,
   (c) an isolated nucleic acid molecule encoding the protein comprising the amino acid sequence as set forth in SEQ ID NO: 12, or the complement thereof, and
   (d) an isolated nucleic acid molecule as defined in any of (a) to (c) characterized in that said nucleic acid molecule is DNA, genomic DNA, cDNA, synthetic DNA or RNA wherein T is replaced by U,
   wherein the isolated nucleic acid molecule is preferentially expressed in the embryo of the plant and wherein said expression increases embryo size or weight.

3. A method for increasing cotyledon size or weight, said method comprising introducing into a plant a nucleic acid molecule encoding a plant cytokinin oxidase selected from the group consisting of:
   (a) an isolated nucleic acid molecule comprising the DNA sequence as set forth in SEQ ID NO:11 or 30, or the complement thereof,
   (b) an isolated nucleic acid molecule comprising the RNA sequence encoding the amino acid sequence of SEQ ID NO:12, or the complement thereof,
   (c) an isolated nucleic acid molecule encoding the protein comprising the amino acid sequence as set forth in SEQ ID NO: 12, or the complement thereof, and (d) an isolated nucleic acid molecule as defined in any of (a) to (c) characterized in that said nucleic acid molecule is DNA, genomic DNA, cDNA, synthetic DNA or RNA wherein T is replaced by U, wherein the isolated nucleic acid molecule is preferentially expressed in the cotyledon of the plant and wherein said expression increases cotyledon size or weight.

4. The method of claim 1 wherein the nucleic acid molecule is under control of a promoter that controls expression preferentially in seeds.

5. The method of claim 2 wherein the nucleic acid molecule is under the control of a promoter that controls expression preferentially in embryos.

6. The method of claim 3 wherein the nucleic acid molecule is under the control of a promoter that controls expression preferentially in cotyledons.

7. The method of claim 4 wherein the promoter is further specific to the endosperm or aleurone.

8. The method of claim 1 wherein said method leads to an increase in yield.

9. The method of claim 1 wherein said method leads to an increase in growth of seedlings or an increase in early vigor.

10. The method of claim 2 wherein said method leads to an increase in yield.

11. The method of claim 2 wherein said method leads to an increase in growth of seedlings or an increase in early vigor.

12. The method of claim 3 wherein said method leads to an increase in yield.

13. The method of claim 3 wherein said method leads to an increase in growth of seedlings or an increase in early vigor.

14. The method of claim 9 wherein the increase in growth of seedlings or early vigor is associated with increased stress tolerance.

15. The method of claim 11 wherein the increase in growth of seedlings or early vigor is associated with increased stress tolerance.

16. The method of claim 13 wherein the increase in growth of seedlings or early vigor is associated with increased stress tolerance.

* * * * *